(12) United States Patent
Chen et al.

(10) Patent No.: US 10,676,473 B2
(45) Date of Patent: Jun. 9, 2020

(54) SOLID STATE FORMS OF FUSED HETEROAROMATIC PYRROLIDINONES

(71) Applicant: TAKEDA PHARMACEUTICAL COMPANY LIMITED, Osaka (JP)

(72) Inventors: Rongliang Chen, San Diego, CA (US); Tomonori Ichibakase, Osaka (JP); Chunrong Ma, San Diego, CA (US); Christopher F. Matthews, San Diego, CA (US); Hajime Motoyoshi, Osaka (JP); Colin O'Bryan, San Diego, CA (US); Kentaro Yaji, Osaka (JP); Naoki Yoshikawa, Osaka (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 119 days.

(21) Appl. No.: 14/973,180

(22) Filed: Dec. 17, 2015

(65) Prior Publication Data

US 2016/0176869 A1 Jun. 23, 2016

Related U.S. Application Data

(60) Provisional application No. 62/093,564, filed on Dec. 18, 2014, provisional application No. 62/115,223, filed on Feb. 12, 2015, provisional application No. 62/180,222, filed on Jun. 16, 2015.

(51) Int. Cl.
| | | |
|---|---|---|
| *C07D 471/04* | (2006.01) | |
| *A61K 9/20* | (2006.01) | |
| *A61K 9/48* | (2006.01) | |

(52) U.S. Cl.
CPC .............. *C07D 471/04* (2013.01); *A61K 9/20* (2013.01); *A61K 9/48* (2013.01)

(58) Field of Classification Search
None
See application file for complete search history.

(56) References Cited

U.S. PATENT DOCUMENTS

| 8,440,689 | B2 * | 5/2013 | Arikawa | ............. | C07D 471/04 |
|---|---|---|---|---|---|
| | | | | | 514/265.1 |
| 9,108,970 | B2 | 8/2015 | Arikawa et al. | | |
| 9,181,255 | B2 | 11/2015 | Arikawa et al. | | |
| 2011/0152273 | A1 | 6/2011 | Arikawa et al. | | |
| 2013/0116260 | A1 | 5/2013 | Arikawa et al. | | |
| 2013/0245031 | A1 | 9/2013 | Arikawa et al. | | |
| 2015/0336964 | A1 | 11/2015 | Arikawa et al. | | |

FOREIGN PATENT DOCUMENTS

| EP | 2 516 434 B1 | 5/2015 | | |
|---|---|---|---|---|
| WO | WO 2011079051 | 6/2011 | | |
| WO | WO 2016048982 | * | 3/2016 | ............ A61K 31/424 |

OTHER PUBLICATIONS

Hygroscopicity Measurement Website, at web address, www.quora.com/Hygroscopy-How-is-the-hygroscopicity-of-a-substance-determined-chemically-What-makes-some-substances-more-hygroscopic-than-others, May 5, 2013.*
J.K. K Guillory, Generation of Polymorphs, Hydrates, Solvates, and Amorphous Solids, in Polymorphism in Pharmaceutical Solids 183-220 (H.G. Brittain ed., 1999).*
S.L. Morissette et al., Advanced Drug Delivery Reviews, 56, 275-300 (2004).*
S.R. Vippagunta et al., Advanced Drug Delivery Reviews, 48, 3-26 (2001).*
Bajpai et al., "Spleen tyrosine kinase: a novel target for therapeutic intervention of rheumatoid arthritis," Expert Opin. Investig. Drugs, 17(5):641-659 (2008).
Baudot et al., "The tyrosine kinase Syk regulates the survival of chronic lymphocytic leukemia B cells through PKCδ and proteasome-dependent regulation of Mcl-1 expression," Oncogene, 28:3261-3273 (2009).
Berge et al, "Pharmaceutical Salts," J. Pharm. Sci., 66(1):1-19 (1977).
Buchner et al., "Spleen Tyrosine Kinase Is Overexpressed and Represents a Potential Therapeutic Target in Chronic Lymphocytic Leukemia," Cancer Research, 69(13):5424-5432 (2009).
Cen et al., "The SYK inhibitor TAK-659 prevents splenomegaly and tumor development in a murine model of EBV-associated lymphoma," Blood (Abstracts & Meeting Program, ASH 58th Annual Meeting) 128(22): Abstract 4179 (2016).
Cen et al., "SYK inhibitor TAK-659 prevents splenomegaly and tumor development in a murine model of EBV-associated lymphoma," Poster presented at the ASH 58th Annual Meeting & Exposition, San Diego, CA, USA, Dec. 3-6, 2016.
Chu et al., "The Syk family of protein tyrosine kinases in T-cell activation and development," Immunol. Rev., 165:167-180 (1998).
Denyer et al., "SYK Kinase Inhibitors in Allergic Diseases," Drug News Perspect., 22(3):146-150 (2009).
Downing, James R., "Can Treating the SYK Cell Cure Leukemia?" Cancer Cell, 16:270-271 (2009).
Feldman et al., "Overexpression of Syk tyrosine kinase in peripheral T-cell lymphomas," Leukemia, 22:1139-1143 (2008).
Hahn et al., "Proteomic and Genetic Approaches Identify Syk as an AML Target," Cancer Cell, 16:281-294 (2009).
Huck et al., "Preclinical and Clinical Development of TAK-659: An Investigational SYK and FLT3 Kinase Inhibitor," Poster presented at the 12th International Ultmann Chicago Lymphoma Symposium, Chicago, IL, USA, Apr. 24-25, 2015.
Huck et al., "Antitumor activity of inhibiting SYK kinase with TAK-659, an investigational agent, in DLBCL models," J. Clin. Oncol. (2014 ASCO Annual Meeting), 32:5s, Abstract 8580 (2014).
Huck et al., "TAK-659, an investigational agent that demonstrates anti-tumor activity in DLBCL models by inhibiting SYK," Poster presented at the 2014 Annual Meeting of the American Society of Clinical Oncology (ASCO), Chicago, IL, USA, May 30-Jun. 3, 2014.

(Continued)

*Primary Examiner* — Jeffrey S Lundgren
*Assistant Examiner* — William Y Lee
(74) *Attorney, Agent, or Firm* — Jones Day

(57) ABSTRACT

Disclosed are chemical entities which are inhibitors of spleen tyrosine kinase (SYK), namely, chemical entities comprising 6-((1R,2S)-2-aminocyclohexylamino)-7-fluoro-4-(1-methyl-1H-pyrazol-4-yl)-1H-pyrrolo[3,4-c]pyridine-3 (2H)-one and certain solid state forms thereof. Also disclosed are methods of using the chemical entities to treat disorders such as a cancer.

8 Claims, 66 Drawing Sheets

(56) References Cited

OTHER PUBLICATIONS

Kaplan et al., "Updated Results from a Phase 1 Study of TAK-659, an Investigational and Reversible SYK Inhibitor, in Patients (Pts) with Advanced Solid Tumor or Lymphoma Malignancies," Blood (Abstracts & Meeting Program, 58th ASH Annual Meeting), 128(22): Abstract 624 (2016).
Kaplan et al., "Updated Results from a Phase 1 Study of TAK-659, an Ivestigational and Reversible SYK Inhibitor, in Patients with Advanced Solid Tumor or Lymphoma Malignancies," Presentation at the 58th ASH Annual Meeting and Exposition on Dec. 5, San Diego, CA, USA, (2016).
Lam, Betty, "Discovery of TAK-659, an Orally Available Investigational Inhibitor of Spleen Tyrosine Kinase (SYK)," Abstracts of Papers, 250th American Chemical Society National Meeting & Exposition, Boston, MA, USA, Aug. 16-20, 2015, Abstract MEDI 30, retrieved on Jan. 26, 2017, retrieved from internet: https://ep70.eventpilotadmin.com/web/page.php?page=IntHtml&project=ACS15fall&id=2286508.
Lam, Betty, "Discovery of TAK-659, an Orally Available Investigational Inhibitor of Spleen Tyrosine Kinase (SYK)," Presentation at the 250th American Chemical Society National Meeting & Exposition, Boston, MA, USA, Aug. 16-20, 2015.
Lam et al., "Discovery of TAK-659 an orally available investigational inhibitor of Spleen Tyrosine Kinase (SYK)," Bioorg. Med. Chem. Lett., 26(24): 5947-5950 (2016).
Masuda et al., "Syk inhibitors as treatment for allergic rhinitis," Pulmonary Pharmacology & Therapeutics, 21:461-467 (2008).
Petrich et al., "Ongoing, First-in-human, Phase 1, Dose-Escalation Study of Investigational SYK Inhibitor TAK-659 in Patients with Advanced Solid Tumors or Lymphoma," Hematological Oncology (Oral Presentations) 33:120, Abstract 039 (2015).
Petrich et al., "Ongoing, First-in-human, Phase 1, Dose-Escalation Study of Investigational SYK Inhibitor TAK-659 in Patients with Advanced Solid Tumors or Lymphoma," Presentation at the 13th International Conference on Malignant Lymphoma on Jun. 17, 2015, Lugano, Switzerland (2015).
Petrich et al., "Phase 1 Dose-Escalation Study of TAK-659, an Investigational SYK Inhibitor, in Patients (Pts) with Advanced Solid Tumor or Lymphoma Malignancies," Blood (Abstracts & Meeting Program, ASH 57th Annual Meeting), 126(23): Abstract 2693 (2015).
Petrich et al., "Phase 1 dose-escalation study of TAK-659, an investigational SYK inhibitor, in patients with advanced solid tumor or lymphoma malignancies," Poster presented at the 57th Annual Meeting of the American Society of Hematology (ASH), Orlando, FL, USA, Dec. 5-8, 2015.
Podolanczuk et al., "Of mice and men: an open-label pilot study for treatment of immune thrombocytopenic purpura by an inhibitor of Syk," Blood, 113(14):3154-3160 (2009).
Purroy et al., "Inhibition of BCR signaling using the Syk inhibitor TAK-659 prevents stroma-mediated signaling in chronic lymphocytic leukemia cells," Oncotarget, 8(1): 742-756 (2017).
Purroy et al., "Effect of Syk Inhibition by TAK-659 on Proliferative, Survival, and Migratory Signals from the Microenvironment in Chronic Lymphocytic Leukemia," J. Clin. Oncol. (2014 ASCO Annual Meeting) 32:5s, Abstract 7058 (2014).
Purroy et al., "Effect of Syk Inhibition by TAK-659 on Proliferative, Survival, and Migratory Signals from the Microenvironment in Chronic Lymphocytic Leukemia," Poster presented at the 2014 Annual Meeting of the American Society of Clinical Oncology (ASCO), Chicago, IL, USA, May 30-Jun. 3, 2014.
Rinaldi et al., "Genomic and expression profiling identifies the B-cell associated tyrosine kinase Syk as a possible therapeutic target in mantle cell lymphoma," Br. J. Haematol., 132:303-316 (2006).
Robertson et al., "Rapid Process Development and Scale-up of a Chiral cis-N-Boc-1,2-Diamine," Poster presented at Chemical Development Symposium, AMRI, Oct. 18-20, 2011.
Sanderson et al., "Syk: A Novel Target for Treatment of Inflammation in Lung Disease," Inflammation & Allergy—Drug Targets, 8:87-95 (2009).
Singh et al., "A Gene Expression Signature Associated with "K-Ras Addiction" Reveals Regulators of EMT and Tumor Cell Survival," Cancer Cell, 15:489-500 (2009).
Streubel et al., "Novel t(5;9)(q33;q22) fuses ITK to SYK in unspecified peripheral T-cell lymphoma," Leukemia, 20:313-318 (2006).
Turner et al., "Tyrosine kinase SYK: essential functions for immunoreceptor signalling," Immunology Today, 21(3):148-154 (2000).
Vanlang, Christopher, "Hygroscopy: How is the hygroscopicity of a substance determined, chemically? What makes some substances more hygroscopic than others?" May 5, 2013, www.quora.com/Hygroscopy-How-is-the-hygroscopicity-of-a-substance-determined-chemically-What-makes-some-substances-more-hygroscopic-than-others.
Wong et al., "Targeting Syk as a treatment for allergic and autoimmune disorders," Expert Opin. Investig. Drugs, 13(7):743-762 (2004).
Ashizawa, "Iyakuhin no takeigensho to shouseki no kagaku," pp. 273, 278, 305-317 (2002).
Australia Patent Office, Examination Report issued in AU Application No. 2015365580, dated Apr. 18, 2019, 5 pages.
Balbach et al., "Pharmaceutical evaluation of early development candidates: 'The 100 mg-approach'," International Journal of Pharmaceutics, 275:1-12 (2004).
Bastin et al., "Salt Selection and Optimisation Procedures for Pharmaceutical New Chemical Entities," Organic Process & Development, 427-435 (2000).
Caira et al., "Crystalline Polymorphism of Organic Compounds," Topics in Current Chemisty: Design of Organic Solids, Weber et al eds., Springer, Berlin, Germany, pp. 163-208 (1998).
Hirayama, "Yuki kagobutsu kessho sakusei handobukku Genri to nohau," pp. 17-23, 3740, 45-51, 57-65 (2008).
Japanese Patent Office, Examination Report issued in JP Application No. 2017-532678, dated Sep. 24, 2019, 5 pages (English Translation only).
Singhal et al., "Drug Polymorphism and Dosage Form Design: A practical perspective," Advanced Drug Delivery Reviews, 56:335-347 (2004).
Takashi, "Effective Solid Form Selection for the Pharmaceutical Development," Journal of pharmaceutical Science and Technology, 68(5):344-349 (2008).
Takata, "API form screening and selection in drug discovery stage," PHARMSTAGE, 6(10):20-25 (2007).

* cited by examiner

FIG. 58

SOLID STATE FORMS OF FUSED HETEROAROMATIC PYRROLIDINONES

CROSS-REFERENCE TO RELATED APPLICATIONS

This application claims the benefit under 35 U.S.C. § 119(e) of U.S. Provisional Application No. 62/093,564 filed on Dec. 18, 2014, U.S. Provisional Application No. 62/115,223 filed on Feb. 12, 2015, and U.S. Provisional Application No. 62/180,222 filed on Jun. 16, 2015. The entire contents of each of the aforesaid applications are incorporated by reference herein in their entireties.

FIELD

This invention relates to compounds, compositions and methods for the treatment of various disorders, particularly disorders of cell proliferation, including cancers, and inflammatory disorders. In particular, the invention provides fused heteroaromatic pyrrolidinone compounds that inhibit the activity of spleen tyrosine kinase (SYK).

BACKGROUND

Spleen tyrosine kinase (SYK) is a 72 kDa non-receptor cytoplasmic tyrosine kinase. SYK has a primary amino acid sequence similar to that of zeta-associated protein-70 (ZAP-70) and is involved in receptor-mediated signal transduction. The N-terminal domain of SYK contains two Src-homology 2 (SH2) domains, which bind to diphosphorylated immunoreceptor tyrosine-based activation motifs (ITAMs) found in the cytoplasmic signaling domains of many immunoreceptor complexes. The C-terminus contains the catalytic domain, and includes several catalytic loop autophosphorylation sites that are responsible for receptor-induced SYK activation and subsequent downstream signal propagation. SYK is expressed in many cell types involved in adaptive and innate immunity, including lymphocytes (B cells, T cells, and NK cells), granulocytes (basophils, neutrophils, and eosinophils), monocytes, macrophages, dendritic cells, and mast cells. SYK is expressed in other cell types, including airway epithelium and fibroblasts in the upper respiratory system. See, e.g., Martin Turner et al., Immunology Today (2000) 21(3):148-54; and Michael P. Sanderson et al., Inflammation & Allergy—Drug Targets (2009) 8:87-95.

SYK's role in ITAM-dependent signaling and its expression in many cell types suggest that compounds which inhibit SYK activity may be useful for treating disorders involving the immune system and inflammation. Such disorders include Type I hypersensitivity reactions (allergic rhinitis, allergic asthma, and atopic dermatitis); autoimmune diseases (rheumatoid arthritis, multiple sclerosis, systemic lupus erythematosus, psoriasis, and immune thrombocytopenic purpura); and inflammation of the lung (chronic obstructive pulmonary disease). See, e.g., Brian R. Wong et al., Expert Opin. Investig. Drugs (2004) 13(7):743-62; Sanderson et al. (2009); Jane Denyer & Vipul Patel, Drug News Perspective (2009) 22(3):146-50; Esteban S. Masuda & Jochen Schmitz, Pulmonary Pharmacology & Therapeutics (2008) 21:461-67; Malini Bajpai et al., Expert Opin. Investig. Drugs (2008) 17(5):641-59; and Anna Podolanczuk et al., Blood (2009) 113:3154-60. Other disorders include hematological malignancies, such as acute myeloid leukemia, B-cell chronic lymphocytic leukemia, B-cell lymphoma (e.g., mantle cell lymphoma), and T-cell lymphoma (e.g., peripheral T-cell lymphoma); as well as epithelial cancers, such as lung cancer, pancreatic cancer, and colon cancer. See, e.g., Cynthia K. Hahn et al., Cancer Cell (2009) 16:281-294; D. H. Chu et al., Immunol. Rev. (1998) 165: 167-180; A. L. Feldman et al., Leukemia (2008) 22:1139-43; A. Rinaldi et al., Br. J. Haematol. (2006) 132:303-316; B. Streubel et al., Leukemia (2006) 20:313-18; Maike Buchner et al., Cancer Research (2009) 69(13):5424-32; A. D. Baudot et al., Oncogene (2009) 28:3261-73; and Anurag Singh et al., Cancer Cell (2009) 15:489-500.

SUMMARY OF THE INVENTION

In certain embodiments, the invention relates to chemical entities comprising 6-((1R,2S)-2-aminocyclohexylamino)-7-fluoro-4-(1-methyl-1H-pyrazol-4-yl)-1H-pyrrolo[3,4-c]pyridine-3(2H)-one. In certain embodiments, the invention relates to 6-((1R,2S)-2-aminocyclohexylamino)-7-fluoro-4-(1-methyl-1H-pyrazol-4-yl)-1H-pyrrolo[3,4-c]pyridine-3(2H)-one citrate.

In certain embodiments, the invention relates to pharmaceutical compositions comprising a chemical entity comprising 6-((1R,2S)-2-aminocyclohexylamino)-7-fluoro-4-(1-methyl-1H-pyrazol-4-yl)-1H-pyrrolo[3,4-c]pyridine-3(2H)-one, and one or more pharmaceutically acceptable carriers.

In certain embodiments, the invention relates to pharmaceutical compositions comprising 6-((1R,2S)-2-aminocyclohexylamino)-7-fluoro-4-(1-methyl-1H-pyrazol-4-yl)-1H-pyrrolo[3,4-c]pyridine-3(2H)-one citrate, and one or more pharmaceutically acceptable carriers.

In certain embodiments, the invention relates to solid state forms of a chemical entity comprising 6-((1R,2S)-2-aminocyclohexylamino)-7-fluoro-4-(1-methyl-1H-pyrazol-4-yl)-1H-pyrrolo[3,4-c]pyridine-3(2H)-one. In certain embodiments, the invention relates to solid state forms of 6-((1R,2S)-2-aminocyclohexylamino)-7-fluoro-4-(1-methyl-1H-pyrazol-4-yl)-1H-pyrrolo[3,4-c]pyridine-3(2H)-one citrate.

In certain embodiments, the invention relates to methods of treating a cancer comprising administering to a patient having a cancer a chemical entity comprising 6-((1R,2S)-2-aminocyclohexylamino)-7-fluoro-4-(1-methyl-1H-pyrazol-4-yl)-1H-pyrrolo[3,4-c]pyridine-3(2H)-one. In certain embodiments, the invention relates to methods of treating a cancer comprising administering to a patient having a cancer 6-((1R,2S)-2-aminocyclohexylamino)-7-fluoro-4-(1-methyl-1H-pyrazol-4-yl)-1H-pyrrolo[3,4-c]pyridine-3(2H)-one citrate.

In certain embodiments, the invention relates to methods of making 6-((1R,2S)-2-aminocyclohexylamino)-7-fluoro-4-(1-methyl-1H-pyrazol-4-yl)-1H-pyrrolo[3,4-c]pyridine-3(2H)-one or a pharmaceutically acceptable salt thereof.

BRIEF DESCRIPTION OF THE FIGURES

FIG. 58 shows an XRPD pattern for crystalline Form 16.

DETAILED DESCRIPTION OF THE INVENTION

Figure 1:
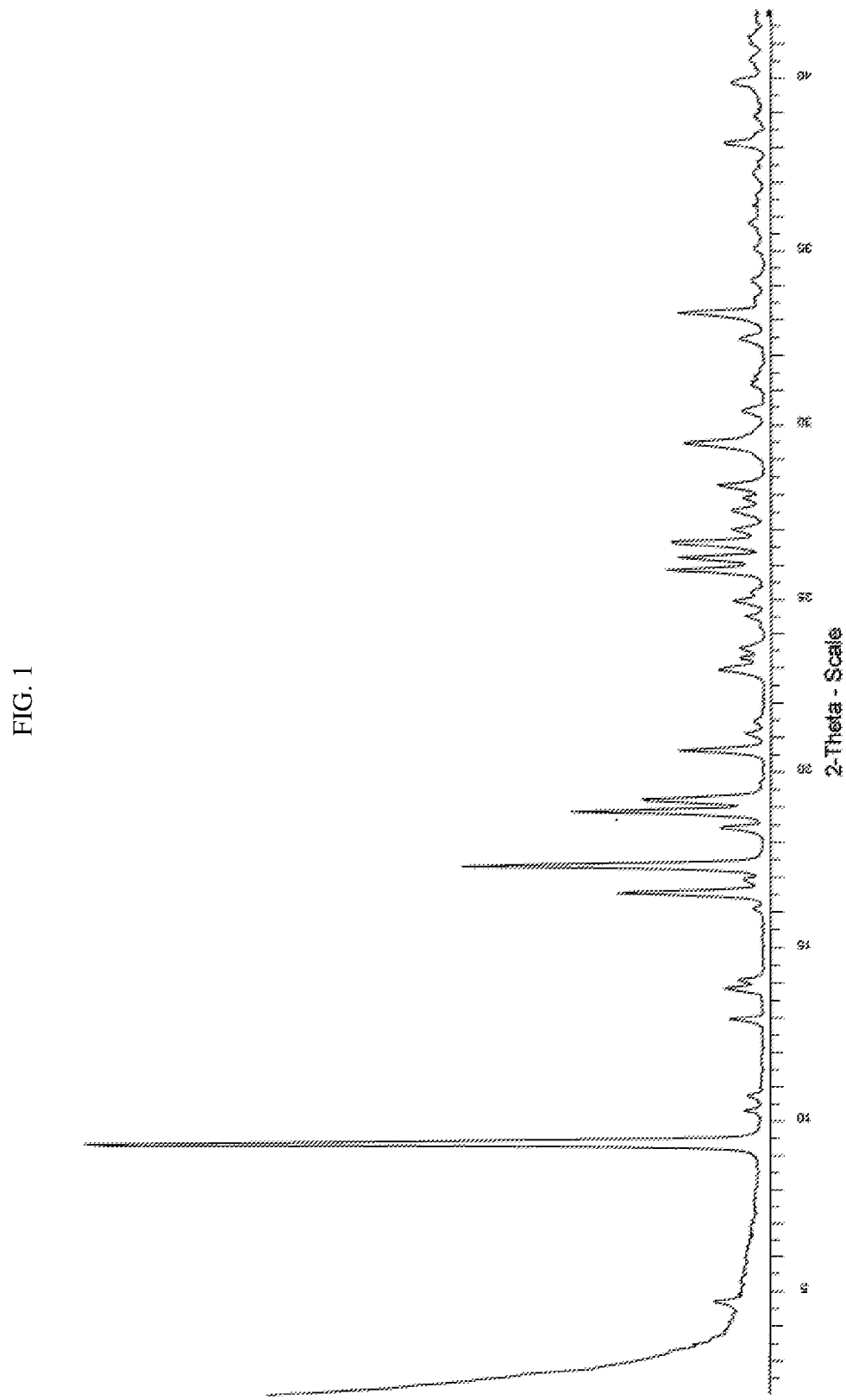
FIG. 1 shows a high resolution X-ray powder diffraction (XRPD) pattern for crystalline Form 1.

In certain embodiments, disclosed herein are chemical entities that are effective as inhibitors of spleen tyrosine kinase (SYK). In certain embodiments, the chemical entities that are disclosed herein are effective as inhibitors of SYK activity in vitro and in vivo, and may useful for the treatment of disorders of cell proliferation (e.g., a cancer). In certain embodiments, such chemical entities comprise one or more of the compounds disclosed in U.S. Pat. No. 8,440,689, which are incorporated herein by reference. In particular, U.S. Pat. No. 8,440,689 discloses fused heteroaromatic pyrrolidinones, such as pyrrolopyrimidinone (e.g., a 6,7-dihydro-5H-pyrrolo[3,4-c]pyrimidin-5-one) and pyrrolo-pyridinone (e.g., a 1H-pyrrolo[3,4-c]pyridine-3(2H)-one) compounds, which are incorporated herein by reference.

In certain embodiments, the chemical entity comprises 6-((1R,2S)-2-aminocyclohexylamino)-7-fluoro-4-(1-methyl-1H-pyrazol-4-yl)-1H-pyrrolo[3,4-c]pyridine-3(2H)-one ("Compound 1"):

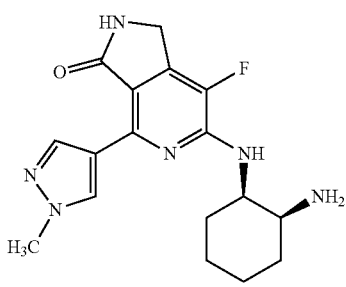

Compound 1 and non-covalently associated molecular entities. A chemical entity comprising Compound 1 thus includes, e.g., the free base; a pharmaceutically acceptable salt of Compound 1, a pharmaceutically acceptable solvate of Compound 1; a pharmaceutically acceptable solvate of a pharmaceutically acceptable salt of Compound 1. In some embodiments, the chemical entity is the free base of Compound 1 or a pharmaceutically acceptable salt thereof. In some embodiments, the chemical entity is a pharmaceutically acceptable salt of Compound 1. In some embodiments, the chemical entity is a solvate of the free base of Compound 1. In some embodiments, the chemical entity is a pharmaceutically acceptable solvate of a pharmaceutically acceptable salt of Compound 1.

The term "about" is used herein to mean approximately, in the region of, roughly, or around. When the term "about" is used in conjunction with a numerical range, it modifies that range by extending the boundaries above and below the numerical values set forth. Unless otherwise specified, the term "about" is used herein to modify a numerical value above and below the stated value by a variance of 10%.

Unless otherwise specified, the terms "include" and "including" and the like are intended to be non-limiting. For example, "including" means including but not limited to, unless otherwise indicated.

In the compounds described herein where relative stereochemistry is defined, the diastereomeric purity of such a compound may be at least 80%, at least 90%, at least 95%, or at least 99%. As used herein, the term "diastereomeric purity" refers to the amount of a compound having the depicted relative stereochemistry, expressed as a percentage of the total amount of all diastereomers present.

In certain embodiments described herein, the enantiomeric purity of the compound may be at least 80%, at least 90%, at least 95%, at least 96%, at least 97%, at least 98%, at least 99%, at least 99.5%, or at least 99.9%. As used herein, the term "enantiomeric purity" refers to the amount of a compound having the depicted absolute stereochemistry, expressed as a percentage of the total amount of the depicted compound and its enantiomer.

Methods for determining diastereomeric and enantiomeric purity are well-known in the art. Diastereomeric purity may be determined by any analytical method capable of quantitatively distinguishing between a compound and its diastereomers. Examples of suitable analytical methods include, without limitation, nuclear magnetic resonance spectroscopy (NMR), gas chromatography (GC), and high performance liquid chromatography (HPLC). Similarly, enantiomeric purity may be determined by any analytical method capable of quantitatively distinguishing between a compound and its enantiomer. Examples of suitable analytical methods include, but are not limited to, GC or HPLC, using a chiral column packing material. Enantiomers may also be distinguishable by NMR if first derivatized with an optically enriched derivatizing agent, e.g., Mosher's acid.

As used herein, "crystalline" refers to a solid in which the constituent atoms, molecules, or ions are packed in a regularly ordered, repeating three-dimensional pattern having a highly regular chemical structure. In particular, a crystalline chemical entity (e.g., a pharmaceutically acceptable salt) may be produced as one or more crystalline forms. For the purposes of this application, the terms "crystalline form" and "polymorph" are synonymous; the terms distinguish between crystals that have different properties (e.g., different XRPD patterns and/or different DSC scan results). Pseudopolymorphs are typically different solvates of a material, and thus their properties differ from one another. Thus, each distinct polymorph and pseudopolymorph is considered to be a distinct crystalline form herein.

"Substantially crystalline" refers to a chemical entity that is at least a particular weight percent crystalline. Particular weight percentages include 50%, 60%, 70%, 75%, 80%, 85%, 87%, 88%, 89%, 90%, 91%, 92%, 93%, 94%, 95%, 96%, 97%, 98%, 99%, 99.5% and 99.9%. In some embodiments, substantially crystalline refers to a chemical entity that is at least 70% crystalline. In some embodiments, substantially crystalline refers to a chemical entity that is at least 80% crystalline. In some embodiments, substantially crystalline refers to a chemical entity that is at least 85% crystalline. In some embodiments, substantially crystalline refers to a chemical entity that is at least at least 90% crystalline. In some embodiments, substantially crystalline refers to a chemical entity that is at least 95% crystalline.

The term "solvate or solvated" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" or "solvated" encompasses both solution-phase and isolable solvates. Representative solvates include, but are not limited to, hydrates, ethanolates, and methanolates.

The term "hydrate" refers to a solvate wherein the solvent molecule is water that is present in a defined stoichiometric amount, and includes, for example, hemihydrates, monohydrates, dihydrates, and trihydrates.

The term "mixture" refers to the combined components of the mixture regardless of the phase-state of the combination (e.g., liquid or liquid/crystalline).

The term "seeding" refers to the addition of crystalline material to a solution or mixture to initiate crystallization.

In certain embodiments, a chemical entity comprising a crystalline form as described herein is substantially free of amorphous forms of the chemical entity, wherein at least a particular percentage by weight of the chemical entity is crystalline. In certain such embodiments, the chemical entity is at least 10%, at least 20%, at least 30%, at least 40%, at least 50%, at least 60%, at least 70%, at least 75%, at least 80%, at least 85%, at least 87%, at least 88%, at least 89%, at least 90%, at least 91%, at least 92%, at least 93%, at least 94%, at least 95%, at least 96%, at least 97%, at least 98%, at least 99%, at least 99.5% or at least 99.9% crystalline. When a particular percentage by weight of the chemical entity is crystalline, the remainder of the chemical entity is amorphous material.

In certain embodiments, a chemical entity comprising a crystalline form as described herein is substantially free of other chemical entities of the chemical entity (e.g., other polymorphs or amorphous material), wherein the chemical entity is at least a particular percentage by weight of the particular crystalline form. In certain such embodiments, a chemical entity comprises at least 10%, at least 20%, at least 30%, at least 40%, at least 50%, at least 60%, at least 70%, at least 75%, at least 80%, at least 85%, at least 87%, at least 88%, at least 89%, at least 90%, at least 91%, at least 92%, at least 93%, at least 94%, at least 95%, at least 96%, at least 97%, at least 98%, at least 99%, at least 99.5% or at least 99.9% of a particular crystalline form. When a particular percentage by weight of the chemical entity is a designated crystalline form, the remainder of the chemical entity may be some combination of amorphous material and one or more other crystalline forms of the chemical entity excluding the particular crystalline form. In some embodiments, the chemical entity is at least 90% by weight of a particular crystalline form. In some embodiments, the chemical entity is at least 95% by weight of a particular crystalline form. In some embodiments, the chemical entity is at least 85% by weight of a particular crystalline form. In some embodiments, the chemical entity is at least 80% by weight of a particular crystalline form.

In certain embodiments, a chemical entity comprising a crystalline form as described herein is not hygroscopic or non-hygroscopic. In certain such embodiments, water sorption at 90% relative humidity (RH) is less than about 0.5%, less than about 0.4%, less than about 0.3%, or less than about 0.2% as shown by a gravimetric vapor sorption (GVS) isotherm plot. In certain such embodiments a chemical entity comprising a crystalline form as described herein exhibits a mass gain of less than about 0.5%, less than about 0.4%, less than about 0.3%, or less than about 0.2% when the RH is increased from about 0% to about 90% as shown by a gravimetric vapor sorption (GVS) isotherm plot. In certain embodiments, the XRPD pattern of a chemical entity comprising a crystalline form as described herein is substantially unchanged after moisture sorption analysis.

Unless otherwise specified, when a particular crystalline form of a chemical entity is identified using one or more XRPD peaks given as angles 2θ, each of the 2θ values is understood to mean the given value±0.2 degrees.

Throughout the specification and claims, when a crystalline form of a chemical entity is identified using one or more temperatures from a DSC profile (e.g., onset of endothermic transition, melt, etc.), each of the temperature values is understood to mean the given value±2° C.

Solid State Forms

Form 1

Provided herein is an assortment of characterizing information to describe a crystalline form of Compound 1 citrate ("Form 1").

FIG. 1 shows an X-ray powder diffraction (XRPD) pattern of Form 1 obtained using CuKα radiation. Peaks identified in FIG. 1 include those listed in Table 1.

TABLE 1

| Angle 2-Theta ° | Intensity % |
| --- | --- |
| 4.68 | 9.8 |
| 9.39 | 100.0 |
| 10.29 | 4.4 |
| 10.72 | 3.8 |
| 12.96 | 7.3 |
| 13.84 | 8.0 |
| 14.09 | 5.5 |
| 16.07 | 3.1 |
| 16.58 | 24.7 |

TABLE 1-continued

| Angle 2-Theta ° | Intensity % |
| --- | --- |
| 16.89 | 4.7 |
| 17.35 | 24.3 |
| 18.40 | 8.8 |
| 18.88 | 24.3 |
| 19.21 | 22.6 |
| 19.70 | 2.0 |
| 20.65 | 16.1 |
| 21.15 | 4.5 |
| 21.49 | 3.0 |
| 22.96 | 9.7 |
| 23.27 | 5.7 |
| 23.60 | 5.7 |
| 24.19 | 2.5 |
| 24.52 | 4.5 |
| 24.97 | 6.7 |
| 25.26 | 3.7 |

In some embodiments, Form 1 is characterized by an XRPD pattern having peaks at 2θ angles of 9.4, 16.6, 17.4, 18.9, and 19.2°. In some embodiments, Form 1 is characterized by an XRPD pattern having peaks at 2θ angles of 9.4, 16.6, 17.4, 18.9, 19.2, and 20.7°. In some embodiments, Form 1 is characterized by an XRPD pattern having peaks at 2θ angles of 4.7, 9.4, 16.6, 17.4, 18.9, 19.2, 20.7, and 23.0°. In some embodiments, Form 1 is characterized by an XRPD pattern having peaks at 2θ angles of 4.7, 9.4, 13.0, 13.8, 14.1, 16.6, 17.4, 18.4, 18.9, 19.2, 20.7, 23.0, 23.3, 23.6, and 25.0°. In some embodiments, Form 1 is characterized by an XRPD pattern substantially as shown in FIG. 1.

Figure 2:
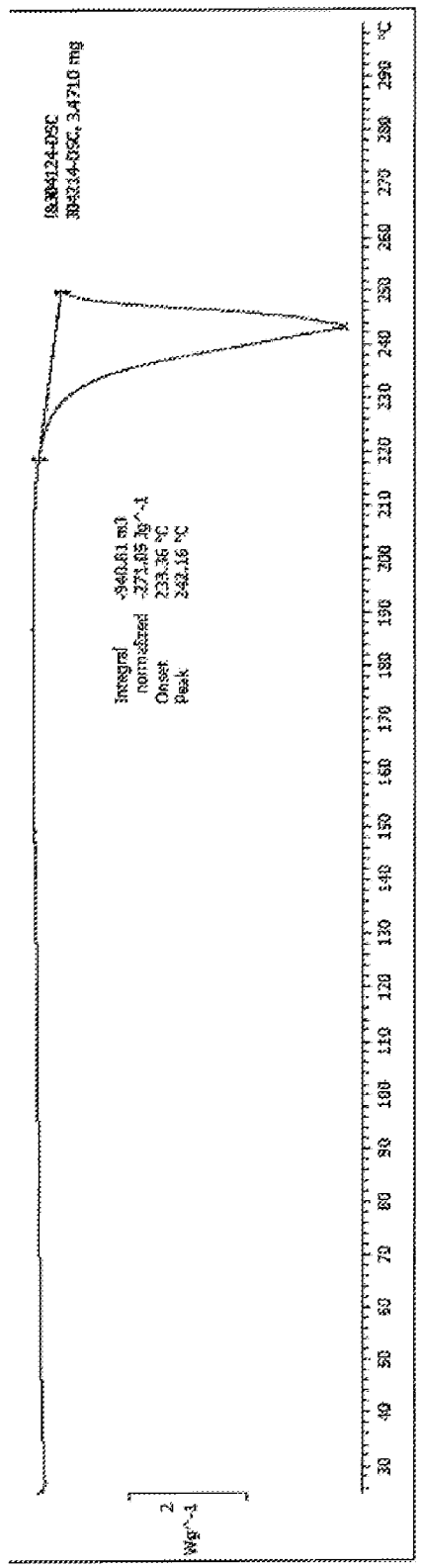
FIG. 2 shows a differential scanning calorimetry (DSC) thermogram for crystalline Form 1.

FIG. 2 shows a differential scanning calorimetry (DSC) profile of Form 1. The DSC thermogram plots the heat flow as a function of temperature from a sample, the temperature rate change being about 10° C./min. FIG. 2 shows an endotherm event with onset of about 233.4° C. and peak at about 242.2° C. In some embodiments, Form 1 is characterized by a DSC profile substantially as shown in FIG. 2.

Figure 3:
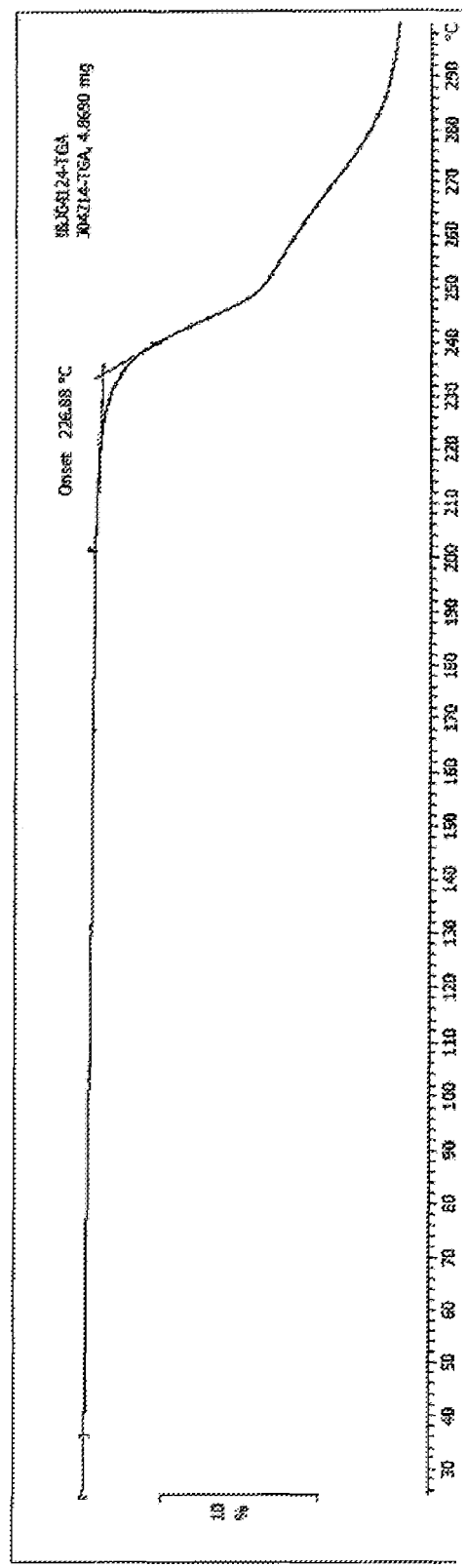
FIG. 3 shows a thermogravimetric analysis (TGA) thermogram for crystalline Form 1.

FIG. 3 shows a thermal gravimetric analysis (TGA) profile of Form 1. The TGA thermogram plots the percent loss of weight of the sample as a function of temperature, the temperature rate change being about 10° C./min. FIG. 3 shows no significant weight loss during heating of the sample, suggesting that Form 1 is not solvated. FIG. 3 also shows onset of decomposition of Form 1 at about 226.9° C. In some embodiments, Form 1 is characterized by a TGA profile substantially as shown in FIG. 3.

Figure 4:
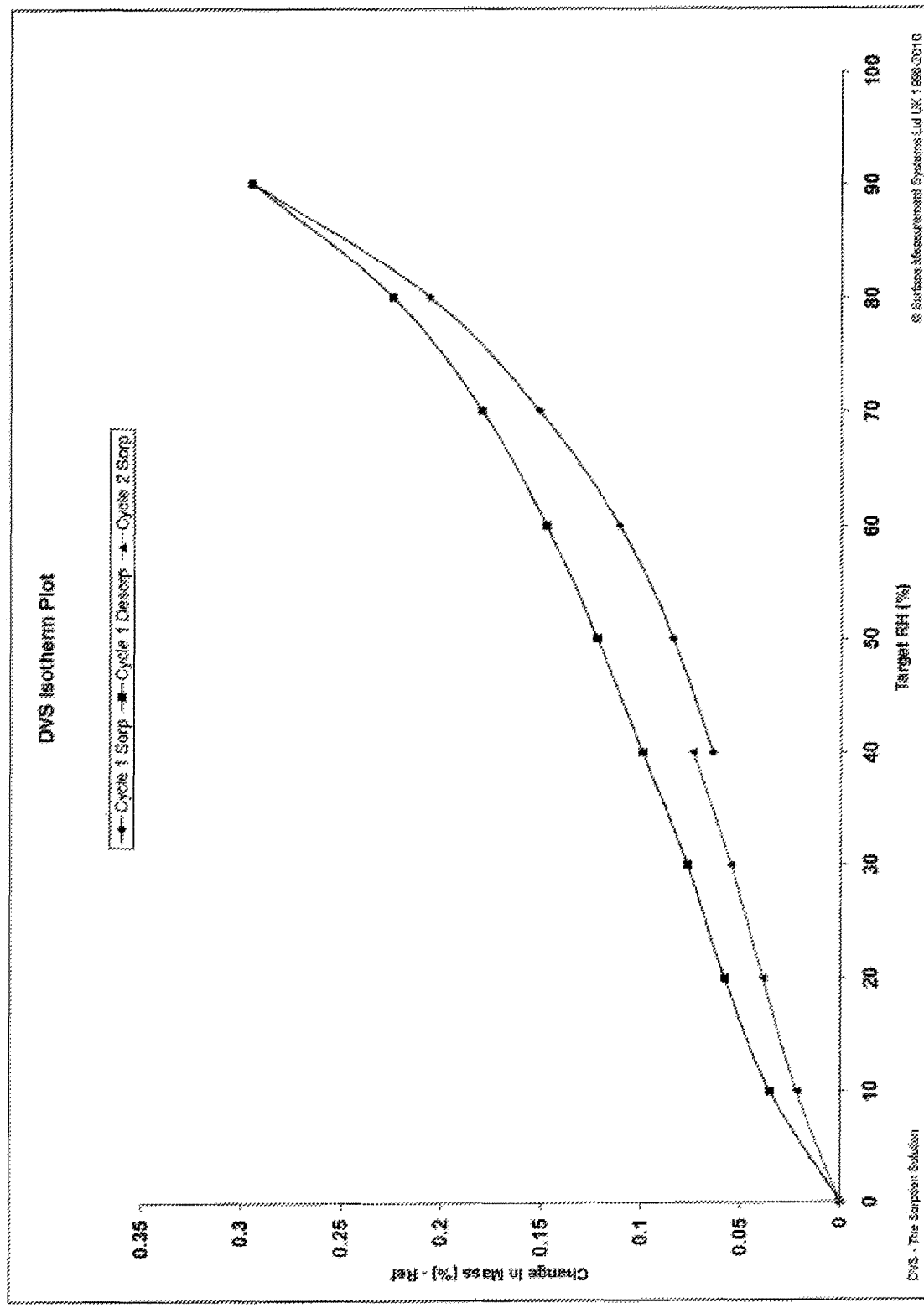
FIG. 4 shows a gravimetric vapor sorption (GVS) isotherm plot for crystalline Form 1.

FIG. 4 shows a gravimetric vapor sorption (GVS) isotherm plot of Form 1. The GVS shows a less than 0.3% w/w variation, indicating that Form 1 is not hygroscopic when subjected to humidity. In some embodiments, Form 1 is characterized by a GVS profile substantially as shown in FIG. 4.

In certain embodiments, Form 1 is a monoclinic crystal form. In certain embodiments, Form 1 belongs to space group $P2_1$. In certain embodiments, Form 1 has the following unit cell dimensions: a=9.35(3) Å, b=6.697(17) Å, c=18.79(5) Å; α=90°, β=92.900, γ=90°.

Form 2

Provided herein is an assortment of characterizing information to describe an amorphous form Compound 1 citrate ("Form 2").

Figure 5:
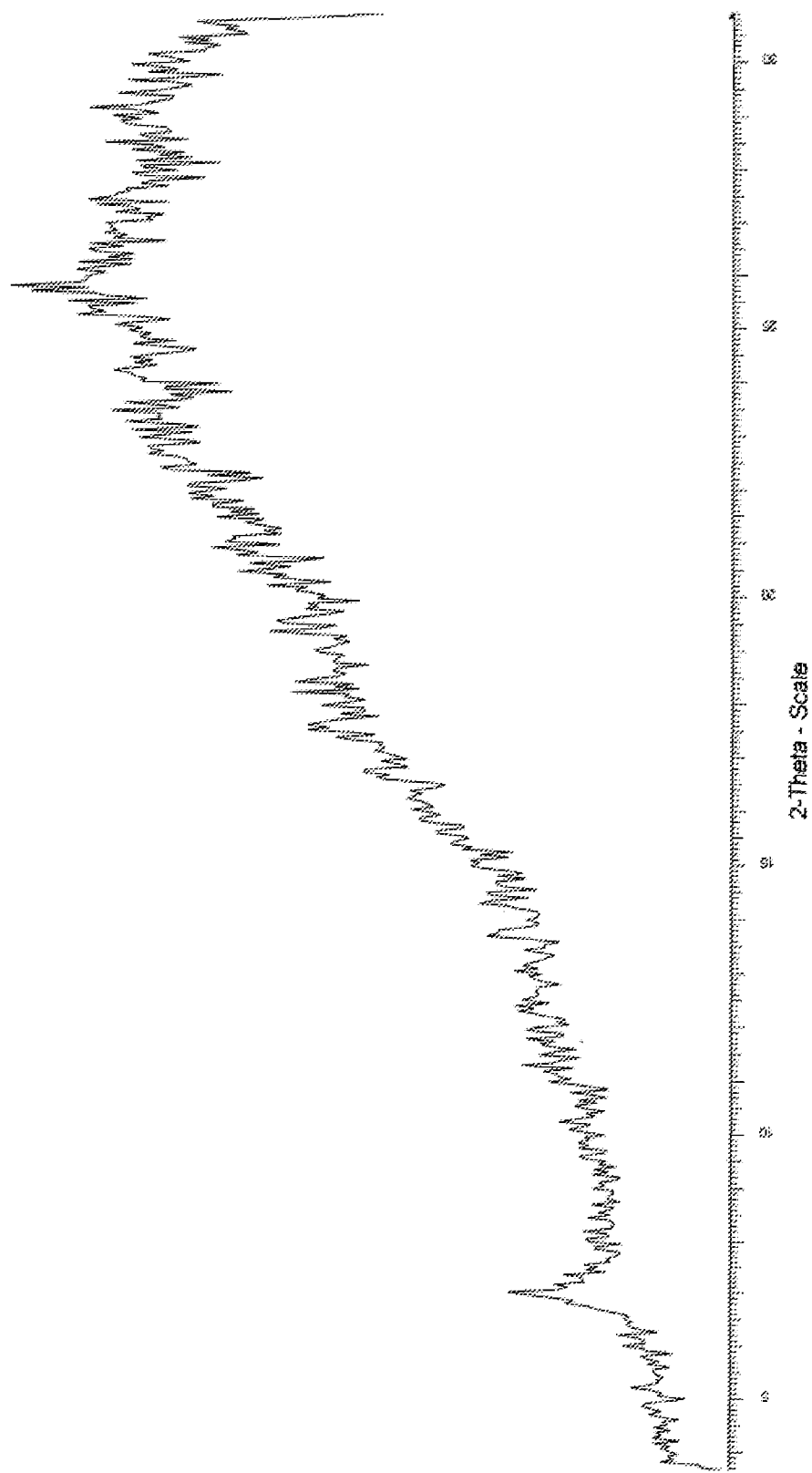
FIG. 5 shows a high resolution XRPD pattern for amorphous Form 2.

FIG. 5 shows an X-ray powder diffraction (XRPD) pattern of Form 2 obtained using CuKα radiation. In some embodiments, Form 2 is characterized by an XRPD pattern substantially as shown in FIG. 5.

Figure 6:
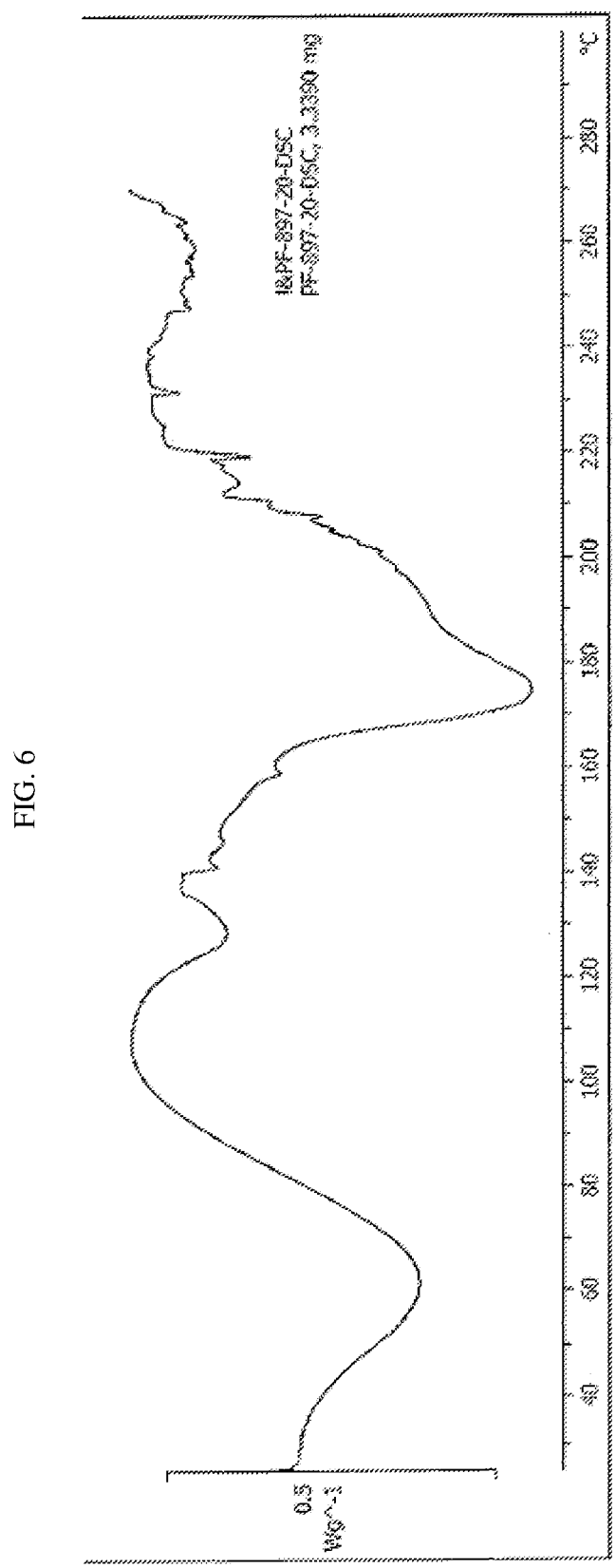
FIG. 6 shows a DSC thermogram for amorphous Form 2.

FIG. 6 shows a differential scanning calorimetry (DSC) profile of Form 2. The DSC thermogram plots the heat flow as a function of temperature from a sample, the temperature rate change being about 10° C./min. In some embodiments, Form 2 is characterized by a DSC profile substantially as shown in FIG. 6.

Figure 7:
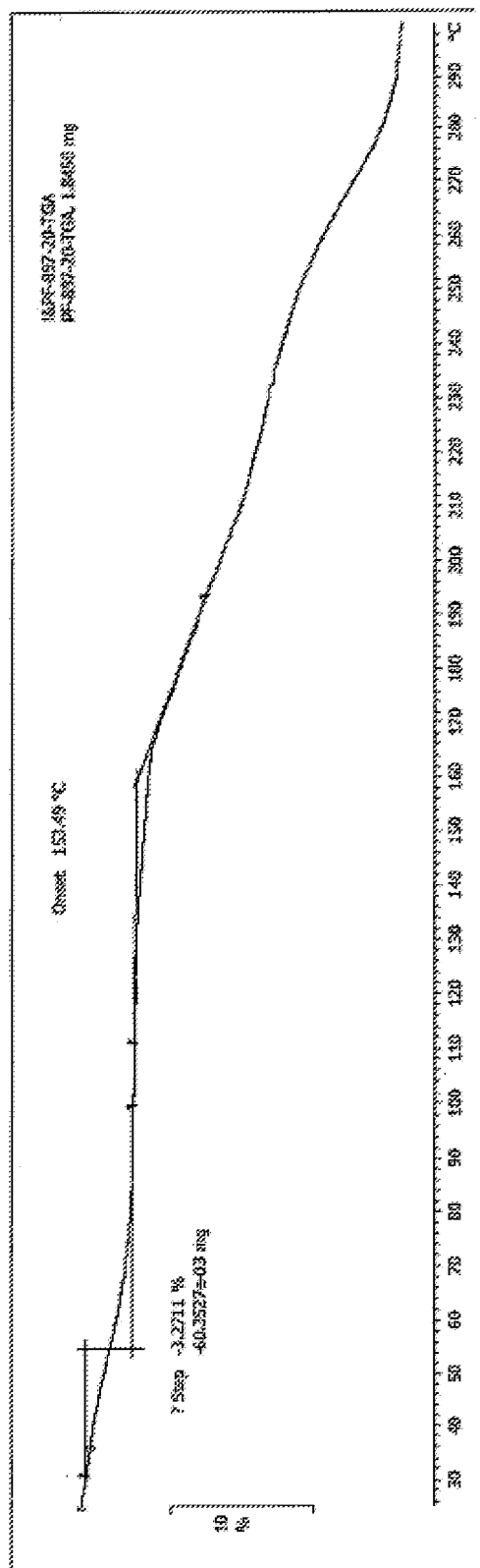
FIG. 7 shows a TGA thermogram for amorphous Form 2.

FIG. 7 shows a thermal gravimetric analysis (TGA) profile of Form 2. The TGA thermogram plots the percent loss of weight of the sample as a function of temperature, the temperature rate change being about 10° C./min. FIG. 7 shows that Form 2 contains approximately 3.3% water. In some embodiments, Form 2 is characterized by a TGA profile substantially as shown in FIG. 7.

Figure 8:
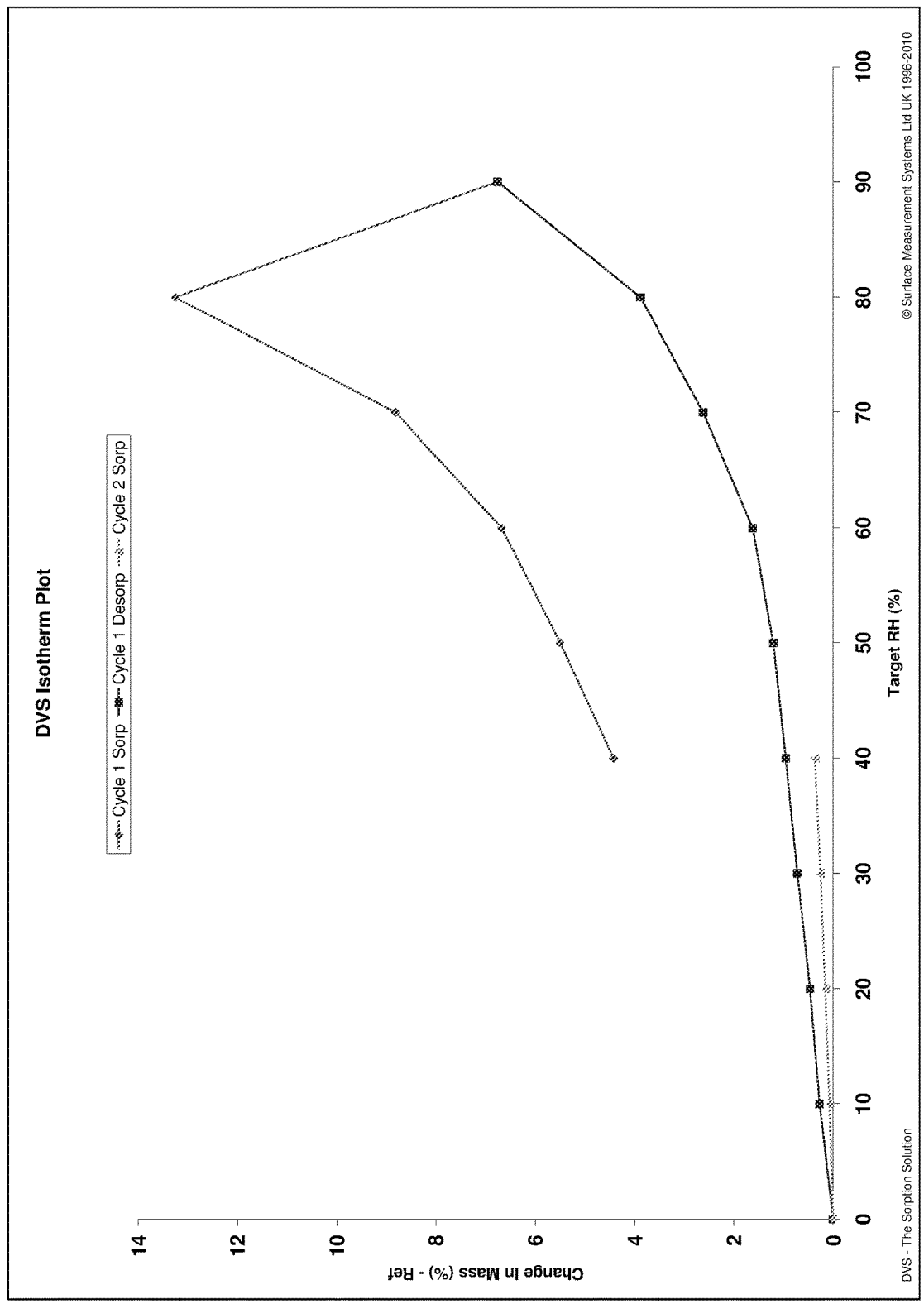
FIG. 8 shows a GVS isotherm plot for amorphous Form 2.

FIG. 8 shows a gravimetric vapor sorption (GVS) isotherm plot of Form 2. The GVS shows that Form 2 adsorbs moisture in the range of 40-80% relative humidity (RH) and undergoes a crystallization event above 80% RH. The crystallization event is accompanied by a weight loss of 7% between 80% and 90% RH. In some embodiments, Form 2 is characterized by a GVS profile substantially as shown in FIG. 8.

Form 3

Provided herein is an assortment of characterizing information to describe a crystalline form of Compound 1 hydrochloride dihydrate ("Form 3").

Figure 9:
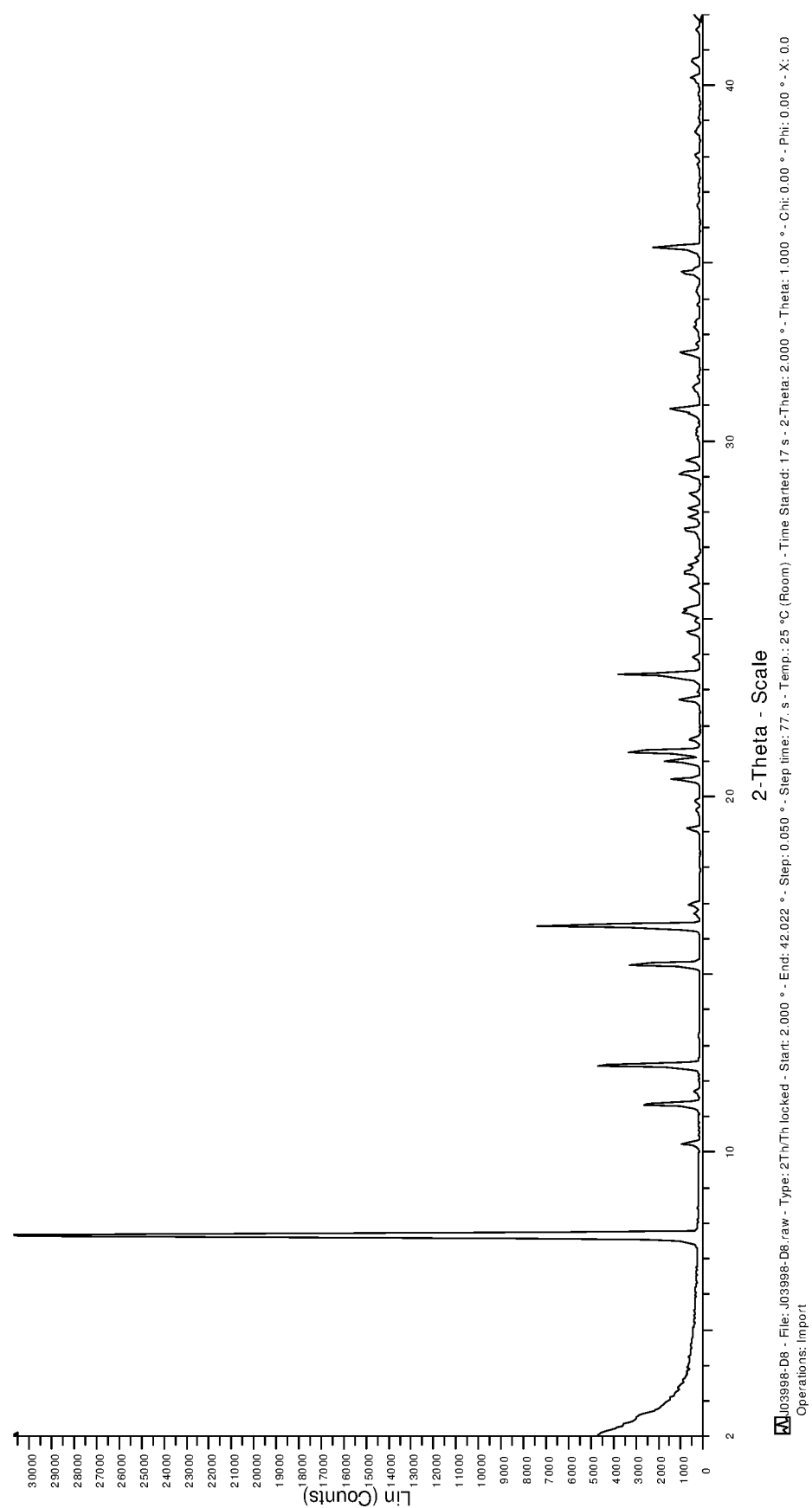
FIG. 9 shows a high resolution XRPD pattern for crystalline Form 3.

FIG. 9 shows an X-ray powder diffraction (XRPD) pattern of Form 3 obtained using CuKα radiation. Peaks identified in FIG. 9 include those listed in Table 2.

TABLE 2

| Angle 2-Theta ° | Intensity % |
|---|---|
| 7.62 | 100.0 |
| 10.21 | 4.4 |
| 11.30 | 8.8 |
| 11.69 | 1.7 |
| 12.40 | 16.1 |
| 13.27 | 0.8 |
| 15.24 | 10.5 |
| 16.34 | 23.9 |
| 16.69 | 1.8 |
| 16.93 | 2.8 |
| 19.07 | 3.1 |
| 19.60 | 1.2 |
| 19.88 | 1.5 |
| 20.48 | 5.0 |
| 20.99 | 5.6 |
| 21.24 | 10.8 |
| 21.59 | 3.0 |
| 22.73 | 3.9 |
| 22.93 | 1.3 |
| 23.43 | 12.6 |
| 23.91 | 2.3 |
| 24.63 | 3.0 |
| 24.96 | 1.5 |
| 25.18 | 4.0 |
| 25.82 | 2.7 |

In some embodiments, Form 3 is characterized by an XRPD pattern having peaks at 2θ angles of 7.6, 12.4, 15.2, 16.3, 21.2, and 23.4°. In some embodiments, Form 3 is characterized by an XRPD pattern having peaks at 2θ angles of 7.6, 11.3, 12.4, 15.2, 16.3, 20.1, 21.2, and 23.4°. In some embodiments, Form 3 is characterized by an XRPD pattern substantially as shown in FIG. 9.

Figure 10:
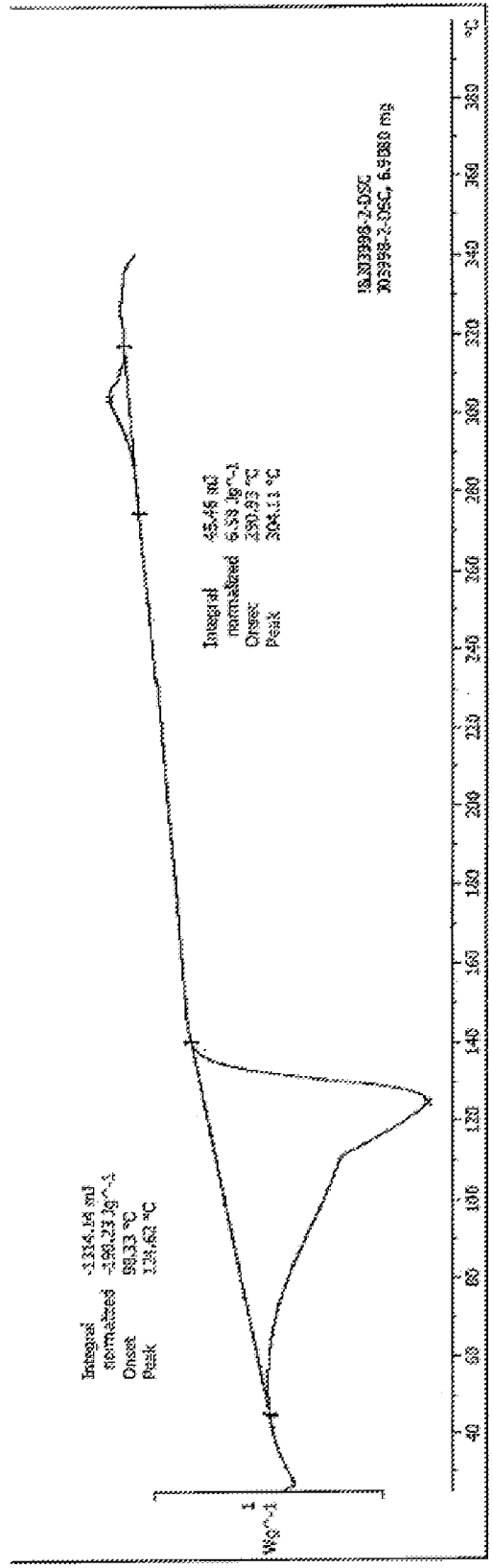
FIG. 10 shows a DSC thermogram for crystalline Form 3.

FIG. 10 shows a differential scanning calorimetry (DSC) profile of Form 3. The DSC thermogram plots the heat flow as a function of temperature from a sample, the temperature rate change being about 10° C./min. FIG. 10 shows a broad endothermic event with onset of about 98.3° C. and peak at about 124.6° C. as well as a solid-solid transition at about 290° C. In some embodiments, Form 3 is characterized by a DSC profile substantially as shown in FIG. 10.

Figure 11:
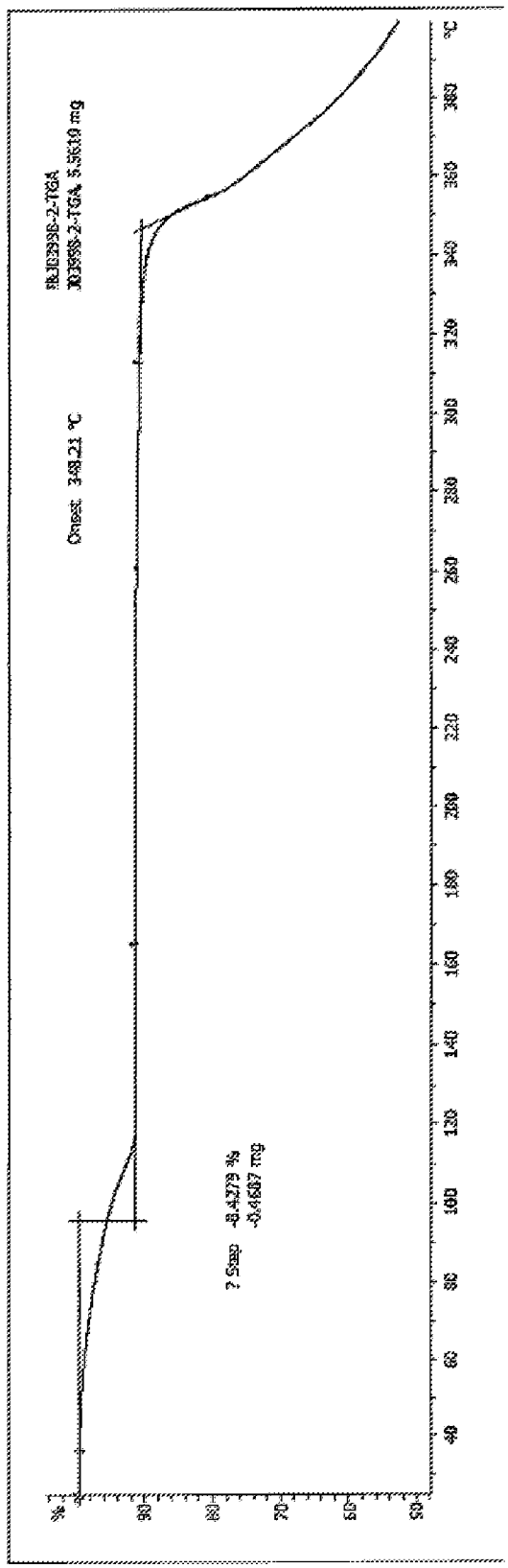
FIG. 11 shows a TGA thermogram for crystalline Form 3.

FIG. 11 shows a thermal gravimetric analysis (TGA) profile of Form 3. The TGA thermogram plots the percent loss of weight of the sample as a function of temperature, the temperature rate change being about 10° C./min. FIG. 11 shows a weight loss of about 8.4%, suggesting that Form 3 is a dihydrate. FIG. 11 also shows a solid-solid transition at about 290° C. In some embodiments, Form 3 is characterized by a TGA profile substantially as shown in FIG. 11. Karl Fischer measurements show a water content of about 8.4%, further suggesting that the weight loss observed in the TGA profile is due to the loss of water, and that Form 3 is a dihydrate.

Figure 12:
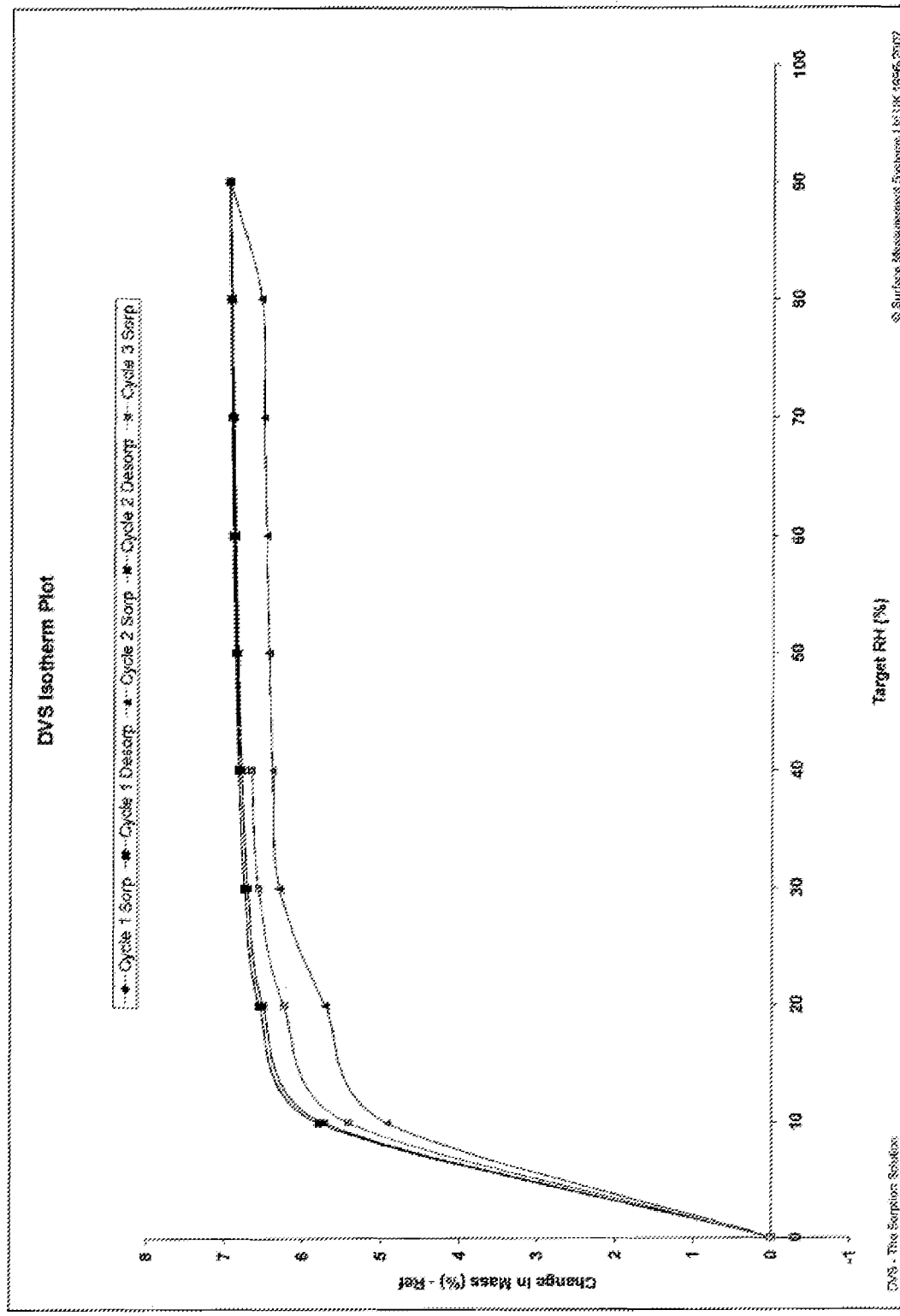
FIG. 12 shows a GVS isotherm plot for crystalline Form 3.

FIG. 12 shows a gravimetric vapor sorption (GVS) isotherm plot of Form 3. The GVS shows that Form 3 is subject to dehydration below 20% RH. A mass change of about 6.5% was observed between 0-20% RH, indicating that water may be removed from the crystal lattice. In certain embodiments, Form 3 may dehydrate to a monohydrate. In certain embodiments, Form 3 may dehydrate to an anhydrous form. In some embodiments, Form 3 is characterized by a GVS profile substantially as shown in FIG. 12.

Form 4

Provided herein is an assortment of characterizing information to describe a crystalline form of Compound 1 hydrochloride ("Form 4").

Figure 13:
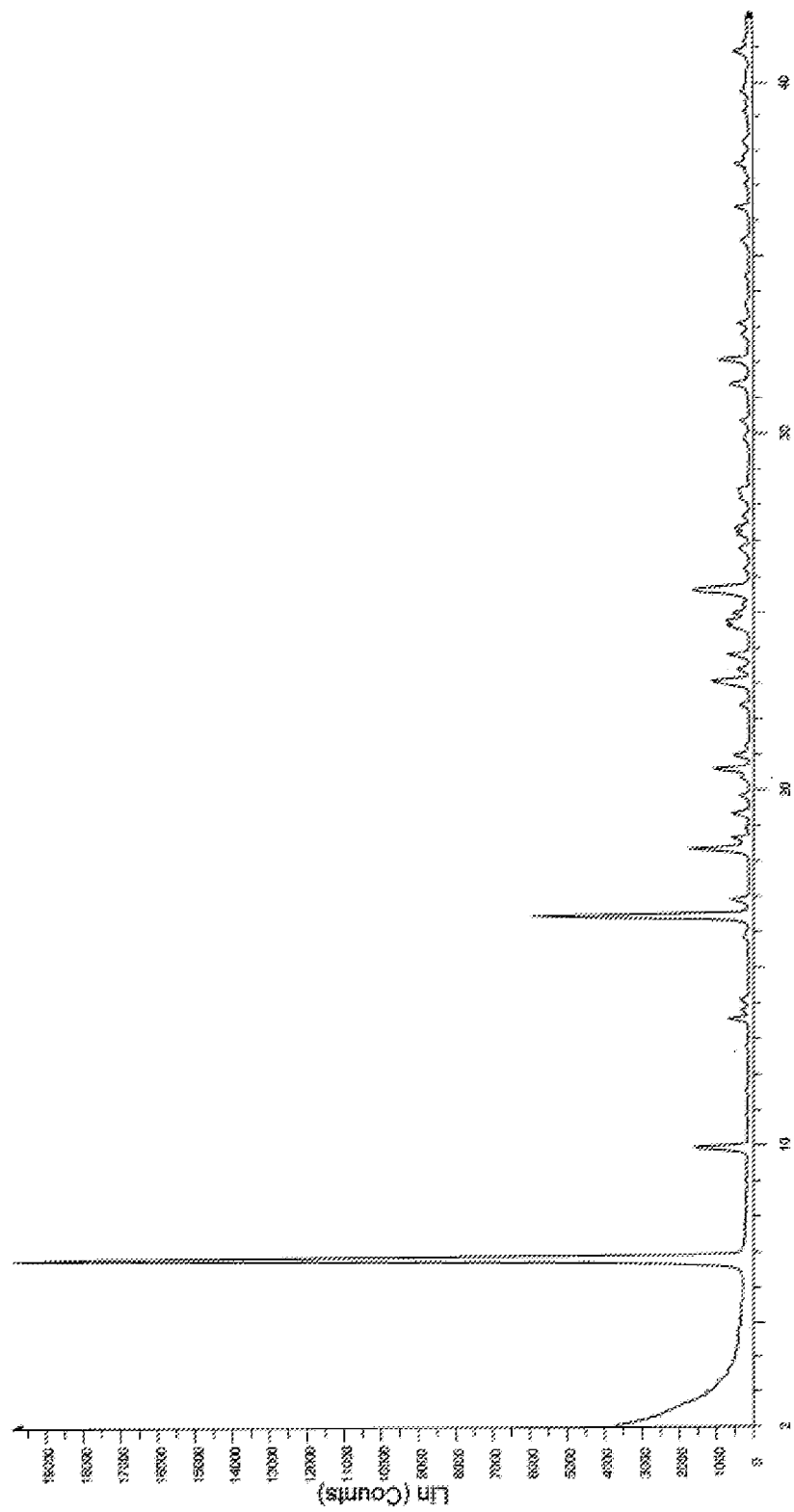
FIG. 13 shows a high resolution XRPD pattern for crystalline Form 4.

FIG. 13 shows an X-ray powder diffraction (XRPD) pattern of Form 4 obtained using CuKα radiation. Peaks identified in FIG. 13 include those listed in Table 3.

TABLE 3

| Angle 2-Theta ° | Intensity % |
|---|---|
| 6.81 | 100.0 |
| 9.94 | 8.4 |
| 13.54 | 3.0 |
| 13.79 | 1.6 |
| 14.10 | 1.6 |
| 16.44 | 30.2 |
| 16.89 | 3.5 |
| 15.82 | 2.2 |
| 18.33 | 9.1 |
| 18.63 | 3.2 |
| 18.94 | 1.5 |
| 19.34 | 3.3 |
| 19.84 | 3.3 |
| 11.54 | 1.0 |
| 20.34 | 1.9 |
| 20.58 | 5.4 |
| 20.98 | 2.7 |
| 21.24 | 1.1 |
| 22.37 | 1.8 |
| 23.08 | 5.6 |
| 23.40 | 2.0 |
| 23.84 | 3.4 |
| 24.63 | 3.4 |
| 24.78 | 3.6 |
| 24.99 | 2.7 |
| 25.24 | 1.4 |
| 25.63 | 7.9 |

In some embodiments, Form 4 is characterized by an XRPD pattern having peaks at 2θ angles of 6.8, 9.9, 16.4, 18.3, 20.6, 23.1, and 25.6°. In some embodiments, Form 4 is characterized by an XRPD pattern having peaks at 2θ angles of 6.8, 9.9, 16.4, 16.9, 18.3, 18.6, 19.3, 19.8, 20.6, 23.1, 23.8, 24.6, 24.8, and 25.6°. In some embodiments, Form 4 is characterized by an XRPD pattern substantially as shown in FIG. 13.

Figure 14:
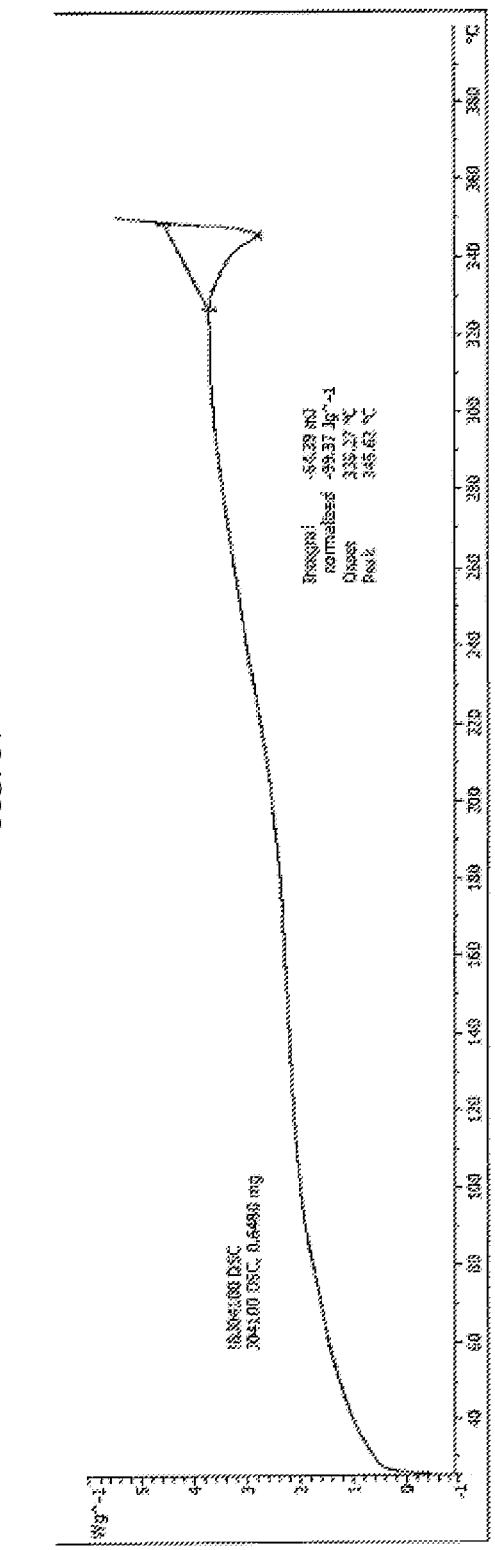
FIG. 14 shows a DSC thermogram for crystalline Form 4.

FIG. 14 shows a differential scanning calorimetry (DSC) profile of Form 4. The DSC thermogram plots the heat flow as a function of temperature from a sample, the temperature rate change being about 10° C./min. FIG. 14 shows an exothermic event at about 353° C. In some embodiments, Form 4 is characterized by a DSC profile substantially as shown in FIG. 14.

Figure 15:
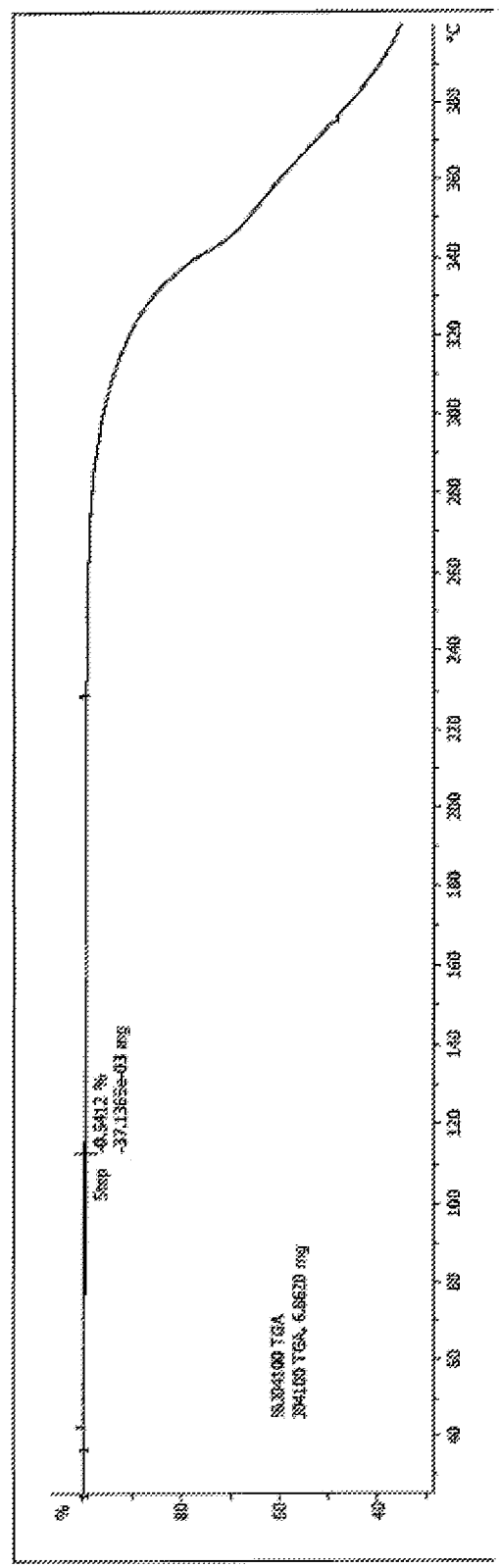
FIG. 15 shows a TGA thermogram for crystalline Form 4.

FIG. 15 shows a thermal gravimetric analysis (TGA) profile of Form 4. The TGA thermogram plots the percent loss of weight of the sample as a function of temperature, the temperature rate change being about 10° C./min. FIG. 15 shows onset of decomposition at about 347° C. In some embodiments, Form 4 is characterized by a TGA profile substantially as shown in FIG. 15.

Figure 16:
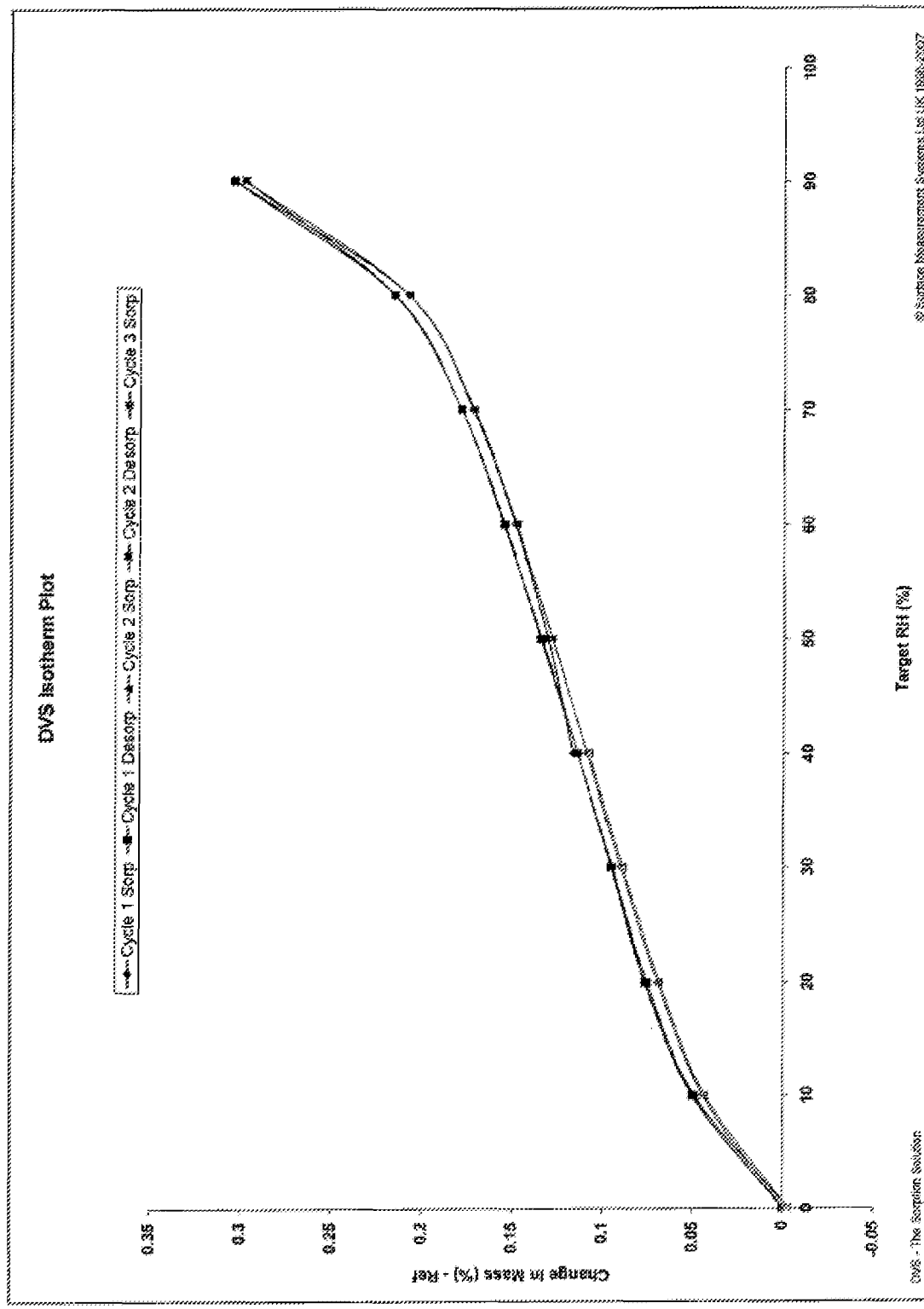
FIG. 16 shows a GVS isotherm plot for crystalline Form 4.

FIG. 16 shows a gravimetric vapor sorption (GVS) isotherm plot of Form 4. The GVS shows that Form 4 is not hygroscopic when subjected to humidity. In some embodiments, Form 4 is characterized by a GVS profile substantially as shown in FIG. 16.

Form 5

Provided herein is an assortment of characterizing information to describe a crystalline form of Compound 1 hydrochloride ("Form 5").

Figure 17:
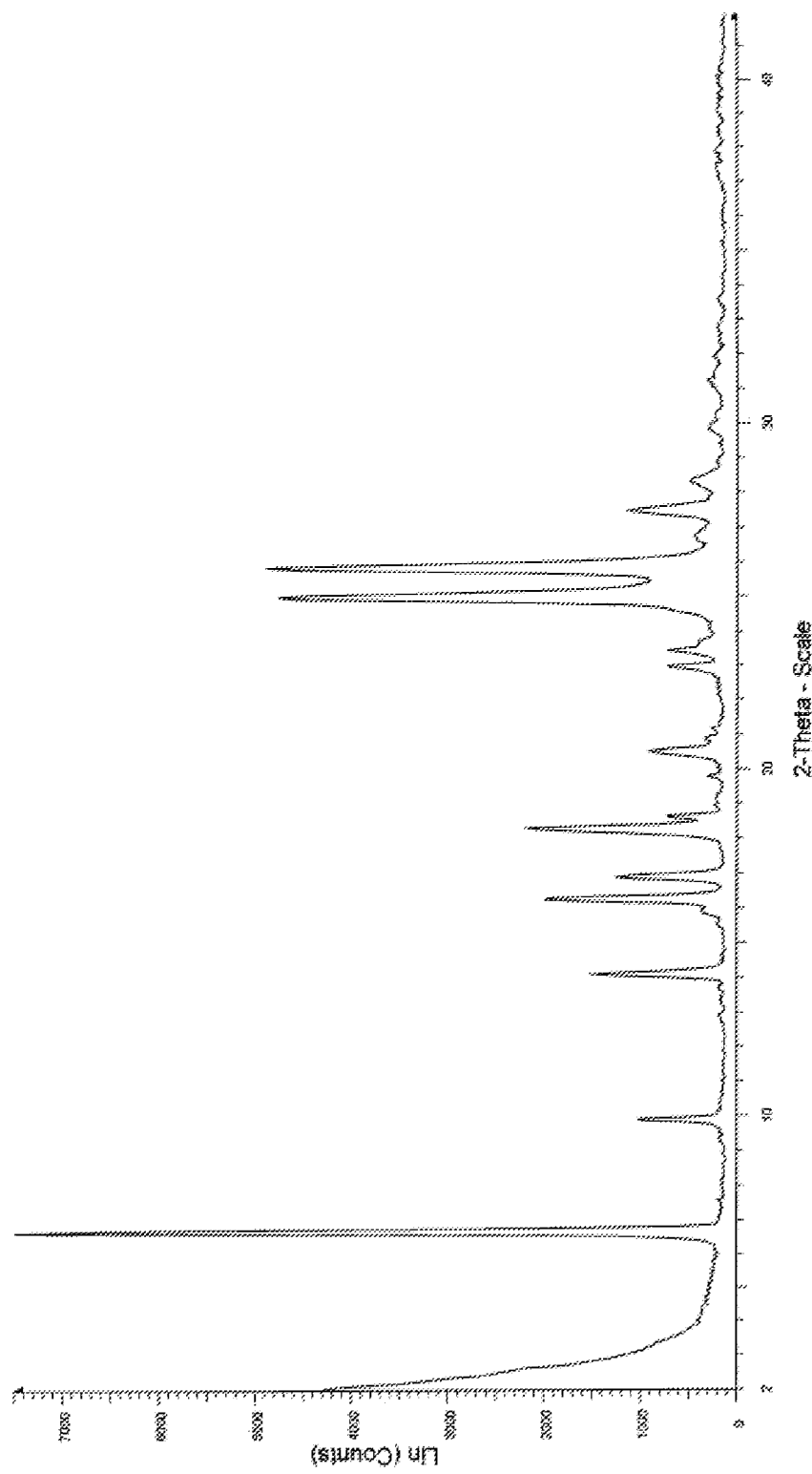
FIG. 17 shows a high resolution XRPD pattern for crystalline Form 5.

FIG. 17 shows an X-ray powder diffraction (XRPD) pattern of Form 5 obtained using CuKα radiation. Peaks identified in FIG. 17 include those listed in Table 4.

TABLE 4

| Angle 2-Theta ° | Intensity % |
|---|---|
| 6.65 | 100.0 |
| 9.89 | 13.6 |
| 14.09 | 20.2 |
| 15.51 | 2.9 |
| 15.91 | 5.4 |
| 16.26 | 27.0 |
| 16.89 | 17.1 |
| 18.29 | 29.2 |
| 18.64 | 9.8 |
| 18.93 | 3.4 |
| 19.79 | 4.4 |
| 20.54 | 12.3 |
| 20.89 | 4.8 |
| 21.19 | 3.8 |
| 22.95 | 9.7 |
| 23.43 | 9.7 |
| 23.74 | 5.7 |
| 24.11 | 4.7 |
| 24.97 | 63.5 |
| 25.83 | 65.4 |
| 26.79 | 6.9 |
| 27.49 | 15.4 |
| 28.33 | 6.6 |

In some embodiments, Form 5 is characterized by an XRPD pattern having peaks at 2θ angles of 6.7, 14.1, 16.3, 18.3, 25.0, and 25.8°. In some embodiments, Form 5 is characterized by an XRPD pattern having peaks at 2θ angles of 6.7, 9.9, 14.1, 16.3, 16.9, 18.3, 20.5, 25.0, 25.8 and 27.5°. In some embodiments, Form 5 is characterized by an XRPD pattern having peaks at 2θ angles of 6.7, 9.9, 14.1, 16.3, 16.9, 18.3, 18.6, 20.5, 23.0, 23.4, 25.0, 25.8 and 27.5°. In some embodiments, Form 5 is characterized by an XRPD pattern substantially as shown in FIG. 17.

Figure 18:
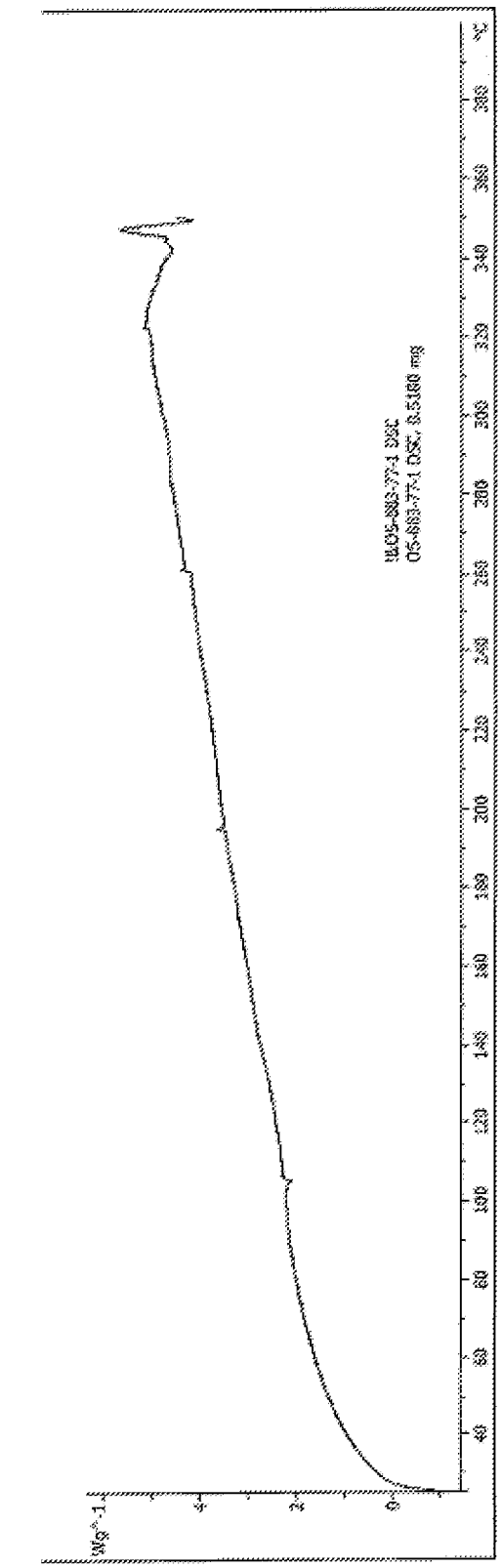
FIG. 18 shows a DSC thermogram for crystalline Form 5.

FIG. 18 shows a differential scanning calorimetry (DSC) profile of Form 5. The DSC thermogram plots the heat flow as a function of temperature from a sample, the temperature rate change being about 10° C./min. FIG. 18 shows a melting event at about 334° C. In some embodiments, Form 5 is characterized by a DSC profile substantially as shown in FIG. 18.

Figure 19:
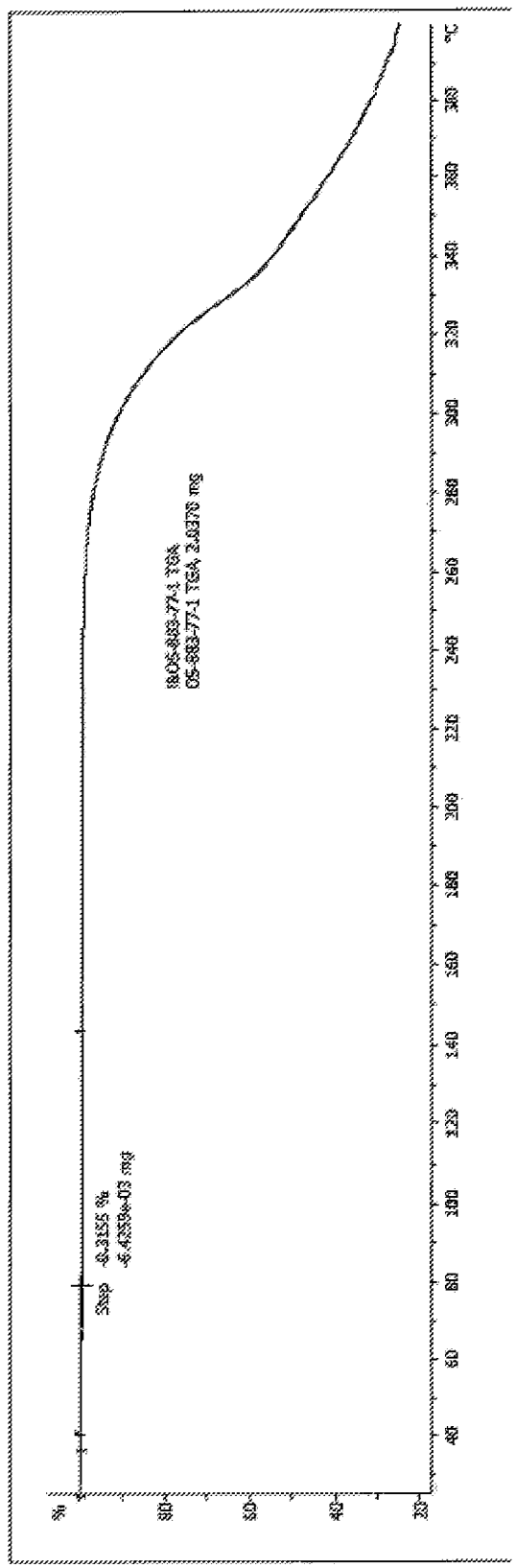
FIG. 19 shows a TGA thermogram for crystalline Form 5.

FIG. 19 shows a thermal gravimetric analysis (TGA) profile of Form 5. The TGA thermogram plots the percent loss of weight of the sample as a function of temperature, the temperature rate change being about 10° C./min. FIG. 19 shows onset of decomposition at about 335° C. In some embodiments, Form 5 is characterized by a TGA profile substantially as shown in FIG. 19.

Figure 20:
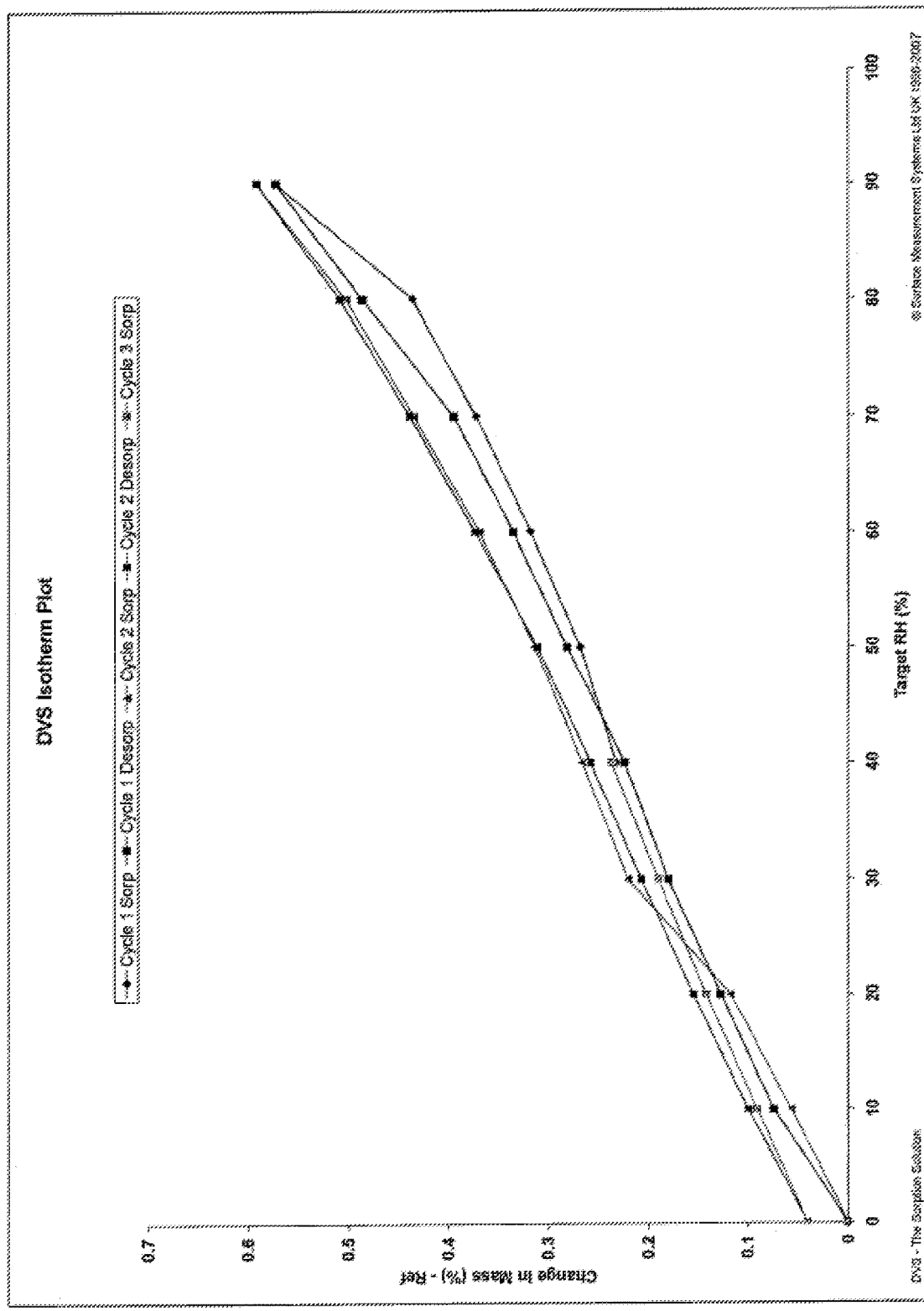
FIG. 20 shows a GVS isotherm plot for crystalline Form 5.

FIG. 20 shows a gravimetric vapor sorption (GVS) isotherm plot of Form 5. The GVS shows that Form 5 is not hygroscopic when subjected to humidity. In some embodiments, Form 5 is characterized by a GVS profile substantially as shown in FIG. 20.

Form 6

Provided herein is an assortment of characterizing information to describe an amorphous form of Compound 1 hydrochloride ("Form 6").

Figure 21:
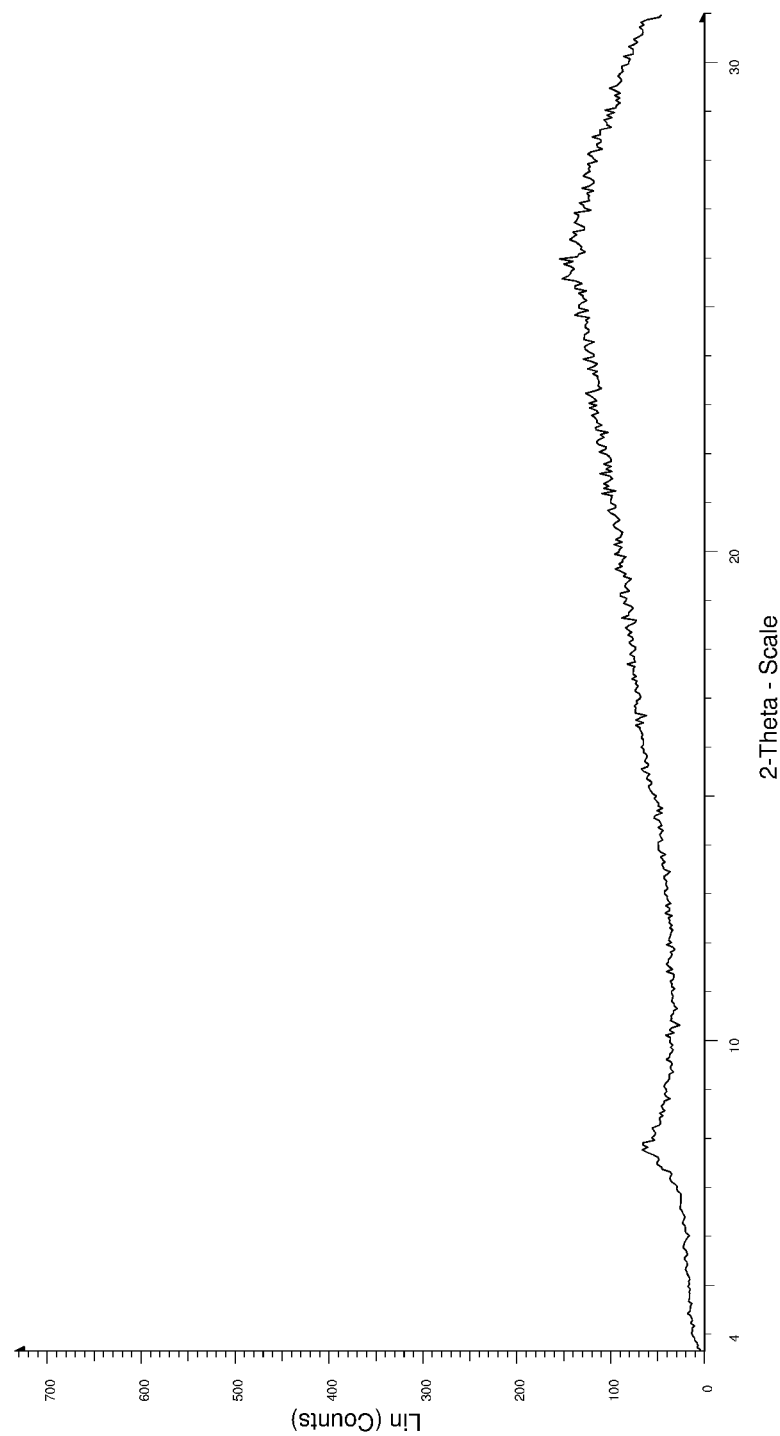
FIG. 21 shows a high resolution XRPD pattern for amorphous Form 6.

FIG. 21 shows an X-ray powder diffraction (XRPD) pattern of Form 6 obtained using CuKα radiation. In some embodiments, Form 6 is characterized by an XRPD pattern substantially as shown in FIG. 21.

Figure 22:
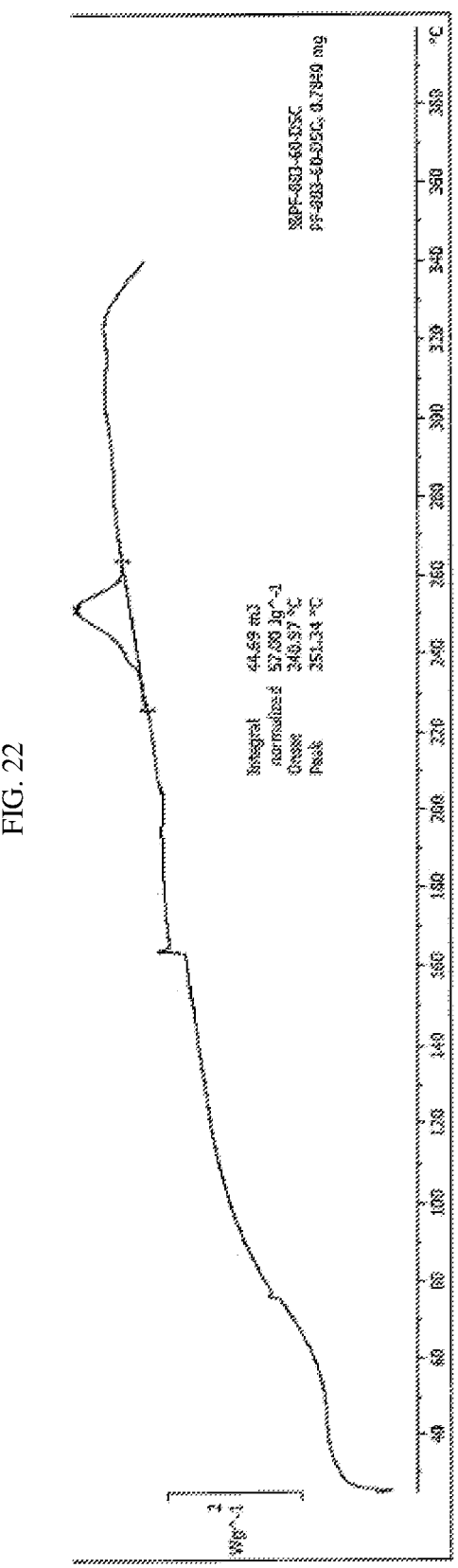
FIG. 22 shows a DSC thermogram for amorphous Form 6.

FIG. 22 shows a differential scanning calorimetry (DSC) profile of Form 6. The DSC thermogram plots the heat flow as a function of temperature from a sample, the temperature rate change being about 10° C./min. FIG. 22 shows a broad exotherm at about 241° C. In some embodiments, Form 6 is characterized by a DSC profile substantially as shown in FIG. 22.

Figure 23:
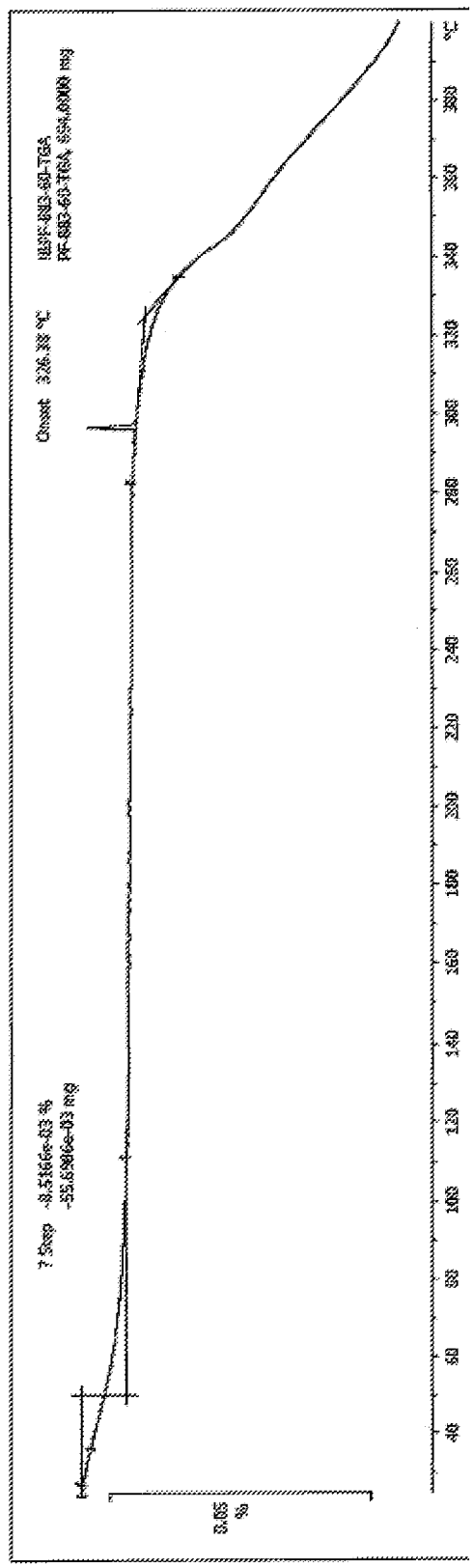
FIG. 23 shows a TGA thermogram for amorphous Form 6.

FIG. 23 shows a thermal gravimetric analysis (TGA) profile of Form 6. The TGA thermogram plots the percent loss of weight of the sample as a function of temperature, the temperature rate change being about 10° C./min. FIG. 23 shows weight loss of 8.5% until sample degradation begins at approximately 300° C. In some embodiments, Form 6 is characterized by a TGA profile substantially as shown in FIG. 23.

Figure 24:
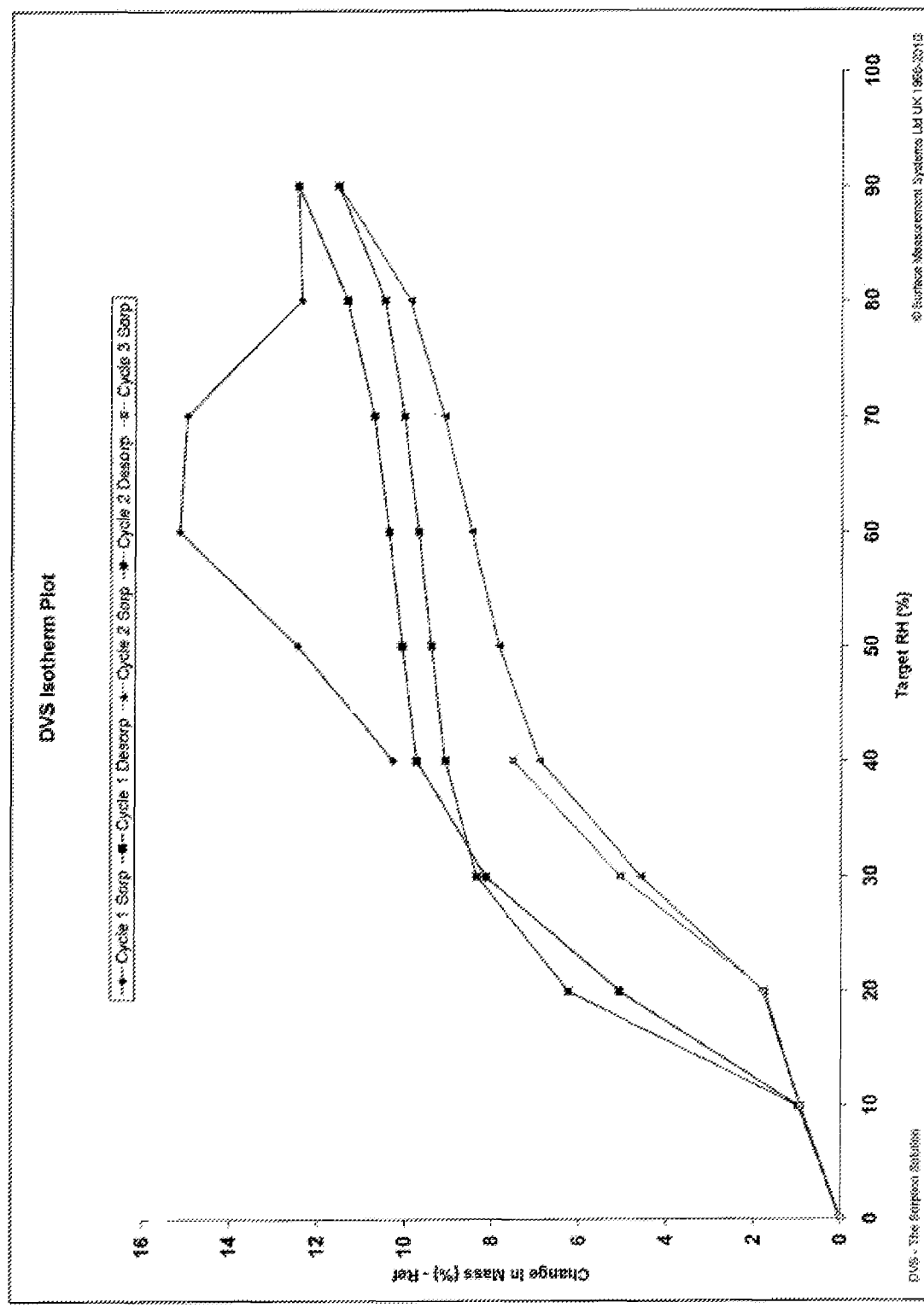
FIG. 24 shows a GVS isotherm plot for amorphous Form 6.

FIG. 24 shows a gravimetric vapor sorption (GVS) isotherm plot of Form 6. The GVS shows 5% w/w water uptake between 40-60% RH and a 3% weight loss between 70-90% RH. In some embodiments, Form 6 is characterized by a GVS profile substantially as shown in FIG. 24.

Form 7

Provided herein is an assortment of characterizing information to describe a crystalline form of Compound 1 hydrochloride ("Form 7").

Figure 25:
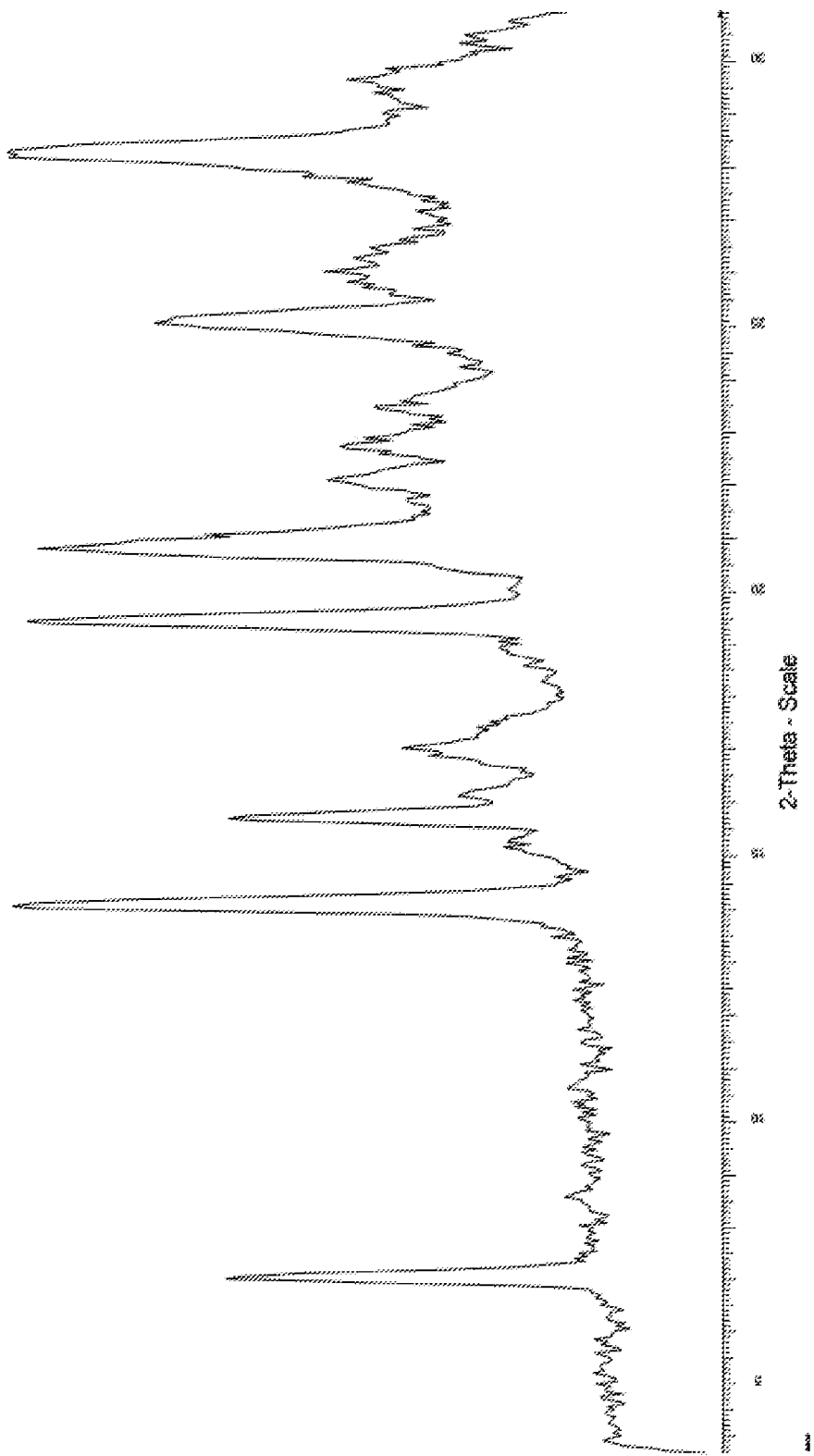
FIG. 25 shows a low resolution XRPD pattern for crystalline Form 7.

FIG. 25 shows an X-ray powder diffraction (XRPD) pattern of Form 7 obtained using CuKα radiation. Peaks identified in FIG. 25 include those listed in Table 5.

TABLE 5

| Angle 2-Theta ° | Intensity % |
|---|---|
| 7.07 | 70.3 |
| 8.62 | 22.4 |
| 14.18 | 100.0 |
| 15.25 | 31.3 |
| 15.76 | 70.3 |
| 16.18 | 37.5 |
| 17.04 | 45.2 |
| 17.51 | 35.2 |
| 18.90 | 31.9 |
| 19.55 | 99.9 |
| 20.90 | 96.7 |
| 21.16 | 74.0 |
| 21.72 | 45.7 |
| 22.18 | 56.0 |
| 22.78 | 54.3 |
| 23.56 | 49.8 |
| 25.17 | 80.1 |

TABLE 5-continued

| Angle 2-Theta ° | Intensity % |
| --- | --- |
| 26.15 | 57.3 |
| 27.75 | 55.8 |
| 28.41 | 98.8 |
| 29.72 | 53.5 |

In some embodiments, Form 7 is characterized by an XRPD pattern having peaks at 2θ angles of 7.1, 14.2, 15.8, 19.6, 20.9, 21.2, 22.2, 22.8, 25.2, 26.2, 27.8, 28.4, and 29.7°. In some embodiments, Form 7 is characterized by an XRPD pattern having peaks at 2θ angles of 7.1, 14.2, 15.3, 15.8, 16.2, 17.0, 17.5, 18.9, 19.6, 20.9, 21.2, 21.7, 22.2, 22.8, 23.6, 25.2, 26.2, 27.8, 28.4, and 29.7°. In some embodiments, Form 7 is characterized by an XRPD pattern substantially as shown in FIG. 25.

Figure 26:
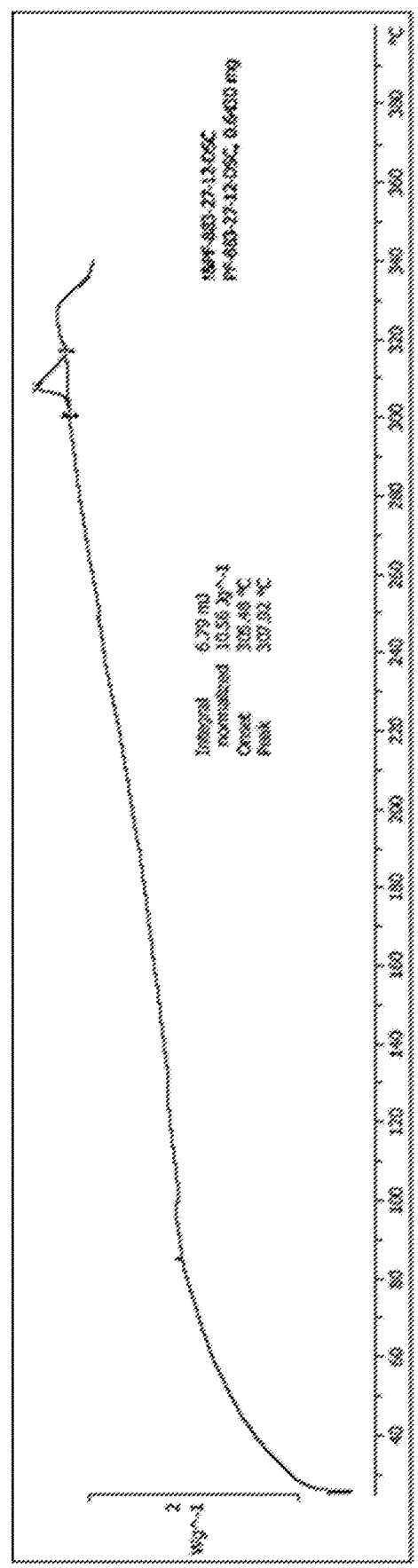
FIG. 26 shows a DSC thermogram for crystalline Form 7.

FIG. 26 shows a differential scanning calorimetry (DSC) profile of Form 7. The DSC thermogram plots the heat flow as a function of temperature from a sample, the temperature rate change being about 10° C./min. FIG. 26 shows a solid-solid exothermic transition at 305° C. Decomposition is observed at about 340° C. In some embodiments, Form 7 is characterized by a DSC profile substantially as shown in FIG. 26.

Figure 27:
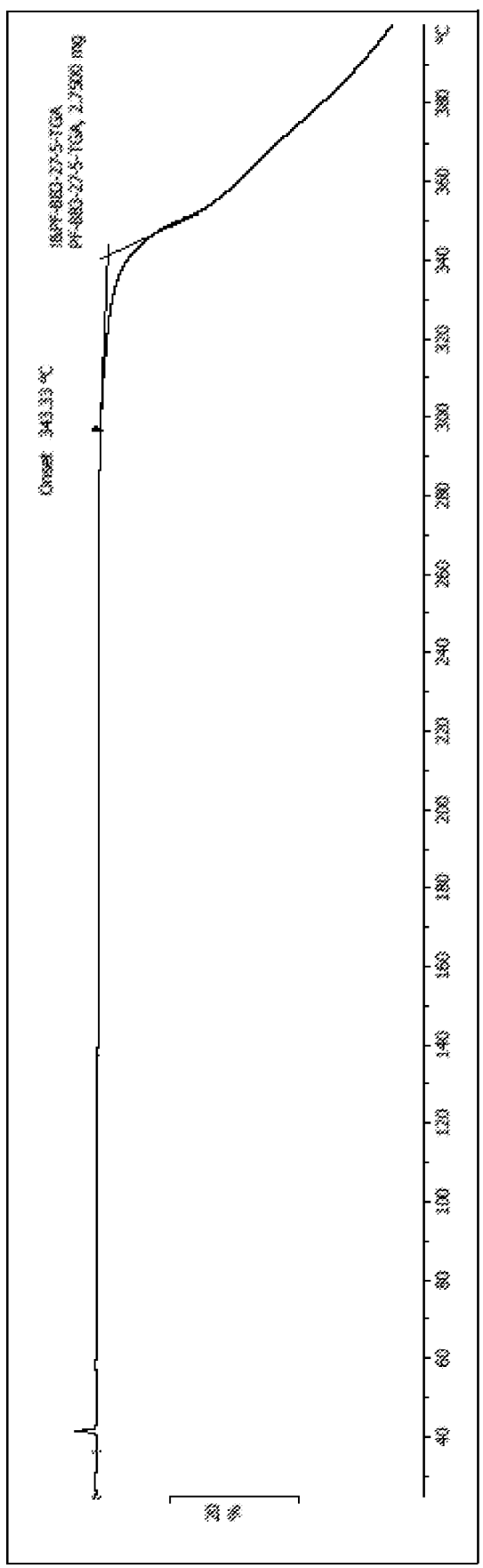
FIG. 27 shows a TGA thermogram for crystalline Form 7.

FIG. 27 shows a thermal gravimetric analysis (TGA) profile of Form 7. The TGA thermogram plots the percent loss of weight of the sample as a function of temperature, the temperature rate change being about 10° C./min. FIG. 27 shows onset of decomposition at about 343° C. In some embodiments, Form 7 is characterized by a TGA profile substantially as shown in FIG. 27.

Figure 28:
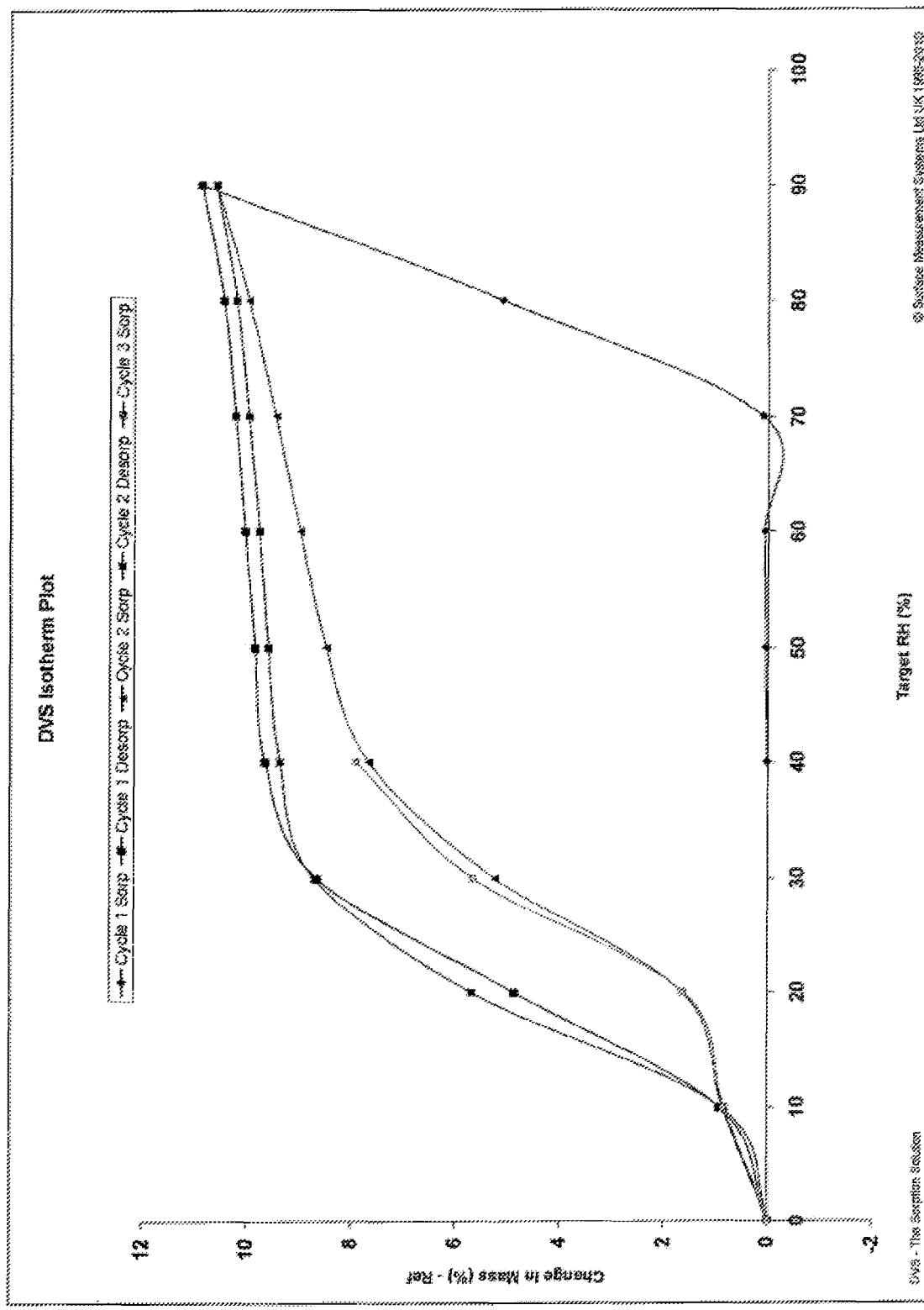
FIG. 28 shows a GVS isotherm plot for crystalline Form 7.

FIG. 28 shows a gravimetric vapor sorption (GVS) isotherm plot of Form 7. The GVS shows that Form 7 has a water uptake of 10.5%, suggesting that Form 7 hydrates to a 2.5 equivalent hydrate. In some embodiments, Form 7 is characterized by a GVS profile substantially as shown in FIG. 28.

Form 8

Provided herein is an assortment of characterizing information to describe a crystalline form of Compound 1 hydrochloride hydrate ("Form 8").

Figure 29:
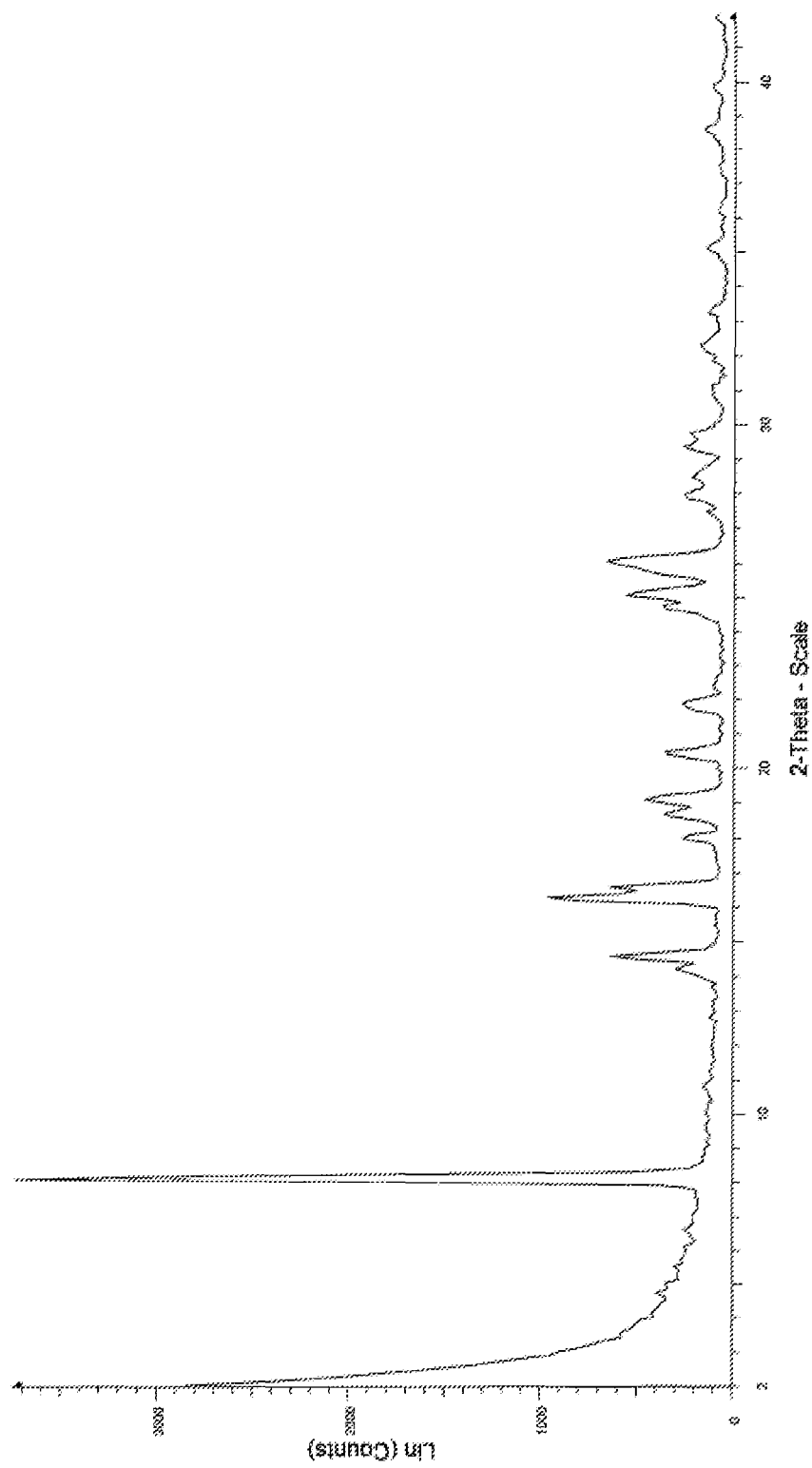
FIG. 29 shows a high resolution XRPD pattern for crystalline Form 8.

FIG. 29 shows an X-ray powder diffraction (XRPD) pattern of Form 8 obtained using CuKα radiation. Peaks identified in FIG. 29 include those listed in Table 6.

TABLE 6

| Angle 2-Theta ° | Intensity % |
| --- | --- |
| 8.09 | 100.0 |
| 10.81 | 4.6 |
| 14.16 | 8.7 |
| 14.58 | 17.6 |
| 16.30 | 27.2 |
| 16.59 | 17.9 |
| 18.02 | 7.5 |
| 18.67 | 10.4 |
| 19.13 | 13.1 |
| 20.46 | 10.1 |
| 21.85 | 8.1 |
| 22.41 | 3.6 |
| 24.78 | 10.6 |
| 25.17 | 16.6 |
| 26.11 | 19.1 |
| 27.47 | 4.8 |
| 27.96 | 8.1 |
| 28.51 | 6.3 |

TABLE 6-continued

| Angle 2-Theta ° | Intensity % |
| --- | --- |
| 29.36 | 8.2 |
| 29.81 | 7.2 |

In some embodiments, Form 8 is characterized by an XRPD pattern having peaks at 2θ angles of 8.1, 14.6, 16.3, 16.6, and 26.10. In some embodiments, Form 8 is characterized by an XRPD pattern having peaks at 2θ angles of 8.1, 14.6, 16.3, 16.6, 18.7, 19.1, 20.5, 24.8, 25.2, and 26.10. In some embodiments, Form 8 is characterized by an XRPD pattern substantially as shown in FIG. 29.

Figure 30:
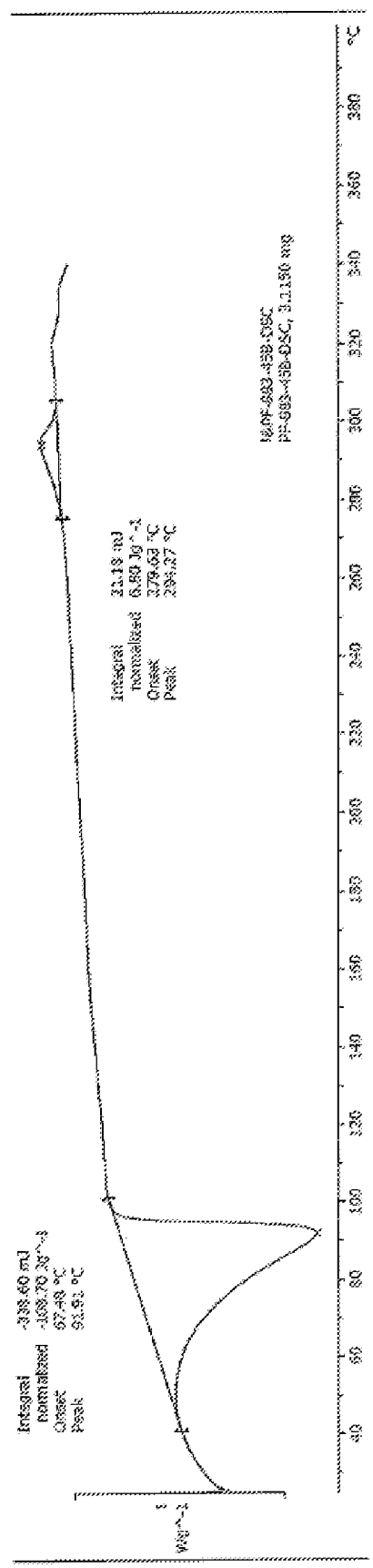
FIG. 30 shows a DSC thermogram for crystalline Form 8.

FIG. 30 shows a differential scanning calorimetry (DSC) profile of Form 8. The DSC thermogram plots the heat flow as a function of temperature from a sample, the temperature rate change being about 10° C./min. FIG. 30 shows a broad endotherm related to loss of water and a solid-solid exothermic transition at about 280° C. Decomposition was observed at about 340° C. In some embodiments, Form 8 is characterized by a DSC profile substantially as shown in FIG. 30.

Figure 31:
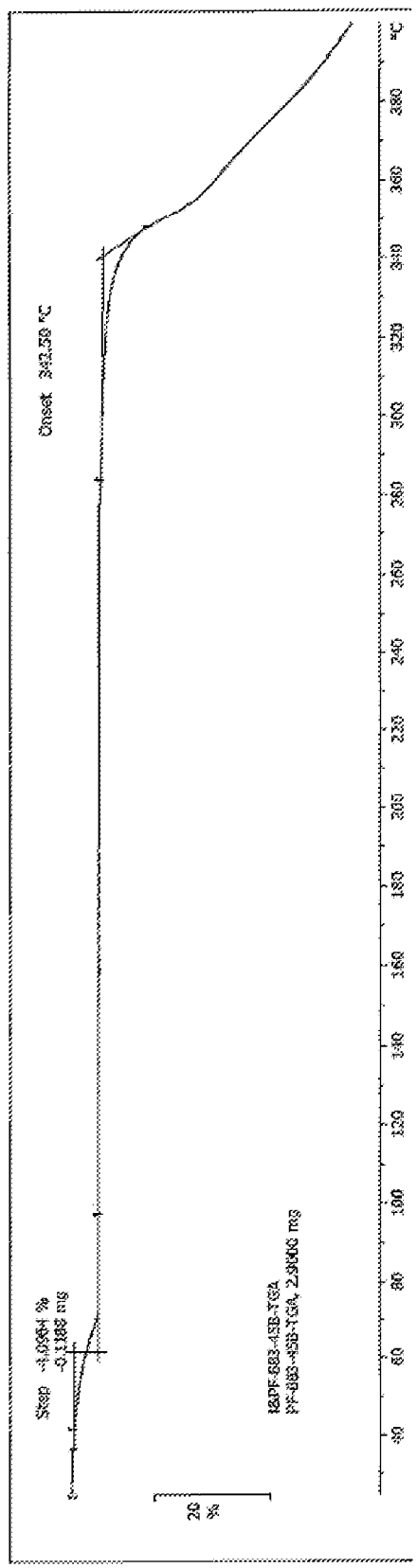
FIG. 31 shows a TGA thermogram for crystalline Form 8.

FIG. 31 shows a thermal gravimetric analysis (TGA) profile of Form 8. The TGA thermogram plots the percent loss of weight of the sample as a function of temperature, the temperature rate change being about 10° C./min. FIG. 31 shows a 4.1% weight loss related to loss of water. Onset of decomposition was seen at about 342° C. In some embodiments, Form 8 is characterized by a TGA profile substantially as shown in FIG. 31.

Figure 32:
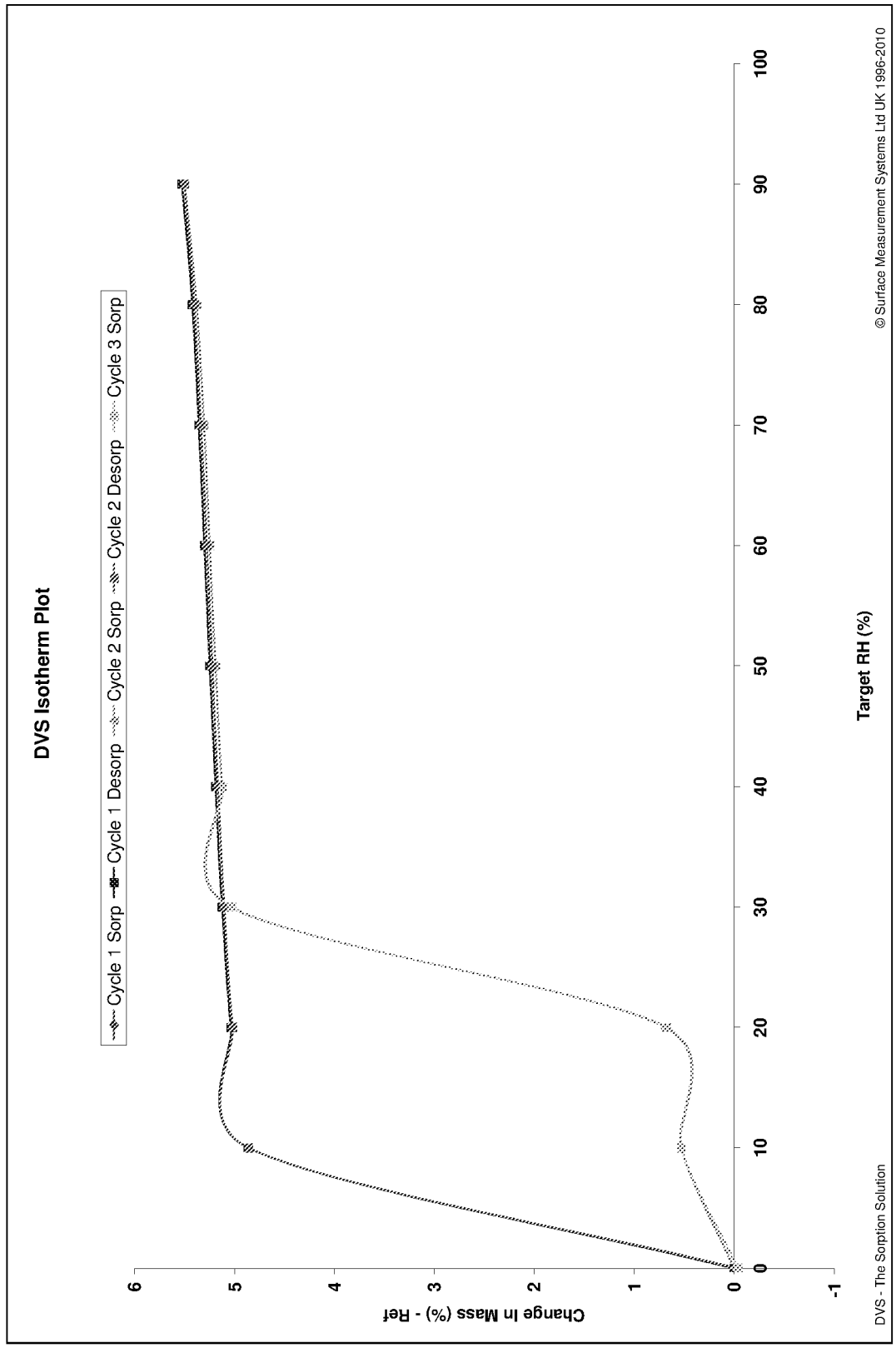
FIG. 32 shows a GVS isotherm plot for crystalline Form 8.

FIG. 32 shows a gravimetric vapor sorption (GVS) isotherm plot of Form 8. The GVS shows that Form 8 has minimal weight variation between 10 and 90% RH. In some embodiments, Form 8 is characterized by a GVS profile substantially as shown in FIG. 32.

Form 9

Provided herein is an assortment of characterizing information to describe a crystalline form of Compound 1 hydrochloride hydrate ("Form 9").

Figure 33:
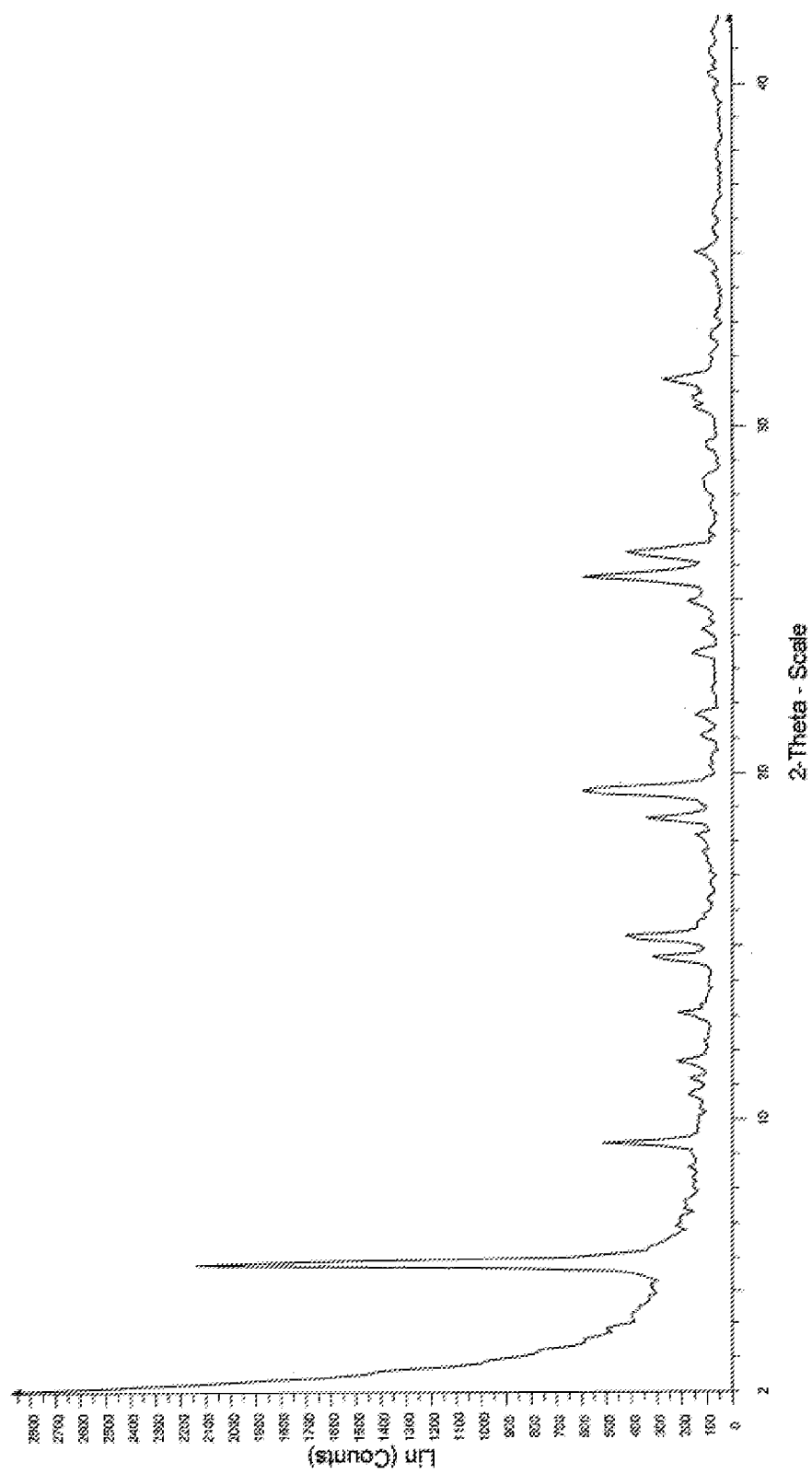
FIG. 33 shows a high resolution XRPD pattern for crystalline Form 9.

FIG. 33 shows an X-ray powder diffraction (XRPD) pattern of Form 9 obtained using CuKα radiation. Peaks identified in FIG. 33 include those listed in Table 7.

TABLE 7

| Angle 2-Theta ° | Intensity % |
| --- | --- |
| 5.81 | 100.0 |
| 9.28 | 24.2 |
| 10.71 | 8.0 |
| 11.23 | 8.2 |
| 11.72 | 10.3 |
| 13.11 | 10.1 |
| 13.34 | 6.5 |
| 14.71 | 15.3 |
| 15.29 | 19.7 |
| 18.21 | 7.3 |
| 18.70 | 16.4 |
| 19.54 | 27.9 |
| 21.10 | 6.1 |
| 21.68 | 7.1 |
| 23.47 | 8.6 |
| 24.18 | 6.9 |
| 24.48 | 4.8 |
| 25.00 | 9.0 |
| 25.71 | 28.2 |
| 26.42 | 20.4 |
| 28.47 | 5.5 |

TABLE 7-continued

| Angle 2-Theta ° | Intensity % |
|---|---|
| 29.54 | 4.8 |
| 30.58 | 7.8 |
| 30.90 | 9.2 |
| 31.39 | 14.1 |

In some embodiments, Form 9 is characterized by an XRPD pattern having peaks at 2θ angles of 5.8, 9.3, 19.5, 25.7, and 26.4°. In some embodiments, Form 9 is characterized by an XRPD pattern having peaks at 2θ angles of 5.8, 9.3, 11.7, 13.1, 14.7, 15.3, 18.7, 19.5, 25.7, 26.4 and 31.4°. In some embodiments, Form 9 is characterized by an XRPD pattern substantially as shown in FIG. 33.

Figure 34:
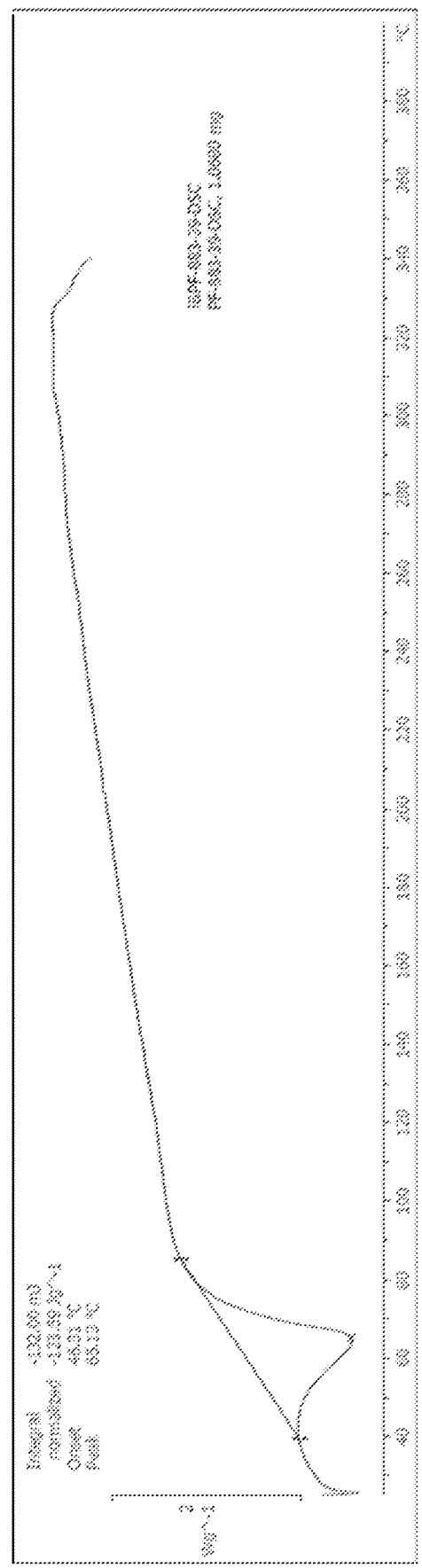
FIG. 34 shows a DSC thermogram for crystalline Form 9.

FIG. 34 shows a differential scanning calorimetry (DSC) profile of Form 9. The DSC thermogram plots the heat flow as a function of temperature from a sample, the temperature rate change being about 10° C./min. FIG. 34 shows a broad endotherm related to loss of water. In some embodiments, Form 9 is characterized by a DSC profile substantially as shown in FIG. 34.

Figure 35:
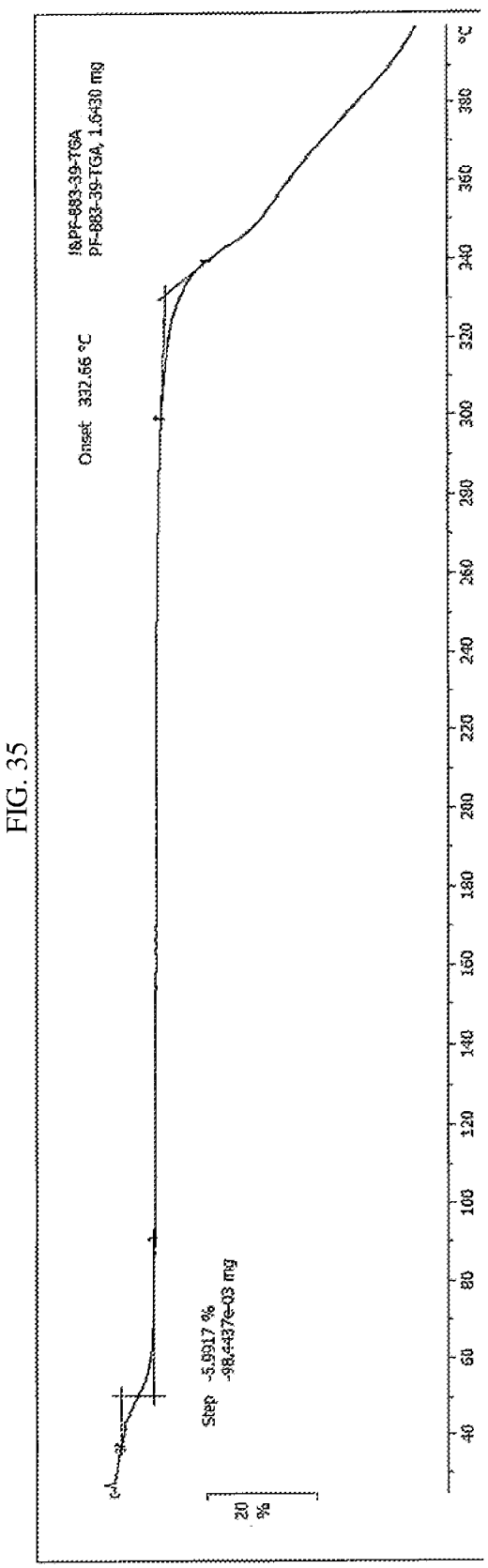
FIG. 35 shows a TGA thermogram for crystalline Form 9.

FIG. 35 shows a thermal gravimetric analysis (TGA) profile of Form 9. The TGA thermogram plots the percent loss of weight of the sample as a function of temperature, the temperature rate change being about 10° C./min. FIG. 35 shows a 6% weight loss related to loss of water (1.5 mol. eq.). Onset of decomposition was at about 333° C. In some embodiments, Form 9 is characterized by a TGA profile substantially as shown in FIG. 35.

Form 10

Provided herein is an assortment of characterizing information to describe a crystalline form of Compound 1 hydrochloride hydrate ("Form 10").

Figure 36:
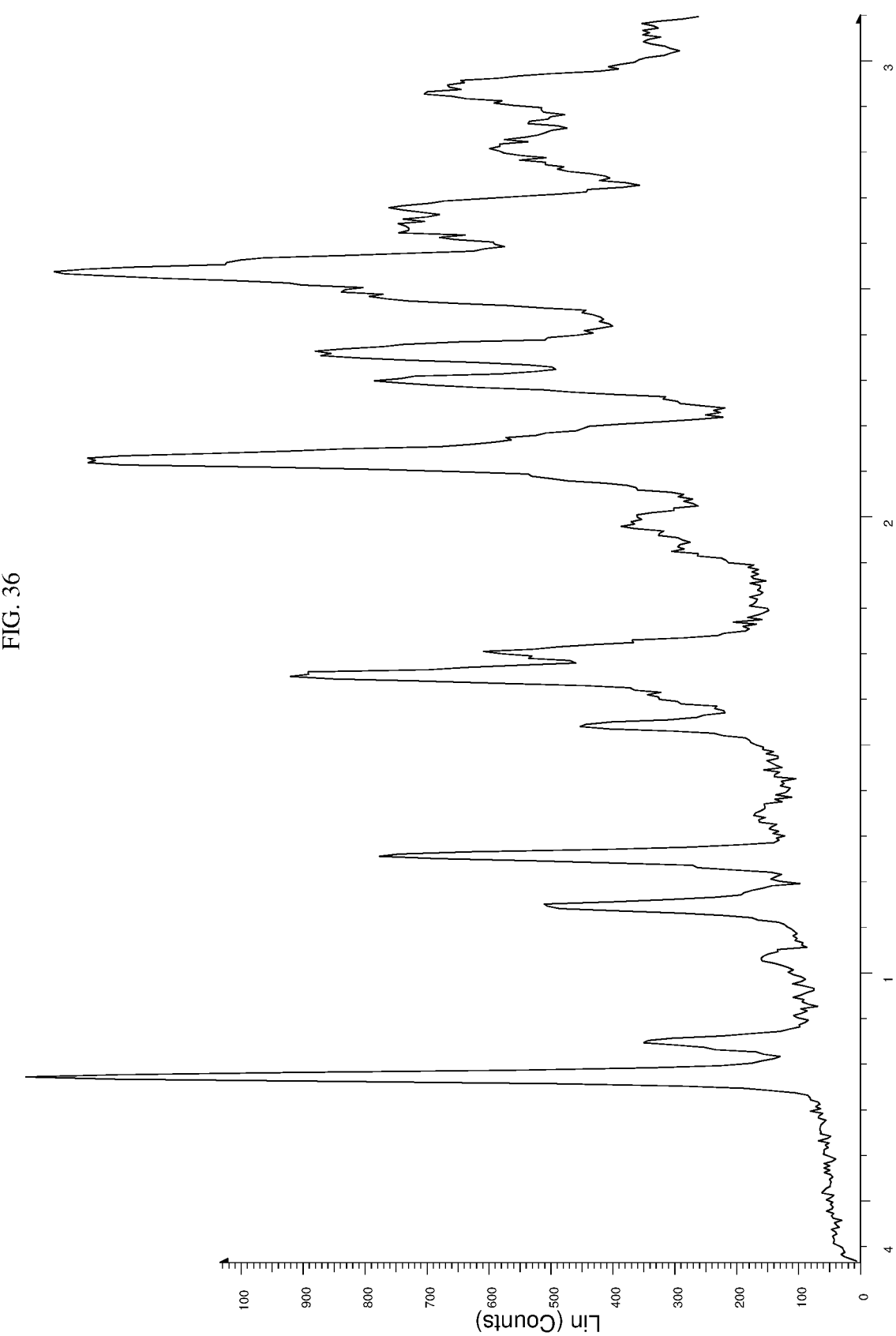
FIG. 36 shows a low resolution XRPD pattern for crystalline Form 10.

FIG. 36 shows an X-ray powder diffraction (XRPD) pattern of Form 10 obtained using CuKα radiation. Peaks identified in FIG. 36 include those listed in Table 8.

TABLE 8

| Angle 2-Theta ° | Intensity % |
|---|---|
| 7.69 | 100.0 |
| 8.46 | 26.2 |
| 10.30 | 12.8 |
| 11.46 | 37.6 |
| 12.54 | 57.9 |
| 13.45 | 13.6 |
| 15.42 | 33.9 |
| 16.11 | 26.2 |
| 16.51 | 68.3 |
| 17.08 | 44.7 |
| 19.36 | 23.1 |
| 19.87 | 29.7 |
| 21.25 | 92.4 |
| 21.80 | 43.3 |
| 23.00 | 57.9 |
| 23.60 | 65.0 |
| 24.88 | 62.2 |
| 25.39 | 96.0 |
| 25.70 | 75.4 |
| 26.32 | 57.3 |
| 26.83 | 57.0 |
| 28.14 | 45.2 |
| 28.67 | 40.7 |
| 29.34 | 52.9 |

In some embodiments, Form 10 is characterized by an XRPD pattern having peaks at 2θ angles of 7.7, 12.5, 16.5, 21.3, 23.0, 23.6, 24.9, 25.4, 25.7, 26.3, 26.8, and 29.3°. In some embodiments, Form 10 is characterized by an XRPD pattern having peaks at 2θ angles of 7.7, 8.5, 11.5, 12.5, 15.4, 16.1, 16.5, 17.1, 19.9, 21.3, 21.8, 23.0, 23.6, 24.9, 25.4, 25.7, 26.3, 26.8, 28.1, 28.7, and 29.3°. In some embodiments, Form 10 is characterized by an XRPD pattern substantially as shown in FIG. 36.

Figure 37:
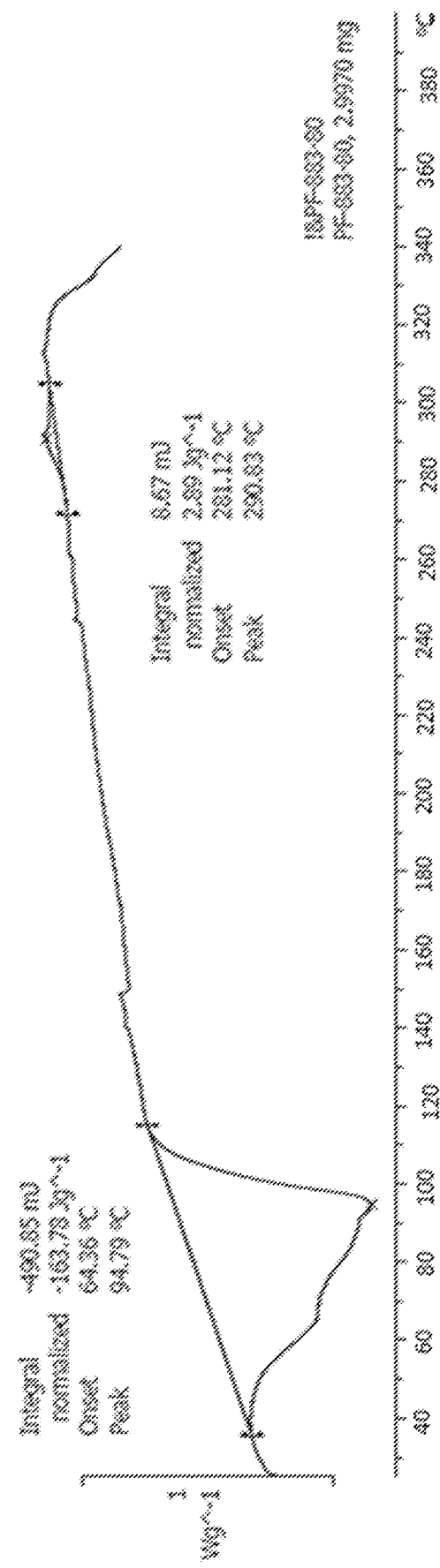
FIG. 37 shows a DSC thermogram for crystalline Form 10.

FIG. 37 shows a differential scanning calorimetry (DSC) profile of Form 10. The DSC thermogram plots the heat flow as a function of temperature from a sample, the temperature rate change being about 10° C./min. In some embodiments, Form 10 is characterized by a DSC profile substantially as shown in FIG. 37.

Figure 38:
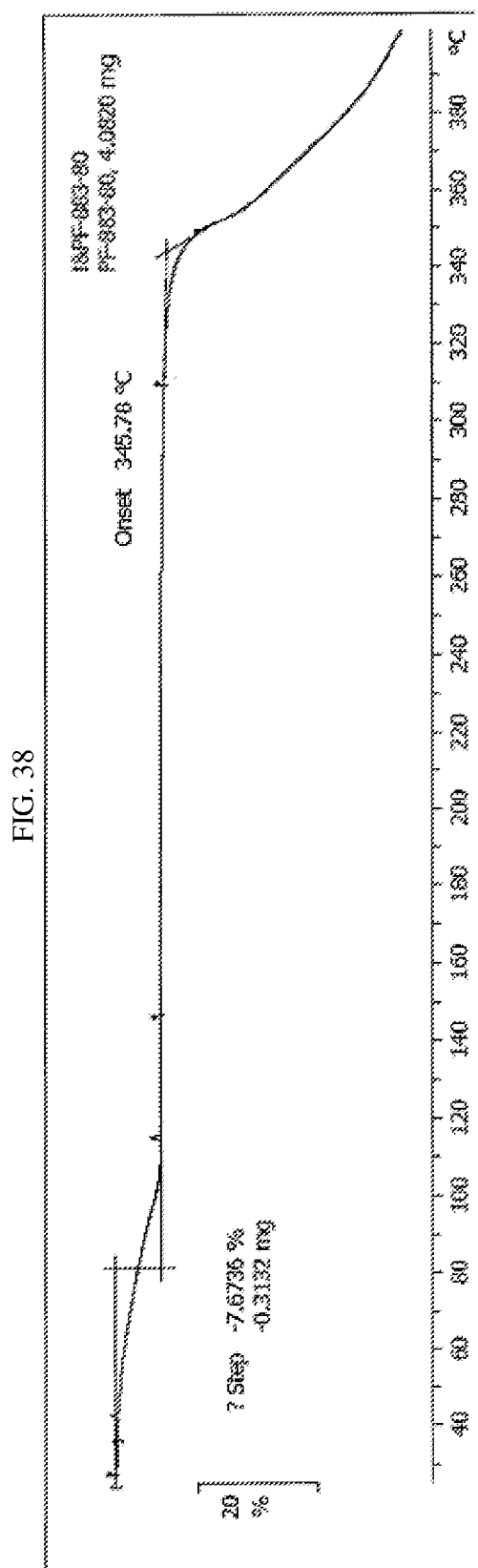
FIG. 38 shows a TGA thermogram for crystalline Form 10.

FIG. 38 shows a thermal gravimetric analysis (TGA) profile of Form 10. The TGA thermogram plots the percent loss of weight of the sample as a function of temperature, the temperature rate change being about 10° C./min. In some embodiments, Form 10 is characterized by a TGA profile substantially as shown in FIG. 38.

Form 11

Provided herein is an assortment of characterizing information to describe a crystalline form of Compound 1 hydrochloride hydrate ("Form 11").

Figure 39:
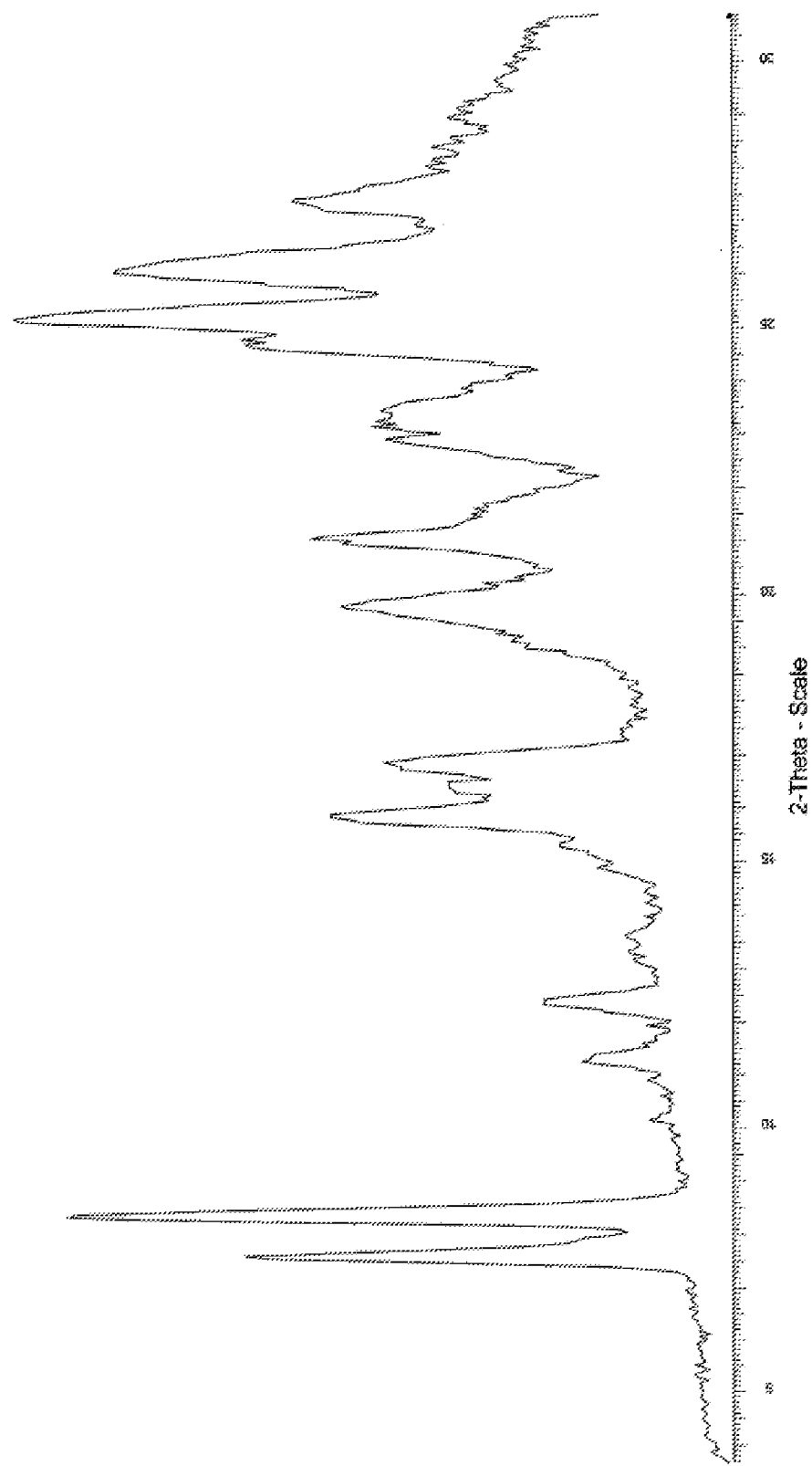
FIG. 39 shows a low resolution XRPD pattern for crystalline Form 11.

FIG. 39 shows an X-ray powder diffraction (XRPD) pattern of Form 11 obtained using CuKα radiation. Peaks identified in FIG. 36 include those listed in Table 9.

TABLE 9

| Angle 2-Theta ° | Intensity % |
|---|---|
| 7.67 | 66.9 |
| 8.42 | 92.1 |
| 10.17 | 12.6 |
| 11.30 | 21.3 |
| 12.43 | 26.4 |
| 13.61 | 15.7 |
| 15.29 | 24.7 |
| 15.91 | 56.8 |
| 16.47 | 41.0 |
| 16.91 | 49.2 |
| 19.10 | 31.5 |
| 19.88 | 54.7 |
| 21.16 | 58.4 |
| 21.69 | 36.0 |
| 22.87 | 48.6 |
| 23.31 | 50.0 |
| 23.96 | 38.2 |
| 24.78 | 66.9 |
| 25.24 | 100.0 |
| 26.13 | 86.0 |
| 27.46 | 60.9 |

In some embodiments, Form 11 is characterized by an XRPD pattern having peaks at 2θ angles of 7.7, 8.4, 15.9, 19.9, 21.2, 23.3, 24.8, 25.2, 26.1, and 27.5°. In some embodiments, Form 11 is characterized by an XRPD pattern having peaks at 2θ angles of 7.7, 8.4, 12.4, 15.9, 16.5, 16.9, 19.9, 21.2, 21.7, 22.9, 23.3, 24.0, 24.8, 25.2, 26.1, and 27.5°. In some embodiments, Form 11 is characterized by an XRPD pattern substantially as shown in FIG. 39.

Figure 40:
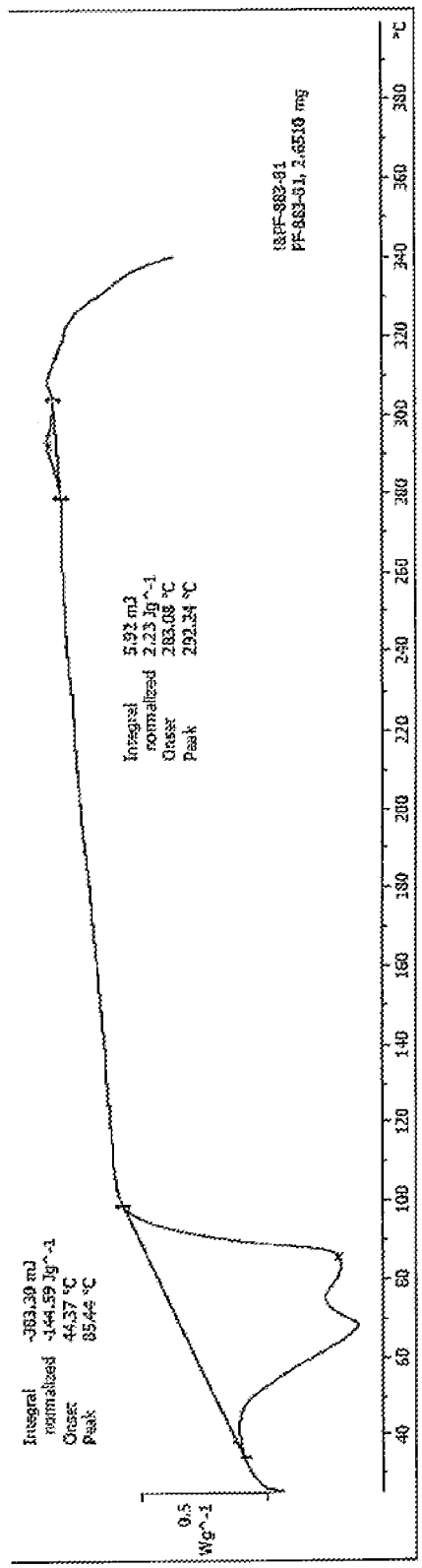
FIG. 40 shows a DSC thermogram for crystalline Form 11.

FIG. 40 shows a differential scanning calorimetry (DSC) profile of Form 11. The DSC thermogram plots the heat flow as a function of temperature from a sample, the temperature rate change being about 10° C./min. In some embodiments, Form 11 is characterized by a DSC profile substantially as shown in FIG. 40.

Figure 41:
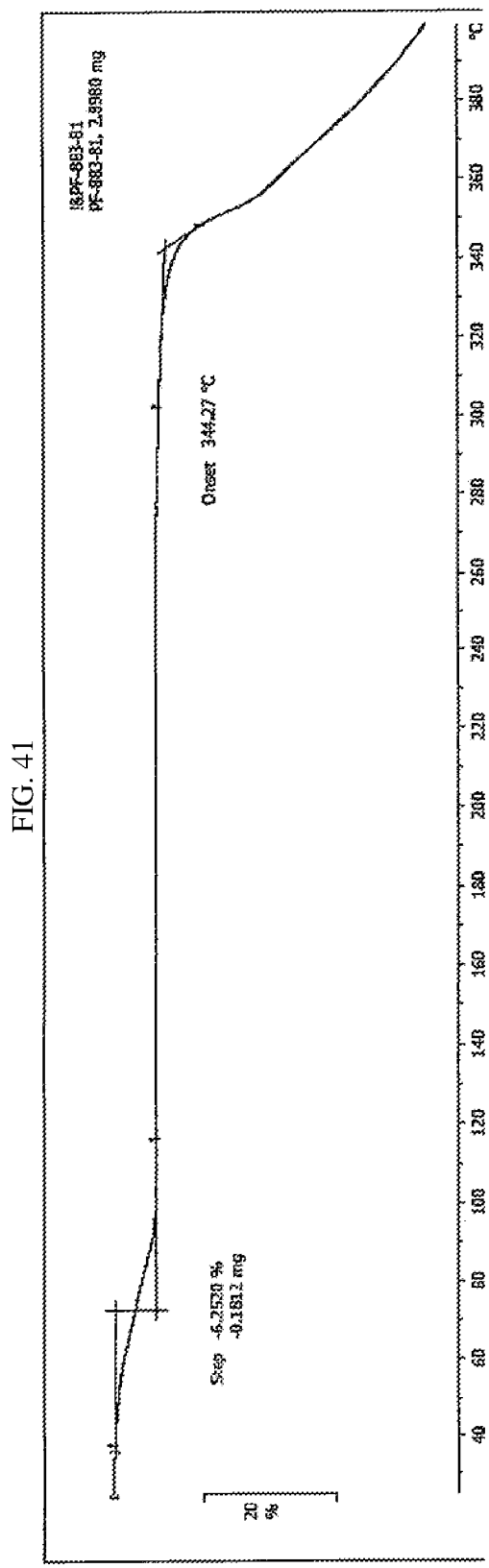
FIG. 41 shows a TGA thermogram for crystalline Form 11.

FIG. 41 shows a thermal gravimetric analysis (TGA) profile of Form 11. The TGA thermogram plots the percent loss of weight of the sample as a function of temperature, the temperature rate change being about 10° C./min. In some embodiments, Form 11 is characterized by a TGA profile substantially as shown in FIG. 41.

Form 12

Provided herein is an assortment of characterizing information to describe a crystalline form of the free base of Compound 1 ("Form 12").

Figure 42:
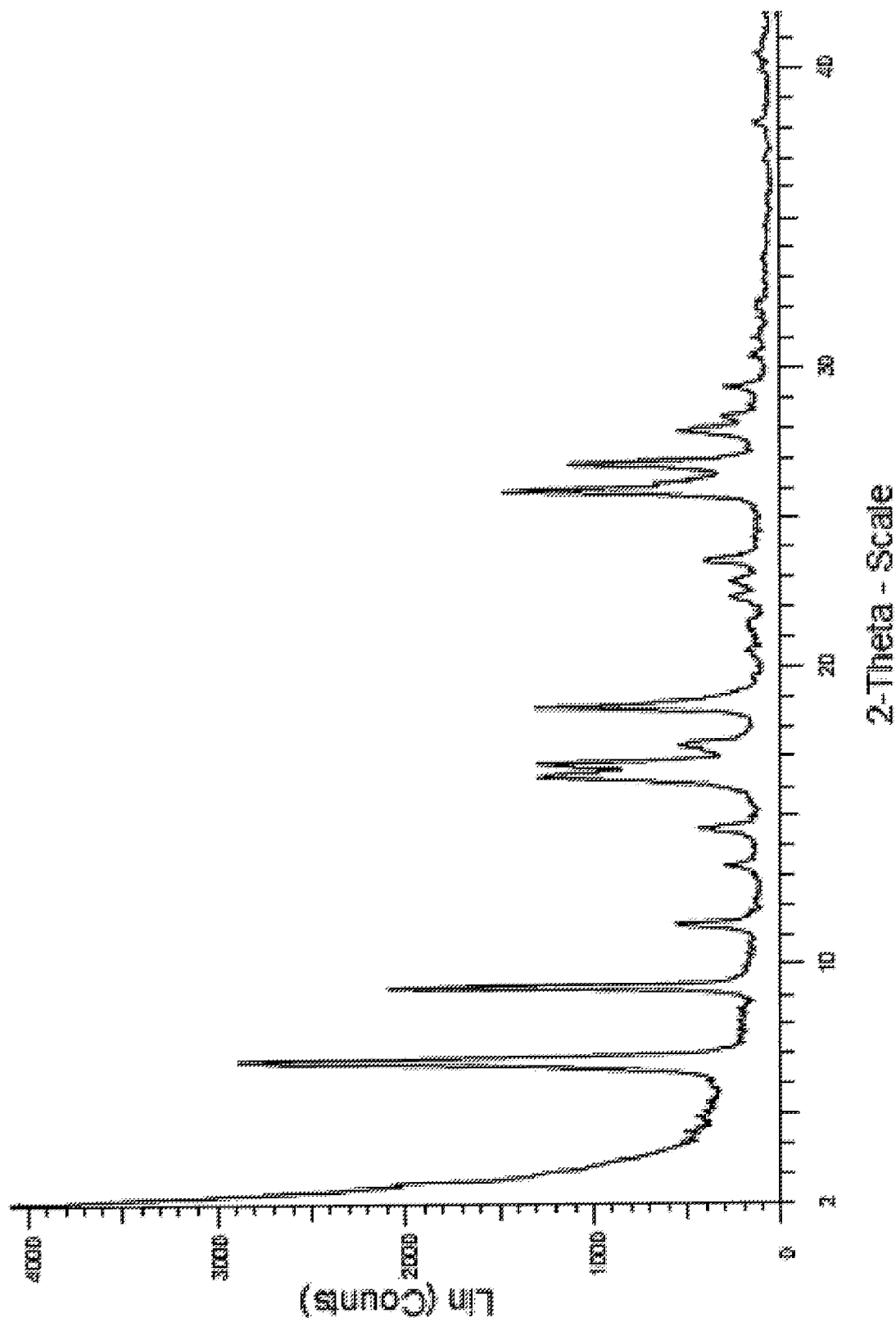
FIG. 42 shows an XRPD pattern for crystalline Form 12.

FIG. 42 shows an X-ray powder diffraction (XRPD) pattern of Form 12 obtained using CuKα radiation. Peaks identified in FIG. 42 include those listed in Table 10.

TABLE 10

| Angle 2-Theta ° | Intensity % |
|---|---|
| 4.4 | 17.8 |
| 4.8 | 15.6 |
| 6.8 | 100.0 |
| 9.2 | 72.3 |
| 11.3 | 19.3 |
| 13.3 | 10.3 |
| 14.5 | 15.1 |
| 16.3 | 44.8 |
| 16.7 | 44.6 |
| 17.4 | 18.6 |
| 18.6 | 45.2 |
| 19.6 | 5.1 |
| 20.6 | 6.5 |
| 21.5 | 6.0 |
| 22.3 | 9.4 |
| 22.9 | 9.3 |
| 23.5 | 14.0 |
| 25.9 | 51.1 |
| 26.8 | 38.8 |
| 27.9 | 18.9 |
| 28.4 | 10.6 |
| 29.4 | 10.1 |
| 30.4 | 5.6 |
| 31.0 | 5.1 |
| 38.2 | 4.8 |
| 40.0 | 3.6 |
| 40.5 | 4.4 |

In some embodiments, Form 12 is characterized by an XRPD pattern having peaks at 2θ angles of 6.8, 9.2, 16.3, 16.7, 18.6, 25.9, and 26.8°. In some embodiments, Form 12 is characterized by an XRPD pattern having peaks at 2θ angles of 6.8, 9.2, 11.3, 16.3, 16.7, 17.4, 18.6, 25.9, 26.8, and 27.9°. In some embodiments, Form 12 is characterized by an XRPD pattern substantially as shown in FIG. 42.

Figure 43:
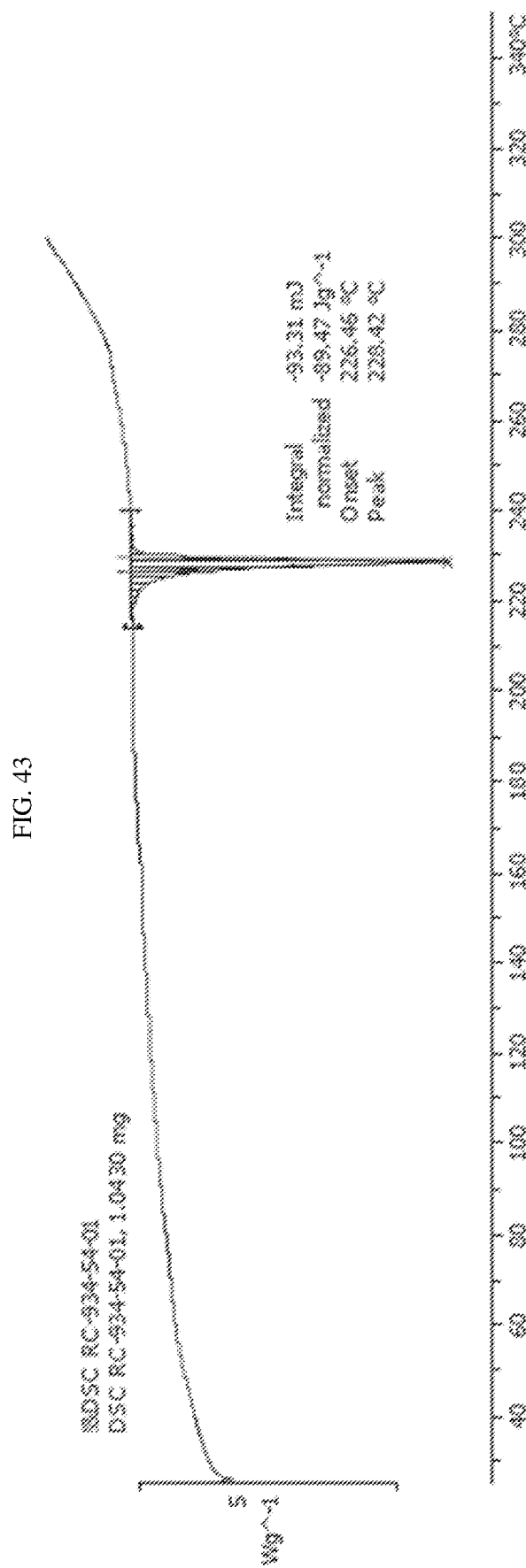
FIG. 43 shows a DSC thermogram for crystalline Form 12.

FIG. 43 shows a differential scanning calorimetry (DSC) profile of Form 12. The DSC thermogram plots the heat flow as a function of temperature from a sample, the temperature rate change being about 10° C./min. FIG. 43 shows an endotherm event with an onset of about 226.5° C. and a peak of about 228.4° C. In some embodiments, Form 12 is characterized by a DSC profile substantially as shown in FIG. 43.

Figure 44:
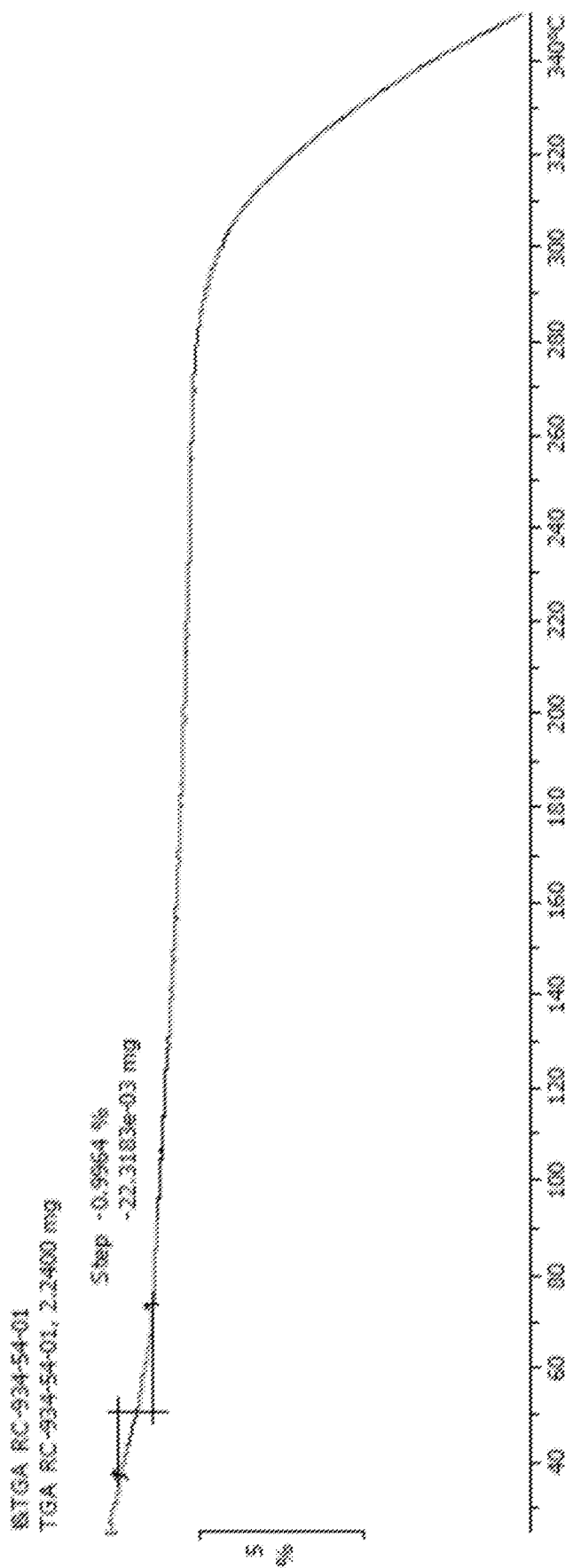
FIG. 44 shows a TGA thermogram for crystalline Form 12.

FIG. 44 shows a thermal gravimetric analysis (TGA) profile of Form 12. The TGA thermogram plots the percent loss of weight of the sample as a function of temperature, the temperature rate change being about 10° C./min. FIG. 44 shows a 1.0% loss up to 70° C. which corresponds to 0.04 equivalents of t-butyl methyl ether. In some embodiments, Form 12 is characterized by a TGA profile substantially as shown in FIG. 44.

Figure 45:
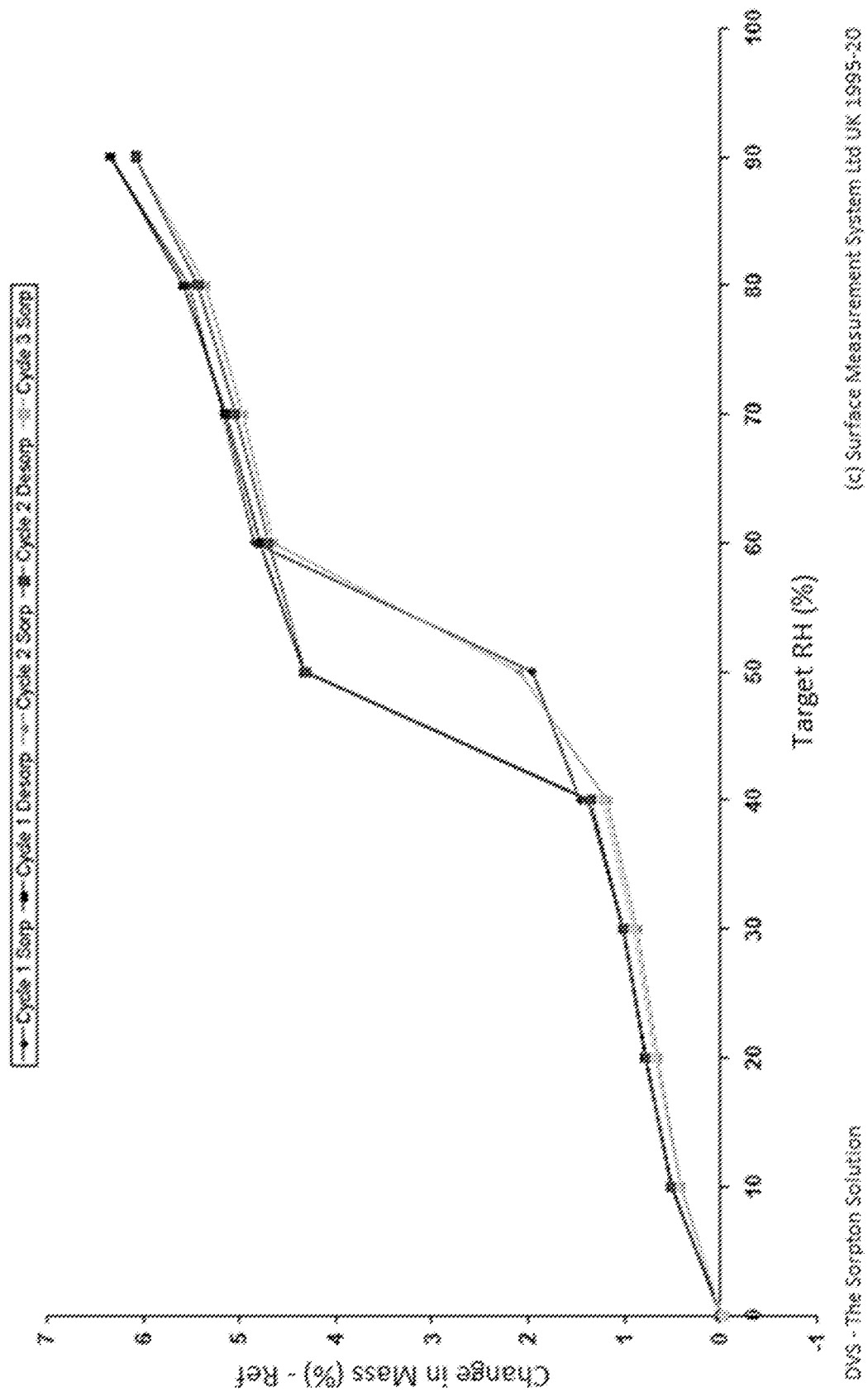
FIG. 45 shows a GVS isotherm plot for crystalline Form 12.

FIG. 45 shows a gravimetric vapor sorption (GVS) isotherm plot of Form 12. The GVS shows that Form 12 has a weight change of about 6% between 0 and 90% RH. Hysterisis was observed between 40 and 60% RH which suggests possible transformation to a hydrate. In some embodiments, Form 12 is characterized by a GVS profile substantially as shown in FIG. 45.

Form 13

Provided herein is an assortment of characterizing information to describe a crystalline form of the free base of Compound 1 ("Form 13").

FIG. 40 shows an X-ray powder diffraction (XRPD) pattern of Form 13 obtained using CuKα radiation. Peaks identified in FIG. 46 include those listed in Table 11.

TABLE 11

| Angle 2-Theta ° | Intensity % |
|---|---|
| 9.4 | 33.9 |
| 13.1 | 6.2 |
| 13.5 | 8.9 |
| 13.9 | 100.0 |
| 15.2 | 6.2 |
| 16.1 | 16.7 |
| 16.5 | 77.6 |
| 18.5 | 44.5 |
| 18.8 | 38.5 |
| 19.1 | 17.8 |
| 19.3 | 36.2 |
| 19.6 | 19.5 |
| 19.8 | 11.9 |
| 20.7 | 13.6 |
| 21.4 | 93.4 |
| 23.0 | 29.0 |
| 23.3 | 28.4 |
| 23.9 | 93.1 |
| 26.5 | 17.1 |
| 26.8 | 6.4 |
| 27.0 | 56.7 |
| 27.3 | 14.9 |
| 27.6 | 6.9 |
| 29.3 | 8.7 |
| 29.7 | 3.6 |
| 30.2 | 6.7 |
| 30.6 | 15.5 |
| 30.8 | 13.2 |
| 31.3 | 8.1 |
| 31.7 | 12.6 |
| 32.3 | 4.4 |
| 32.6 | 5.2 |
| 33.1 | 5.4 |
| 33.4 | 6.5 |
| 35.0 | 3.6 |
| 35.8 | 4.4 |
| 36.3 | 4.5 |
| 37.5 | 3.2 |
| 37.8 | 5.7 |
| 38.7 | 5.7 |
| 39.1 | 4.6 |
| 39.7 | 2.5 |
| 40.0 | 2.7 |
| 40.2 | 7.6 |
| 40.7 | 2.3 |
| 41.6 | 2.7 |
| 41.9 | 3.8 |

Figure 46:
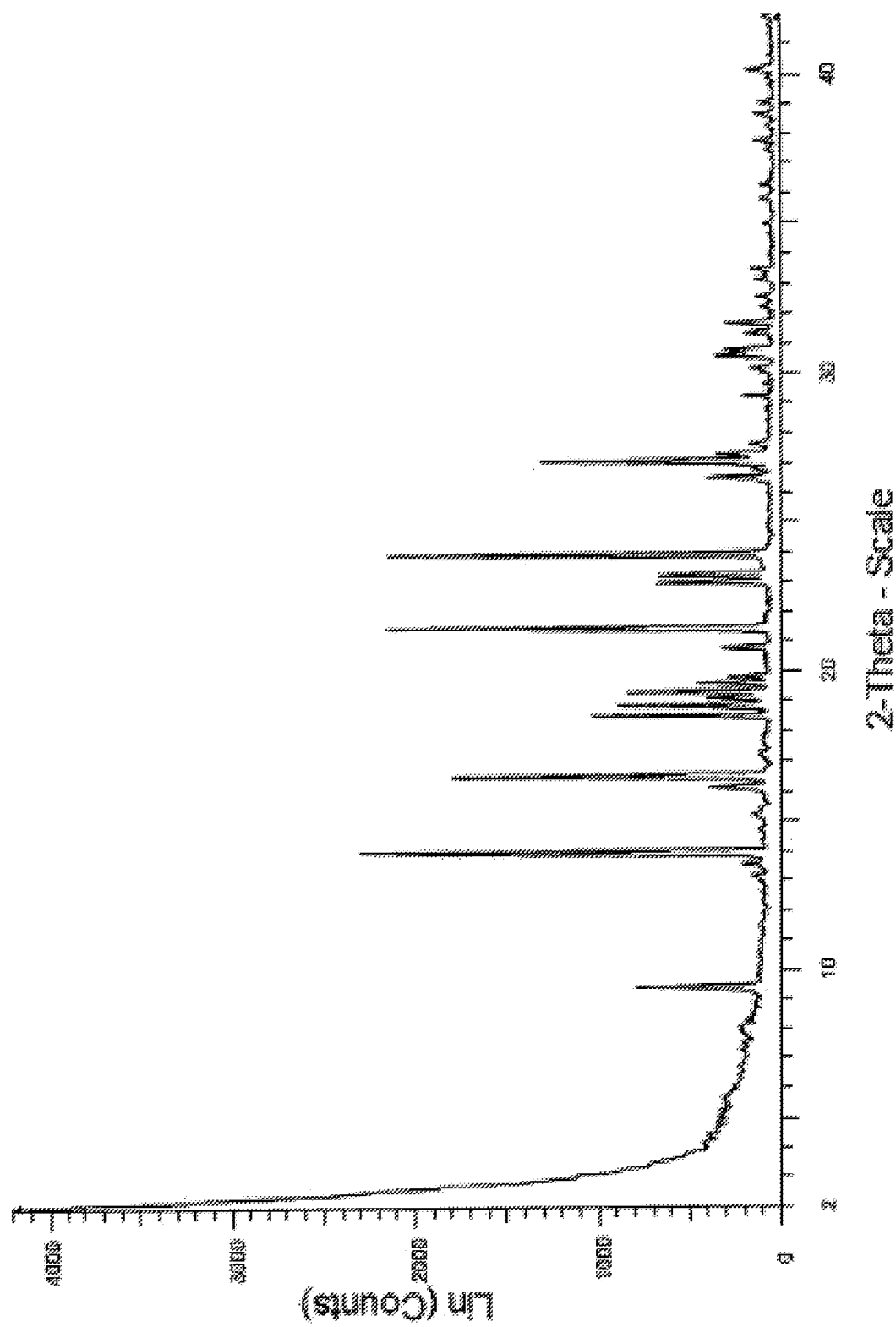
FIG. 46 shows an XRPD pattern for crystalline Form 13.

In some embodiments, Form 13 is characterized by an XRPD pattern having peaks at 2θ angles of 9.4, 13.9, 16.5, 18.5, 18.8, 19.3, 21.4, 23.0, 23.3, 23.9, and 27.0°. In some embodiments, Form 13 is characterized by an XRPD pattern having peaks at 2θ angles of 9.4, 13.9, 16.1, 16.5, 18.5, 18.8, 19.1, 19.3, 19.6, 21.4, 23.0, 23.3, 23.9, 26.5, 27.0, and 30.6°. In some embodiments, Form 13 is characterized by an XRPD pattern substantially as shown in FIG. 46.

Figure 47:
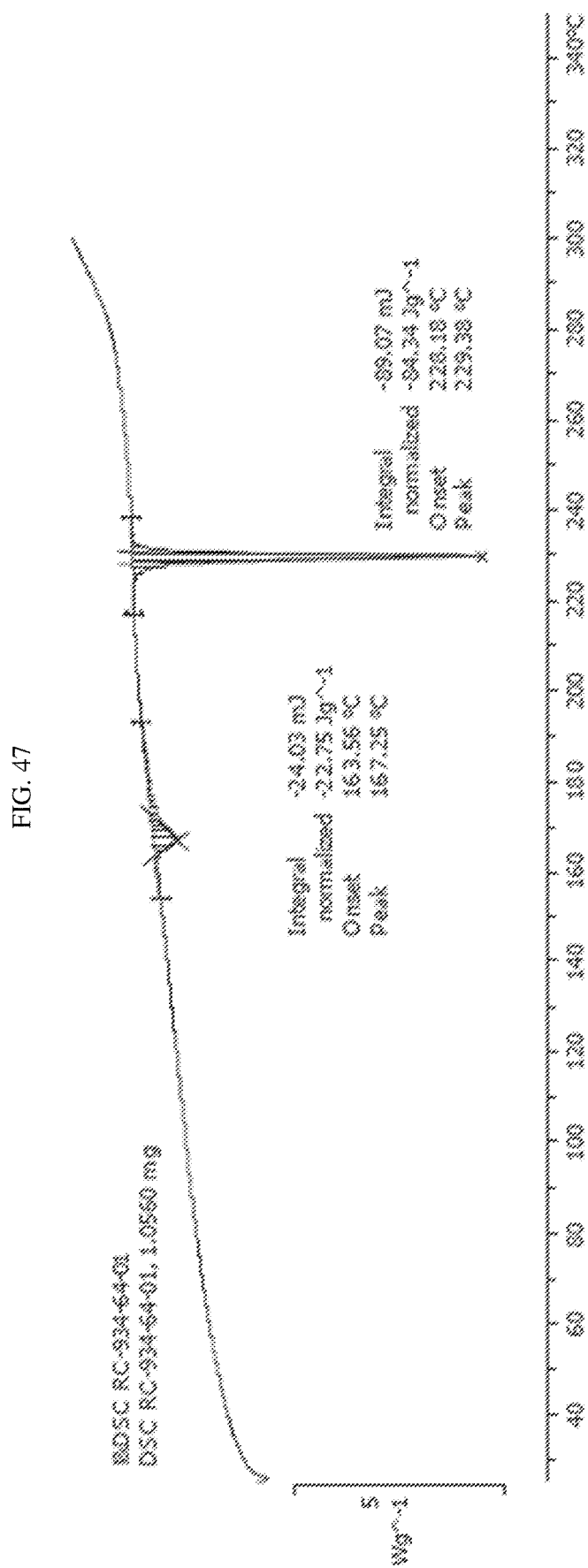
FIG. 47 shows a DSC thermogram for crystalline Form 13.

FIG. 47 shows a differential scanning calorimetry (DSC) profile of Form 13. The DSC thermogram plots the heat flow as a function of temperature from a sample, the temperature rate change being about 10° C./min. FIG. 47 shows an endotherm event with an onset of about 163.6° C. and an endotherm event with an onset of about 228.2° C. In some embodiments, Form 13 is characterized by a DSC profile substantially as shown in FIG. 47.

Figure 48:
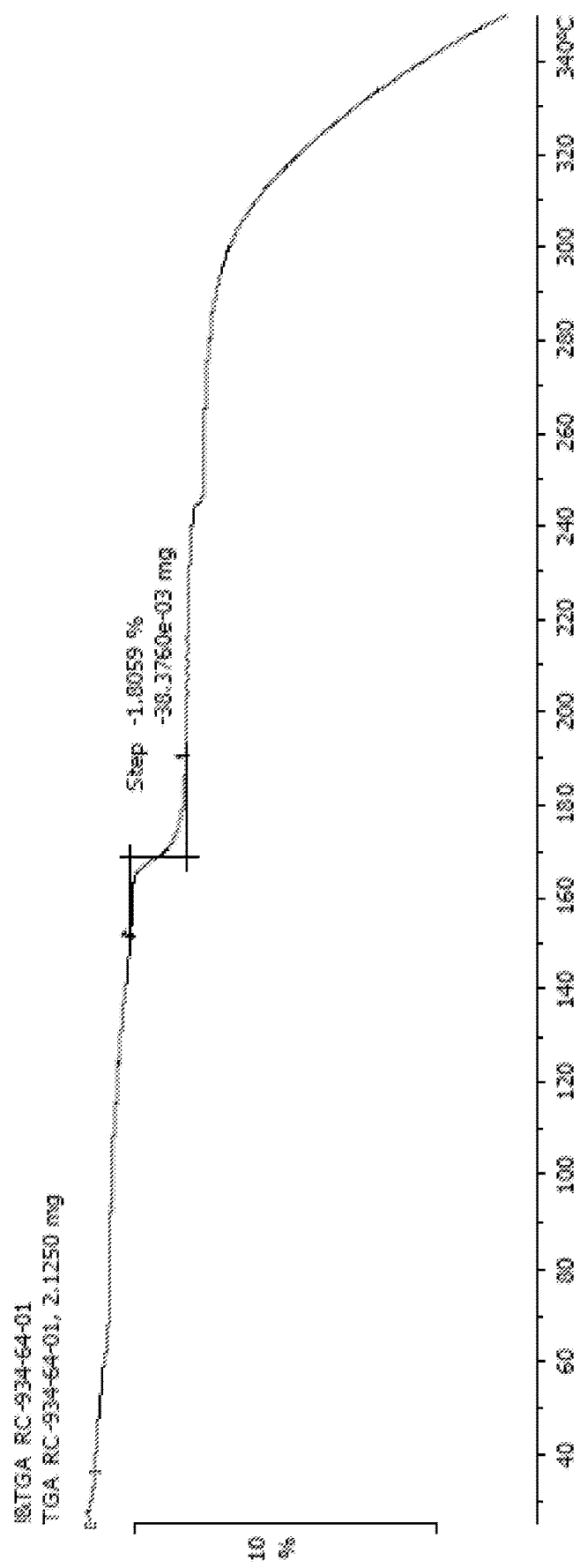
FIG. 48 shows a TGA thermogram for crystalline Form 13.

FIG. 48 shows a thermal gravimetric analysis (TGA) profile of Form 13. The TGA thermogram plots the percent loss of weight of the sample as a function of temperature, the temperature rate change being about 10° C./min. FIG. 48 shows weight loss of about 1.8% between 150 and 190° C. In some embodiments, Form 13 is characterized by a TGA profile substantially as shown in FIG. 48.

Figure 49:
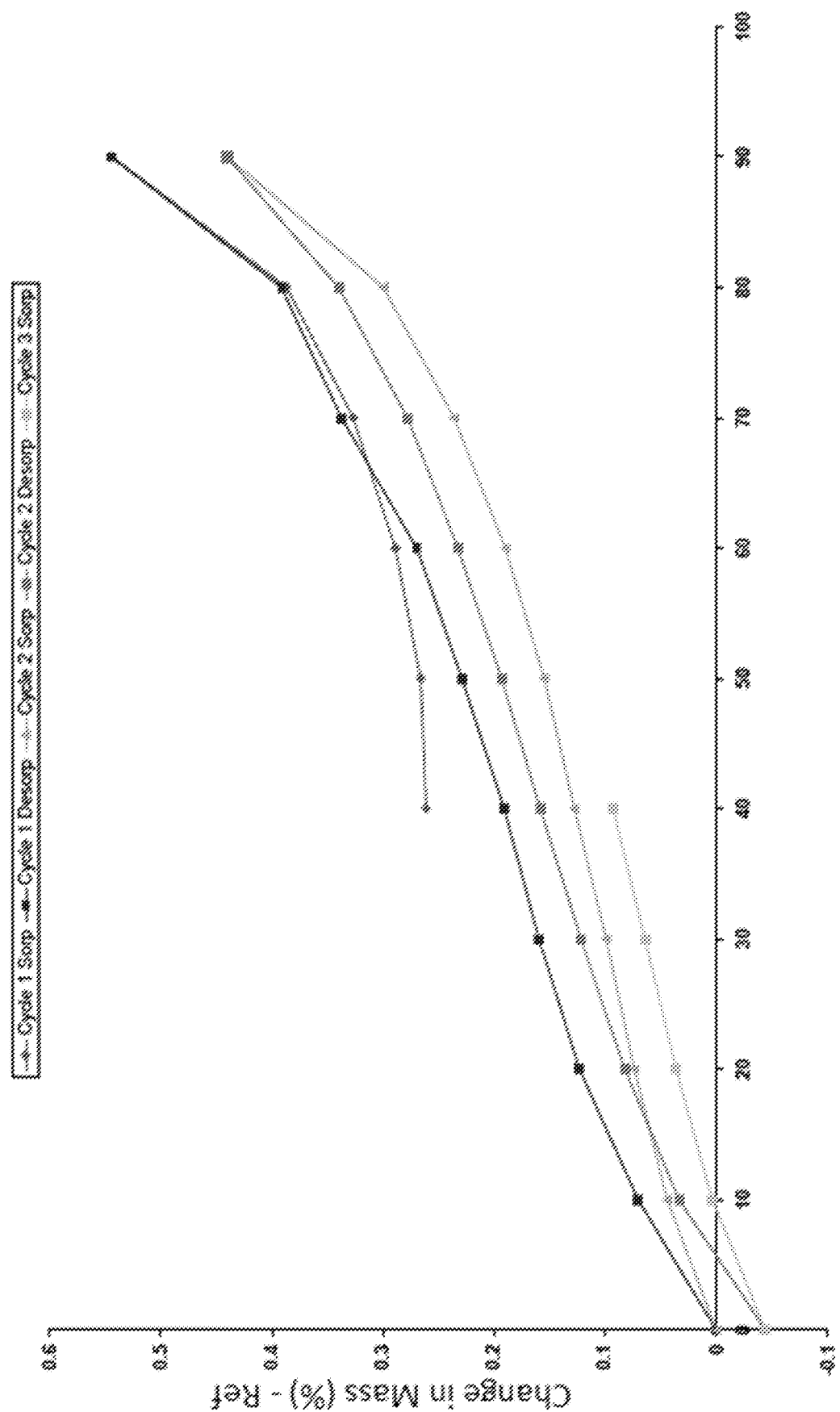
FIG. 49 shows a GVS isotherm plot for crystalline Form 13.

FIG. 49 shows a gravimetric vapor sorption (GVS) isotherm plot of Form 13. The GVS shows that Form 13 has a total weight change of less than 0.6% between 0 to 90% RH suggesting that Form 13 is not hygroscopic when subjected to humidity. In some embodiments, Form 13 is characterized by a GVS profile substantially as shown in FIG. 49.

Form 14

Provided herein is an assortment of characterizing information to describe a crystalline form of Compound 1 free base hemihydrate ("Form 14").

Figure 50:
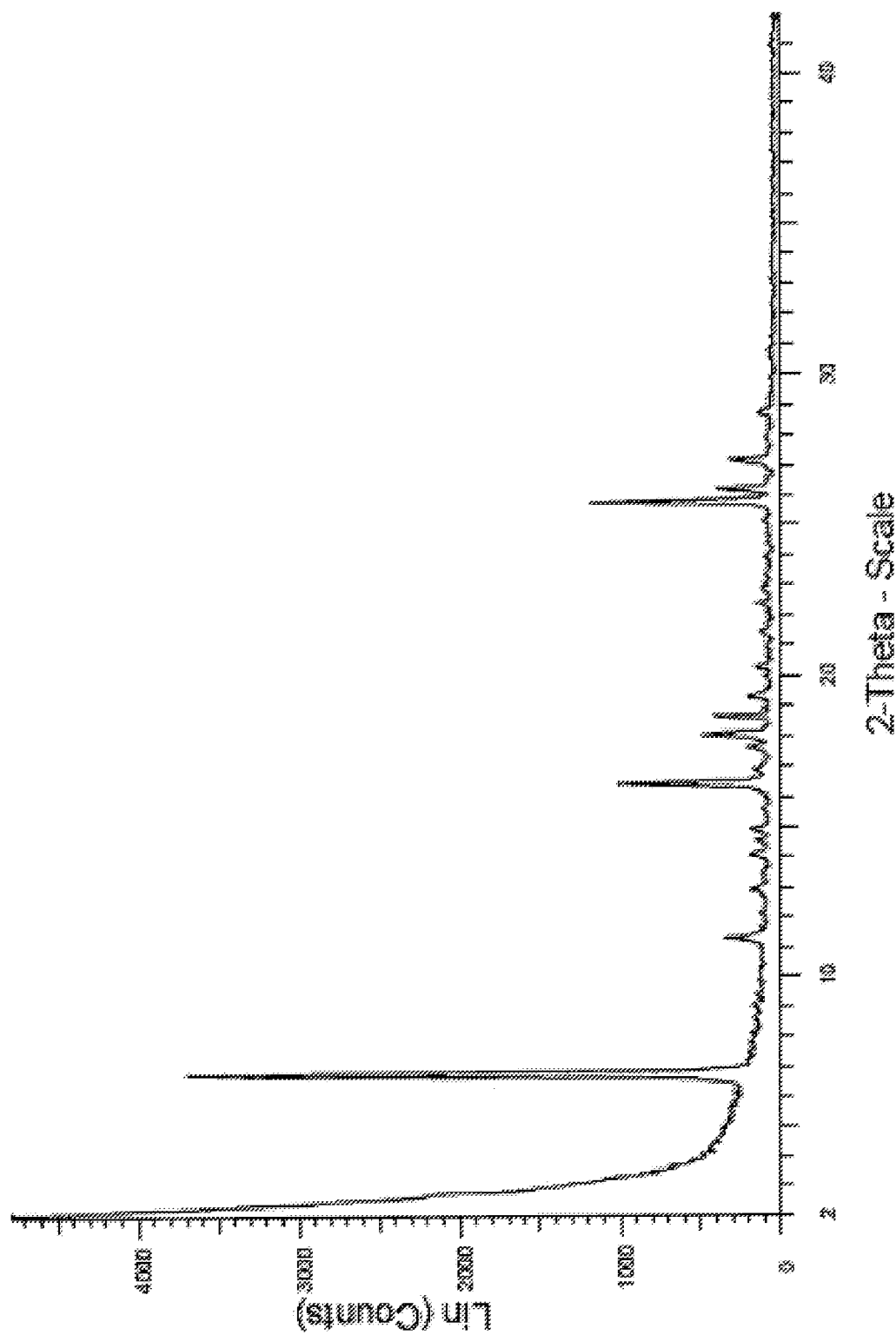
FIG. 50 shows an XRPD pattern for crystalline Form 14.

FIG. 50 shows an X-ray powder diffraction (XRPD) pattern of Form 14 obtained using CuKα radiation. Peaks identified in FIG. 50 include those listed in Table 12.

TABLE 12

| Angle 2-Theta ° | Intensity % |
|---|---|
| 6.7 | 100.0 |
| 7.7 | 5.1 |
| 8.6 | 4.1 |
| 9.0 | 4.5 |
| 9.4 | 3.8 |
| 11.3 | 9.2 |
| 12.1 | 3.2 |
| 12.9 | 4.8 |
| 13.5 | 3.0 |
| 14.0 | 5.0 |
| 14.5 | 3.9 |
| 14.9 | 5.0 |
| 15.6 | 2.7 |
| 16.4 | 27.2 |
| 16.9 | 4.3 |
| 17.6 | 5.6 |
| 18.0 | 12.9 |
| 18.6 | 10.9 |
| 18.9 | 2.7 |
| 19.3 | 5.3 |
| 19.9 | 2.4 |
| 20.3 | 4.0 |
| 21.4 | 3.3 |
| 21.7 | 2.1 |
| 22.4 | 4.0 |
| 22.9 | 2.8 |
| 23.3 | 2.3 |
| 24.0 | 2.6 |
| 25.1 | 2.8 |
| 25.8 | 31.8 |
| 26.2 | 10.7 |
| 27.1 | 8.4 |
| 27.9 | 2.4 |
| 28.7 | 3.5 |
| 30.8 | 1.7 |
| 31.3 | 1.5 |
| 36.5 | 1.3 |
| 41.0 | 1.4 |
| 41.3 | 1.1 |

In some embodiments, Form 14 is characterized by an XRPD pattern having peaks at 2θ angles of 6.7, 16.4, 18.0, 18.6, 25.8, and 26.2°. In some embodiments, Form 14 is characterized by an XRPD pattern having peaks at 2θ angles of 6.7, 7.7, 11.3, 14.0, 14.9, 16.4, 17.6, 18.0, 18.6, 19.3, 25.8, 26.2, and 27.10. In some embodiments, Form 14 is characterized by an XRPD pattern substantially as shown in FIG. 50.

Figure 51:
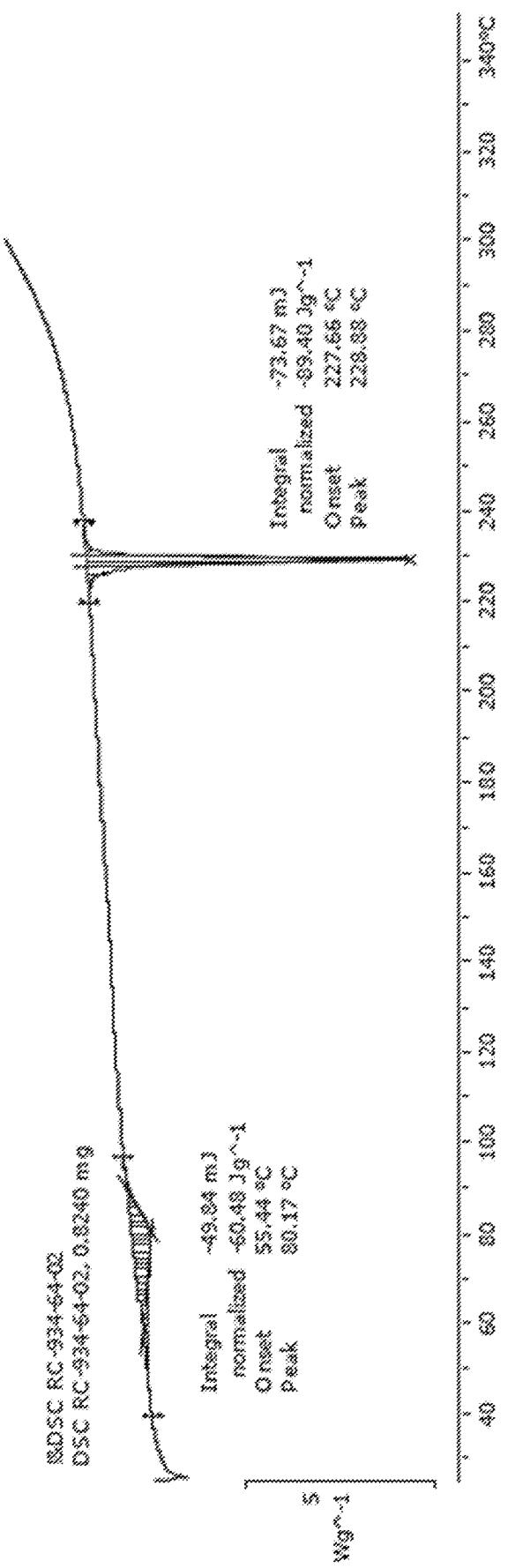
FIG. 51 shows a DSC thermogram for crystalline Form 14.

FIG. 51 shows a differential scanning calorimetry (DSC) profile of Form 14. The DSC thermogram plots the heat flow as a function of temperature from a sample, the temperature rate change being about 10° C./min. FIG. 51 shows a desolvation endotherm event with an onset of about 55.4° C. and a sharp melting endotherm event with an onset of about 227.7° C. In some embodiments, Form 14 is characterized by a DSC profile substantially as shown in FIG. 51.

Figure 52:
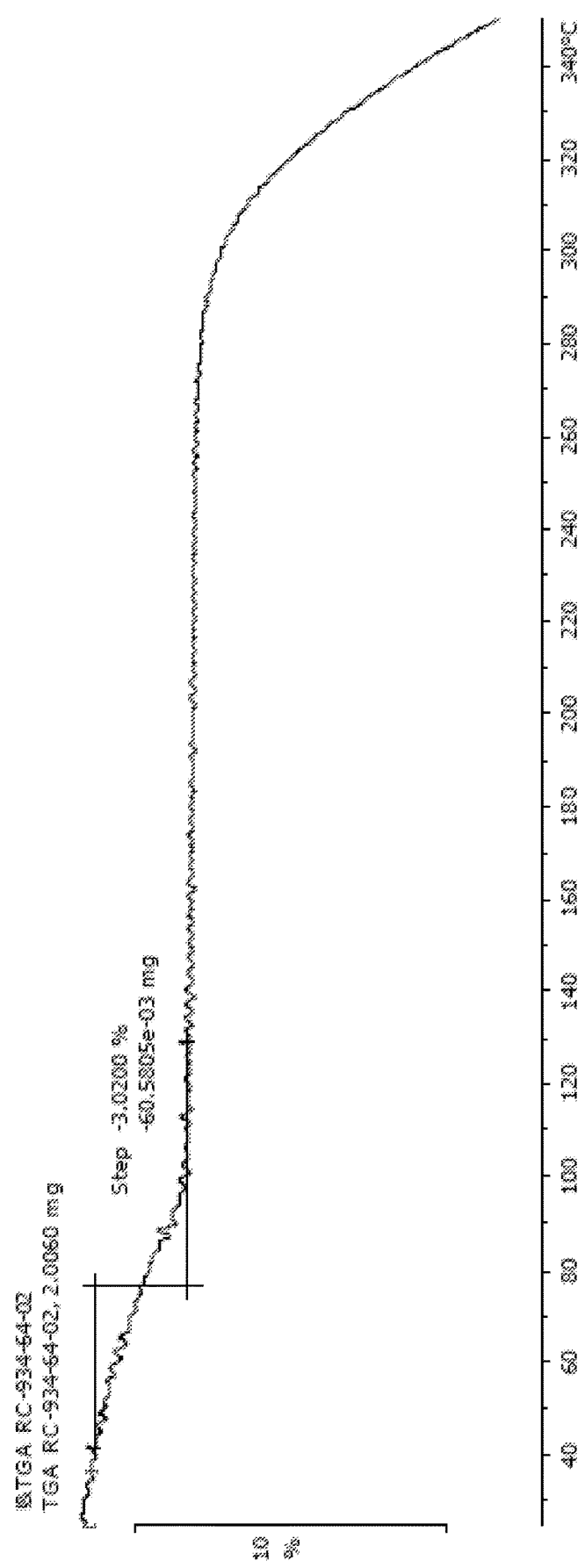
FIG. 52 shows a TGA thermogram for crystalline Form 14.

FIG. 52 shows a thermal gravimetric analysis (TGA) profile of Form 14. The TGA thermogram plots the percent loss of weight of the sample as a function of temperature, the temperature rate change being about 10° C./min. FIG. 52 shows a 3.0% weight loss between 40 and 130° C., wherein 2.9% of the weight loss is attributed to loss of water, suggesting that Form 14 is a hemihydrate. In some embodiments, Form 14 is characterized by a TGA profile substantially as shown in FIG. 52. Karl Fischer measurements show a water content of about 2.7%, further suggesting that the weight loss observed in the TGA profile is due to the loss of water, and that Form 14 is a hemihydrate.

Figure 53:
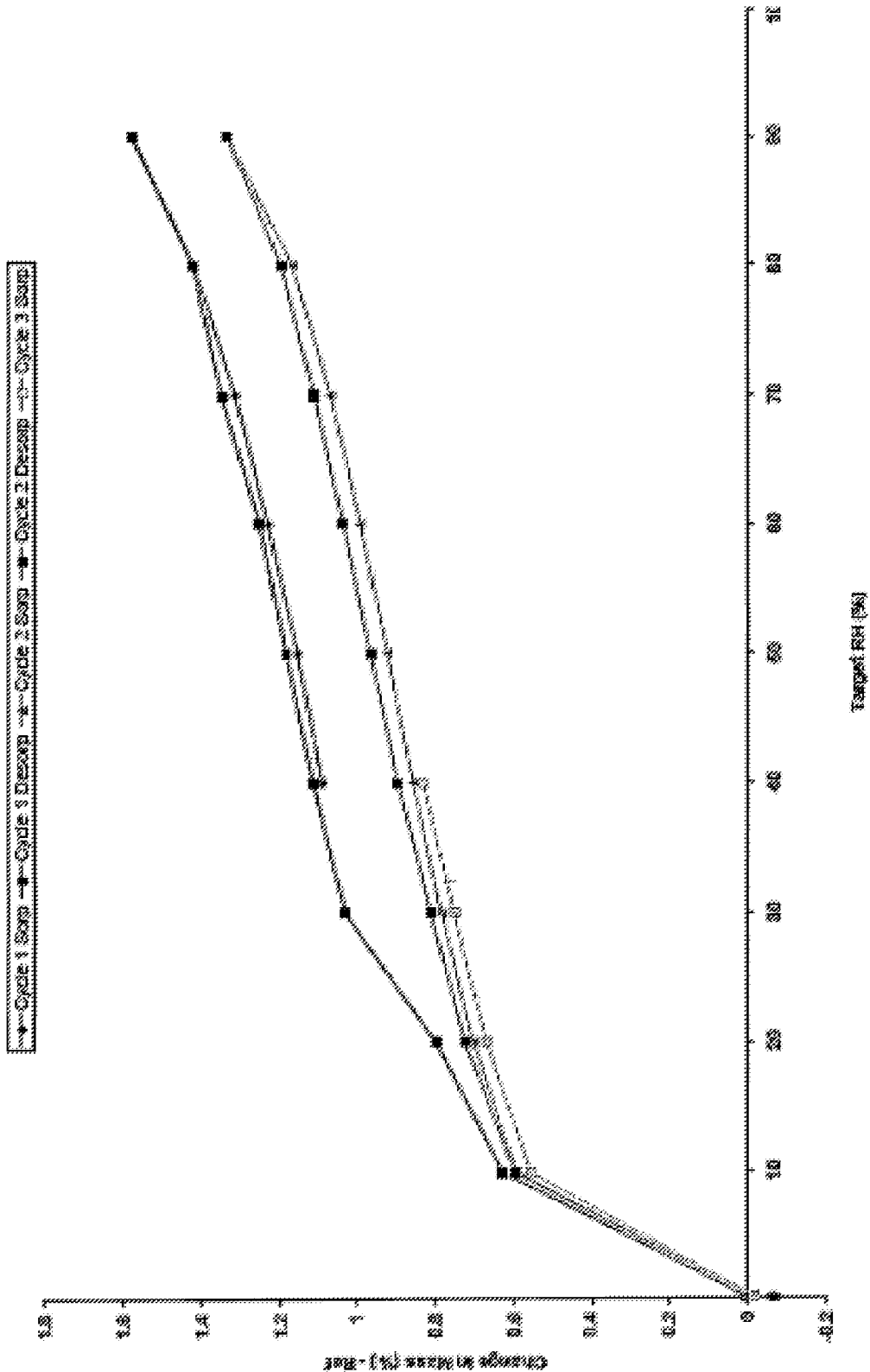
FIG. 53 shows a GVS isotherm plot for crystalline Form 14.

FIG. 53 shows a gravimetric vapor sorption (GVS) isotherm plot of Form 14. The GVS shows that Form 14 has a total weight change of 1.5% between 0 to 90% RH. In some embodiments, Form 14 is characterized by a GVS profile substantially as shown in FIG. 53.

Form 15

Provided herein is an assortment of characterizing information to describe a crystalline form of Compound 1 free base monohydrate ("Form 15").

Figure 54:
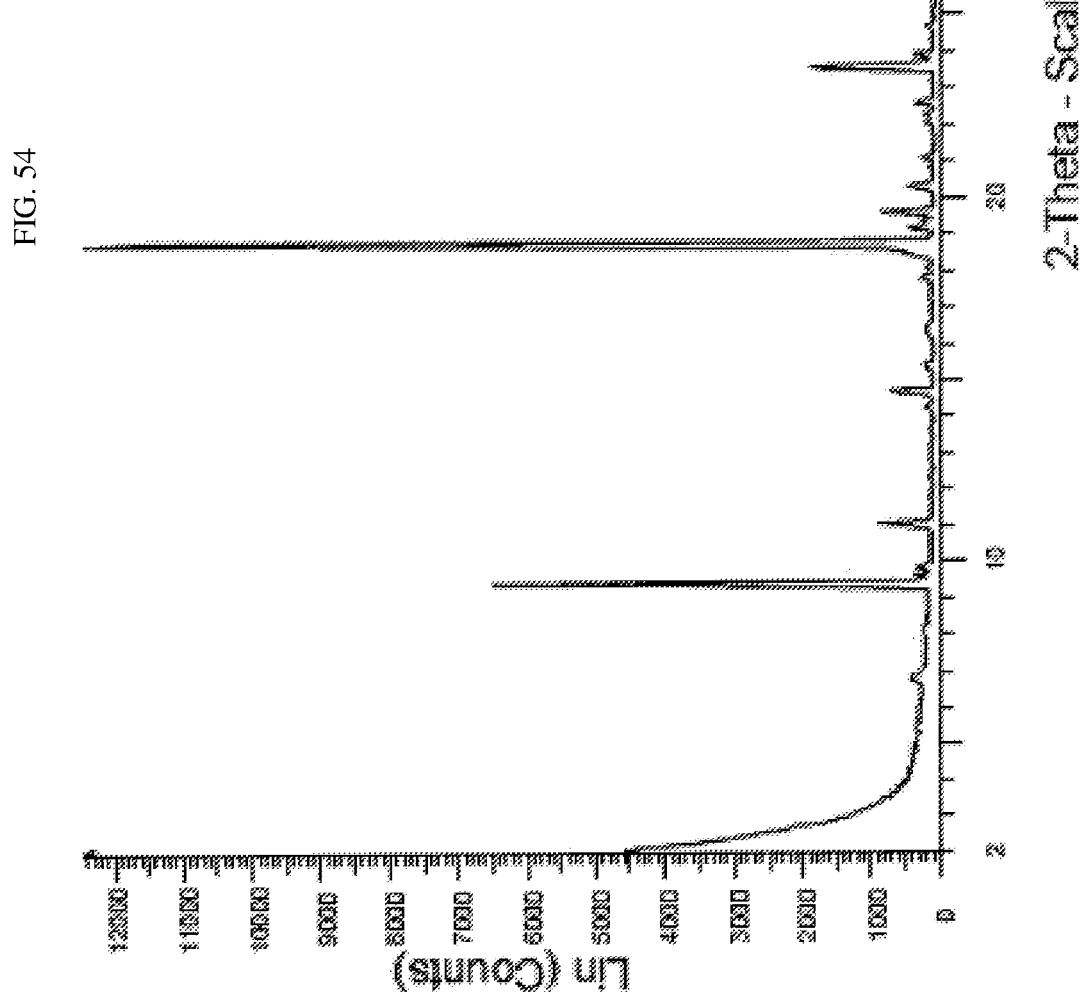
FIG. 54 shows an XRPD pattern for crystalline Form 15.

FIG. 54 shows an X-ray powder diffraction (XRPD) pattern of Form 15 obtained using CuKα radiation. Peaks identified in FIG. 54 include those listed in Table 13.

TABLE 13

| Angle 2-Theta ° | Intensity % |
|---|---|
| 6.8 | 3.3 |
| 8.1 | 1.7 |
| 9.3 | 52.0 |
| 9.6 | 2.8 |
| 9.8 | 2.4 |
| 11.0 | 7.0 |
| 14.2 | 1.5 |
| 14.6 | 5.7 |
| 15.4 | 1.6 |
| 16.3 | 1.3 |
| 17.8 | 2.1 |
| 18.1 | 1.3 |
| 18.4 | 4.3 |
| 18.7 | 100.0 |
| 19.1 | 3.6 |
| 19.3 | 2.1 |
| 19.6 | 6.7 |
| 20.3 | 3.6 |
| 21.1 | 2.0 |
| 22.1 | 1.6 |
| 22.2 | 1.7 |
| 22.6 | 2.8 |
| 23.6 | 15.1 |
| 23.9 | 2.8 |
| 24.6 | 1.3 |
| 25.8 | 1.5 |
| 26.0 | 2.5 |
| 26.2 | 3.5 |
| 26.4 | 11.0 |
| 26.7 | 2.4 |
| 27.3 | 1.5 |
| 27.6 | 0.9 |

TABLE 13-continued

| Angle 2-Theta ° | Intensity % |
| --- | --- |
| 28.2 | 3.6 |
| 28.7 | 1.0 |
| 29.2 | 1.0 |
| 29.5 | 1.2 |
| 30.4 | 1.3 |
| 31.0 | 2.1 |
| 31.3 | 1.9 |
| 31.5 | 1.2 |
| 31.9 | 0.9 |
| 32.3 | 3.0 |
| 32.6 | 1.7 |
| 32.9 | 1.5 |
| 35.3 | 0.8 |
| 37.9 | 0.9 |
| 38.3 | 2.3 |
| 38.8 | 0.9 |
| 39.2 | 1.5 |
| 39.7 | 1.4 |
| 40.9 | 0.9 |
| 41.1 | 0.9 |

In some embodiments, Form 15 is characterized by an XRPD pattern having peaks at 2θ angles of 9.3, 18.7, 23.6, and 26.4°. In some embodiments, Form 15 is characterized by an XRPD pattern having peaks at 2θ angles of 9.3, 14.6, 18.7, 23.6, and 26.4°. In some embodiments, Form 15 is characterized by an XRPD pattern substantially as shown in FIG. 54.

Figure 55:
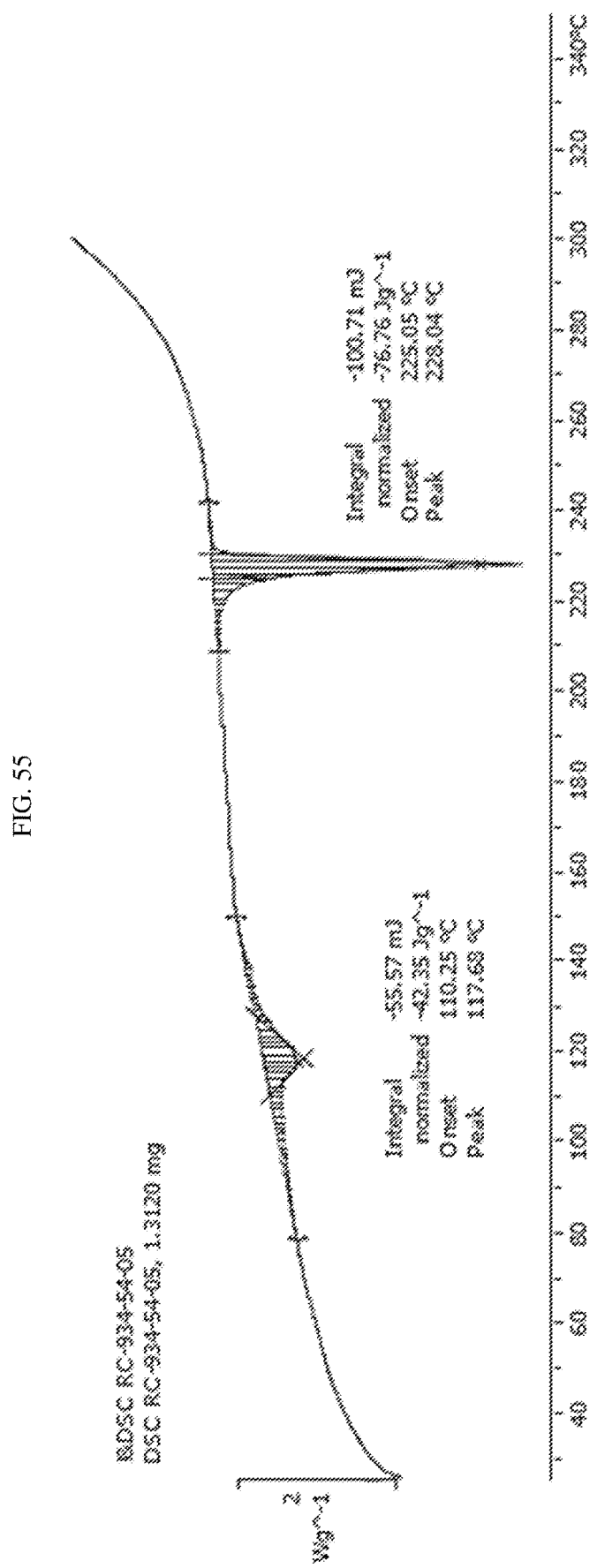
FIG. 55 shows a DSC thermogram for crystalline Form 15.

FIG. 55 shows a differential scanning calorimetry (DSC) profile of Form 15. The DSC thermogram plots the heat flow as a function of temperature from a sample, the temperature rate change being about 10° C./min. FIG. 55 shows a desolvation endotherm event with an onset of about 110.2° C. and a sharp melting endotherm event with an onset of about 225.1° C. In some embodiments, Form 15 is characterized by a DSC profile substantially as shown in FIG. 55.

Figure 56:
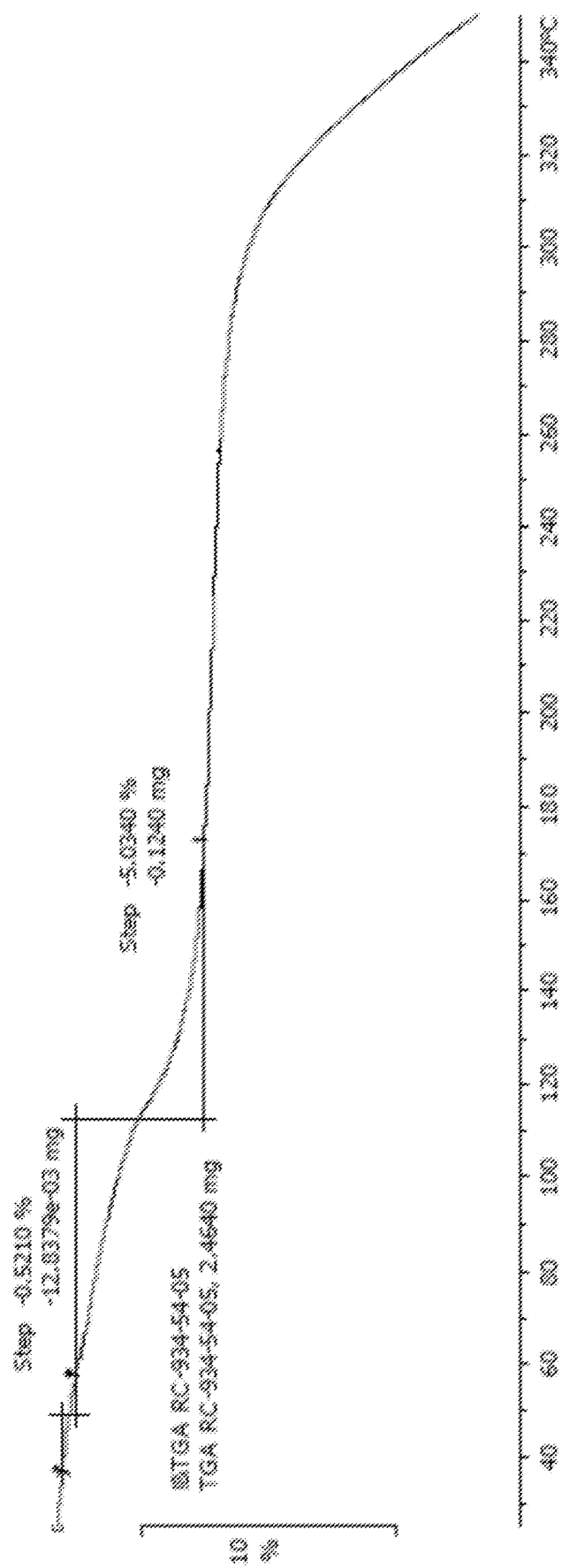
FIG. 56 shows a TGA thermogram for crystalline Form 15.

FIG. 56 shows a thermal gravimetric analysis (TGA) profile of Form 15. The TGA thermogram plots the percent loss of weight of the sample as a function of temperature, the temperature rate change being about 10° C./min. FIG. 50 shows a 5.0% weight loss between 60 and 180° C., wherein 4.5% is attributed to loss of water, suggesting the Form 15 is a mono-hydrate.

In some embodiments, Form 15 is characterized by a TGA profile substantially as shown in FIG. 56. Karl Fischer measurements show a water content of about 3.6%, further suggesting that the weight loss observed in the TGA profile is due to the loss of water, and that Form 15 is a monohydrate.

FIG. 51 shows a gravimetric vapor sorption (GVS) isotherm plot of Form 15. The GVS shows that Form 15 has a total weight change of 2.0% between 0 to 90% RH. In some embodiments, Form 15 is characterized by a GVS profile substantially as shown in FIG. 51.

Form 16

Provided herein is an assortment of characterizing information to describe a crystalline form of Compound 1 free base trihydrate ("Form 16").

Figure 58:
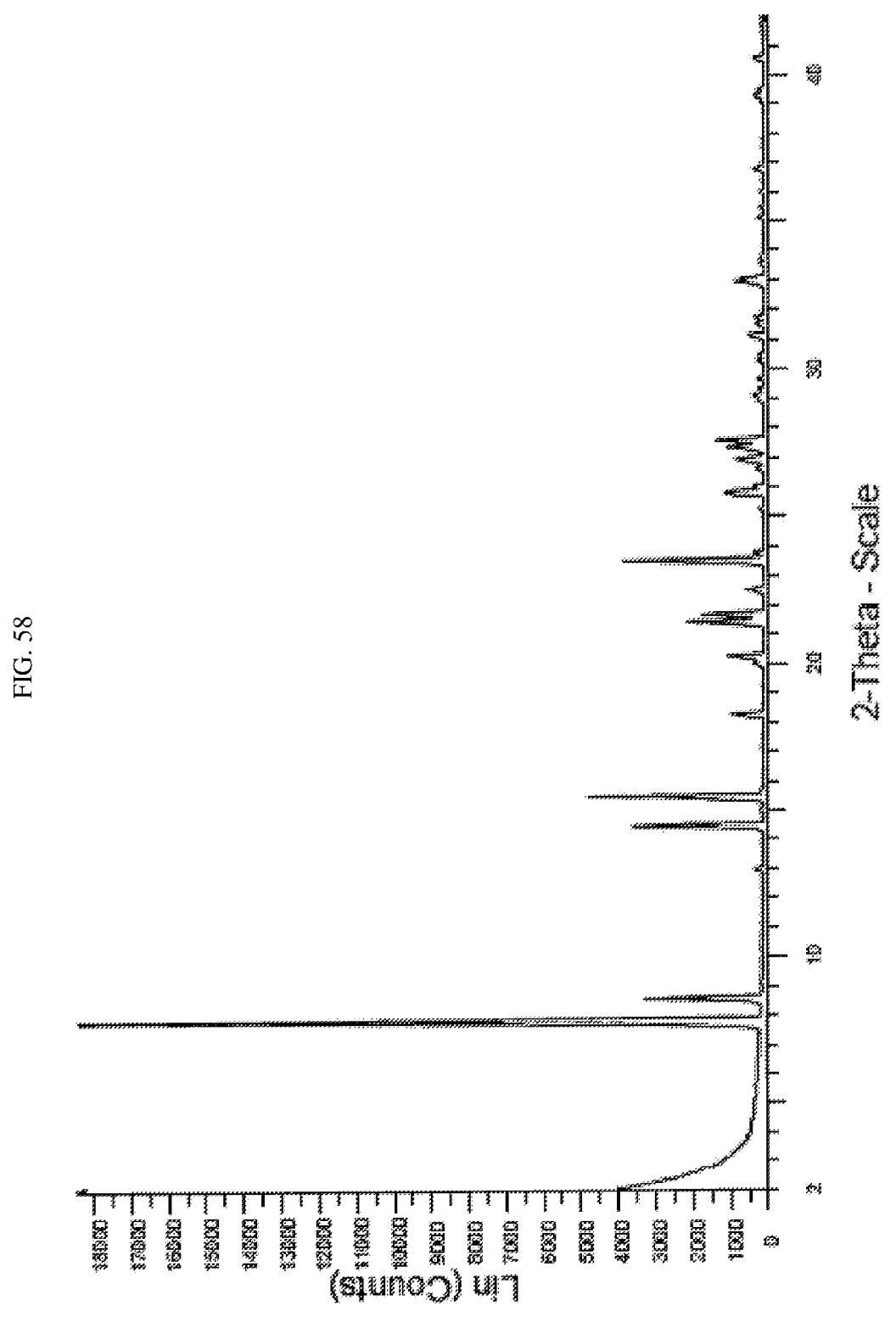

FIG. 58 shows an X-ray powder diffraction (XRPD) pattern of Form 16 obtained using CuKα radiation. Peaks identified in FIG. 58 include those listed in Table 14.

TABLE 14

| Angle 2-Theta ° | Intensity % |
| --- | --- |
| 7.8 | 100.0 |
| 8.5 | 17.6 |
| 12.9 | 1.7 |
| 14.4 | 19.4 |
| 15.0 | 0.8 |
| 15.4 | 25.8 |
| 18.2 | 5.2 |
| 20.0 | 2.0 |
| 20.2 | 5.7 |
| 21.4 | 11.4 |
| 21.6 | 9.4 |
| 22.5 | 3.1 |
| 23.5 | 20.9 |
| 23.8 | 1.8 |
| 25.3 | 1.0 |
| 25.8 | 6.2 |
| 26.1 | 2.1 |
| 26.6 | 1.5 |
| 26.9 | 4.5 |
| 27.3 | 5.8 |
| 27.6 | 7.3 |
| 28.9 | 1.4 |
| 29.1 | 2.1 |
| 29.4 | 1.2 |
| 29.7 | 1.3 |
| 30.3 | 1.4 |
| 30.5 | 1.2 |
| 31.2 | 2.7 |
| 31.5 | 1.6 |
| 31.8 | 1.9 |
| 33.0 | 4.6 |
| 33.1 | 3.9 |
| 33.6 | 1.0 |
| 33.8 | 1.0 |
| 34.2 | 0.6 |
| 35.1 | 1.4 |
| 35.5 | 1.0 |
| 36.0 | 0.9 |
| 36.5 | 0.8 |
| 36.8 | 2.1 |
| 37.1 | 0.7 |
| 37.5 | 0.7 |
| 37.8 | 0.7 |
| 38.7 | 0.5 |
| 39.1 | 1.0 |
| 39.3 | 1.9 |
| 39.5 | 1.4 |
| 40.6 | 2.0 |
| 41.4 | 0.7 |
| 41.7 | 0.8 |

In some embodiments, Form 16 is characterized by an XRPD pattern having peaks at 2θ angles of 7.8, 8.5, 14.4, 15.4, and 23.5°. In some embodiments, Form 16 is characterized by an XRPD pattern having peaks at 2θ angles of 7.8, 8.5, 14.4, 15.4, 21.4, 21.6, and 23.5°. In some embodiments, Form 16 is characterized by an XRPD pattern substantially as shown in FIG. 58.

Figure 59:
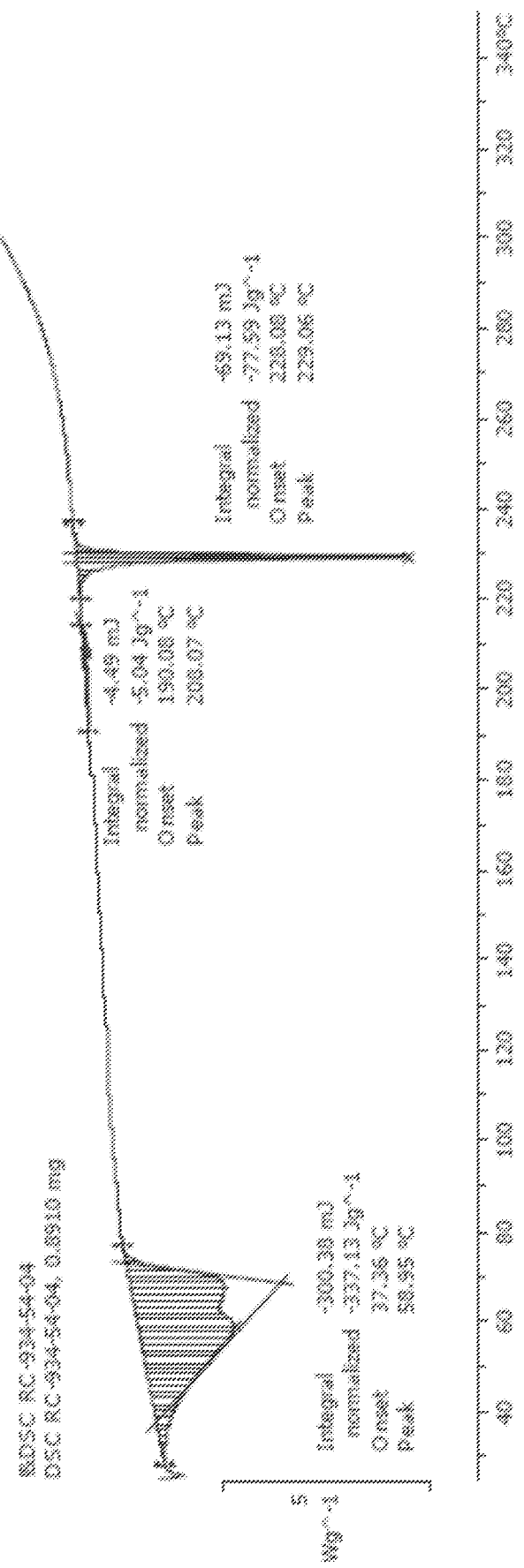
FIG. 59 shows a DSC thermogram for crystalline Form 16.

FIG. 59 shows a differential scanning calorimetry (DSC) profile of Form 16. The DSC thermogram plots the heat flow as a function of temperature from a sample, the temperature rate change being about 10° C./min. FIG. 59 shows overlapping endotherms with an onset of about 37.4° C., a broad endotherm with an onset of about 190.1° C., and a sharp endothermic event at about 228.1° C. associated with melting. In some embodiments, Form 16 is characterized by a DSC profile substantially as shown in FIG. 59.

Figure 60:
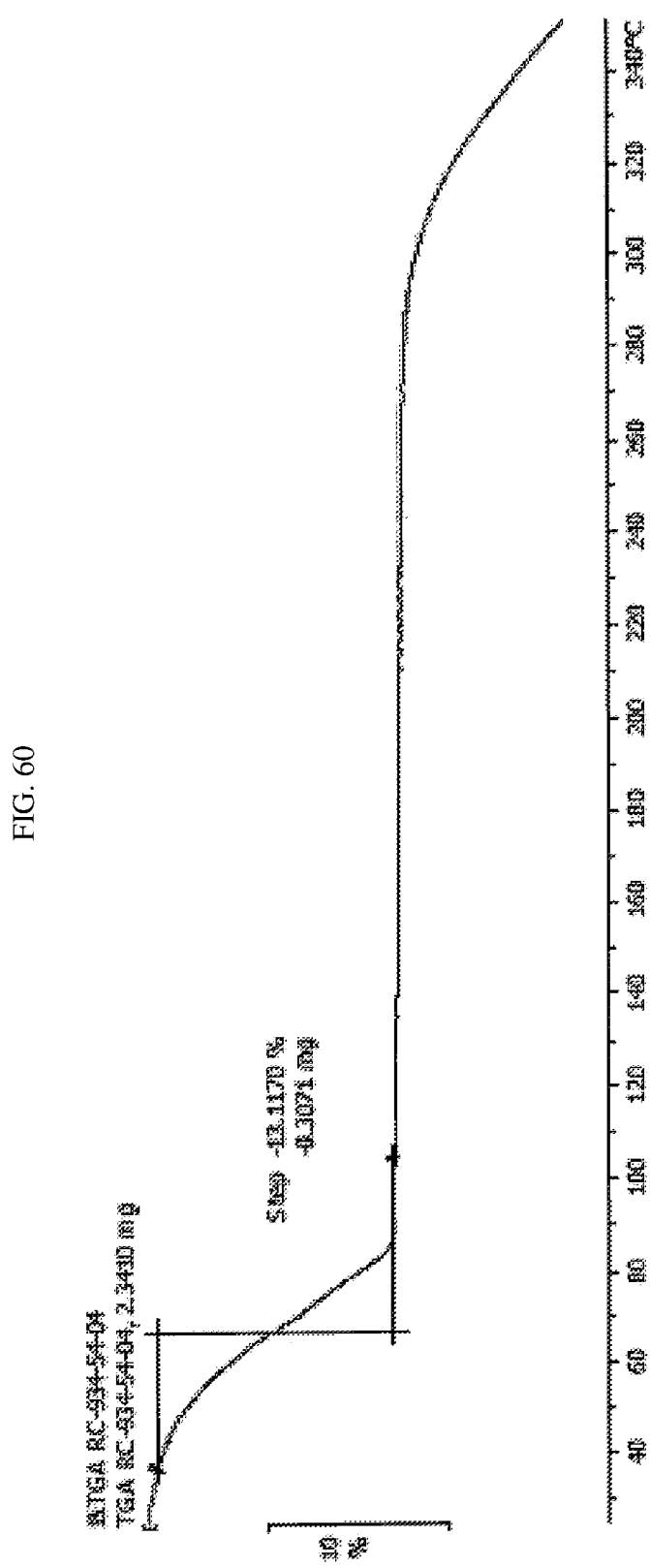
FIG. 60 shows a TGA thermogram for crystalline Form 16.

FIG. 60 shows a thermal gravimetric analysis (TGA) profile of Form 16. The TGA thermogram plots the percent loss of weight of the sample as a function of temperature, the temperature rate change being about 10° C./min. FIG. 60 shows a 13.1% weight loss between 40 and 85° C., suggesting that Form 16 is a trihydrate. In some embodiments, Form 16 is characterized by a TGA profile substantially as shown in FIG. 60. Karl Fischer measurements show a water content of about 13.3%, further suggesting that the weight loss observed in the TGA profile is due to the loss of water, and that Form 16 is a trihydrate.

Figure 61:
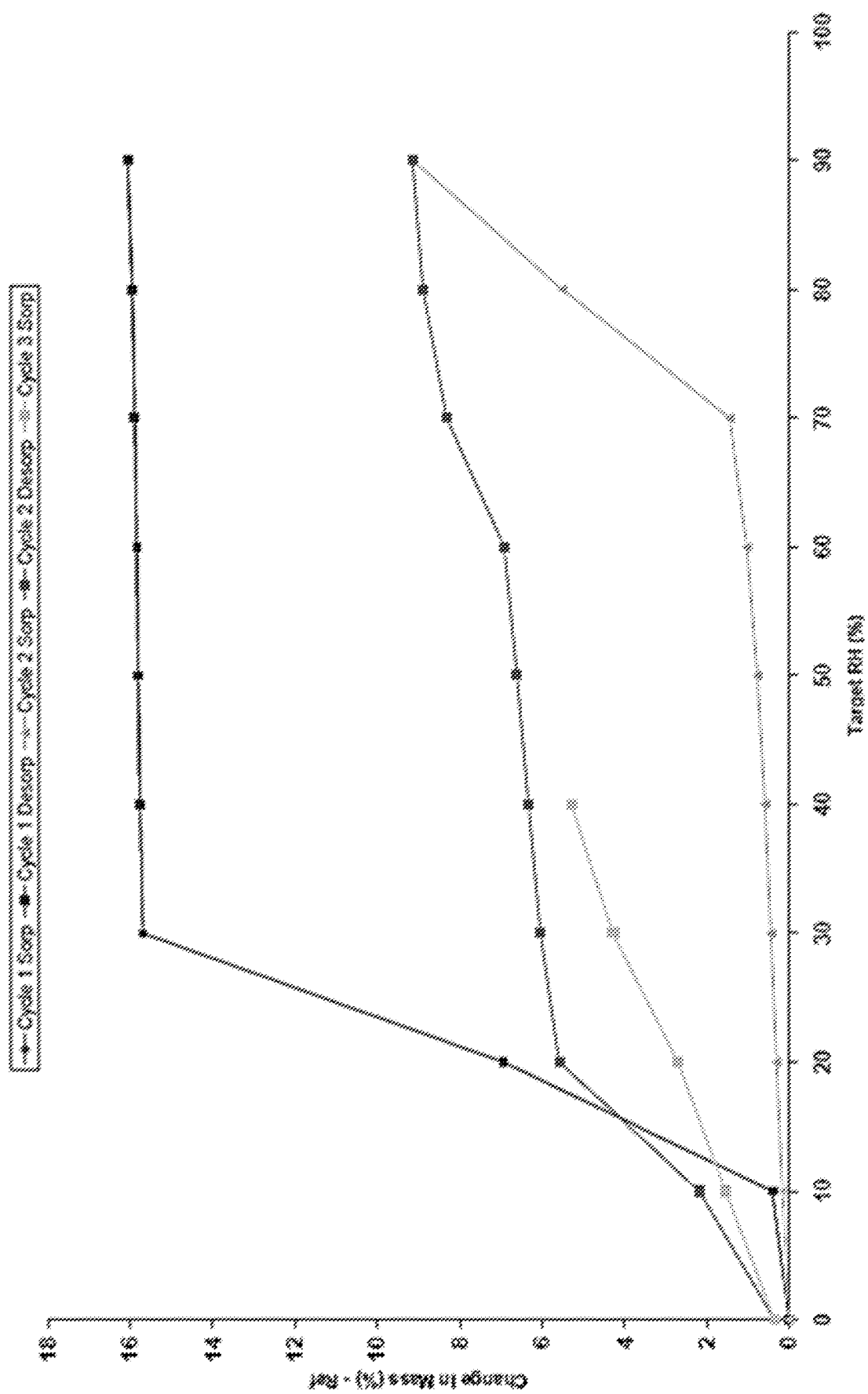
FIG. 61 shows a GVS isotherm plot for crystalline Form 16.

FIG. 61 shows a gravimetric vapor sorption (GVS) isotherm plot of Form 16. The GVS shows dehydration below 30% RH. In some embodiments, Form 16 is characterized by a GVS profile substantially as shown in FIG. 61.

Form 17

Provided herein is an assortment of characterizing information to describe a crystalline form of Compound 1 free base monohydrate ("Form 17").

Figure 62:
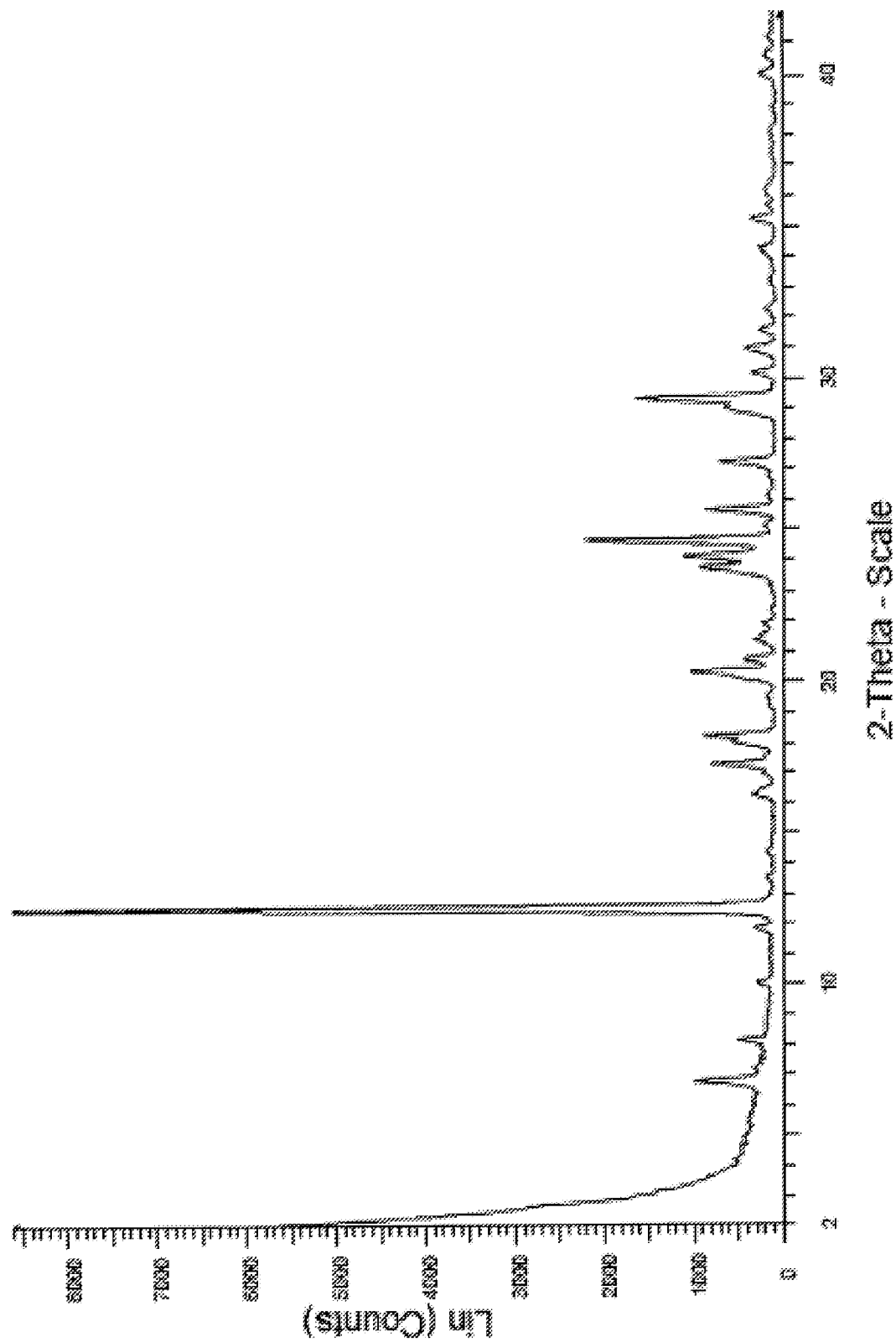
FIG. 62 shows an XRPD pattern for crystalline Form 17.

FIG. 62 shows an X-ray powder diffraction (XRPD) pattern of Form 17 obtained using CuKα radiation. Peaks identified in FIG. 56 include those listed in Table 15.

TABLE 15

| Angle 2-Theta ° | Intensity % |
|---|---|
| 6.7 | 11.4 |
| 7.1 | 3.7 |
| 8.1 | 5.7 |
| 10.0 | 3.1 |
| 11.8 | 3.5 |
| 12.5 | 100.0 |
| 13.5 | 1.9 |
| 14.3 | 1.9 |
| 16.2 | 3.8 |
| 17.0 | 2.5 |
| 17.3 | 9.1 |
| 18.0 | 6.3 |
| 18.2 | 10.1 |
| 18.7 | 1.4 |
| 19.2 | 1.7 |
| 19.3 | 1.7 |
| 19.5 | 1.9 |
| 20.1 | 6.2 |
| 20.3 | 11.7 |
| 20.7 | 4.8 |
| 21.2 | 2.5 |
| 21.4 | 3.5 |
| 21.6 | 2.8 |
| 21.9 | 2.5 |
| 23.8 | 10.5 |
| 24.1 | 12.7 |
| 24.7 | 25.4 |
| 25.7 | 9.8 |
| 27.2 | 8.0 |
| 28.9 | 6.8 |
| 29.0 | 7.6 |
| 29.3 | 18.8 |
| 30.2 | 3.7 |
| 30.9 | 4.5 |
| 31.6 | 2.8 |
| 32.3 | 2.0 |
| 34.2 | 2.8 |
| 34.3 | 2.8 |
| 35.3 | 3.7 |
| 35.7 | 1.9 |
| 36.1 | 2.0 |
| 40.1 | 2.7 |
| 40.7 | 2.1 |
| 41.2 | 1.8 |

In some embodiments, Form 17 is characterized by an XRPD pattern having peaks at 2θ angles of 6.7, 12.5, 18.2, 20.3, 23.8, 24.1, 24.7, and 29.3°. In some embodiments, Form 17 is characterized by an XRPD pattern having peaks at 2θ angles of 6.7, 12.5, 17.3, 18.2, 20.3, 23.8, 24.1, 24.7, 25.7, and 29.3°. In some embodiments, Form 17 is characterized by an XRPD pattern substantially as shown in FIG. 62.

Figure 63:
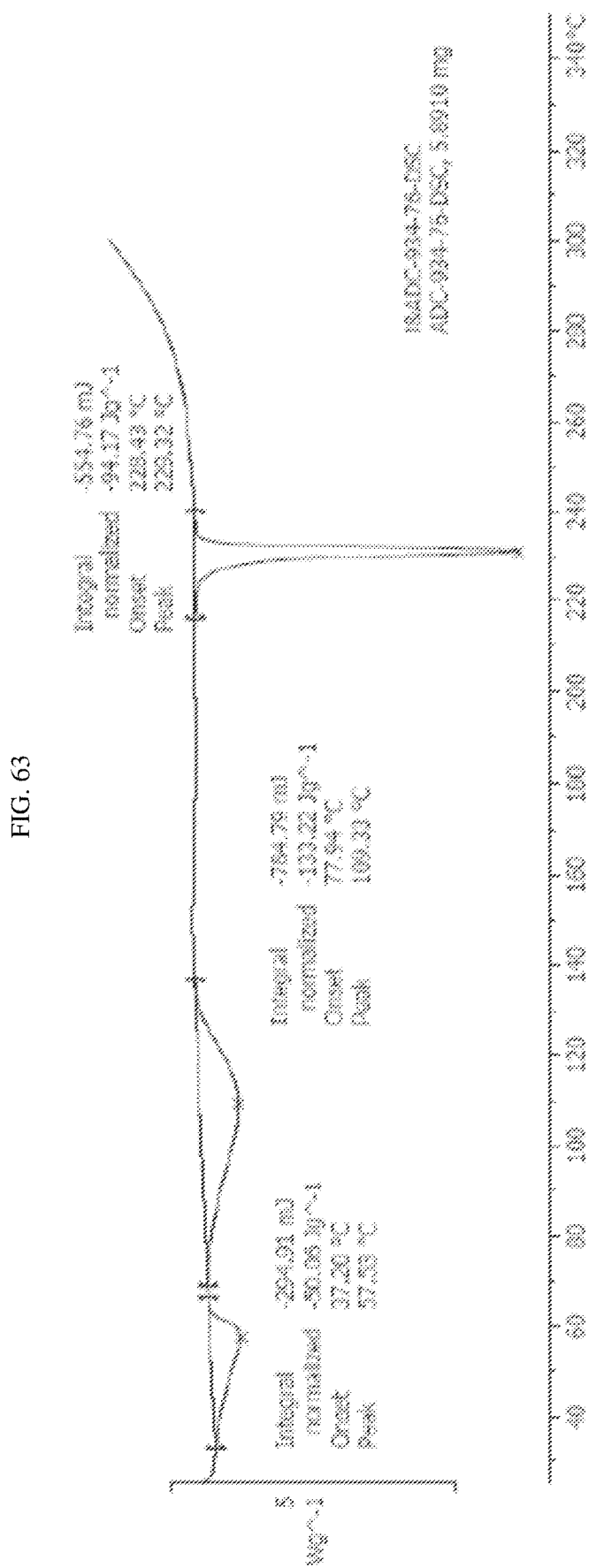
FIG. 63 shows a DSC thermogram for crystalline Form 17.

FIG. 63 shows a differential scanning calorimetry (DSC) profile of Form 17. The DSC thermogram plots the heat flow as a function of temperature from a sample, the temperature rate change being about 10° C./min. FIG. 63 shows an endotherm event with an onset at about 37° C., a followed by a second endotherm with an onset at about 78° C., and a sharp endothermic event at about 228° C. associated with melting. In some embodiments, Form 17 is characterized by a DSC profile substantially as shown in FIG. 63.

Figure 64:
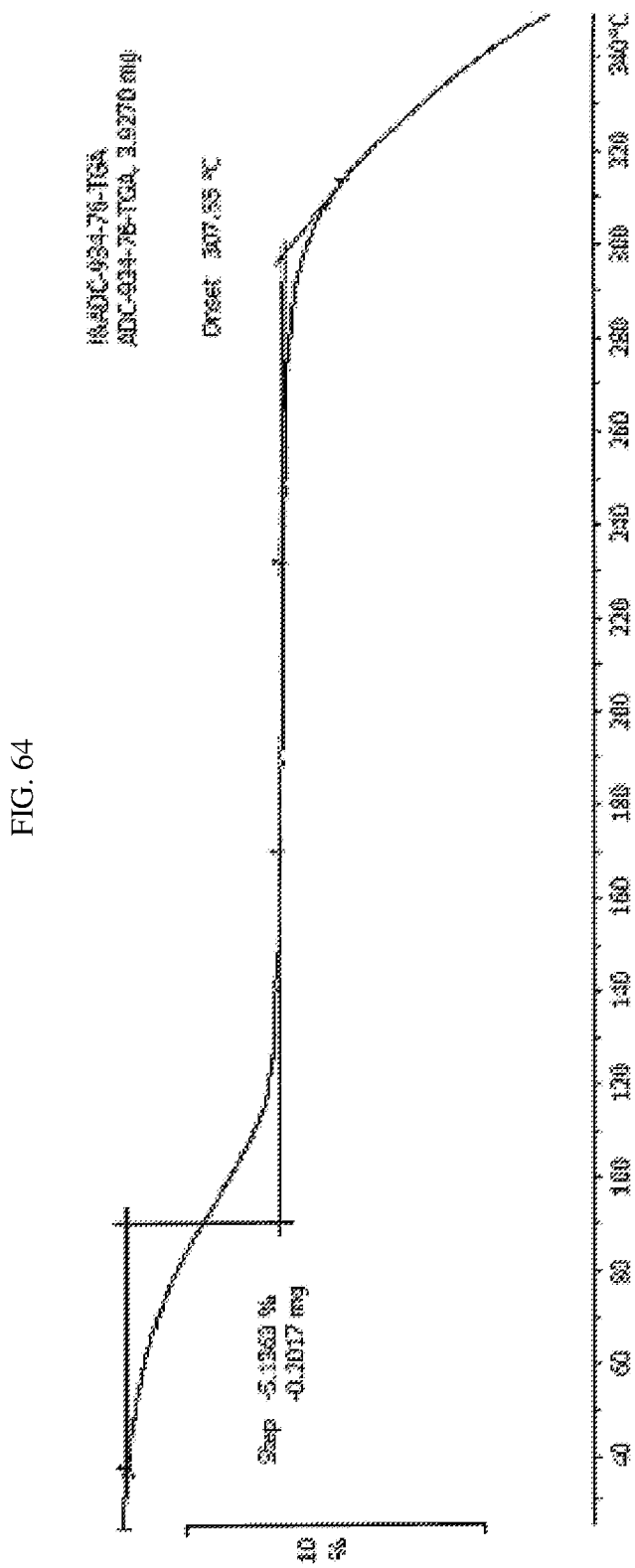
FIG. 64 shows a TGA thermogram for crystalline Form 17.

FIG. 64 shows a thermal gravimetric analysis (TGA) profile of Form 17. The TGA thermogram plots the percent loss of weight of the sample as a function of temperature, the temperature rate change being about 10° C./min. FIG. 64 shows a 5.1% weight loss between room temperature and 170° C., suggesting that Form 17 is a monohydrate. In some embodiments, Form 17 is characterized by a TGA profile substantially as shown in FIG. 64. Karl Fischer measurements show a water content of about 6.5%, further suggesting that the weight loss observed in the TGA profile is due to the loss of water, and that Form 17 is a monohydrate.

Figure 65:
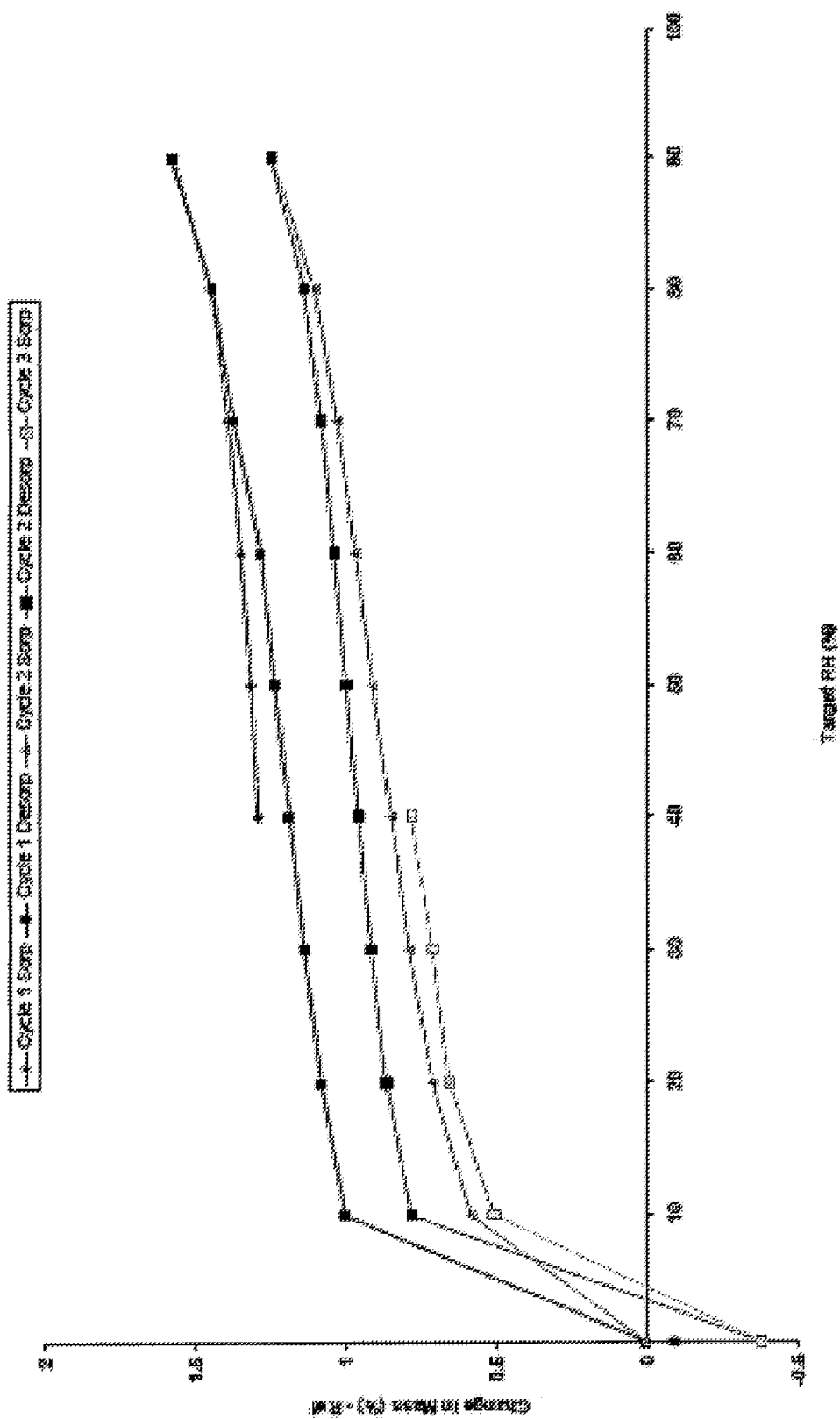
FIG. 65 shows a GVS isotherm plot for crystalline Form 17.
Figure 66:
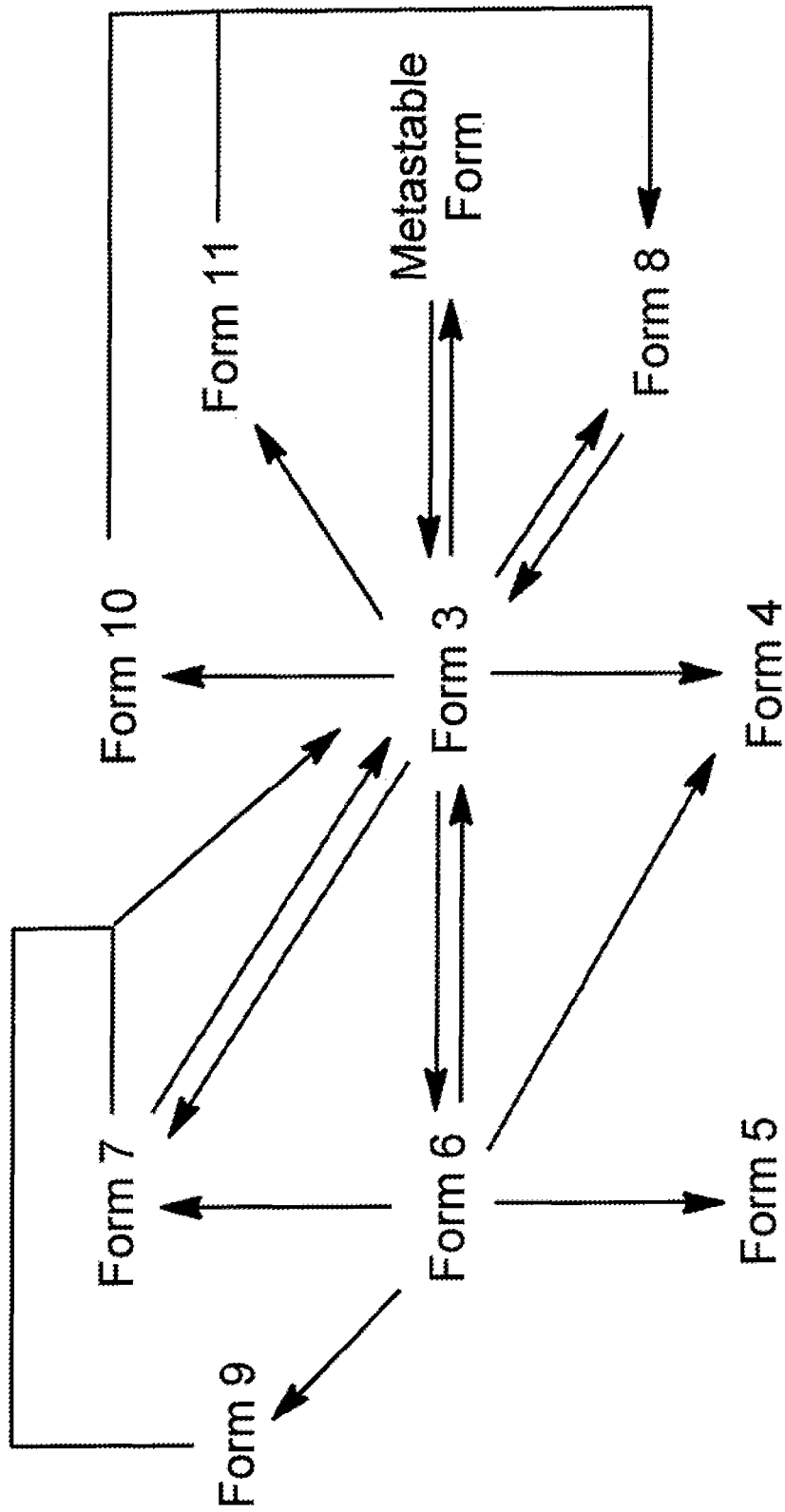
FIG. 66 shows the interconversions between Compound 1 hydrochloride forms.

FIG. 65 shows a gravimetric vapor sorption (GVS) isotherm plot of Form 17. In some embodiments, Form 17 is characterized by a GVS profile substantially as shown in FIG. 65.

Synthetic Methods

A chemical entity comprising Compound 1 may be prepared by methods known to one skilled in the art and/or by reference to the schemes shown below and the examples that follow. Exemplary synthetic routes are set forth in Schemes 1 to 8, and in the Examples below.

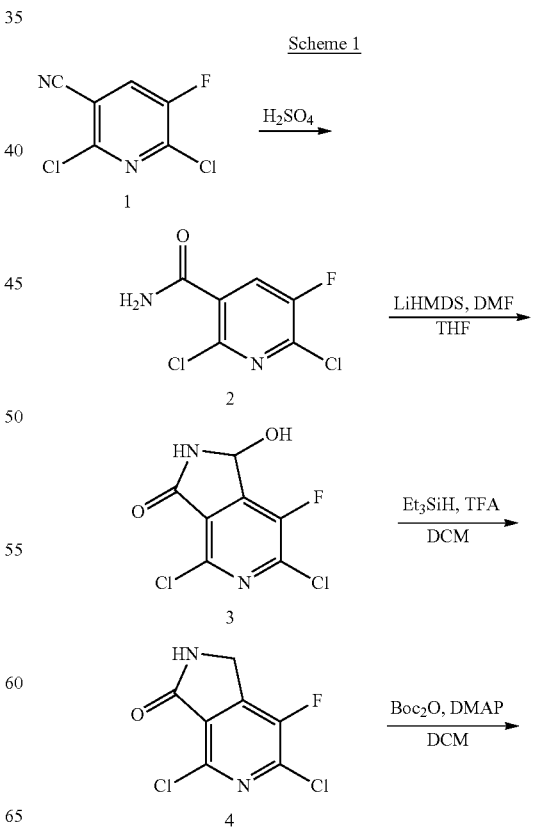

Scheme 1

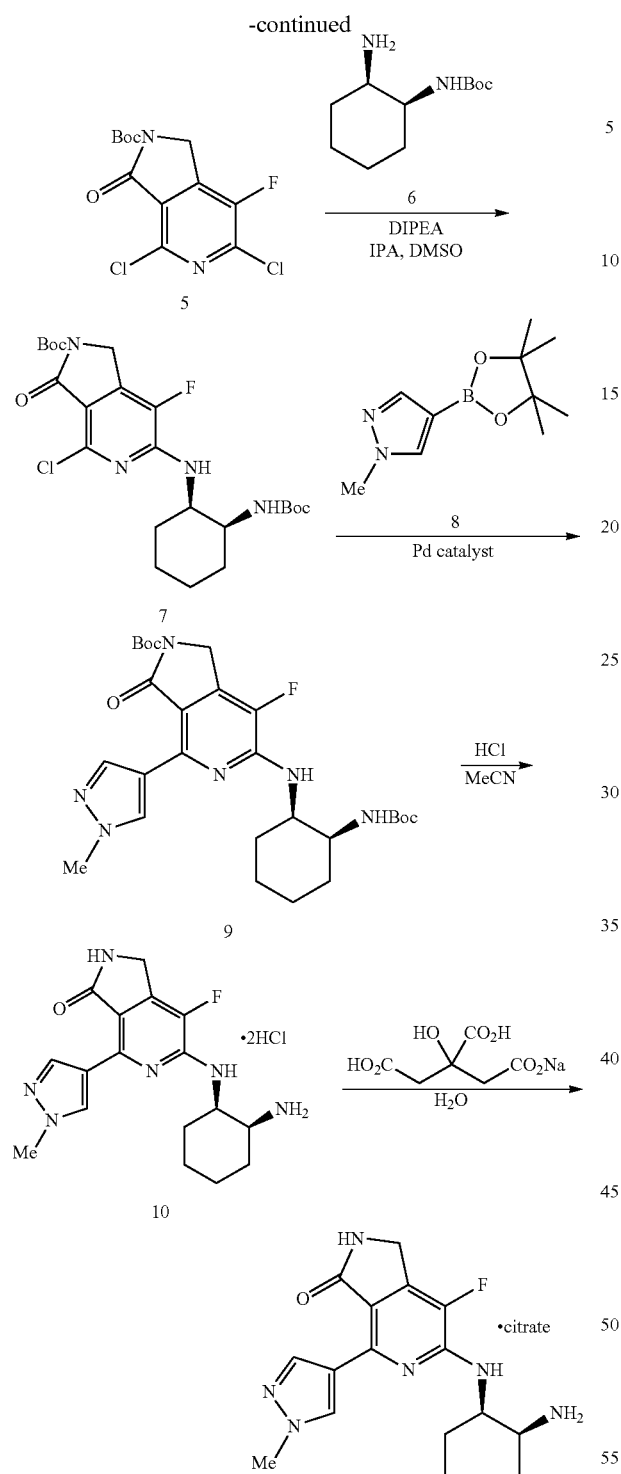

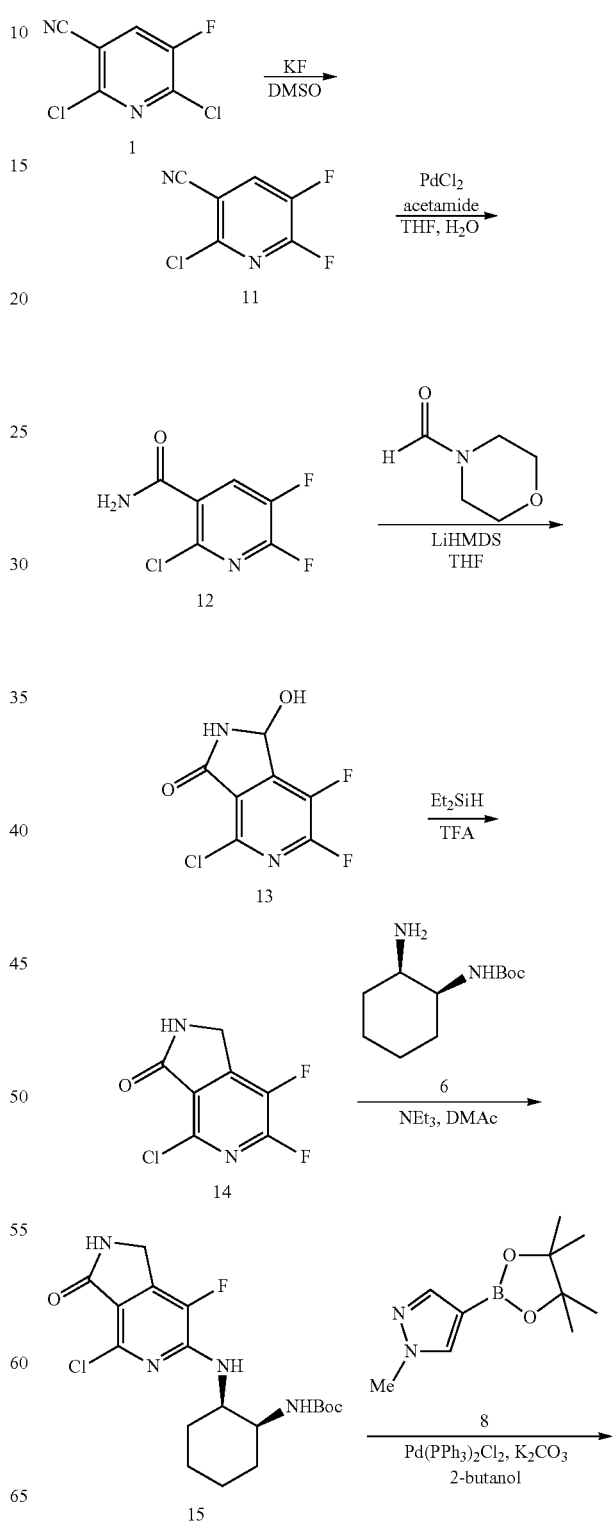

be found in U.S. Pat. No. 8,440,689, which is incorporated herein in its entirety. Suzuki coupling of (7) with borane (8) to provide (9). Deprotection of (9) resulted in Compound 1 dihydrochloride (10) which was converted to Compound 1 citrate.

Scheme 2

Scheme 1 describes the synthesis of Compound 1 citrate which is further exemplified in Example 1 below. 2,6-Dichloro-3-cyano-5-fluoropyridine (1) was treated with sulfuric acid to give carboxamide (2) which was treated with LiHMDS and DMF to provide (3) which was reduced with triethylsilane and TFA to give 4,6-dichloro-7-fluoro-1H-pyrrolo[3,4-c]pyridin-3(2H)-one (4). Boc protection of (4) was followed by coupling with diaminocyclohexane (6) to provide (7). The synthesis of diaminocyclohexane (6) may

27

-continued

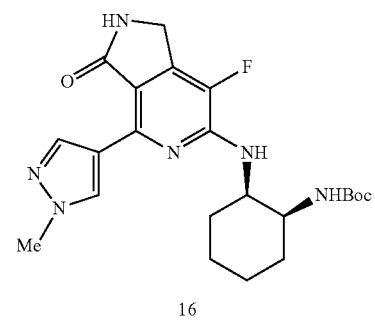

16

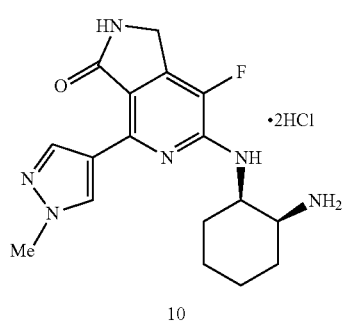

10

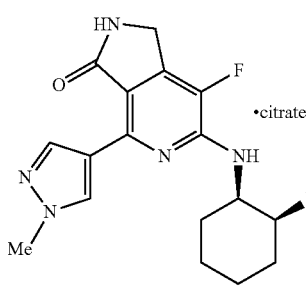

10

Scheme 2 describes the synthesis of Compound 1 citrate which is further exemplified in Example 2 below. 2,6-Dichloro-3-cyano-5-fluoropyridine (1) was treated with potassium fluoride to give 2-chloro-3-cyano-4,5-difluoropyridine (11). 2-Chloro-3-cyano-4,5-difluoropyridine (11) was then treated with acetamide to provide carboxamide (12). Carboxamide (12) was treated with LiHMDS and 4-formylmorpholine to give (13) which was reduced with triethylsilane and TFA to give 4-chloro-6,7-difluoro-1H-pyrrolo[3,4-c]pyridin-3(2H)-one (14). Coupling with diaminocyclohexane (6) and Suzuki coupling with borane (8) provided (16). Deprotection of (16) resulted in Compound 1 dihydrochloride (10) which was converted to Compound 1 citrate.

Scheme 3

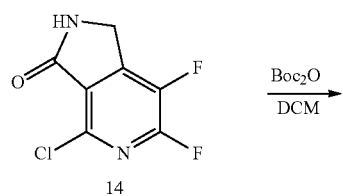

14

28

-continued

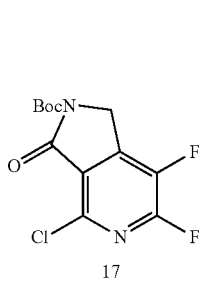

17

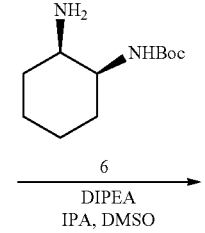

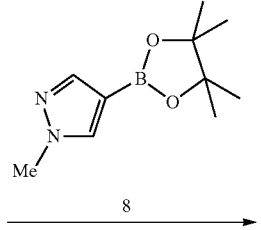

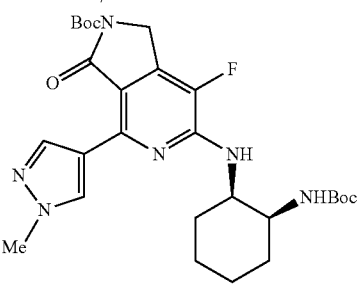

9

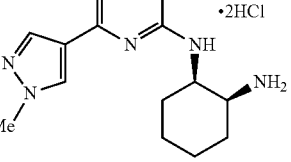

10

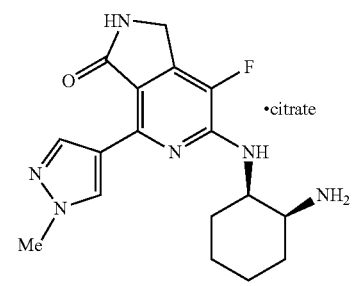

Scheme 3 describes another alternative synthesis of (10) which is further exemplified in Example 3 below. 4-Chloro-6,7-difluoro-1H-pyrrolo[3,4-c]pyridin-3 (2H)-one (14) was prepared as described above and was then Boc protected and coupled with diaminocyclohexane (6) to provide (7). As described above, Suzuki coupling of (7) with borane (8) to provide (9). Deprotection of (9) resulted in Compound 1 dihydrochloride (10) which was converted to Compound 1 citrate.

Scheme 4

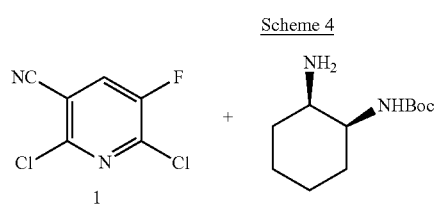
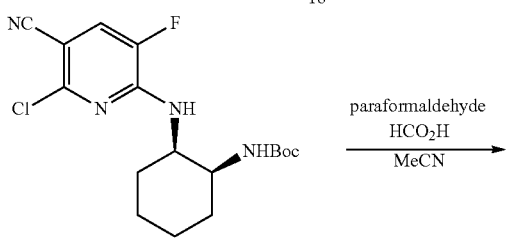
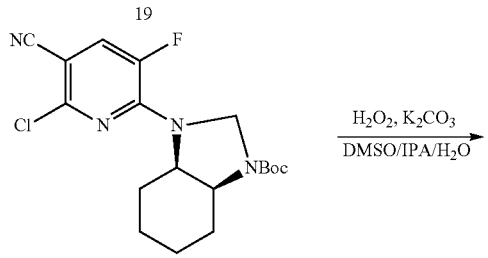
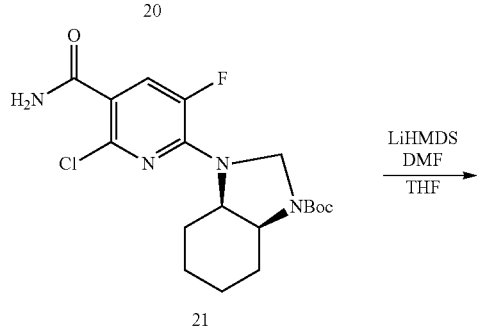
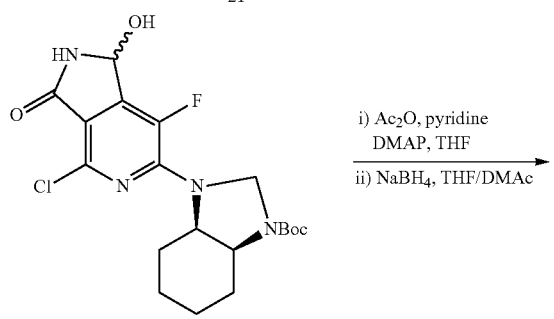
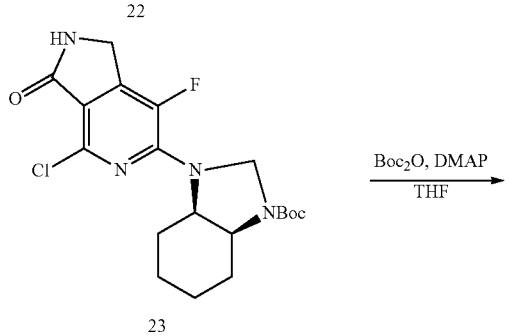
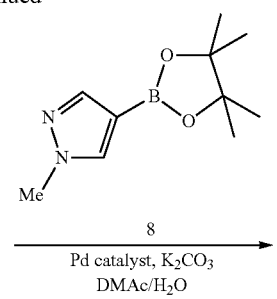
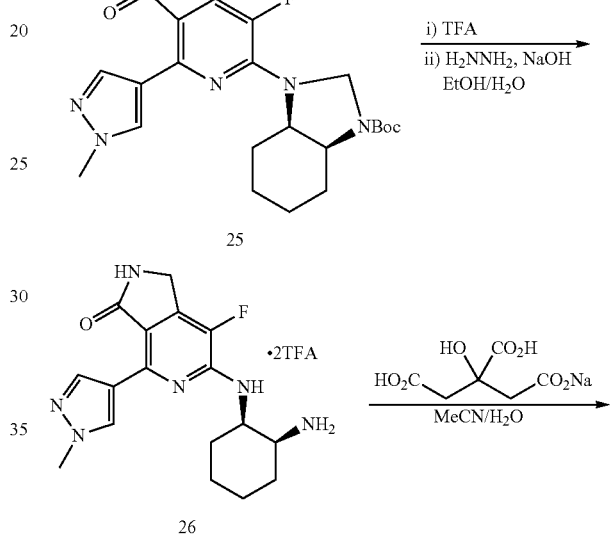
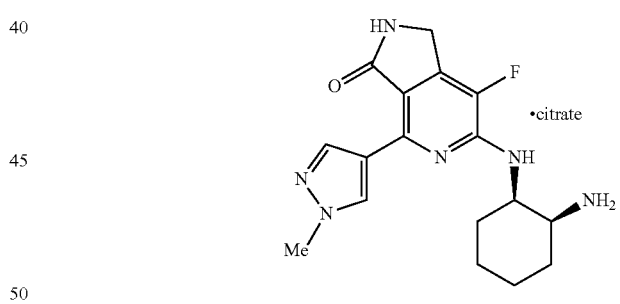

Scheme 4 describes another alternative synthesis of Compound 1 citrate which is further exemplified in Example 4 below. 2,6-Dichloro-3-cyano-5-fluoropyridine (1) was treated with diisopropylethylamine (DIPEA) and Boc diaminocyclohexane (18) to provide (19). tert-Butyl ((1S, 2R)-2-((6-chloro-5-cyano-3-fluoropyridin-2-yl)amino)cyclohexyl)carbamate (19) was then treated with paraformaldehyde and formic acid to provide protected (20). Treatment of (20) with hydrogen peroxide and potassium carbonate provided carboxamide (21). Treatment with LiHMDS and DMF provided (22) which was reduced to give (23). Boc protection of (23) then provided (24). Suzuki coupling with borane (8) provided (25) which was deprotected to provide Compound 1 trifluoroacetate (26) which was converted to Compound 1 citrate.

Scheme 5

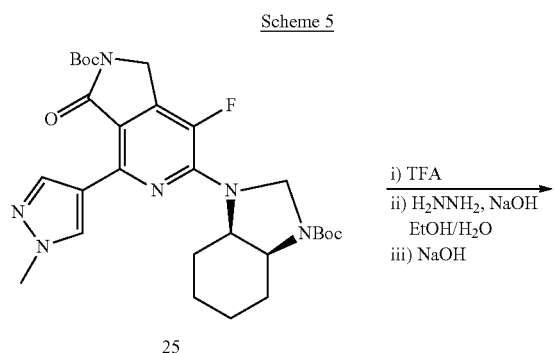

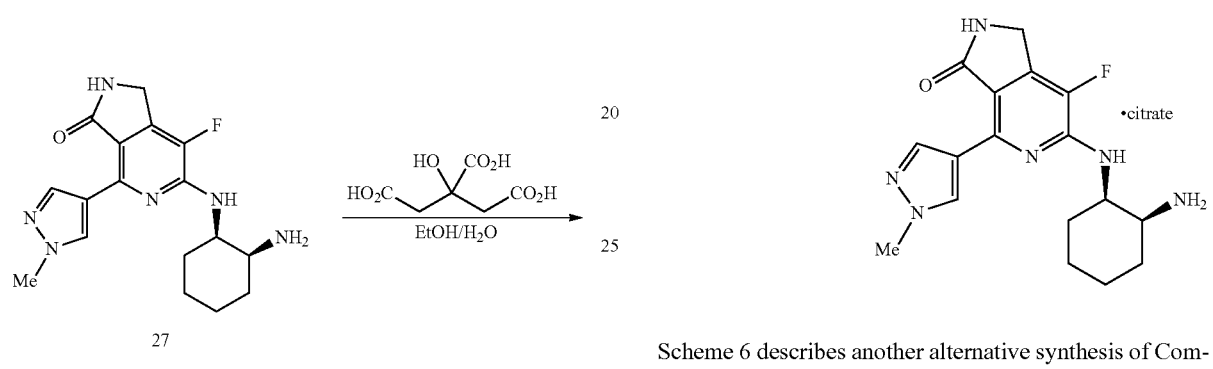

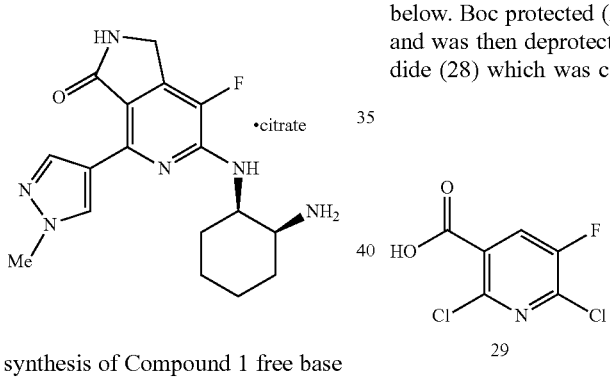

Scheme 5 describes a synthesis of Compound 1 free base as well as another alternative synthesis of Compound 1 citrate which is further exemplified in Example 5 below. Boc protected (25) was prepared as described above and was then deprotected and treated with sodium hydroxide to provide Compound 1 free base (27) which was converted to Compound 1 citrate.

Scheme 6

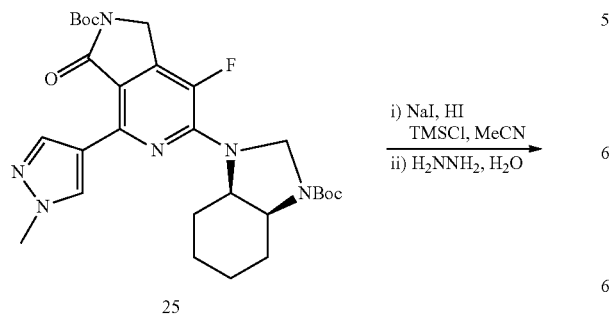

Scheme 6 describes another alternative synthesis of Compound 1 citrate which is further exemplified in Example 5 below. Boc protected (25) was prepared as described above and was then deprotected to provide Compound 1 hydroiodide (28) which was converted to Compound 1 citrate.

Scheme 7

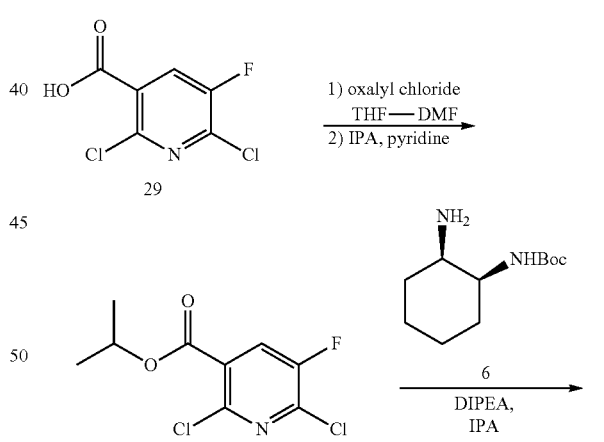

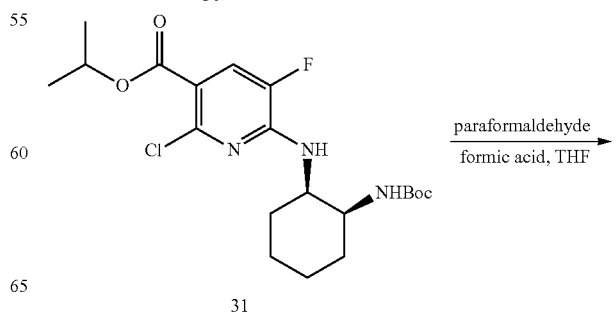

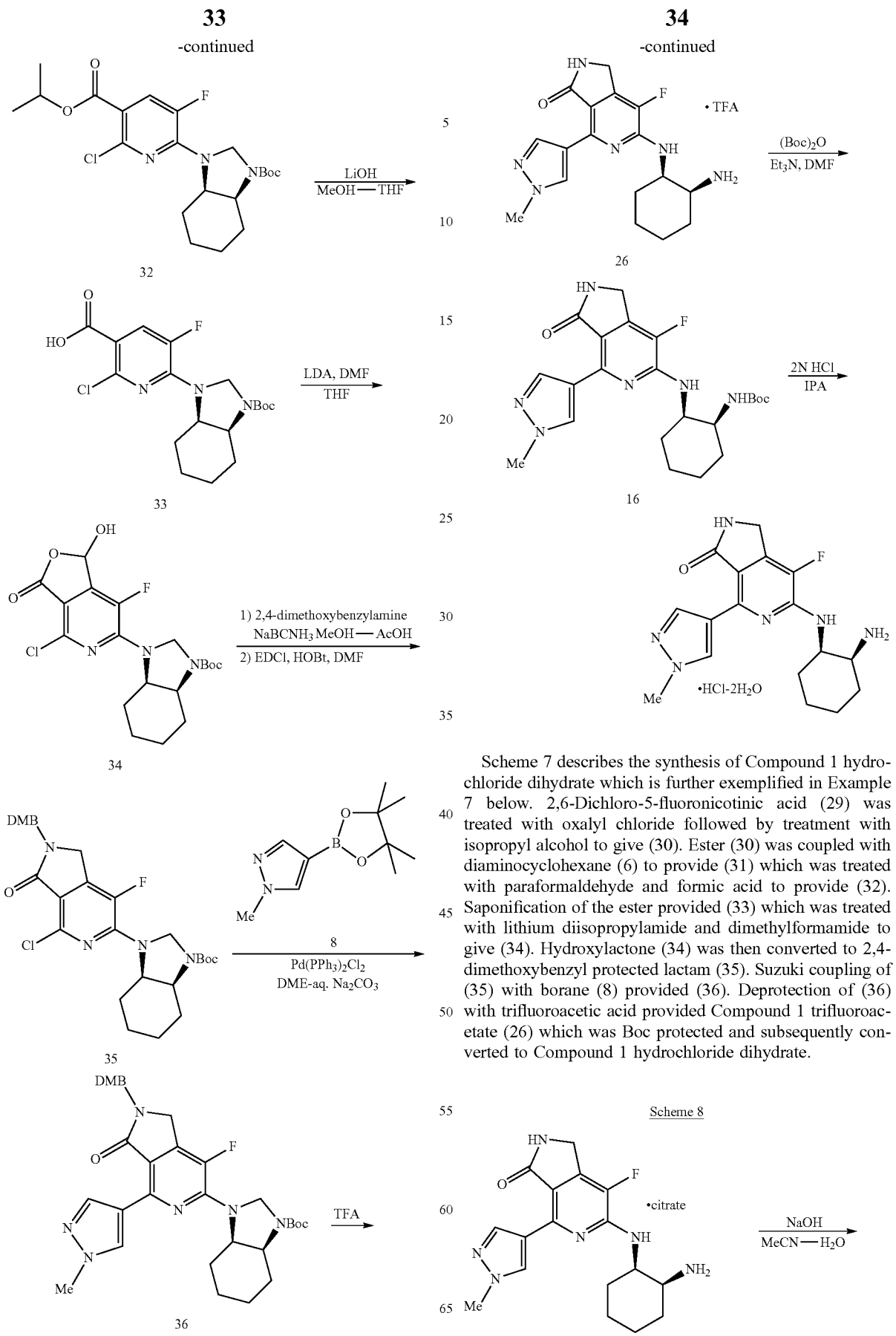

Scheme 7 describes the synthesis of Compound 1 hydrochloride dihydrate which is further exemplified in Example 7 below. 2,6-Dichloro-5-fluoronicotinic acid (29) was treated with oxalyl chloride followed by treatment with isopropyl alcohol to give (30). Ester (30) was coupled with diaminocyclohexane (6) to provide (31) which was treated with paraformaldehyde and formic acid to provide (32). Saponification of the ester provided (33) which was treated with lithium diisopropylamide and dimethylformamide to give (34). Hydroxylactone (34) was then converted to 2,4-dimethoxybenzyl protected lactam (35). Suzuki coupling of (35) with borane (8) provided (36). Deprotection of (36) with trifluoroacetic acid provided Compound 1 trifluoroacetate (26) which was Boc protected and subsequently converted to Compound 1 hydrochloride dihydrate.

-continued

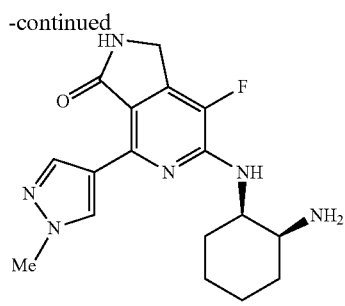

Scheme 8 describes an alternative synthesis of Compound 1 free base which is further exemplified in Example 8 below. Compound 1 citrate was prepared as described above and was then treated with NaOH to provide Compound 1 free base.

In certain embodiments, the invention relates to a method of making a compound of Formula I

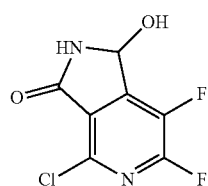

(I)

or a pharmaceutically acceptable salt thereof, comprising reacting a compound of Formula Ia

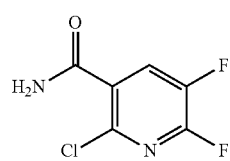

(Ia)

or a pharmaceutically acceptable salt thereof, with a formylation reagent.

In certain embodiments, the formylation reagent is a compound of Formula Ib

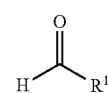

(Ib)

or a pharmaceutically acceptable salt thereof, wherein $R^1$ is $NR^aR^b$ wherein $R^a$ and $R^b$ are each independently alkyl or $R^a$ and $R^b$ together with the nitrogen to which they are attached form a five to seven membered ring. In certain embodiments, $R^a$ and $R^b$ are independently alkyl. In certain embodiments, $R^a$ and $R^b$ are both methyl. In certain embodiments, $R^a$ and $R^b$ together with the nitrogen to which they are attached form a five- to seven-membered ring. In certain embodiments, $R^a$ and $R^b$ together with the nitrogen to which they are attached form a six-membered ring. In certain embodiments, $R^a$ and $R^b$ together with the nitrogen to which they are attached for a morpholino ring. Accordingly, in certain embodiments the formylation reagent is 4-formyl-morpholine.

In certain embodiments, the reacting a compound of Formula Ia with a formylation reagent is performed in the presence of a base. In certain such embodiments, the base is selected from lithium hexamethyldisilazane (LiHMDS), sodium hexamethyldisilazane (NaHMDS), and potassium hexamethyldisilazane (KHMDS). In certain embodiments, the base is LiHMDS.

In certain embodiments, the invention relates to a compound of Formula I

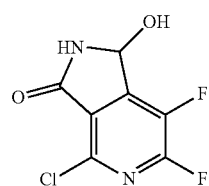

(I)

or a pharmaceutically acceptable salt thereof.

In certain embodiments, the invention relates to a method of making a compound of Formula II

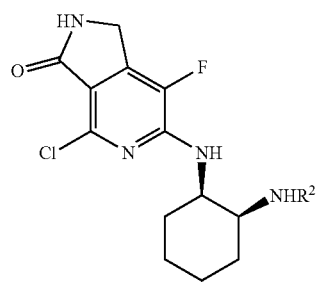

(II)

or a pharmaceutically acceptable salt thereof, wherein $R^2$ is a protecting group, comprising reacting a compound of Formula IIa

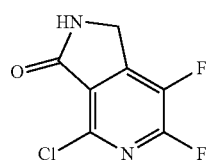

(IIa)

or a pharmaceutically acceptable salt thereof, with a compound of Formula IIb

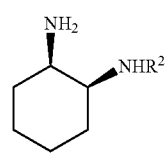

(IIb)

or a pharmaceutically acceptable salt thereof, wherein $R^2$ is a protecting group.

In certain embodiments, $R^2$ is an N-acyl protecting group. In certain embodiments, $R^2$ is selected from methoxycarbonyl, ethoxycarbonyl, tert-butoxycarbonyl (Boc), benzyloxycarbonyl (Cbz), allyloxycarbonyl (Aloc), 9-fluorenyl-methoxycarbonyl (Fmoc), 2-(trimethylsilyl)ethoxycarbonyl (Teoc), and 2,2,2-trichloroethoxycarbonyl (Troc). In certain embodiments, $R^2$ is Boc.

In certain embodiments, the reacting a compound of Formula IIa with a compound of Formula IIb is performed in the presence of a base. In certain such embodiments, the base is selected from triethylamine, diisopropylethylamine, and N-methylmorpholine. In certain embodiments, the base is triethylamine.

In certain embodiments, the invention relates to a compound of Formula II

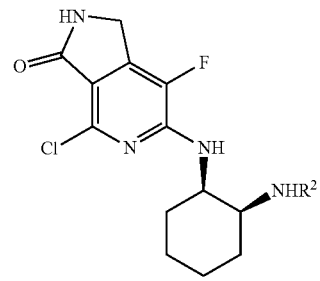

(II)

or a pharmaceutically acceptable salt thereof, wherein $R^2$ is a protecting group.

In certain embodiments, $R^2$ is an N-acyl protecting group. In certain embodiments, $R^2$ is selected from methoxycarbonyl, ethoxycarbonyl, tert-butoxycarbonyl (Boc), benzyloxycarbonyl (Cbz), allyloxycarbonyl (Aloc), 9-fluorenyl-methoxycarbonyl (Fmoc), 2-(trimethylsilyl)ethoxycarbonyl (Teoc), and 2,2,2-trichloroethoxycarbonyl (Troc). In certain embodiments, $R^2$ is Boc.

In certain embodiments, the invention relates to a method of making a compound of Formula III

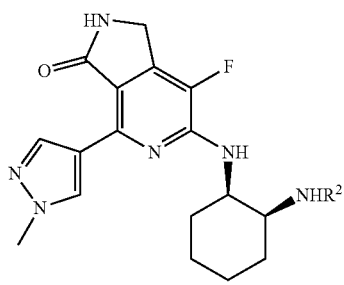

(III)

or a pharmaceutically acceptable salt thereof, wherein $R^2$ is a protecting group, comprising reacting a compound of Formula II

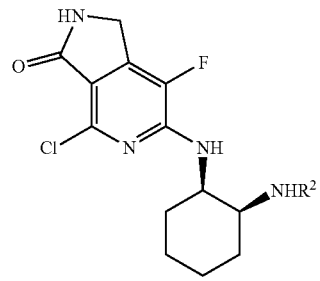

(II)

or a pharmaceutically acceptable salt thereof, wherein $R^2$ is a protecting group with a compound of Formula IIIa or a pharmaceutically acceptable salt thereof.

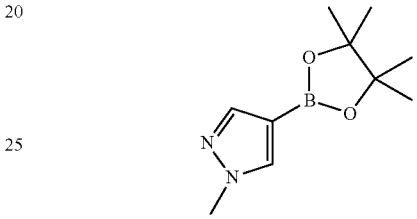

(IIIa)

In certain embodiments, $R^2$ is an N-acyl protecting group. In certain embodiments, $R^2$ is selected from methoxycarbonyl, ethoxycarbonyl, tert-butoxycarbonyl (Boc), benzyloxycarbonyl (Cbz), allyloxycarbonyl (Aloc), 9-fluorenyl-methoxycarbonyl (Fmoc), 2-(trimethylsilyl)ethoxycarbonyl (Teoc), and 2,2,2-trichloroethoxycarbonyl (Troc). In certain embodiments, $R^2$ is Boc.

In certain embodiments, the reacting a compound of Formula II with a compound of Formula IIIa is performed in the presence of a palladium catalyst. In certain such embodiments the palladium catalyst is selected from $Pd(PCy_3)_2Cl_2$, $Pd(dppf)Cl_2$, $Pd(dtbpf)Cl_2$ and $Pd(PPh_3)_2Cl_2$. In certain embodiments, the palladium catalyst is $Pd(PPh_3)_2Cl_2$.

In certain embodiments, the invention relates to a compound of Formula III

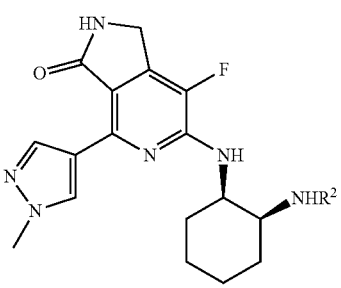

(III)

or a pharmaceutically acceptable salt thereof, wherein $R^2$ is a protecting group.

In certain embodiments, $R^2$ is an N-acyl protecting group. In certain embodiments, $R^2$ is selected from methoxycarbonyl, ethoxycarbonyl, tert-butoxycarbonyl (Boc), benzyloxycarbonyl (Cbz), allyloxycarbonyl (Aloc), 9-fluorenyl-methoxycarbonyl (Fmoc), 2-(trimethylsilyl)ethoxycarbonyl (Teoc), and 2,2,2-trichloroethoxycarbonyl (Troc). In certain embodiments, $R^2$ is Boc.

In certain embodiments, the invention relates to a method of making a chemical entity comprising Compound 1 (e.g., Compound 1 or a pharmaceutically acceptable salt thereof), comprising reacting a compound of Formula III

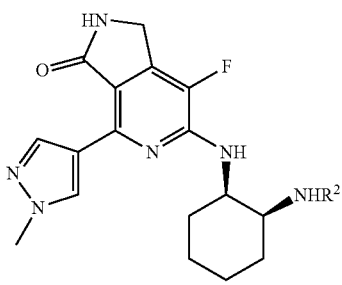

or a pharmaceutically acceptable salt thereof, wherein $R^2$ is a protecting group, with a deprotecting agent.

In certain embodiments, $R^2$ is an N-acyl protecting group. In certain embodiments, $R^2$ is selected from methoxycarbonyl, ethoxycarbonyl, tert-butoxycarbonyl (Boc), benzyloxycarbonyl (Cbz), allyloxycarbonyl (Aloc), 9-fluorenylmethoxycarbonyl (Fmoc), 2-(trimethylsilyl)ethoxycarbonyl (Teoc), and 2,2,2-trichloroethoxycarbonyl (Troc). In certain embodiments, $R^2$ is Boc.

In certain embodiments, the deprotecting agent is an acid. In certain such embodiments, the acid is selected from hydrochloric acid and trifluoroacetic acid. In certain such embodiments, the acid is hydrochloric acid. In certain such embodiments, the acid is trifluoroacetic acid.

In certain embodiments, the method further comprises forming Compound 1 citrate. In certain such embodiments, forming Compound 1 citrate comprises (i) treating with a base, thereby providing Compound 1 free base, followed by treating citric acid. In certain such embodiments, the base is sodium hydroxide. In certain alternative such embodiments, forming Compound 1 citrate comprises treating with sodium dihydrogencitrate.

Accordingly, in certain embodiments the invention relates to a method of making Compound 1 or a pharmaceutically acceptable salt thereof, comprising
(i) reacting a compound of Formula IIa

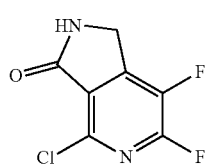

or a pharmaceutically acceptable salt thereof, with a compound of Formula IIb

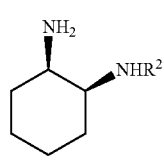

or a pharmaceutically acceptable salt thereof, wherein $R^2$ is a protecting group to provide a compound of Formula II

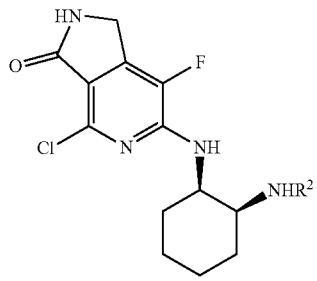

or a pharmaceutically acceptable salt thereof, wherein $R^2$ is a protecting group;
(ii) reacting a compound of Formula II with a compound of Formula IIIa

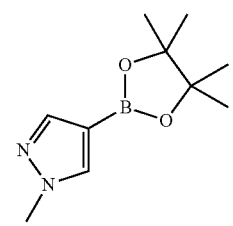

or a pharmaceutically acceptable salt thereof to provide a compound of Formula III;

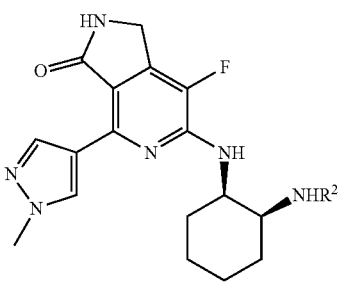

or a pharmaceutically acceptable salt thereof, wherein $R^2$ is a protecting group;
(iii) reacting a compound of Formula III with a deprotecting agent.

In certain embodiments, $R^2$ is an N-acyl protecting group. In certain embodiments, $R^2$ is selected from methoxycarbonyl, ethoxycarbonyl, tert-butoxycarbonyl (Boc), benzyloxycarbonyl (Cbz), allyloxycarbonyl (Aloc), 9-fluorenylmethoxycarbonyl (Fmoc), 2-(trimethylsilyl)ethoxycarbonyl (Teoc), and 2,2,2-trichloroethoxycarbonyl (Troc). In certain embodiments, $R^2$ is Boc.

In certain embodiments, the deprotecting agent is an acid. In certain such embodiments, the acid is selected from hydrochloric acid and trifluoroacetic acid. In certain such embodiments, the acid is hydrochloric acid. In certain such embodiments, the acid is trifluoroacetic acid.

In certain embodiments, the method further comprises forming Compound 1 citrate. In certain such embodiments, forming Compound 1 citrate comprises (i) treating with a base, thereby providing Compound 1 free base, followed by treating citric acid. In certain such embodiments, the base is sodium hydroxide. In certain alternative such embodiments, forming Compound 1 citrate comprises treating with sodium dihydrogencitrate.

In certain embodiments, the invention relates to a method for making a compound of Formula IV

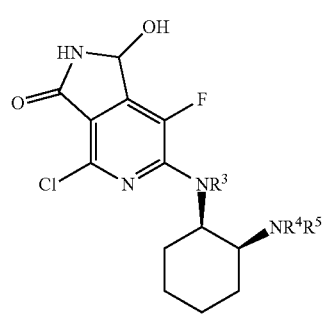

(IV)

or a pharmaceutically acceptable salt thereof, wherein $R^3$ and $R^4$ are each independently protecting groups or $R^3$ and $R^4$ together are a protecting group and $R^5$ is a protecting group, comprising reacting a compound of Formula IVa

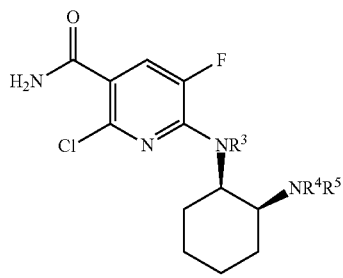

(IVa)

or a pharmaceutically acceptable salt thereof, wherein $R^3$ and $R^4$ are each independently protecting groups or $R^3$ and $R^4$ together are a protecting group and $R^5$ is a protecting group, with a formylation reagent.

In certain embodiments, $R^3$ and $R^4$ are each independently protecting groups. In certain embodiments, $R^3$ and $R^4$ together are a protecting group. In certain such embodiments, $R^3$ and $R^4$ together are $C_{1-4}$ alkylene, such as methylene (—CH$_2$—), dimethylmethylene (—C(CH$_3$)$_2$—), or benzylidene. In certain embodiments, $R^3$ and $R^4$ together are methylene.

In certain embodiments, $R^5$ is an N-acyl protecting group. In certain embodiments, $R^5$ is selected from methoxycarbonyl, ethoxycarbonyl, tert-butoxycarbonyl (Boc), benzyloxycarbonyl (Cbz), allyloxycarbonyl (Aloc), 9-fluorenylmethoxycarbonyl (Fmoc), 2-(trimethylsilyl)ethoxycarbonyl (Teoc), and 2,2,2-trichloroethoxycarbonyl (Troc). In certain embodiments, $R^5$ is Boc.

In certain embodiments, the reacting a compound of Formula IVa with a formylation reagent is performed in the presence of a base. In certain such embodiments, the base is selected from lithium hexamethyldisilazane (LiHMDS), sodium hexamethyldisilazane (NaHMDS), potassium hexamethyldisilazane (KHMDS), and lithium diisopropylamide (LDA). In certain embodiments, the base is LiHMDS. In certain embodiments, the formylation reagent is N,N-dimethylformamide (DMF).

In certain embodiments, the invention relates to a compound of Formula IV

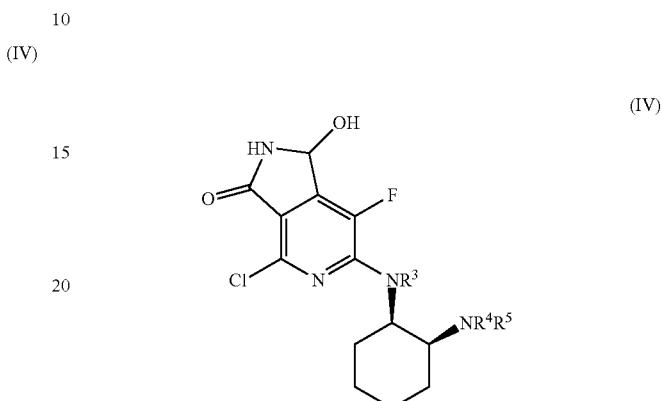

(IV)

or a pharmaceutically acceptable salt thereof, wherein $R^3$ and $R^4$ are each independently protecting groups or $R^3$ and $R^4$ together are a protecting group and $R^5$ is a protecting group.

In certain embodiments, $R^3$ and $R^4$ are each independently protecting groups. In certain embodiments, $R^3$ and $R^4$ together are a protecting group. In certain such embodiments, $R^3$ and $R^4$ together are $C_{1-4}$ alkylene, such as methylene (—CH$_2$—), dimethylmethylene (—C(CH$_3$)$_2$—), or benzylidene. In certain embodiments, $R^3$ and $R^4$ together are methylene.

In certain embodiments, $R^5$ is an N-acyl protecting group. In certain embodiments, $R^5$ is selected from methoxycarbonyl, ethoxycarbonyl, tert-butoxycarbonyl (Boc), benzyloxycarbonyl (Cbz), allyloxycarbonyl (Aloc), 9-fluorenylmethoxycarbonyl (Fmoc), 2-(trimethylsilyl)ethoxycarbonyl (Teoc), and 2,2,2-trichloroethoxycarbonyl (Troc). In certain embodiments, $R^5$ is Boc.

In certain embodiments, the invention relates to a method for making a compound of Formula V

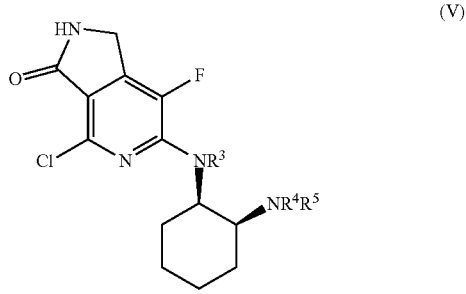

(V)

or a pharmaceutically acceptable salt thereof, wherein $R^3$ and $R^4$ are each independently protecting groups or $R^3$ and $R^4$ together are a protecting group and $R^5$ is a protecting group, comprising reducing a compound of Formula (IV)

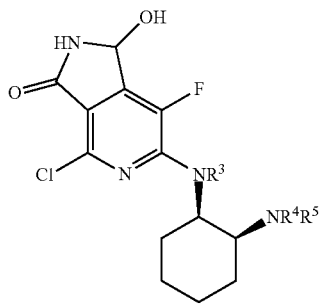

(IV)

or a pharmaceutically acceptable salt thereof, wherein $R^3$ and $R^4$ are each independently protecting groups or $R^3$ and $R^4$ together are a protecting group and $R^5$ is a protecting group, under reducing conditions.

In certain embodiments, $R^3$ and $R^4$ are each independently protecting groups. In certain embodiments, $R^3$ and $R^4$ together are a protecting group. In certain such embodiments, $R^3$ and $R^4$ together are $C_{1-4}$ alkylene, such as methylene (—$CH_2$—), dimethylmethylene (—$C(CH_3)_2$—), or benzylidene. In certain embodiments, $R^3$ and $R^4$ together are methylene.

In certain embodiments, $R^5$ is an N-acyl protecting group. In certain embodiments, $R^5$ is selected from methoxycarbonyl, ethoxycarbonyl, tert-butoxycarbonyl (Boc), benzyloxycarbonyl (Cbz), allyloxycarbonyl (Aloc), 9-fluorenylmethoxycarbonyl (Fmoc), 2-(trimethylsilyl)ethoxycarbonyl (Teoc), and 2,2,2-trichloroethoxycarbonyl (Troc). In certain embodiments, $R^5$ is Boc.

In certain embodiments, the reducing conditions comprise conversion of the hydroxyl group to a leaving group followed by treatment with a reducing agent. In certain embodiments, the leaving group is selected from alkanoate, aryloate, formate, phosphate, carbonate, and sulfate. In certain embodiments, the leaving group is acetate. In certain embodiments, the reducing agent is selected from sodium borohydride, sodium cyanoborohydride, lithium borohydride, lithium aluminum hydride, and sodium triacetoxyborohydride. In certain embodiments, the reducing agent is sodium borohydride.

In certain embodiments, the invention relates a compound of Formula V

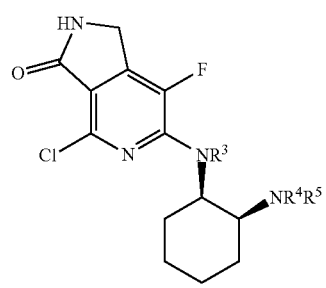

(V)

or a pharmaceutically acceptable salt thereof, wherein $R^3$ and $R^4$ are each independently protecting groups or $R^3$ and $R^4$ together are a protecting group and $R^5$ is a protecting group.

In certain embodiments, $R^3$ and $R^4$ are each independently protecting groups. In certain embodiments, $R^3$ and $R^4$ together are a protecting group. In certain such embodiments, $R^3$ and $R^4$ together are $C_{1-4}$ alkylene, such as methylene (—$CH_2$—), dimethylmethylene (—$C(CH_3)_2$—), or benzylidene. In certain embodiments, $R^3$ and $R^4$ together are methylene.

In certain embodiments, $R^5$ is an N-acyl protecting group. In certain embodiments, $R^5$ is selected from methoxycarbonyl, ethoxycarbonyl, tert-butoxycarbonyl (Boc), benzyloxycarbonyl (Cbz), allyloxycarbonyl (Aloc), 9-fluorenylmethoxycarbonyl (Fmoc), 2-(trimethylsilyl)ethoxycarbonyl (Teoc), and 2,2,2-trichloroethoxycarbonyl (Troc). In certain embodiments, $R^5$ is Boc.

In certain embodiments, the invention relates to a method of making a chemical entity comprising Compound 1 (e.g., Compound 1 or a pharmaceutically acceptable salt thereof), comprising deprotecting a compound of Formula VI

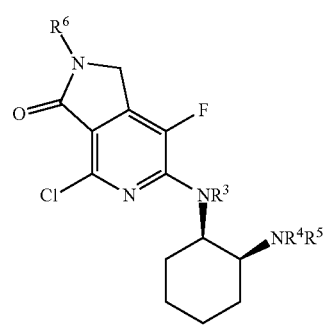

(VI)

or a pharmaceutically acceptable salt thereof, wherein $R^3$ and $R^4$ are each independently protecting groups or $R^3$ and $R^4$ together are a protecting group and $R^5$ and $R^6$ are each independently a protecting group, under deprotecting conditions.

In certain embodiments, $R^3$ and $R^4$ are each independently protecting groups. In certain embodiments, $R^3$ and $R^4$ together are a protecting group. In certain such embodiments, $R^3$ and $R^4$ together are $C_{1-4}$ alkylene, such as methylene (—$CH_2$—), dimethylmethylene (—$C(CH_3)_2$—), or benzylidene. In certain embodiments, $R^3$ and $R^4$ together are methylene.

In certain embodiments, $R^5$ and $R^6$ are each independently an N-acyl protecting group. In certain embodiments, $R^5$ and $R^6$ are each independently selected from methoxycarbonyl, ethoxycarbonyl, tert-butoxycarbonyl (Boc), benzyloxycarbonyl (Cbz), allyloxycarbonyl (Aloc), 9-fluorenylmethoxycarbonyl (Fmoc), 2-(trimethylsilyl)ethoxycarbonyl (Teoc), and 2,2,2-trichloroethoxycarbonyl (Troc). In certain embodiments, $R^5$ is Boc. In certain embodiments, $R^6$ is Boc.

In certain embodiments, the deprotecting conditions comprise treating a compound of Formula VI with an acid, followed by treatment with a base. In certain such embodiments, the acid is selected from trifluoroacetic acid, hydroiodic acid, and trimethylsilyl iodide. In certain embodiments, the trimethylsilyl iodide may be generated by reacting trimethylsilyl chloride with an iodide salt. In certain such embodiments, the acid is trifluoroacetic acid. In certain such embodiments, the acid is a mixture of trimethylsilyl chloride, sodium iodide, and hydroiodic acid. In certain embodiments, the base is selected from sodium hydroxide, potassium hydroxide, ammonium hydroxide, hydroxylamine, and hydrazine. In certain such embodiments, the base is a mixture of sodium hydroxide and hydrazine.

In certain embodiments, the method further comprises forming Compound 1 citrate. In certain such embodiments, forming Compound 1 citrate comprises treating with a base, thereby providing Compound 1 free base, followed by treatment with citric acid. In certain such embodiments, the base is sodium hydroxide. In certain alternative such embodiments, forming Compound 1 citrate comprises treating with sodium dihydrogencitrate.

In certain embodiments, the invention relates to a compound of Formula VI

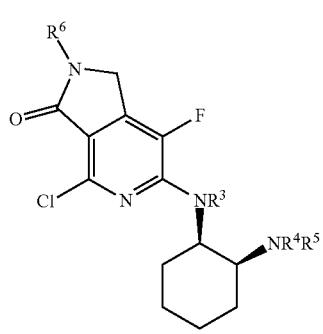

(VI)

or a pharmaceutically acceptable salt thereof or a pharmaceutically acceptable salt thereof, wherein $R^3$ and $R^4$ are each independently protecting groups or $R^3$ and $R^4$ together are a protecting group, and $R^5$ and $R^6$ are each independently a protecting group.

In certain embodiments, $R^3$ and $R^4$ are each independently protecting groups. In certain embodiments, $R^3$ and $R^4$ together are a protecting group. In certain such embodiments, $R^3$ and $R^4$ together are $C_{1-4}$ alkylene, such as methylene (—$CH_2$—), dimethylmethylene (—$C(CH_3)_2$—), or benzylidene. In certain embodiments, $R^3$ and $R^4$ together are methylene.

In certain embodiments, $R^5$ and $R^6$ are each independently an N-acyl protecting group. In certain embodiments, $R^5$ and $R^6$ are each independently selected from methoxycarbonyl, ethoxycarbonyl, tert-butoxycarbonyl (Boc), benzyloxycarbonyl (Cbz), allyloxycarbonyl (Aloc), 9-fluorenylmethoxycarbonyl (Fmoc), 2-(trimethylsilyl)ethoxycarbonyl (Teoc), and 2,2,2-trichloroethoxycarbonyl (Troc). In certain embodiments, $R^5$ is Boc. In certain embodiments, $R^6$ is Boc.

Uses

In certain embodiments, the chemical entities of this invention may be useful as inhibitors of SYK. Thus, the chemical entities of this invention may be assayed for their ability to inhibit the SYK in vitro or in vivo, or in cells or animal models according to methods provided in further detail herein, or methods known in the art. The chemical entities may be assessed for their ability to bind or mediate SYK enzyme activity directly. Alternatively, the activity of the chemical entities may be assessed through indirect cellular assays, or assays measuring downstream effects of SYK activation to assess inhibition of downstream effects of SYK inhibition.

If a pharmaceutically acceptable salt is the chemical entity of the invention utilized in these compositions, the salts preferably are derived from inorganic or organic acids and bases. For reviews of suitable salts, see, e.g., Berge et al, *J. Pharm. Sci.* 66:1-19 (1977) and Remington: The Science and Practice of Pharmacy, 20th Ed., A. Gennaro (ed.), Lippincott Williams & Wilkins (2000) ("Remington's").

Examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

In certain embodiments, the invention relates to a pharmaceutical composition comprising a chemical entity comprising Compound 1. The pharmaceutical compositions of the invention preferably are in a form suitable for administration to a recipient subject, preferably a mammal, more preferably a human. The term "pharmaceutically acceptable carrier" is used herein to refer to a material that is compatible with the recipient subject, and is suitable for delivering an active agent to the target site without terminating the activity of the agent. The toxicity or adverse effects, if any, associated with the carrier preferably are commensurate with a reasonable risk/benefit ratio for the intended use of the active agent. Many such pharmaceutically acceptable carriers are known in the art. See, e.g., *Remington's; Handbook of Pharmaceutical Excipients*, 6th Ed., R. C. Rowe et al. (eds.), Pharmaceutical Press (2009).

The pharmaceutical compositions of the invention may be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutically acceptable carriers that may be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In certain embodiments, the compositions of this invention may be formulated for pharmaceutical administration to a mammal, such as a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. Preferably, the compositions are administered orally, intravenously, or subcutaneously. In certain embodiments, a pharmaceutical composition is suitable for oral administration. The pharmaceutical compositions of the invention may be designed to be short-acting, fast-releasing, or long-acting. Still further, pharmaceutical compositions may be suitable for local administration or rather than systemic administration.

Pharmaceutical compositions may be prepared as liquid suspensions or solutions using a liquid, such as an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons such as mineral oil and petrolatum; and water may also be used in suspension formulations.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including capsules, tablets, aqueous suspensions or solutions, preferably capsules or tablets. In certain embodiments, the oral dosage form is a tablet. In certain embodiments, the oral dosage form is a caplet. When aqueous suspensions are required for oral use, the active ingredient is combined with emulsifying and suspending agents. If desired, certain sweetening, flavoring or coloring agents may also be added. In certain solid dosage forms, the active chemical entity is mixed with at least one inert, pharmaceutically acceptable excipient or carrier such as sodium citrate or dicalcium phosphate and/or a) fillers or extenders including, but not limited to, starches, lactose, sucrose, glucose, mannitol, microcrystalline cellulose and silicic acid, b) binders including, but not limited to, hydroxypropyl cellulose, carboxymethylcellulose, alginates, gelatin, sucrose, and acacia, c) humectants including, but not limited to, glycerol, d) disintegrating agents including, but not limited to, agar-agar, calcium carbonate, polyvinylpyrrolidinone, croscarmellose, sodium starch glycolate, potato or tapioca starch, alginic acid, certain silicates, and sodium carbonate, e) solution retarding agents including, but not limited to, paraffin, f) absorption accelerators including, but not limited to, quaternary ammonium compounds, g) wetting agents including, but not limited to, cetyl alcohol and glycerol monostearate, h) absorbents including, but not limited to, kaolin and bentonite clay, and/or i) lubricants including, but not limited to, talc, calcium stearate, magnesium stearate, sodium stearyl fumarate, solid polyethylene glycols, sodium lauryl sulfate, silicon dioxide and mixtures thereof. In the case of capsules, tablets and pills, the dosage form may also comprise buffering agents. In certain embodiments, tablets may be manufactured using a wet granulation process. In certain embodiments, tablets may be manufactured using a dry granulation process. In certain embodiments, tablets may be manufactured using a direct compression process.

In certain embodiments, the invention relates to a pharmaceutical composition comprising a chemical entity comprising Compound 1. In certain embodiments, the invention relates to a pharmaceutical composition suitable for oral administration, such as a tablet or a capsule, comprising a chemical entity comprising Compound 1. In certain such embodiments, the chemical entity comprising Compound 1 is selected from Form 1, Form 2, Form 3, Form 4, Form 5, Form 6, Form 7, Form 8, Form 9, Form 10, Form 11, Form 12, Form 13, Form 14, Form 15, Form 16, and Form 17, or any combination thereof. In certain embodiments, the chemical entity comprising Compound 1 is a citrate salt of Compound 1. In certain embodiments, the chemical entity comprising Compound 1 is Form 1. In certain embodiments, the chemical entity comprising Compound 1 is a hydrochloride salt of Compound 1. In certain embodiments, the chemical entity comprising Compound 1 is Form 3. Accordingly, in certain embodiments, the invention relates to a tablet comprising Compound 1 citrate, such as Form 1. In certain such embodiments, the tablet comprises about 20 mg, about 60 mg, or about 100 mg of Compound 1 citrate, such as Form 1.

In certain embodiments, a dose of the chemical entity comprising Compound 1 is from about 1 mg to about 3000 mg, from about 1 mg to about 1000 mg, from about 1 mg to about 500 mg, from about 10 mg to about 200 mg, from about 50 mg to about 150 mg, from about 60 mg to about 120 mg, or from about 60 mg to about 100 mg. In certain embodiments, a dose of the chemical entity comprising Compound 1 is about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, or about 150 mg. Such a dose may comprise one or more tablets or capsules (e.g., a total daily dose of 60 mg may comprise a single 60 mg tablet or may comprise three 20 mg tablets). In certain embodiments, a dose is the total daily dose of the chemical entity comprising Compound 1. In certain embodiments, the total daily dose may be given once daily or may be divided such that the chemical entity comprising Compound 1 is given twice daily or three times daily. In certain such embodiments, the chemical entity comprising Compound 1 is selected from Form 1, Form 2, Form 3, Form 4, Form 5, Form 6, Form 7, Form 8, Form 9, Form 10, Form 11, Form 12, Form 13, Form 14, Form 15, Form 16, and Form 17, or any combination thereof. In certain embodiments, the chemical entity comprising Compound 1 is a citrate salt of Compound 1. In certain embodiments, the chemical entity comprising Compound 1 is Form 1. In certain embodiments, the chemical entity comprising Compound 1 is a hydrochloride salt of Compound 1. In certain embodiments, the chemical entity comprising Compound 1 is Form 3.

The active chemical entity may also be in micro-encapsulated form with one or more excipients as noted above. The solid dosage forms of tablets, dragees, capsules, pills, and granules may be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and may also be of a composition that they release the active ingredient(s) only, or preferentially, in a certain part of the intestinal tract, optionally, in a delayed manner. Examples of embedding compositions that may be used include polymeric substances and waxes.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a composition suitable for administration by rectal suppository or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to disorders as described herein (e.g., proliferation disorders, e.g., cancers, inflammatory, neurodegenerative disorders). The term "subject" as used herein, means an animal, preferably a mammal, more preferably a human. The term "patient" as used herein, means a human.

Preferably, the composition is formulated for administration to a patient or subject having or at risk of developing or experiencing a recurrence of the relevant disorder being treated. Preferred pharmaceutical compositions of the invention are those formulated for oral, intravenous, or subcutaneous administration. However, any of the above dosage forms containing a chemical entity of the invention are well within the bounds of routine experimentation and therefore, well within the scope of the instant invention. In certain embodiments, the pharmaceutical composition of the invention may further comprise another therapeutic agent. Preferably, such other therapeutic agent is one normally administered to patients with the disorder, disease or condition being treated.

A chemical entity of the invention may be used to treat disorders, diseases, and conditions for which inhibition of SYK is indicated. Such disorders, diseases, and conditions generally relate to any unhealthy or abnormal state in a subject for which the inhibition of SYK provides a therapeutic benefit. More particularly, such disorders, diseases, and conditions may involve the immune system and inflammation, including Type I hypersensitivity (allergic) reactions (allergic rhinitis, allergic asthma, and atopic dermatitis); autoimmune diseases (rheumatoid arthritis, multiple sclerosis, systemic lupus erythematosus, psoriasis, and immune thrombocytopenic purpura); inflammation of the lung (chronic obstructive pulmonary disease) and thrombosis. A chemical entity of the invention may also be used to treat disorders, diseases, and conditions related to abnormal cell growth, including hematological malignancies, such as acute myeloid leukemia, B-cell chronic lymphocytic leukemia, B-cell lymphoma (e.g., mantle cell lymphoma), and T-cell lymphoma (e.g., peripheral T-cell lymphoma), as well as epithelial cancers (i.e., carcinomas), such as lung cancer (small cell lung cancer and non-small cell lung cancer), pancreatic cancer, and colon cancer.

As used herein, the term "treating" or "treatment" includes reversing, reducing, or arresting the symptoms, clinical signs, and underlying pathology of a condition in manner to improve or stabilize a subject's condition.

In addition to the hematological malignancies and epithelial cancers noted above, a chemical entity of the invention may also be used to treat other types of cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, a chemical entity of the invention may also be used to treat other diseases related to abnormal cell growth, including non-malignant proliferative diseases such as benign prostatic hypertrophy, restinosis, hyperplasia, synovial proliferation disorder, retinopathy or other neovascular disorders of the eye, among others.

A chemical entity of the invention may also be used to treat autoimmune disorders in addition to those listed above. Such disorders, diseases, and conditions include Crohns disease, dermatomyositis, diabetes mellitus type 1, Goodpasture's syndrome, Graves' disease, Guillain-Barre syndrome, Hashimoto's disease, mixed connective tissue damage, myasthenia gravis, narcolepsy, pemphigus vulgaris, pernicious anemia, polymyositis, primary biliary cirrhosis, Sjrgren's syndrome, temporal arteritis, ulcerative colitis, vasculitis, and Wegener's granulomatosis, among others.

Furthermore, a chemical entity of the invention may be used to treat inflammatory disorders including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, vasculitis, and systemtic inflammatory response syndrome.

A chemical entity of the invention may also be used to treat specific diseases that may fall within one or more general disorders described above, including arthritis. In addition to rheumatoid arthritis, Sjögren's syndrome, systemic lupus erythematosus, SLE in children and adolescents, a chemical entity of the invention may also be used to treat other arthritis diseases, including ankylosing spondylitis, avascular necrosis, Bechet's disease, bursitis, calcium pyrophosphate dihyrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, scleroderma, spinal stenosis, Still's disease, and tendinitis, among others.

Accordingly, in certain embodiments, the invention relates to a method of treating a cancer comprising administering to a patient having a cancer a chemical entity comprising Compound 1. In certain embodiments, the invention relates to a method of treating a cancer comprising administering to a patient having a cancer a pharmaceutical composition comprising a chemical entity comprising Compound 1. In certain such embodiments, the chemical entity comprising Compound 1 is selected from Form 1, Form 2, Form 3, Form 4, Form 5, Form 6, Form 7, Form 8, Form 9, Form 10, Form 11, Form 12, Form 13, Form 14, Form 15, Form 16, and Form 17, or any combination thereof. In certain embodiments, the chemical entity comprising Compound 1 is a citrate salt of Compound 1. In certain embodiments, the chemical entity comprising Compound 1 is Form 1. In certain embodiments, the chemical entity comprising Compound 1 is a hydrochloride salt of Compound 1. In certain embodiments, the chemical entity comprising Compound 1 is Form 3.

In certain embodiments, the invention relates to a method of treating a hematological cancer comprising administering to a patient having a hematological cancer a chemical entity comprising Compound 1. In certain embodiments, the invention relates to a method of treating a hematological cancer comprising administering to a patient having a cancer a pharmaceutical composition comprising a chemical entity comprising Compound 1. In certain such embodiments, the chemical entity comprising Compound 1 is selected from Form 1, Form 2, Form 3, Form 4, Form 5, Form 6, Form 7, Form 8, Form 9, Form 10, Form 11, Form 12, Form 13, Form 14, Form 15, Form 16, and Form 17, or any combination thereof. In certain embodiments, the chemical entity comprising Compound 1 is a citrate salt of Compound 1. In certain embodiments, the chemical entity comprising Compound 1 is Form 1. In certain embodiments, the chemical entity comprising Compound 1 is a hydrochloride salt of Compound 1. In certain embodiments, the chemical entity comprising Compound 1 is Form 3.

In certain embodiments, the invention relates to a method of treating a leukemia or lymphoma comprising administering to a patient having a leukemia or lymphoma a chemical entity comprising Compound 1. In certain embodiments, the invention relates to a method of treating a cancer comprising administering to a patient having a leukemia or lymphoma a pharmaceutical composition comprising a chemical entity comprising Compound 1. In certain such embodiments, the chemical entity comprising Compound 1 is selected from Form 1, Form 2, Form 3, Form 4, Form 5, Form 6, Form 7, Form 8, Form 9, Form 10, Form 11, Form 12, Form 13, Form 14, Form 15, Form 16, and Form 17, or any combination thereof. In certain embodiments, the chemical entity comprising Compound 1 is a citrate salt of Compound 1. In certain embodiments, the chemical entity comprising Compound 1 is Form 1. In certain embodiments, the chemical entity comprising Compound 1 is a hydrochloride salt of Compound 1. In certain embodiments, the chemical entity comprising Compound 1 is Form 3.

In certain embodiments, the invention relates to a method of treating a cancer selected from peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, lymphoma, gastric carcinoma, breast cancer, ovarian cancer, lung cancer (e.g., small cell lung cancer) and a post-transplant lymphoproliferative disorder (PT-LPD), comprising administering to a patient having a cancer selected from peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, lymphoma, gastric carcinoma, breast cancer, ovarian cancer, lung cancer (e.g., small cell lung cancer) and a post-transplant lymphoproliferative disorder (PT-LPD) a chemical entity comprising Compound 1.

In certain embodiments, the invention relates to a method of treating a cancer selected from indolent non-Hodgkin's lymphoma (iNHL), peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, gastric carcinoma, breast cancer, ovarian cancer, lung cancer (e.g., small cell lung cancer) and a post-transplant lymphoproliferative disorder (PT-LPD), comprising administering to a patient having a cancer selected from indolent non-Hodgkin's lymphoma (iNHL), peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, gastric carcinoma, breast cancer, ovarian cancer, lung cancer (e.g., small cell lung cancer) and a post-transplant lymphoproliferative disorder (PT-LPD) a chemical entity comprising Compound 1.

In certain embodiments, the invention relates to a method of treating a cancer selected from peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, lymphoma, gastric carcinoma, breast cancer, ovarian cancer, lung cancer (e.g., small cell lung cancer) and a post-transplant lymphoproliferative disorder (PT-LPD), comprising administering to a patient having a cancer selected from peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, lymphoma, gastric carcinoma, breast cancer, ovarian cancer, lung cancer (e.g., small cell lung cancer) and a post-transplant lymphoproliferative disorder (PT-LPD) a pharmaceutical composition comprising a chemical entity comprising Compound 1.

In certain embodiments, the invention relates to a method of treating a cancer selected from indolent non-Hodgkin's lymphoma (iNHL), peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, gastric carcinoma, breast cancer, ovarian cancer, lung cancer (e.g., small cell lung cancer) and a post-transplant lymphoproliferative disorder (PT-LPD), comprising administering to a patient having a cancer selected from indolent non-Hodgkin's lymphoma (iNHL), peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, gastric carcinoma, breast cancer, ovarian cancer, lung cancer (e.g., small cell lung cancer) and a post-transplant lymphoproliferative disorder (PT-LPD) a pharmaceutical composition comprising a chemical entity comprising Compound 1.

In certain embodiments, the invention relates to a method of treating a cancer selected from iNHL, MCL, PT-LPD, DLBCL, CLL, and AML. In certain such embodiments, the cancer is selected from iNHL, MCL, PT-LPD, DLBCL, and AML. In certain such embodiments, the cancer is selected from DLBCL, CLL, and AML. In certain such embodiments, the cancer is selected from DLBCL and AML. In certain embodiments, the cancer is PTCL. In certain embodiments, the cancer is DLBCL. In certain embodiments, the cancer is FL. In certain embodiments, the cancer is MCL. In certain embodiments, the cancer is CLL. In certain embodiments, the cancer is AML. In certain embodiments, the cancer is MDS. In certain embodiments, the cancer is nasopharyngeal carcinoma. In certain embodiments, the cancer is lymphoma. In certain embodiments, the cancer is gastric carcinoma. In certain embodiments, the cancer is breast cancer. In certain embodiments, the cancer is ovarian cancer. In certain embodiments, the cancer is lung cancer (e.g., small cell lung cancer). In certain embodiments, the cancer is a post-transplant lymphoproliferative disorder. In certain embodiments, the cancer is iNHL.

In certain such embodiments, the chemical entity comprising Compound 1 is selected from Form 1, Form 2, Form 3, Form 4, Form 5, Form 6, Form 7, Form 8, Form 9, Form 10, Form 11, Form 12, Form 13, Form 14, Form 15, Form 16, and Form 17, or any combination thereof. In certain embodiments, the chemical entity comprising Compound 1 is a citrate salt of Compound 1. In certain embodiments, the chemical entity comprising Compound 1 is Form 1. In certain embodiments, the chemical entity comprising Compound 1 is a hydrochloride salt of Compound 1. In certain embodiments, the chemical entity comprising Compound 1 is Form 3.

In certain such embodiments, the invention relates to a method of treating a cancer selected from peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, lymphoma, gastric carcinoma, breast cancer, ovarian cancer, lung cancer (e.g., small cell lung cancer) and a post-transplant lymphoproliferative disorder (PT-LPD), comprising administering to a patient having a cancer selected from peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, lymphoma, gastric carcinoma, breast cancer, ovarian cancer, lung cancer (e.g., small cell lung cancer) and a post-transplant lymphoproliferative disorder (PT-LPD) a dose, such as a total daily dose, of a chemical entity comprising Compound 1 of from about 1 mg to about 3000 mg, from about 1 mg to about 1000 mg, from about 1 mg to about 500 mg, from about 10 mg to about 200 mg, from about 50 mg to about 150 mg, from about 60 mg to about 120 mg, or from about 60 mg to about 100 mg. In certain such embodiments, the dose is administered orally.

In certain such embodiments, the invention relates to a method of treating a cancer selected from indolent non-Hodgkin's lymphoma (iNHL), peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, gastric carcinoma, breast cancer, ovarian cancer, lung cancer (e.g., small cell lung cancer) and a post-transplant lymphoproliferative disorder (PT-LPD), comprising administering to a patient having a cancer selected from indolent non-Hodgkin's lymphoma (iNHL), peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, gastric carcinoma, breast cancer, ovarian cancer, lung cancer (e.g., small cell lung cancer) and a post-transplant lymphoproliferative disorder (PT-LPD) a dose, such as a total daily dose, of a chemical entity comprising Compound 1 of from about 1 mg to about 3000 mg, from about 1 mg to about 1000 mg, from about 1 mg to about 500 mg, from about 10 mg to about 200 mg, from about 50 mg to about 150 mg, from about 60 mg to about 120 mg, or from about 60 mg to about 100 mg. In certain such embodiments, the dose is administered orally.

In certain such embodiments, the invention relates to a method of treating a cancer selected from peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, lymphoma, gastric carcinoma, breast cancer, ovarian cancer, lung cancer (e.g., small cell lung cancer) and a post-transplant lymphoproliferative disorder (PT-LPD), comprising administering to a patient having a cancer selected from peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, lymphoma, gastric carcinoma, breast cancer, ovarian cancer, lung cancer (e.g., small cell lung cancer) and a post-transplant lymphoproliferative disorder (PT-LPD) a dose, such as a total daily dose, of a chemical entity comprising Compound 1 of about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, or about 150 mg of a chemical entity comprising Compound 1. In certain such embodiments, the dose is administered orally.

In certain such embodiments, the invention relates to a method of treating a cancer selected from indolent non-Hodgkin's lymphoma (iNHL), peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, gastric carcinoma, breast cancer, ovarian cancer, lung cancer (e.g., small cell lung cancer) and a post-transplant lymphoproliferative disorder (PT-LPD), comprising administering to a patient having a cancer selected from indolent non-Hodgkin's lymphoma (iNHL), peripheral T-cell lymphoma (PTCL), diffuse large B-cell lymphoma (DLBCL), follicular lymphoma (FL), mantle cell lymphoma (MCL), chronic lymphocytic leukemia (CLL), acute myeloid leukemia (AML), myelodysplastic syndrome (MDS), nasopharyngeal carcinoma, gastric carcinoma, breast cancer, ovarian cancer, lung cancer (e.g., small cell lung cancer) and a post-transplant lymphoproliferative disorder (PT-LPD) a dose, such as a total daily dose, of a chemical entity comprising Compound 1 of about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, or about 150 mg of a chemical entity comprising Compound 1. In certain such embodiments, the dose is administered orally.

In certain such embodiments, the cancer is selected from iNHL, MCL, PT-LPD, DLBCL, CLL, and AML. In certain such embodiments, the cancer is selected from iNHL, MCL, PT-LPD, DLBCL, and AML. In certain embodiments, the invention relates to a method of treating a cancer selected from DLBCL, CLL, and AML, comprising administering to a patient having a cancer selected from DLBCL, CLL, and AML a chemical entity comprising Compound 1. In certain embodiments, the invention relates to a method of treating a cancer selected from DLBCL, CLL, and AML, comprising administering to a patient having a cancer selected from DLBCL, CLL, and AML a pharmaceutical composition comprising a chemical entity comprising Compound 1. In certain embodiments, the cancer is selected from DLBCL and AML. In certain embodiments, the cancer is CLL. In certain embodiments, the cancer is AML. In certain embodiments, the cancer is DLBCL. In certain embodiments, the cancer is PTCL. In certain embodiments, the cancer is FL. In certain embodiments, the cancer is MCL. In certain embodiments, the cancer is MDS. In certain embodiments, the cancer is nasopharyngeal carcinoma. In certain embodiments, the cancer is lymphoma. In certain embodiments, the cancer is gastric carcinoma. In certain embodiments, the cancer is breast cancer. In certain embodiments, the cancer is ovarian cancer. In certain embodiments, the cancer is lung cancer (e.g., small cell lung cancer). In certain embodiments, the cancer is a post-transplant lymphoproliferative disorder. In certain embodiments, the cancer is iNHL.

In certain such embodiments, the chemical entity comprising Compound 1 is selected from Form 1, Form 2, Form 3, Form 4, Form 5, Form 6, Form 7, Form 8, Form 9, Form 10, Form 11, Form 12, Form 13, Form 14, Form 15, Form 16, and Form 17, or any combination thereof. In certain embodiments, the chemical entity comprising Compound 1 is a citrate salt of Compound 1 (e.g., Form 1 or Form 2). In certain such embodiments the citrate salt of Compound 1 is Form 1. In certain embodiments, the chemical entity comprising Compound 1 is a hydrochloride salt of Compound 1 (e.g., Form 3 or Form 4). In certain such embodiments the hydrochloride salt of Compound 1 is Form 3.

In certain such embodiments, the invention relates to a method of treating a cancer selected from DLBCL, CLL, and AML, comprising administering to a patient having a cancer selected from DLBCL, CLL, and AML a dose, such as a total daily dose, of a chemical entity comprising Compound 1 of from about 1 mg to about 3000 mg, from about 1 mg to about 1000 mg, from about 1 mg to about 500 mg, from about 10 mg to about 200 mg, from about 50 mg to about 150 mg, from about 60 mg to about 120 mg, or from about 60 mg to about 100 mg. In certain such embodiments, the dose is administered orally.

In certain such embodiments, the invention relates to a method of treating a cancer selected from indolent non-Hodgkin's lymphoma (iNHL), mantle cell lymphoma, post-transplant lymphoproliferative disorder (PT-LPD), diffuse large B-cell lymphoma (DLBCL), chronic lymphocytic leukemia (CLL), and acute myeloid leukemia (AML), comprising administering to a patient having a cancer selected from indolent non-Hodgkin's lymphoma (iNHL), mantle cell lymphoma, post-transplant lymphoproliferative disorder (PT-LPD), diffuse large B-cell lymphoma (DLBCL), chronic lymphocytic leukemia (CLL), and acute myeloid leukemia (AML) a dose, such as a total daily dose, of a chemical entity comprising Compound 1 of from about 1 mg to about 3000 mg, from about 1 mg to about 1000 mg, from about 1 mg to about 500 mg, from about 10 mg to about 200 mg, from about 50 mg to about 150 mg, from about 60 mg to about 120 mg, or from about 60 mg to about 100 mg. In certain such embodiments, the dose is administered orally.

In certain such embodiments, the invention relates to a method of treating a cancer selected from DLBCL, CLL, and AML, comprising administering to a patient having a cancer selected from DLBCL, CLL, and AML a dose, such as a total daily dose, of a chemical entity comprising Compound 1 of about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, or about 150 mg of a chemical entity comprising Compound 1. In certain such embodiments, the dose is administered orally.

In certain such embodiments, the invention relates to a method of treating a cancer selected from indolent non-Hodgkin's lymphoma (iNHL), mantle cell lymphoma, post-transplant lymphoproliferative disorder (PT-LPD), diffuse large B-cell lymphoma (DLBCL), chronic lymphocytic leukemia (CLL), and acute myeloid leukemia (AML), comprising administering to a patient having a cancer selected from indolent non-Hodgkin's lymphoma (iNHL), mantle cell lymphoma, post-transplant lymphoproliferative disorder (PT-LPD), diffuse large B-cell lymphoma (DLBCL), chronic lymphocytic leukemia (CLL), and acute myeloid leukemia (AML) a dose, such as a total daily dose, of a chemical entity comprising Compound 1 of about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, or about 150 mg of a chemical entity comprising Compound 1. In certain such embodiments, the dose is administered orally.

In order that this invention be more fully understood, the following preparative and testing examples are set forth. These examples are for the purpose of illustration only and are not intended to be construed as limiting the scope of the invention in any way.

EXAMPLES

Example 1. Synthesis of 6-(((1R,2S)-2-aminocyclohexyl)amino)-7-fluoro-4-(1-methyl-1H-pyrazol-4-yl)-1H-pyrrolo[3,4-c]pyridin-3 (2H)-one citrate (Compound 1 Citrate)

Step 1. 2,6-dichloro-5-fluoronicotinamide (2)

2,6-dichloro-5-fluoronicotinonitrile (1) was charged into a 50 L, jacketed, cylindrical reactor equipped with an overhead stirrer, thermocouple and $N_2$ inlet and outlet. Concentrated sulfuric acid (27.22 kg, 4.93 vol) was added to the flask and agitation was started. The brown mixture was heated to 65° C. and stirred for 1 h and a clear brown solution was obtained. The dark brown mixture was then cooled to ambient temperature and then to <10° C. While cooling, a separate 100 L, jacketed reactor was charged with deionized (DI) water (74.0 L, 24.7 vol) and the water was cooled to 0-5° C. The reaction mixture was then transferred to the cooled water over one hour and thirty five minutes and the internal temperature was kept below 20° C. The resulting slurry was filtered through an 18" Hastelloy Nutsche funnel with a polypropylene (PP) filter cloth. The 50 L reactor was rinsed with water (3×12 L, 3×4 vol) and the rinses were transferred to the funnel to wash the filter cake. The filter cake was conditioned for 16 hours and transferred to drying trays. The solid was dried under high vacuum at 40-50° C. for 29 h to give 2.856 kg of (2) as a beige solid in 87% yield. $^1$H NMR (500 MHz, $d_6$-DMSO) δ 8.23 (d, J=7.9 Hz, 1H), 8.10 (s, 1H), 7.94 (s, 1H).

Step 2. 4,6-dichloro-7-fluoro-1-hydroxy-1H-pyrrolo [3,4-c]pyridin-3 (2H)-one (3)

A 50 L, jacketed reactor equipped with a data logger, thermocouple, and nitrogen inlet and outlet was charged with lithium bis(trimethylsilyl)amide (LiHMDS, 20.22 kg, 2.50 equiv) as a 1 M solution in tetrahydrofuran (THF) with external cooling to −3° C. A 100 L, jacketed reactor was charged with (2), anhydrous THF (18 L, 11.85 kg, 7.0 vol), and N,N-dimethylformamide (DMF, 1.99 kg, 3.0 equiv) at ambient temperature. The batch in the 100 L reactor was charged to the LiHMDS in the 50 L reactor while maintaining an internal batch temperature below 5° C. over 1 h. After 1 h the reaction was slowly quenched into the 100 L reactor containing a 2 N hydrochloric acid (HCl, 4.8 L) solution in DI water (24.0 L, 6.25 vol) at 0° C. while maintaining an internal temperature below 20° C. over 2 h. The batch was extracted into isopropyl acetate (IPAc) (38.0 L, 20.0 vol) and the organic extract was concentrated under reduced pressure at 38° C. to approximately ≈8.0 L (5.0 vol). An additional portion of IPAc (28.5 L, 15.0 vol) was charged and the batch was further reduced to approximately 5.0 vol (9.0 L) to afford a yellow slurry. Heptanes (38.0 L, 20.0 vol) were charged to the batch over 1 h and the solids were isolated using an 18" Hastelloy Nutsche filter equipped with a PP cloth and vacuum receiver. The filter cake was rinsed twice with heptanes (2×9.50 L, 5.0 vol) and conditioned under a blanket of nitrogen for 30 min. The solids were further dried under vacuum at 25° C. for 24 h to afford (3) (1.9358 kg) in 89.8% yield. $^1$H NMR (500 MHz, $d_6$-DMSO) δ 9.52 (s, 1H), 6.91 (d, J=9.6 Hz, 1H), 6.10 (dd, $J_1$=2.6 Hz, $J_2$=9.5 Hz, 1H).

Step 3. 4,6-dichloro-7-fluoro-1H-pyrrolo[3,4-c]pyridin-3(2H)-one (4)

A 50 L, jacketed reactor equipped with a data logger, thermocouple, and nitrogen inlet and outlet was charged with (3) (1.92 kg, 8.10 mol) and dichloromethane (DCM, 9.60 L, 5.0 vol) at ambient temperature. Trifluoroacetic acid (10.86 kg, 11.76 equiv) and triethyl silane (4.68 kg, 4.97 equiv) were charged over 10 min while maintaining an internal temperature below 20° C. The reaction was heated to an internal temperature of 40° C. and held for 10 h. The reaction was then cooled to 10° C. for the slow addition of methyl t-butyl ether (MTBE, 28.80 L, 15.0 vol) over 2 h. The resultant slurry was aged at 10° C. for 15 min and filtered through an 18" Hastelloy Nutsche filter equipped with PP cloth and a vacuum receiver. The filter cake was rinsed twice with MTBE (2×7.68 L, 4.0 vol) and conditioned over 2 h. The solids were further dried in vacuo at 25° C. to afford (4) (1.699 kg) in 95% yield as a white solid. $^1$H NMR (300 MHz, $d_6$-DMSO) δ 9.16 (s, 1H), 4.55 (s, 2H).

Step 4. tert-butyl 4,6-dichloro-7-fluoro-3-oxo-1H-pyrrolo[3,4-c]pyridine-2(3H)-carboxylate (5)

A 50 L, jacketed reactor equipped with a data logger, thermocouple, and nitrogen inlet and outlet was charged with (4) (3.4 kg), DCM (13.7 L, 4.0 vol), and 4-dimethylaminopyridine (DMAP, 38 g, 0.02 equiv) at ambient temperature. A solution of Boc-anhydride (3.91 kg, 1.1 equiv) in DCM (3.4 L, 1.0 vol) was charged over a 15 min period while maintaining an internal temperature below 25° C. The carboy containing Boc anhydride solution was rinsed with DCM (3.4 L, 1 vol) into the batch. The reaction was stirred at ambient temperature for 17 h and was then concentrated under reduced pressure to 9 L remaining in the reactor. Ethanol (34.0 L, 10.0 vol) was added and the mixture was distilled to approximately 6.0 vol (21 L) under reduced pressure. The batch temperature was adjusted to 18° C. and the resultant slurry was isolated via vacuum filtration through an 18" Hastelloy Nutsche filter equipped with a PP cloth and vacuum receiver. The filter cake was rinsed three times with EtOH (3×6.8 L, 3×2.0 vol) and conditioned over 23 h. The solids were deemed dry to afford (5) (4.184 kg) in 84% yield as a pink solid. $^1$H NMR (500 MHz, $d_6$-DMSO) δ 4.91 (s, 2H), 1.53 (s, 9H).

Step 5. tert-butyl 6-(((1R,2S)-2-((tert-butoxycarbonyl)amino)cyclohexyl)amino)-4-chloro-7-fluoro-3-oxo-1H-pyrrolo[3,4-c]pyridine-2(3H)-carboxylate (7)

A nitrogen-flushed, 30 L, cylindrical, jacketed reactor was charged with MTBE (6.84 L) and (6) mandelate (1.703 kg) and stirred at 20±5° C. 2 N NaOH was charged to the reactor while maintaining a batch temperature of <25° C. The mixture was stirred for 30 minutes after which time the phases were separated and were transferred to carboys. The aqueous phase was returned to the reactor and back-extracted with MTBE (6.84 L). The resulting organic phase was combined with the previous organic phase and washed with DI water (6 L) followed by brine (6 L). The batch was concentrated to 5 L with the jacket set at 50° C., 7.6 inHg vacuum, and a batch temperature of 24.2-24.3° C. The vacuum was released and 7.2 L of isopropyl alcohol (IPA) was charged to the reaction. Vacuum was reapplied to the reactor at 6 inHg with an initial internal temperature of 35.9° C. (jacket temperature 50° C.). After concentration from 12 L to 8 L, the vacuum was increased to 2.9 inHg for an additional hour and increased again to 2.5 inHg until reaching the endpoint at 3 L. The batch was held overnight under nitrogen at 20±5° C. prior to the next distillation. 7.2 L of IPA was then charged to the batch and the jacket was heated to 50° C. Vacuum was applied at 2.4 inHg for 3.5 hours until the targeted endpoint of 5 L was reached. The batch maintained a temperature of 35-40° C. throughout the distillation. The vacuum was removed and the jacket cooled to 20±5° C.

(5) (1.2 kg), IPA (1.2 L), DIPEA (0.85 L), and DMSO (1.2 L) were charged to the 30 L reactor. The batch was heated to 76° C. and stirred for a total of 46 h. The v/v ratio of DMSO/IPA was then adjusted to 6:1 by the addition of IPA (3.8 L). $H_2O$ (4.8 L) was added to the reaction via transfer pump while maintaining the batch temperature above 65° C. After addition, no solid precipitate was observed. The reactor was seeded with (7) (7.5 g) and the reaction was cooled to 25° C. over 3 h. After 2 h, the batch was observed as a suspension. The batch was then stirred at 25° C. for 1 h and the product was isolated by vacuum filtration. The solid was washed with 6:4:1 IPA/$H_2O$/DMSO (2.4 L) and 3:2 IPA/$H_2O$ (2×2.4 L). The product was conditioned for 30 min and dried under vacuum at 45° C. for 2 days to afford (7) (798 g, 43% yield) as a bright pink solid.

(7) (22.6 kg), isopropanol (17.7 kg), and n-heptane (46.5 kg) were charged to a 400 L Hastelloy reactor and the reactor was purged with nitrogen. The batch was heated to 75±5° C. over 2-3 hours and then stirred at 75±5° C. for at least 3-6 hours. The batch temperature was adjusted to 20±5° C. and agitated for a minimum of 12 hours while maintaining 20±5° C. The batch was filtered and washed twice with 3:1 n-heptane/IPA (23.0 kg/9.2 kg) and then conditioned for at least 1 hour. The filtered solids were then dried in a vacuum oven at 50±5° C. to afford 20.3 kg of (7) in 96% yield. $^1$H NMR (300 MHz, $CDCl_3$) δ 6.18-5.98 (m, 1H), 4.94-4.76 (m, 1H), 4.28-4.15 (m, 1H), 4.11-3.96 (m, 1H), 2.08-1.92 (m, 1H), 1.80-1.67 (m, 2H), 1.66-1.53 (m, 11H), 1.53-1.32 (m, 13H), 1.21 (d, J=10 Hz, 1H).

Step 6. tert-butyl 6-(((1R,2S)-2-((tert-butoxycarbonyl)amino)cyclohexyl)amino)-7-fluoro-4-(1-methyl-1H-pyrazol-4-yl)-3-oxo-1H-pyrrolo[3,4-c]pyridine-2 (3H)-carboxylate (9)

A nitrogen-flushed, 30 L, cylindrical, jacketed reactor was charged with (7) (660 g), (8) (330 g), $K_2CO_3$ (370 g), and 80% (2.8 L) of a premixed solution containing dimethylactetamide (DMAc, 3.3 L) and $H_2O$ (0.23 L). The mixture was stirred at 22±5° C. The reactor was degassed under vacuum to 50 mbars and backfilled with $N_2$ (×5). Pd-118 (8.6 g) and the remaining 20% (1 L) of the DMAc/H2O solution were charged to the reactor. The reactor was degassed under vacuum to 50 mbars and backfilled with $N_2$ (×5). The batch was heated to 80° C. and stirred for 8 h. The batch was then cooled to 65° C. and a solution of N-acetylcysteine (22 g) in $H_2O$ (0.2 L) was charged to the reactor. The batch was stirred at 65° C. for 1 h. $H_2O$ (5.3 L) was charged to the reactor over 1 h while maintaining a batch temperature of 60±5° C. The batch was stirred at 60° C. for 1.5 h, cooled to 25° C. over 3 h, and stirred overnight at 25° C. The product was isolated by vacuum filtration and washed with $H_2O$ (3 vol) and 1:1 IPA/$H_2O$ (2×3 vol). The solid was dried under vacuum at 58° C. to afford (9) (616 g, 86% yield) as a light brown solid.

A 12 L, three-neck, round-bottom flask equipped with a mechanical overhead stirrer, thermocouple, and $N_2$ inlet was charged with (9) (488 g) and 4.9 L (10 vol) of 1:4 THF/MTBE (premixed). The mixture was stirred at ambient (24° C.) for 18 h. The product was isolated by vacuum filtration and the solids were washed with 1:4 THF/MTBE (2×5 vol) and conditioned for 2.5 h. The isolated solid was dried under vacuum at 60° C. to afford (9) (416 g, 85% yield) as a brown solid. $^1$H NMR (500 MHz, $d_6$-DMSO) δ 8.67 (s, 1H), 8.23 (s, 1H), 6.75 (dd, $J_1$=6.8 Hz, $J_2$=39.3 Hz, 2H), 4.73 (s, 2H), 4.38-4.27 (m, 1H), 3.91 (s, 3H), 3.90-3.82 (m, 1H), 1.88-1.74 (m, 2H), 1.65-1.53 (m, 13H), 1.43-1.28 (m, 11H).

Step 7. 6-(((1R,2S)-2-aminocyclohexyl)amino)-7-fluoro-4-(1 i-methyl-1H-pyrazol-4-yl)-1H-pyrrolo[3,4-c]pyridin-3(2H)-one dihydrochloride (10)

A 50 L, glass-jacketed reactor was charged with (9) (708 g), MeCN (12 L, 17 vol), and THMS-05 resin (70 g, 0.1 wt %). The mixture was heated to 65° C. and stirred for 16 h. The batch was filtered through Celite over a glass-fritted funnel and transferred to a 30 L reactor through a 1 micron in-line filter. Once the filtration was complete, the 50 L reactor and filter lines were rinsed with MeCN (2.1 L, 3 vol). The filtered batch was heated to 65° C. and formed a dark solution. The batch was cooled to 45° C. and 2 N HCl (2 L, 3 equiv) was charged to the batch over 1 h. After addition, a portion of (10) seed (2.7 g, 0.5 wt %) was slurried in MeCN (54 mL) and charged to the batch. The batch was stirred at 45° C. for 1 h and gradually formed a suspension. The batch was warmed to 65° C. over 1 h and stirred at 65° C. for 1 h followed by cooling to 25° C. and stirring for 18 h. The product was isolated by vacuum filtration and the solids were washed with MeCN (5 vol) and conditioned for 1.5 h. The isolated solid was dried under vacuum at 60° C. to afford (10) (377 g, 69% yield) as an off-white solid. $^1$H NMR (500 MHz, $d_6$-DMSO) δ 8.83 (s, 1H), 8.36 (s, 1H), 8.29 (s, 1H), 7.88 (br, 1H), 6.75 (d, J=6.5 Hz, 1H), 4.45-4.34 (m, 6H), 3.89 (s, 3H), 3.67 (m, 1H), 1.91-1.81 (m, 3H), 1.70-1.63 (m, 3H), 1.46-1.45 (m, 2H).

Step 8. 6-(((1R,2S)-2-aminocyclohexyl)amino)-7-fluoro-4-(1-methyl-1H-pyrazol-4-yl)-1H-pyrrolo[3,4-c]pyridin-3(2H)-one citrate (Compound 1 Citrate)

A 12 L, half-jacketed, round-bottom reactor equipped with a mechanical overhead stirrer, thermocouple, reflux condenser, and $N_2$ inlet was charged with (10) (275 g), THMS-05 resin (28 g, 0.1 wt %), and $H_2O$ (4.68 L, 17 vol). The batch was heated to 85° C. and stirred for 19 h. A filtration apparatus, including a bench-top fritted filter and 1 micron in-line filter, was assembled and preheated using water at 85° C. The batch was transferred through both filters to a 30 L reactor with the jacket preheated to 85° C. Water (280 mL, 1 vol) was charged to the 12 L reactor as a rinse and transferred through the filter apparatus to the 30 L reactor. After transfer, the batch temperature was 71° C. and was heated back to 85° C. The 12 L reactor was cleaned and charged with sodium citrate monobasic (320 g, 2.1 equiv) and $H_2O$ (830 mL, 3 vol). This mixture was heated to 60° C. and formed a solution. The sodium citrate monobasic solution was transferred to the jacketed reactor over 5 min. The batch began to crystallize halfway through the addition. The suspension was stirred at 85° C. for 2 h, cooled to 25° C., and stirred for 16 h. The product was isolated by vacuum filtration and the solids were washed with $H_2O$ (3 vol) and conditioned for 3 h. The isolated solid was dried under vacuum at 55° C. to afford Compound 1 citrate (297 g, 94% yield) as an off-white solid. $^1$H NMR (500 MHz, d-TFA) δ 8.10 (s, 1H), 8.00 (s, 1H), 3.95 (s, 1H), 3.72 (s, 2H), 3.30 (s, 3H), 2.98-2.96 (m, 1H), 2.24 (d, J=16.5 Hz, 2H), 2.17 (d, J=16.5 Hz, 2H), 1.10-0.95 (m, 5H), 0.93-0.76 (m, 3H).

Example 2. Synthesis of 6-(((1R,2S)-2-aminocyclohexyl)amino)-7-fluoro-4-(1-methyl-1H-pyrazol-4-yl)-1H-pyrrolo[3,4-c]pyridin-3(2H)-one citrate (Compound 1 Citrate)

Step 1. 2-chloro-3-cyano-4,5-difluoropyridine (11)

(1) (100 g, 524 mmol) was dissolved in DMSO (150 mL) at 25±10° C. under inert atmosphere. Potassium fluoride (36.5 g, 628 mmol) was added and rinsed with DMSO (100 mL). The resulting suspension was stirred for 18 hours at 25±5° C. To the reaction mixture was added water (1.0 L) over 2 hours. The resulting slurry was aged for 3 hours and then filtered. The filter cake was washed with water (500 mL) and dried on the filter (centrifugal). The wet cake was used in the following reaction without further drying. 83.0 g of (11) was obtained as a white solid (91%). $^1$H NMR (500 MHz, $CDCl_3$): δ (ppm) 7.90-7.95 (m, 1H).

Step 2. 2-chloro-5,6-difluoropyridine-3-carboxamide (12)

To a stirred solution of THF (138 mL) and water (86 mL) were added (11) (69.0 g, 395 mmol) and acetamide (93.4 g, 1.58 mol) at 25±10° C. under inert atmosphere. The reaction vessel was rinsed with THF (121 mL). The resulting mixture was degassed by repeating evacuation and back-filling with nitrogen. Palladium (II) chloride (1.40 g, 7.91 mmol) was added and the mixture was reacted for 6 hours at 60-65° C. The reaction mixture was cooled to 25±10° C. and then diluted with EtOAc (518 mL) and 10% NaCl solution (345 mL). The organic layer was separated and washed with 10% NaCl solution (345 mL) twice. The solvent was then switched to EtOAc (155 mL) by solvent-chasing technique and then heated to 55±5° C. To the resulting solution was added n-heptane (690 mL) over 2.5 hours at 55±5° C. The obtained slurry was cooled to 20-25° C. over 1 hour, aged at this temperature for 3 hours, and then filtered. The filter cake was washed with n-heptane (138 mL) and dried in vacuo at 40±10° C. for 3 hours. 64.2 g of (12) was obtained as an off-white solid (84%). $^1$H NMR (500 MHz, $CDCl_3$): δ (ppm) 6.34 (br s, 1H), 6.80 (br s, 1H), 8.25 (t, J=8.4 Hz, 1H).

Step 3. 4-chloro-6,7-difluoro-1-hydroxy-1H-pyrrolo[3,4-c]pyridin-3 (2H)-one (13)

To a cooled (−5±5° C.) solution of LiHMDS (1.0 M in THF, 46.7 mL, 46.7 mmol) was added a pre-mixed solution of (12) (30.0 g, 156 mmol) and 4-formyl morpholine (17.2 mL, 171 mmol) in THF (150 mL) over 1.5 hours at −5±5° C. under inert atmosphere. The vessel was rinsed with THF (15 mL). The reaction mixture was stirred for 30 minutes at −5±5° C. and then transferred onto a pre-cooled (0-5° C.) and well-agitated mixture of isopropyl acetate (IPAc, 510 mL) and 2 M aq. HCl solution (630 mL) at such a rate that the internal temperature is kept below 5° C. (over approximately 30 minutes). The resulting mixture was stirred for 15 min at −5±5° C. and then allowed to stand at 25±10° C. The organic layer was separated and washed with 10% NaCl solution (300 mL) two times. The solvent was switched into IPAc (150 mL) by solvent-chasing technique. To the resulting slurry was added n-heptane (300 mL) over 1 hour at 20~25° C. The obtained slurry was aged at this temperature for 3 hours, and then filtered. The filter cake was washed with n-heptane (60 mL) and dried in vacuo at 40±10° C. for 3 hours. 29.9 g of (13) was obtained as an off-white solid (87%). $^1$H NMR (500 MHz, DMSO-$d_6$): δ (ppm) 6.12 (d, J=8.5 Hz, 1H), 6.97 (d, J=9.5 Hz, 1H), 9.48 (s, 1H).

Step 4. 4-chloro-6,7-difluoro-1H-pyrrolo[3,4-c]pyridin-3(2H)-one (14)

To a heated (55±5° C.) slurry of (13) (27.0 g, 122 mmol) in trifluoroacetic acid (108 mL) was added triethylsilane (97.5 mL, 612 mmol) over 3 hours at this temperature. The reaction mixture was stirred for 2 hours at 55±5° C. and then cooled to 0±5° C. MTBE (702 mL) was added to the mixture over 2 hours at 0±5° C. The resulting slurry was aged for 2 hours at this temperature and then filtered. The filter cake was washed with MTBE (81 mL) and dried in vacuo at 40±10° C. for 3 hours. 20.8 g of (14) was obtained as an off-white solid (83%). $^1$H NMR (500 MHz, DMSO-$d_6$): δ (ppm) 4.57 (s, 2H), 9.10 (br s, 1H).

Step 5. tert-butyl ((1S,2R)-2-((4-chloro-7-fluoro-3-oxo-2,3-dihydro-1H-pyrrolo[3,4-c]pyridin-6-yl)amino)cyclohexyl)carbamate (15)

A 1:1 salt mixture of (2S)-hydroxy(phenyl)acetic acid and tert-butyl [(1S,2R)-2-aminocyclohexyl]carbamate (18.8 g, 51.3 mmol) which may be prepared as disclosed in U.S. Pat. No. 8,440,689, incorporated herein in its entirety, was suspended in MTBE (75 mL) at 25±10° C. under inert atmosphere with stirring. Water (94 mL) and 2 M aq. NaOH solution (51.3 mL) were then added. The resulting mixture was stirred vigorously for 30 minutes at 25±10° C. and then allowed stand. The phases were separated and the aqueous layer was extracted with MTBE (75 mL). These organic layers were combined and washed successively with water (75 mL) and with 5% NaCl solution (75 mL). At this point, one of two alternative processes was selected: (A) The solvent was switched to DMAc (50 mL) using a solvent-chasing technique and the resulting DMAc solution was used in the following reaction without further purification; or (B) The solution was evaporated to dryness under high-vacuum to furnish (6) as a colorless oil that was used in the following reaction without further purification.

The solution of (6) in DMAc (50 mL) obtained above was diluted with DMAc (30 mL) under inert atmosphere at 25±10° C. followed by addition of (14) (10.0 g, 48.9 mmol) with stirring at 30±15° C. and the vessel was rinsed with DMAc (20 mL). After stirring for 10 min at this temperature, triethylamine (8.18 mL, 58.7 mmol) was added. The resulting mixture was reacted for 30 min at 30±15° C., reacted for 5 hours at 65±5° C., and then cooled to 50±5° C. To the reaction mixture was added water (70 mL) over 30 min at 50±5° C. After aging at this temperature for 3 hours, another portion of water (70 mL) was added over 30 min. The resultant slurry was aged for 30 minutes at 50±5° C. and for overnight at 25±10° C., and then filtered. The filter cake was washed with a pre-mixed solution of DMAc-water (1:4, 50 mL), and with water (100 mL, ×2). The obtained wet solid was dried in vacuo at 40±10° C. for 3 hours. 17.2 g of (15) was obtained as a grey solid (88%). $^1$H NMR (500 MHz, DMSO-$d_6$): δ (ppm) 1.10-1.85 (m, 8H), 1.36 (s, 9H), 3.83 (br s, 1H), 4.09 (br s, 1H), 4.34 (s, 2H), 6.68 (br d, J=7.5 Hz, 1H), 6.83 (br d, J=7.0 Hz, 1H), 8.39 (s, 1H).

Step 6. tert-butyl ((1S,2R)-2-((7-fluoro-4-(1-methyl-1H-pyrazol-4-yl)-3-oxo-2,3-dihydro-1H-pyrrolo[3,4-c]pyridin-6-yl)amino)cyclohexyl)carbamate (16)

To a stirred solution of 2-butanol (120 mL) and water (90 mL) were added (15) (30.0 g, 75.2 mmol), 1-methyl-4-(4,4,5,5-tetramethyl-1,3,2-dioxaborolan-2-yl)-1H-pyrazole (22.0 g, 105 mmol), and potassium carbonate (22.9 g, 166 mmol) under inert atmosphere at 25±10° C. The vessel was then rinsed with 2-butanol (30 mL). The resulting mixture was degassed by repeating evacuation and back-filling with nitrogen. Pd(PPh$_3$)$_2$Cl$_2$ (528 mg, 0.75 mmol, 1 mol %) was added, and the vessel was rinsed with 2-butanol (30 mL). Degassing was conducted again. The resulting mixture was heated to 95±10° C., and allowed to react for 4 hours at this temperature. The reaction mixture was cooled to 60±10° C., and a solution of L-cysteine (911 mg, 7.52 mmol) in water (270 mL) was added in one portion at this temperature. After stirring for 1 hour, n-heptane (360 mL) was added over 1 hour at 60±10° C. The resulting slurry was cooled to 25±5° C. over 1 hour, aged for 18 hours at this temperature, and filtered. The filter cake was washed with a pre-mixed solution of n-heptane and 2-butanol (5:1, 90 mL), and with water (150 mL). The obtained wet solid was dried in vacuo at 50±10° C. for 10 hours. 28.4 g of (16) was obtained as an off-white solid (85%). $^1$H NMR (500 MHz, DMSO-$d_6$): δ (ppm) 1.10-1.85 (m, 8H), 1.34 (s, 9H), 3.87 (br s, 1H), 3.89 (s, 3H), 4.28 (br s, 1H), 4.35 (s, 2H), 6.44 (br d, J=6.5 Hz, 1H), 6.72 (br d, J=7.5 Hz, 1H), 8.27 (s, 2H), 8.77 (s, 1H).

Step 7. 6-(((1R,2S)-2-aminocyclohexyl)amino)-7-fluoro-4-(1-methyl-1H-pyrazol-4-yl)-1H-pyrrolo[3,4-c]pyridin-3(2H)-one dihydrochloride (10)

To a solution of THF (1500 mL) and water (200 mL) were added (16) (50.0 g, 113 mmol) and palladium-scavenging resin (5 g) under inert atmosphere. The vessel was rinsed with THF (50 mL) and the resulting mixture was heated to 65±5° C. and stirred for 3 hours. The resin was filtered and washed with THF (100 mL) and the filtrate and the washings were combined. The solvent was switched to acetonitrile (500 mL) using a solvent-chasing technique. The resulting slurry was diluted with acetonitrile (1000 mL) and heated to 45±5° C. with stirring under inert atmosphere. A 4 M HCl solution (84.4 mL, 338 mmol) was then added over 40 min and the resulting mixture was heated to 65±5° C. and stirred for 5 hours. The obtained slurry was cooled to 25±5° C., aged for overnight at this temperature with stirring, and then filtered. The filter cake was washed with acetonitrile (250 mL). The obtained wet solid was dried in vacuo at 50±10° C. for 3 hours. 51.3 g of (10) was obtained as an off-white solid (105%). This compound has 1.5-2 eq of associated water. $^1$H NMR (500 MHz, DMSO-$d_6$): δ (ppm) 1.45 (d, J=7.6 Hz, 2H), 1.68 (d, J=7.6 Hz, 3H), 1.79-1.92 (m, 2H), 1.92-1.99 (m, 1H), 3.65 (br s, 1H), 3.89 (s, 3H), 4.37 (d, J=3.8 Hz, 2H), 4.44 (br s, 1H), 6.80 (d, J=5.7 Hz, 1H), 8.10 (br s, 3H), 8.30 (s, 1H), 8.36 (br s, 1H), 8.83 (s, 1H).

Step 8. 6-(((1R,2S)-2-aminocyclohexyl)amino)-7-fluoro-4-(1-methyl-1H-pyrazol-4-yl)-1H-pyrrolo[3,4-c]pyridin-3(2H)-one citrate (Compound 1 Citrate)

To a suspension of (10) (10.0 g, 23.0 mmol) in water (170 mL) was added palladium-scavenging resin (1.0 g) at 25±10° C. The resulting mixture was heated to 85±5° C. and stirred for 15 hours at this temperature. The resin was filtered and washed with hot water (10 mL). The filtrate and the washings were combined, cooled to 50±5° C., and then diluted with THF (60 mL). To the resulting mixture was added 4 M NaOH solution (12.1 mL, 48.2 mmol) over 15 min at 50±5° C. with stirring. After stirring for 5 minutes, a solution of citric acid monohydrate (10.1 g, 48.2 mmol) in water (20 mL) was added over 4 hours at 50±5° C. The resultant slurry was stirred at 50±5° C. for 3 hours, and then at 25±5° C. for 19 hours. The slurry was filtered, and the filter cake was washed with a pre-mixed solution of THF-water (1:1, 30 mL). The obtained wet solid was dried in vacuo at 50±10° C. for 18 hours. 10.2 g Compound 1 citrate was obtained as a white solid (86%). $^1$H NMR (500 MHz, DMSO-$d_6$): δ (ppm) 1.42-1.50 (m, 2H), 1.57-1.65 (m, 1H), 1.65-1.73 (m, 2H), 1.78-1.92 (m, 3H), 2.50 (dd, J=15, 15 Hz, 4H), 3.66 (br s, 1H), 3.89 (s, 3H), 4.37 (d, J=5.0 Hz, 2H), 4.44 (br s, 1H), 6.74 (d, J=6.6 Hz, 1H), 8.29 (s, 1H), 8.36 (br s, 1H), 8.83 (s, 1H).

Example 3. Synthesis of 6-(((1R,2S)-2-aminocyclohexyl)amino)-7-fluoro-4-(1-methyl-1H-pyrazol-4-yl)-1H-pyrrolo[3,4-c]pyridin-3(2H)-one dihydrochloride (Compound 1 dihydrochloride)

Step 1. tert-butyl 4-chloro-6,7-difluoro-3-oxo-1H-pyrrolo[3,4-c]pyridine-2(3H)-carboxylate (17)

To a cooled (5±5° C.) suspension of (14) (500 mg, 2.44 mmol) in dichloromethane (2 mL) were added triethylamine (0.68 mL, 4.89 mmol) and 4-dimethylaminopyridine (6.0 mg, 0.049 mmol) with stirring under inert atmosphere. A solution of (Boc)$_2$O (0.63 ml, 2.93 mL) in dichloromethane (0.5 mL) was added over 20 minutes and rinsed with dichloromethane (0.5 mL). The resulting mixture was warmed to 25±5° C. and stirred for 24 hours at this temperature. 2-Propanol (20 mL) was then added over 30 minutes. The resulting slurry was aged for 5 hours and then filtered. The filter cake was washed with 2-propanol (1.0 mL×3). The obtained wet solid was dried in vacuo at 40±10° C. for 2 hours. 562 mg of (17) was obtained as a pale pink solid (75%). $^1$H NMR (500 MHz, DMSO-d$_6$): δ (ppm) 1.53 (s, 9H), 4.94 (s, 2H).

Step 2. tert-butyl 6-(((1R,2S)-2-((tert-butoxycarbonyl)amino)cyclohexyl)amino)-4-chloro-7-fluoro-3-oxo-1H-pyrrolo[3,4-c]pyridine-2(3H)-carboxylate (7)

To a solution of (6) (crude oil, 373 mg, 1.74 mmol) in 2-propanol (2.3 mL) were added (17) (500 mg, 1.64 mmol) and N-methylmorpholine (0.22 mL, 1.97 mmol) at 25±5° C. The reaction mixture was heated to 65±5° C. and stirred for 18 hours at this temperature. Water (4 mL) was added over 40 min. The resulting slurry was aged for 1 hour at 65±5° C., and for 3 hours at 25±5° C. After filtration of the slurry, the filter cake was washed with a pre-mixed solution of 2-propanol-water (1:2, 2 mL), and with water (2 mL). The obtained wet solid was dried in vacuo at 40±10° C. for 6 hours. 690 mg of (7) was obtained as a white solid (84%). $^1$H NMR (500 MHz, DMSO-d$_6$): δ (ppm) 1.10-1.81 (m, 8H), 1.36 (br s, 9H), 1.50 (s, 9H), 3.83 (br s, 1H), 4.12 (br s, 1H), 4.72 (s, 2H), 6.68 (br d, J=7.5 Hz, 1H), 7.18 (br d, J=5.5 Hz, 1H).

Step 3. tert-butyl 6-(((1R,2S)-2-((tert-butoxycarbonyl)amino)cyclohexyl)amino)-7-fluoro-4-(1-methyl-1H-pyrazol-4-yl)-3-oxo-1H-pyrrolo[3,4-c]pyridine-2(3H)-carboxylate (9)

To a solution of DMAc (2.0 mL) and water (0.14 mL) were added (7) (500 mg, 1.00 mmol), 1-methyl-4-(4,4,5,5-tetramethyl-1,3,2-dioxaborolan-2-yl)-1H-pyrazole (250 mg, 1.20 mmol), and potassium carbonate (277 mg, 2.00 mmol) under inert atmosphere at 25±10° C. The resulting mixture was degassed by repeating evacuation and back-filling with nitrogen. 1,1'-bis(di-tert-butylphosphino)ferrocene palladium dichloride (Pd-118 catalyst, 6.5 mg, 0.010 mmol, 1 mol %) was then added, and the vessel was rinsed with a solution of DMAc (0.5 mL) and water (0.04 mL). Degassing was conducted again. The resulting mixture was heated to 85±5° C., and stirred for 3 hours at this temperature. The reaction mixture was cooled to 60±5° C., and a solution of N-acetyl-L-cysteine (16 mg, 0.10 mmol) in water (0.15 mL) was added in one portion at this temperature. After stirring for 1 hour, water (4 mL) was added over 1 hour at 60±5° C. The resulting slurry was stirred for 1 hour at 60±5° C. and then for 18 hours at 25±5° C. After filtration of the slurry, the filter cake was washed with water (1.5 mL), and with a pre-mixed solution of 2-propanol-water (1:1, 1.5 mL, ×2). The obtained wet solid was dried in vacuo at 40±10° C. for 5 hours. 554 mg of (9) was obtained as a brown solid (102%). $^1$H NMR (500 MHz, DMSO-d$_6$): δ (ppm) 1.34 (s, 9H), 1.47-1.57 (m, 13H), 1.58-1.66 (m, 2H), 1.72-1.86 (m, 2H), 3.86 (br s, 1H), 3.91 (s, 3H), 4.31 (br s, 1H), 4.73 (s, 2H), 6.71 (d, J=10 Hz, 1H), 6.79 (d, J=10 Hz, 1H), 8.23 (s, 1H), 8.67 (s, 1H).

Step 4. 6-(((1R,2S)-2-aminocyclohexyl)amino)-7-fluoro-4-(1-methyl-1H-pyrazol-4-yl)-1H-pyrrolo[3,4-c]pyridin-3(2H)-one dihydrochloride (10)

(9) (10.0 g, 18.4 mmol) was suspended in acetonitrile (200 mL) and heated to 50±5° C. with stirring. A 4 M HCl solution (13.8 mL, 55.1 mmol) was then added over 14 minutes. The reaction mixture was stirred for 1 hour at 50±5° C. and then for 16 hours at 70±5° C. The resultant slurry was cooled to 25±5° C., aged for 5 hours at this temperature, and filtered. The filter cake was washed with acetonitrile (30 mL). The obtained wet solid was dried in vacuo at 50±10° C. for 18 hours. 8.04 g of the title compound was obtained as an off-white solid (105%). This compound was found to have 1.5-2 eq of associated water.

Example 4. Synthesis of 6-(((1R,2S)-2-aminocyclohexyl)amino)-7-fluoro-4-(1-methyl-1H-pyrazol-4-yl)-1H-pyrrolo[3,4-c]pyridin-3(2H)-one citrate (Compound 1 Citrate)

Step 1. tert-butyl ((1S,2R)-2-((6-chloro-5-cyano-3-fluoropyridin-2-yl)amino)cyclohexyl)carbamate (19)

To a solution of (18) which may be prepared as disclosed in U.S. Pat. No. 8,440,689, incorporated herein in its entirety (102.5 g, 1.2 eq) in IPA (228 mL) at RT, were added DMSO (152 mL), DIPEA (97.3 mL, 1.4 eq), and (1) (76.11 g, 0.399 mol). The resulting solution was stirred at RT for 25 min and was heated gradually to 70° C. over 40 min, followed by stirring at 70° C. for 2 h.

The reaction mixture was then cooled to RT and diluted with IPA (152 mL) and H$_2$O (76 mL). The resulting solution was seeded and stirred at RT for 1 h to give a thick slurry. H$_2$O (228 mL) was added at RT over 40 min, and the resulting slurry was stirred at RT for 20 min. H$_2$O (76 mL) was added over 30 min, followed by stirring at RT for 2 h. The solids were collected by filtration, washed with 2:3 (v/v) IPA/H$_2$O (532 mL), and dried in a vacuum oven to afford 140.82 g of (19) as pale yellow solid. 96% isolated yield. $^1$H NMR (DMSO-d$_6$, 500 MHz): δ (ppm) 1.14-1.25 (m, 2H), 1.35 (s, 9H), 1.45-1.65 (m, 4H), 1.70-1.80 (m, 2H), 3.87 (br s, 0.85H), 3.98 (br s, 0.30H), 4.08 (br s, 0.85H), 6.32 (br s, 0.15H), 6.67 (d, J=7.9 Hz, 0.85H), 7.49 (d, J=5.7 Hz, 0.85H), 7.79 (br s, 0.15H), 7.95 (d, J$_{HF}$=10.4 Hz, 1H).

Step 2. (3aR,7aS)-tert-butyl 3-(6-chloro-5-cyano-3-fluoropyridin-2-yl)octahydro-1H-benzo[d]imidazole-1-carboxylate (20)

A mixture of (19) (140.14 g, 0.380 mol), MeCN (700.7 mL), paraformaldehyde (22.82 g, 2 eq) and formic acid (57.35 mL, 4 eq) was stirred at RT for 1 h and then heated to 60° C. followed by stirring at 60° C. for 16 h. The reaction was then cooled to RT followed by addition of H$_2$O (140.1 mL). The resulting solution was seeded and stirred at RT for 30 min to form a seed bed. H$_2$O (560.6 mL) was added at RT over 1.5 h, and the resulting slurry was stirred at RT for 3.5 h. The solid was collected by filtration, washed with 2:3 (v/v) MeCN/H$_2$O (560 mL) and dried in a vacuum oven to give 136.31 g of (20) as pale yellow solid. 94% isolated yield. $^1$H NMR (CDCl$_3$, 500 MHz): δ (ppm) 1.31-1.39 (m, 1H), 1.43-1.50 (m, 2H), 1.50 (s, 9H), 1.56-1.72 (m, 3H), 1.86-1.93 (m, 1H), 2.43 (br s, 1H), 4.91 (dd, J=8.5, 1.3 Hz, 1H), 5.11 (d, J=6.9 Hz, 1H), 7.38 (d, J=11.7 Hz, 1H).

Step 3. (3aR,7aS)-tert-butyl 3-(5-carbamoyl-6-chloro-3-fluoropyridin-2-yl)octahydro-1H-benzo[d]imidazole-1-carboxylate (21)

To a stirred mixture of (20) (131.79 g, 0.3461 mol), IPA (659 mL), DMSO (264 mL) and K$_2$CO$_3$ (35.88 g, 0.75 eq) at RT was added hydrogen peroxide (30%, 53.0 mL, 1.5 eq) over 30 min while maintaining the internal temperature between 16° C. and 23° C. (exothermic). After stirring at 17-18° C. for 40 min, the reaction was allowed to warm to 26° C. over 80 min (moderately exothermic). The reaction was further stirred at RT for 20 h, and H$_2$O (527 mL) was added over 5 min while maintaining the batch temperature between 23° C. and 28° C. (exothermic). The resulting hazy solution was seeded and stirred at RT for 1 h to give a seed bed. H$_2$O (791 mL) was added at RT over 1 h, and the resulting slurry was cooled to 4° C., followed by stirring at 4° C. for 20 min. The solid was collected by filtration, washed with 1:3 (v/v) IPA/H$_2$O (395 mL), suction-dried at RT, and was further dried in a vacuum oven (40° C.) for 4 h to afford 135.25 g of (21) as colorless solid. 98% isolated yield (uncorrected). $^1$H NMR (CDCl$_3$, 500 MHz): δ (ppm) 1.30-1.38 (m, 1H), 1.43-1.47 (m, 2H), 1.50 (s, 9H), 1.55-1.60 (m, 1H), 1.66-1.74 (m, 2H), 1.83-1.90 (m, 1H), 2.36 (br s, 1H), 4.00 (dt, J=5.4, 5.0 Hz, 1H), 4.40 (dt, J=7.9, 5.7 Hz, 1H), 4.90 (dd, J=7.9, 1.3 Hz, 1H), 5.08 (d, J=6.9 Hz, 1H), 5.95 (br s, 1H), 7.05 (br s, 1H), 7.98 (d, J=12.9 Hz, 1H).

Step 4. (3aR,7aS)-tert-butyl 3-(4-chloro-7-fluoro-1-hydroxy-3-oxo-2,3-dihydro-1H-pyrrolo[3,4-c]pyridin-6-yl)octahydro-1H-benzo[d]imidazole-1-carboxylate (22)

To a THF solution of LiHMDS (1035 mL, 1.0 M, 3.3 eq) under nitrogen atmosphere was added a degassed solution of (22) (125.15 g, 0.3138 mol) and anhydrous DMF (72.89 mL, 3 eq) in THF (325 mL+50 mL rinse) over 15 min during which the internal temperature increased from 20° C. to 31° C. without external cooling (moderately exothermic). The resulting solution was stirred at 25-30° C. for 2 h and poured into a stirred mixture of THF (250.3 mL) and 1 M HCl aq (1.41 L, 4.5 eq) over 40 min while maintaining the temperature below 10.5° C. (exothermic). After addition of isopropyl acetate (375 mL), the resulting biphasic solution was allowed to warm to RT with stirring, followed by addition of isopropyl acetate (375 mL). The organic layer was separated, diluted with isopropyl acetate (375 mL), and washed with 5% NaCl aq (625 mL). The solution was solvent-switched to isopropyl acetate on rotavap while feeding a total of 1.2 L isopropyl acetate. The net weight of the resulting slurry was adjusted to 789 g by addition of isopropyl acetate. Heptane (1.0 L) was added over 1.5 h, and the resulting slurry was stirred at RT overnight. Heptane (251 mL, 2 vol) was then added at RT over 20 min, and the slurry was stirred at RT for 1 h. The solid was collected by filtration, washed with 1:2 (v/v) isopropyl acetate/heptane (625 mL), and suction-dried at RT to afford 111.8 g of (22) as a mixture of diastereomers (1:1). 84% isolated yield. $^1$H NMR (DMSO-d$_6$, 500 MHz): δ (ppm) 1.25-1.40 (m, 3H), 1.44 (s, 9H), 1.45-1.51 (m, 1H), 1.53-1.70 (m, 2H), 1.74-1.82 (m, 1H), 2.27 (br s, 1H), 3.95-3.99 (m, 1H), 4.36-4.41 (m, 1H), 4.84-4.87 (m, 1H), 4.96 (dd, J=7.6, 1.9 Hz, 0.5H), 4.98 (dd, J=7.9, 2.2 Hz, 0.5H), 5.96 (br s, 0.5H), 5.98 (br s, 0.5H), 6.60 (d, J=9.5 Hz, 0.5H), 6.69 (d, J=9.1 Hz, 0.5H), 8.95 (br s, 1H).

Step 5. (3aR,7aS)-tert-butyl 3-(4-chloro-7-fluoro-3-oxo-2,3-dihydro-1H-pyrrolo[3,4-c]pyridin-6-yl)octahydro-1H-benzo[d]imidazole-1-carboxylate (23)

To a solution of (22) (111.01 g, 0.260 mol) in THF (555 mL) at 5° C., were added 4-dimethylaminopyridine (DMAP) (635 mg, 0.02 eq), pyridine (27.3 mL, 1.3 eq), and Ac$_2$O (27.0 mL, 1.1 eq) while maintaining the internal temperature below 5° C. The resulting hazy solution was stirred at 0-5° C. for 1 h. The reaction mixture was then diluted with methyl t-butyl ether (MTBE) (555 mL) while maintaining the internal temperature below 5° C. and quenched by addition of 5% NaCl aq (333 mL). The resulting biphasic solution was allowed to warm to RT over 10 min with stirring, followed by stirring at RT for 30 min. The organic layer was separated and washed with 5% NaCl aq (333 mL) and 15% citric acid aq (333 mL). The solution was azeotropically dried on rotavap by feeding a total of 3.8 L THF. The net weight of the solution was adjusted to 802 g by addition of THF. The solution was cooled to 3° C., and dry DMAc (111 mL) was added. NaBH$_4$ (11.8 g, 1.2 eq) was added in four portions over 36 min (exothermic), while maintaining the internal temperature below 8.5° C. The resulting mixture was stirred at 0-5° C. for 3.5 h. NaBH$_4$ (0.49 g, 0.05 eq) was added, and the reaction was further stirred at 0-5° C. for 45 min. The reaction was quenched by carefully adding 5% NaCl aq (333 mL) over 7 min while maintaining the internal temperature below 15° C. (exothermic and gas evolution). The resulting mixture was stirred at RT until the gas evolution almost ceased (20-30 min). The aqueous layer was discarded. The organic layer was diluted with IPA (555 mL) and concentrated on rotavap to ca. 777 mL to give a thin suspension. The resulting suspension was further solvent-switched to IPA by feeding a total of 888 mL IPA. The net weight of the resulting slurry was adjusted to 634 g by addition of IPA. H$_2$O (333 mL) was added at RT over 1 h, and the resulting slurry was stirred at RT for 20 h. The solid was collected by filtration, washed with 1:1 (v/v) IPA/H$_2$O (444 mL), dried in a vacuum oven to afford 96.4 g of (23). 90% isolated yield. $^1$H NMR (DMSO-d$_6$, 500 MHz): δ (ppm) 1.25-1.40 (m, 3H), 1.44 (s, 9H), 1.45-1.51 (m, 1H), 1.60-1.72 (m, 2H), 1.75-1.82 (m, 1H), 2.25 (br s, 1H), 3.97 (q, J=5.0 Hz, 1H), 4.36 (dt, J=6.9, 6.3 Hz, 1H), 4.40 (s, 2H), 4.84 (d, J=7.3 Hz, 1H), 4.97 (dd, J=7.6, 1.9 Hz, 1H), 8.56 (br s, 1H).

Step 6. (3aR,7aS)-tert-butyl 3-(2-(tert-butoxycarbonyl)-4-chloro-7-fluoro-3-oxo-2,3-dihydro-1H-pyrrolo[3,4-c]pyridin-6-yl)octahydro-1H-benzo[d]imidazole-1-carboxylate (24)

To a stirred solution of (23) (93.38 g, 0.2267 mol) in THF (654 mL) at 3° C., were added DMAP (1.38, 0.05 eq) and a solution of (Boc)$_2$O (51.95 g, 1.05 eq) in THF (80 mL+13 mL rinse) over 1 h. The resulting pinkish hazy solution was stirred at 0° C. for 40 min. The reaction was diluted with IPA and solvent-switched to IPA on rotavap by feeding a total of 1.3 L IPA. The net weight of the solution was adjusted to 556 g by addition of IPA. The solution was then seeded (115 mg) and stirred at RT for 1 h to give a seed bed. H$_2$O (560 mL) was added over 1 h, and the resulting slurry was stirred at RT for 17 h. The solid was collected by filtration, washed with 1:2 (v/v) IPA/H$_2$O (466 mL) and suction-dried at RT for 3 h to afford 108.62 g of (24) as off-white to pale pinkish solid. 94% isolated yield. $^1$H NMR (DMSO-d$_6$, 500 MHz): δ (ppm) 1.27-1.41 (m, 4H), 1.44 (s, 9H), 1.51 (s, 9H), 1.58-1.70 (m, 2H), 1.78-1.84 (m, 1H), 2.31 (br s, 1H), 3.97 (dt, J=5.4, 5.0 Hz, 1H), 4.39-4.43 (m, 1H), 4.76 (s, 2H), 4.88 (d, J=7.3 Hz, 1H), 5.02 (dd, J=7.9, 2.5 Hz, 1H).

Step 7. (3aR,7aS)-tert-butyl 3-(2-(tert-butoxycarbonyl)-7-fluoro-4-(1-methyl-1H-pyrazol-4-yl)-3-oxo-2,3-dihydro-1H-pyrrolo[3,4-c]pyridin-6-yl)octahydro-1H-benzo[d]imidazole-1-carboxylate (25)

To a flask containing (24) (105.16 g), were added DMAc/H$_2$O (525.8 mL/36.8 mL, pre-mixed), K$_2$CO$_3$ (56.89 g, 2 eq)

and (8) (51.38 g, 1.2 eq). The resulting suspension was degassed by repeating an evacuation-$N_2$ refill cycle five times, followed by addition of dichloro[1,1'-bis(di-tert-butylphosphino)ferrocene]palladium(II) (939 mg, 0.7 mol %). The mixture was degassed again (×5) and gradually heated to 80° C. over 20 min, followed by heating to 80° C. for 70 min. The reaction mixture was cooled to 5° C. and diluted with EtOAc (1050 mL). $H_2O$ (735 mL) was added while maintaining the batch temperature below 25° C. (exothermic). The organic layer was separated, washed with $H_2O$ (525 mL), filtered through a pad of Celite (rinsed with 150 mL of EtOAc), and solvent-switched to IPA on rotavap by feeding a total of 1.5 L IPA. The net weight of the solution was adjusted to 775 g by addition of IPA. The solution was heated to 45° C., and $H_2O$ (420 mL) was added over 5 min. The resulting solution was seeded (115 mg) and stirred at 45° C. for 1.5 h to form a seed bed. $H_2O$ (630 mL) was added at 45° C. over 1 h, and the resulting slurry was allowed to cool to RT, followed by stirring at RT overnight. The solid was collected by filtration, washed with 2:3 (v/v) IPA/$H_2O$ (525 mL), and dried in a vacuum oven to afford 106.15 g of (25). 93% isolated yield. $^1$H NMR (DMSO-$d_6$, 500 MHz): δ (ppm) 1.45 (s, 9H), 1.53 (s, 9H), 1.31-1.65 (m, 4H), 1.67-1.76 (m, 2H), 1.81-1.88 (m, 1H), 2.24 (br s, 1H), 3.92 (s, 3H), 3.99 (q, J=5.3 Hz, 1H), 4.44-4.49 (m, 1H), 4.75 (s, 2H), 4.91 (d, J=7.0 Hz, 1H), 5.06 (dd, J=7.9, 2.2 Hz, 1H), 8.18 (s, 1H), 8.69 (s, 1H).

Step 8. 6-(((1R,2S)-2-aminocyclohexyl)amino)-7-fluoro-4-(1-methyl-1H-pyrazol-4-yl)-1H-pyrrolo[3,4-c]pyridin-3(2H)-one trifluoroacetate (26)

To a flask containing (25) (2.00 g) was added TFA (8.00 mL, 30 eq) without stirring. The resulting mixture was stirred at RT for 30 min to give a homogeneous solution. After cooling to 4° C., a solution of hydrazine monohydrate (1.74 mL, 10 eq) in EtOH (6.0 mL) was added dropwise over 10 min followed by slow addition of 8 N NaOH aq (11.2 mL, 25 eq) over 10 min while maintaining the internal temperature below 10° C. The resulting hazy solution was gradually heated to 55° C. over 15 min and further stirred at 52-57° C. for 6.5 h. The resulting suspension was allowed to cool to RT and stirred at RT for 1 h. The solid was collected by filtration, washed with 20% EtOH/$H_2O$ (12 mL) and suction-dried under air at RT for 3 h to afford (26) (1.57 g). 97% isolated yield (corrected for output purity). $^1$H NMR (DMSO-$d_6$, 500 MHz): δ (ppm) 1.42-1.50 (m, 2H), 1.60-1.73 (m, 3H), 1.80-1.95 (m, 3H), 3.66-3.70 (m, 1H), 3.89 (s, 3H), 4.37 (d, J=17.7 Hz, 1H), 4.38 (d, J=17.7 Hz, 1H), 4.45-4.50 (m, 1H), 6.78 (d, J=6.6 Hz, 1H), 7.88 (br s, 3H), 8.30 (s, 1H), 8.35 (s, 1H), 8.82 (s, 1H).

Step 9. 6-(((1R,2S)-2-aminocyclohexyl)amino)-7-fluoro-4-(1-methyl-1H-pyrazol-4-yl)-1H-pyrrolo[3,4-c]pyridin-3(2H)-one (Compound 1 Citrate)

A suspension of (26) (1.00 g, 76.4 wt % as free base) in 40% MeCN/$H_2O$ (20.0 mL) was heated to 72-74° C. for 30 min to give a clear solution containing a small amount of black particles. The solution was filtered hot into a separate flask via a syringe filter (rinsed with 2 mL of 40% MeCN/$H_2O$). The combined filtrate was heated back to 70° C. and then cooled to 55° C. to give a thin suspension. A solution of sodium dihydrogencitrate monohydrate (0.618 g, 1.2 eq, dissolved at a high temperature) in $H_2O$ (2.0 mL) was added over 5 min. The resulting slurry was stirred at 55-57° C. for 2 h, gradually cooled to 4° C. over 4 h and stirred at 1-4° C. for 2 h. The solid was collected by filtration, washed with $H_2O$ (10 mL and 6 mL) and suction-dried to afford Compound 1 citrate (1.09 g). 92% isolated yield (corrected for input and output purity). $^1$H NMR (DMSO-$d_6$, 500 MHz): δ (ppm) 1.42-1.50 (m, 2H), 1.58-1.73 (m, 3H), 1.79-1.95 (m, 3H), 2.49 (d, J=15.1 Hz, 2H), 2.55 (d, J=15.1 Hz, 2H), 3.65-3.69 (m, 1H), 3.89 (s, 3H), 4.38 (d, J=17.7 Hz, 1H), 4.39 (d, J=17.7 Hz, 1H), 4.43-4.49 (m, 1H), 6.75 (d, J=6.6 Hz, 1H), 8.29 (s, 1H), 8.35 (s, 1H), 8.82 (s, 1H), 9.61 (brs, 5H).

Example 5. Synthesis of 6-(((1R,2S)-2-aminocyclohexyl)amino)-7-fluoro-4-(1-methyl-1H-pyrazol-4-yl)-1H-pyrrolo[3,4-c]pyridin-3 (2H)-one citrate (Compound 1 Citrate)

Step 1. 6-(((1R,2S)-2-aminocyclohexyl)amino)-7-fluoro-4-(1-methyl-1H-pyrazol-4-yl)-1H-pyrrolo[3,4-c]pyridin-3(2H)-one (27, Compound 1 Free Base)

To a flask containing (25) (2.00 g) was added TFA (8.00 mL, 30 eq) without stirring. The resulting mixture was stirred at RT for 30 min to give a homogeneous solution. After cooling to 4° C., a solution of hydrazine monohydrate (1.74 mL, 10 eq) in EtOH (2.0 mL) was added dropwise over 20 min followed by slow addition of 8 N NaOH aq (11.2 mL, 25 eq) over 15 min while maintaining the internal temperature below 10° C. (both additions were exothermic). The resulting hazy solution was gradually heated to 58° C. over 15 min and further stirred at 58-60° C. for 22 h. The suspension was allowed to cool to 41° C., and 8 N NaOH aq (1.7 mL, 3.8 eq) was added dropwise over 5 min at the same temperature to afford a hazy solution, which turned into a slurry again within a minute. After aging the slurry at 41° C. for 20 min, 8 N NaOH aq (0.55 mL, 1.2 eq) was added dropwise over 10 min at the same temperature. The resulting slurry was stirred at 41° C., allowed to cool to RT, and stirred at RT for 3 h to afford a thick slurry. The solid was collected by filtration, washed with 5% EtOH/$H_2O$ (12 mL) and suction-dried under air at RT for 5 h to afford (27, Compound 1 free base) (1.29 g). 96% isolated yield (corrected for output purity). $^1$H NMR (DMSO-$d_6$, 500 MHz): δ (ppm) 1.32-1.41 (m, 2H), 1.55-1.74 (m, 6H), 3.11-3.15 (m, 1H), 3.31 (br s, 4H), 3.89 (s, 3H), 4.06-4.12 (m, 1H), 4.35 (s, 2H), 6.38 (d, J=6.9 Hz, 1H), 8.24 (s, 1H), 8.25 (s, 1H), 8.78 (s, 1H).

Step 2. 6-(((1R,2S)-2-aminocyclohexyl)amino)-7-fluoro-4-(1-methyl-1H-pyrazol-4-yl)-1H-pyrrolo[3,4-c]pyridin-3(2H)-one (Compound 1 Citrate)

A 50 mL flask was charged with (27, Compound 1 free base) (1.00 g, 91.0 wt %, 0.910 g assay) and 95% EtOH/$H_2O$ (14.0 mL). The resulting mixture was heated to 57° C. to give a red purple solution, which turned into a pale yellow solution containing a small amount of black particles after aging at 57° C. for 10 min. The solution was further stirred at 57° C. for 20 min and then heated to 67° C. for 20 min. The solution was filtered hot into a separate 50 mL flask via a syringe filter (rinsed with 4 mL of 95% EtOH/$H_2O$). The combined filtrate was heated to 57° C. and a solution of citric acid monohydrate (0.666 g, 1.2 eq) in 95% EtOH/$H_2O$ (3.0 mL) was added dropwise over 10 min. The resulting thick slurry was diluted with 95% EtOH/$H_2O$ (2 mL) to aid the agitation and stirred at 55-60° C. for 2 h. The slurry was then gradually cooled to RT over 1 h and stirred at RT for 1 h. The solid was collected by filtration, washed with 95%

EtOH/H$_2$O (15 mL) and suction-dried to afford Compound 1 citrate (1.36 g). HPLC assay revealed a free base content of 65.9 wt % (theoretical: 64.2 wt %). 98% isolated yield (corrected for input and output purity).

Example 6. Synthesis of 6-(((1R,2S)-2-aminocyclohexyl)amino)-7-fluoro-4-(1-methyl-1H-pyrazol-4-yl)-1H-pyrrolo[3,4-c]pyridin-3(2H)-one citrate (Compound 1 Citrate)

Step 1. 6-(((1R,2S)-2-aminocyclohexyl)amino)-7-fluoro-4-(1-methyl-1H-pyrazol-4-yl)-1H-pyrrolo[3,4-c]pyridin-3 (2H)-one hydroiodide (28)

A 50 mL round bottom flask was charged with (25) (1.00 g), NaI (1.62 g, 6 eq), and MeCN (7.0 mL). The resulting mixture was cooled to 0° C. before 57% HI (0.040 mL, 0.17 eq) and TMSCl (1.37 mL, 6 eq) were added. The resulting suspension was stirred at 0° C. for 20 min and allowed to warm to RT, followed by stirring at RT for 50 min. The reaction was then cooled to 0° C. and quenched by addition of a mixture of hydrazine monohydrate (1.74 mL, 20 eq) and H$_2$O (10 mL). The resulting biphasic solution was stirred at RT for 100 min to give a thin suspension. H$_2$O (11 mL) was added at RT, and the resulting slurry was cooled to 0° C. and stirred at the same temperature for 2 h. The solids were collected by filtration and suction-dried to afford 0.810 g of (28) as an off-white solid. 67.6 wt % as free base by LC assay. 88% isolated yield. $^1$H NMR (DMSO-d$_6$, 500 MHz): δ (ppm) 1.40-1.49 (m, 2H), 1.57-1.70 (m, 3H), 1.76-1.90 (m, 3H), 3.60-3.64 (m, 1H), 3.89 (s, 3H), 4.37 (d, J=18.0 Hz, 1H), 4.39 (d, J=18.0 Hz, 1H), 4.40-4.44 (m, 1H), 6.68 (d, J=6.6 Hz, 1H), 7.23 (br s, 3H), 8.29 (s, 1H), 8.33 (s, 1H), 8.82 (s, 1H).

Step 2. 6-(((1R,2S)-2-aminocyclohexyl)amino)-7-fluoro-4-(1-methyl-1H-pyrazol-4-yl)-1H-pyrrolo[3,4-c]pyridin-3(2H)-one (Compound 1 Citrate)

A 20 mL vial was charged with (28) (200 mg, 67.6 wt % as free base) and H$_2$O (3.4 mL) and heated to 80° C. to give a suspension. A solution of sodium dihydrogencitrate monohydrate (147 mg, 1.6 eq) in H$_2$O (1.2 mL) was added. The resulting slurry was heated to 80° C. for 15 min and allowed to cool to RT, followed by aging at RT overnight. The solids were collected by filtration, washed with H$_2$O (2 mL) and suction-dried to afford 0.19 g of Compound 1 citrate as fine pale yellow powder. 66.3 wt % as free base by LC assay. 93% isolated yield (corrected).

Example 7. Synthesis of 6-(((1R,2S)-2-aminocyclohexyl)amino)-7-fluoro-4-(1-methyl-1H-pyrazol-4-yl)-1H-pyrrolo[3,4-c]pyridin-3(2H)-one hydrochloride dihydrate (Compound 1 Hydrochloride Dihydrate)

Step 1. Isopropyl 2,6-dichloro-5-fluoronicotinate (30)

To a solution of (29) (200 g, 952.43 mmol) in THF (dry) (2000 mL) was added oxalyl chloride (86 ml, 1000.05 mmol) and DMF (0.696 g, 9.52 mmol) at 0° C. dropwise. The mixture was stirred at 0° C. for 30 min and then warmed to rt, and stirred for 1 h. The reaction mixture was then concentrated in vacuo. The residue was dissolved in THF (dry) (2000 mL) and isopropanol (109 mL, 1428.64 mmol) and pyridine (92 mL, 1142.91 mmol) were added to the solution at 0° C. The mixture was stirred at room temperature for 1 h and then quenched with 1N HCl aq. (150 mL) at 0° C. and extracted with EtOAc (400 mL), water (400 mL) and brine (400 mL). The organic layer was separated, washed with brine (600 mL×2), dried over MgSO4 and concentrated in vacuo. The residue was purified by column chromatography (NH-silica gel, eluted with 20% EtOAc in Hexane), concentrated, and dried to give (30) (225 g, 894 mmol, 94%) as (a) colorless oil.

Step 2. Isopropyl 6-(((1R,2S)-2-((tert-butoxycarbonyl)amino)cyclohexyl)amino)-2-chloro-5-fluoronicotinate (31)

To a solution of (30) (106 g, 419.96 mmol) in 2-propanol (1.5 L) were added (18) (108 g, 503.96 mmol) and N,N-diisopropylethylamine (0.219 L, 1259.89 mmol) at room temperature. The mixture was stirred for 3.5 days at reflux. The reaction solvent was then removed in vacuo and the residue was dissolved in EtOAc (1000 mL). The solution was washed with 1N HCl, sat. NaHCO$_3$ aq., and brine, dried over Na$_2$SO$_4$, and concentrated in vacuo. The resulting residue was dissolved in isopropyl ether (500 mL) and hexane (100 mL) and the solution was seeded. The resulting precipitate was collected through filtration and washed with isopropyl ether to give (31) (99.6 g, 232 mmol, 55.2%).

Step 3. (3aR,7aS)-tert-butyl 3-(6-chloro-3-fluoro-5-(isopropoxycarbonyl)pyridin-2-yl)octahydro-1H-benzo[d]imidazole-1-carboxylate (32)

To a solution of isopropyl (31) (129.3 g, 300.76 mmol) in THF (1.4 L) were added paraformaldehyde (45.2 g, 1503.79 mmol) and formic acid (280 mL, 7300.32 mmol) at room temperature. The mixture was stirred for 3 h at reflux and then neutralized with 4N NaOH (1.8 L) at 25° C. The organic layer was separated and the aqueous layer was extracted with EtOAc (×500 mL). The combined organic layers were washed with 0.5N NaOH (1 L), brine (1 L), dried over Na$_2$SO$_4$, and concentrated in vacuo to provide (32) which was carried on to the next reaction without further purification.

Step 4. 6-((3aS,7aR)-3-(tert-butoxycarbonyl)octahydro-1H-benzo[d]imidazol-1-yl)-2-chloro-5-fluoronicotinic acid (33)

To a solution of (32) (300.76 mmol) in a mixture of THF (600 mL), MeOH (600 mL) and water (150 mL) was added a 4M lithium hydroxide (113 ml, 451.14 mmol) solution at room temperature. The mixture was stirred at the same temperature for 1 day. The mixture was then diluted with EtOAc (500 ml), acidified with a 1N HCl (400 mL) solution and extracted with EtOAc. The organic layer was washed with water and brine, dried over Na$_2$SO$_4$ and concentrated in vacuo. The crude product was washed with isopropyl ether and collected through filtration to give (33) (111.9 g, 280 mmol, 93% in 2 steps) as a white solid.

Step 5. (3aR,7aS)-tert-butyl 3-(4-chloro-7-fluoro-1-hydroxy-3-oxo-1,3-dihydrofuro[3,4-c]pyridin-6-yl)octahydro-1H-benzo[d]imidazole-1-carboxylate (34)

To a solution of n-Butyllithium (419 mL, 670.46 mmol) in THF (dry) (1120 mL) was added a solution of diisopropylamine (96 mL, 684.43 mmol) in THF (dry) (110 mL) at −40° C. under N$_2$. The mixture was then stirred at −40° C.

for 10 min. To the reaction mixture was added a solution (33) (111.7 g, 279.36 mmol) in THF (dry) (670 ml) at −40° C. The mixture was stirred at −25° C. for 30 min. To the reaction mixture was added DMF (87 mL, 1117.43 mmol) at −60° C. and the mixture was stirred at −40° C. for 1 h. The reaction mixture was then poured into 1N HCl (1680 mL) at 0° C. and extracted with EtOAc (600 mL). The organic layer was separated and the aqueous layer was extracted with EtOAc (400 mL). The combined organic layers were washed with water and brine, dried over $MgSO_4$ and concentrated in vacuo. The residue was purified by column chromatography (silica gel, eluted with 50% EtOAc in hexane) and concentrated in vacuo. The residue was then crystallized from 25% EtOAc in hexane (480 mL) to give (34) (109 g, 255 mmol, 91%) as a pale yellow solid.

Step 6. (3aR,7aS)-tert-butyl 3-(4-chloro-2-(2,4-dimethoxybenzyl)-7-fluoro-3-oxo-2,3-dihydro-1H-pyrrolo[3,4-c]pyridin-6-yl)octahydro-1H-benzo[d]imidazole-1-carboxylate (35)

To a solution of 2,4-dimethoxybenzylamine (33.2 mL, 220.87 mmol) in MeOH (1100 mL) and AcOH (11.11 mL) was added (34) (90 g, 210.35 mmol) at room temperature. The mixture was stirred in a water bath for 2 h. Sodium cyanoborohydride (26.4 g, 420.70 mmol) was then added in small portions. The mixture was stirred for further 2 h. The mixture was then quenched with water (360 mL) and brine (360 mL). The mixture was extracted with EtOAc (500 mL×3) and the combined organic layers were washed with brine, dried over $Na_2SO_4$ and concentrated in vacuo and carried on to the next reaction without further purification.

To a solution of (3aR,7aS)-tert-butyl 3-(4-chloro-2-(2,4-dimethoxybenzyl)-7-fluoro-3-oxo-2,3-dihydro-1H-pyrrolo[3,4-c]pyridin-6-yl)octahydro-1H-benzo[d]imidazole-1-carboxylate (210.35 mmol) in DMF (1.2 L) was added 1-(3-dimethylaminopropyl)-3-ethylcarbodiimide hydrochloride (EDCI, 54.4 g, 283.97 mmol) and 1-hydroxybenzotriazole hydrate (HOBt, 43.5 g, 283.97 mmol) at room temperature. The mixture was stirred at the same temperature overnight. The mixture was quenched with water (1.2 L) and extracted with EtOAc (1.2 L×2). The organic layer was separated, washed with brine, dried over $Na_2SO_4$ and concentrated in vacuo. The residue was rinsed with isopropyl ether to give (35) (105.7 g, 188 mmol, 90% in 2 steps).

Step 7. (3aR,7aS)-tert-butyl 3-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-yl)octahydro-1H-benzo[d]imidazole-1-carboxylate (36)

To a solution of (35) (155.9 g, 277.87 mmol) in dimethoxyethane (DME, 1500 mL) and water (750 mL) were added (8) (69.4 g, 333.45 mmol), sodium carbonate (70.7 g, 666.90 mmol) and trans-dichlorobis(triphenylphosphine)palladium(II) (7.80 g, 11.11 mmol) at room temperature. The mixture was stirred at 90° C. under Ar for 4 h. The reaction mixture was then treated with EtOAc (1000 mL) and water (500 mL) and the mixture was extracted with EtOAc. The combined organic layers were washed with 1N NaOH aq. and brine and dried over $Na_2SO_4$. The solution was passed through a pad of NH silica gel to remove Pd residue and the filtrate was concentrated in vacuo to provide (36) which was carried on to the next reaction without further purification.

Step 8. 6-(((1R,2S)-2-aminocyclohexyl)amino)-7-fluoro-4-(1-methyl-1H-pyrazol-4-yl)-1H-pyrrolo[3,4-c]pyridin-3(2H)-one trifluoroacetate (26)

(36) (171 g, 281.86 mmol) was dissolved in trifluoroacetic acid (860 mL, 11162.63 mmol) and water (9 mL) at room temperature. The mixture was stirred at reflux overnight. The reaction solvent was then removed in vacuo to provide (26) which was carried on to the next reaction without further purification.

Step 9. tert-butyl ((1S,2R)-2-((7-fluoro-4-(1-methyl-1H-pyrazol-4-yl)-3-oxo-2,3-dihydro-1H-pyrrolo[3,4-c]pyridin-6-yl)amino)cyclohexyl)carbamate (16)

To a solution of (26) (95 g, 207.24 mmol) in DMF (950 mL) was added triethylamine (43.2 mL, 310.86 mmol) and $Boc_2O$ (52.4 mL, 227.96 mmol) at 0° C. After stirring at 0° C. for 10 min, the reaction mixture was treated with EtOAc (1 L), 1M citric acid (210 mL) and water (1 L). The organic layer was separated, washed with water and brine, dried over $Na_2SO_4$. The solution was passed through silica gel (500 g) and the silica gel was washed with EtOAc. The eluate was concentrated in vacuo and the residue was washed with isopropyl ether. The residue was then dissolved in THF (2100 mL) and MeOH (700 mL) and 1N Sodium hydroxide (370 mL, 370.00 mmol) was added at room temperature. After stirring at the same temperature for 30 min, the reaction mixture was treated with EtOAc and brine and the organic layer was separated. The aqueous layer was extracted with EtOAc (×2) and the combined organic layers were washed with brine, dried over $Na_2SO_4$ and concentrated in vacuo. The residue was suspended in acetone (1100 mL) and water (220 mL). The mixture was stirred at reflux for 6 h and filtered through filter paper. The precipitate was washed with isopropyl ether to give (16) (64.3 g, 145 mmol, 86%).

Step 10. 6-(((1R,2S)-2-aminocyclohexyl)amino)-7-fluoro-4-(1-methyl-1H-pyrazol-4-yl)-1H-pyrrolo[3,4-c]pyridin-3(2H)-one hydrochloride dihydrate (Compound 1 Hydrochloride Dihydrate)

A suspension of (16) (146.5 g, 329.58 mmol) in 2-propanol (1450 mL) was heated to 70° C. at which point 2M hydrochloric acid (675 mL, 1350.00 mmol) was added. The reaction mixture was heated at 65° C. for 3 h and then cooled in an ice water bath for 1 h. The resulting solid was filtered, rinsed with cold isopropanol and dried by airflow to give Compound 1 hydrochloride dihydrate (132.3 g, 317 mmol, 96%). $^1$H NMR (300 MHz, $d_6$-DMSO) δ (ppm) 1.36-2.02 (m, 8H), 3.62-3.71 (m, 1H), 3.89 (s, 3H), 4.32-4.53 (m, 3H), 6.79 (d, J=6.4 Hz, 1H), 7.96 (brs, 3H), 8.37 (s, 1H), 8.84 (s, 1H).

Example 8. Synthesis of 6-(((1R,2S)-2-aminocyclohexyl)amino)-7-fluoro-4-(1-methyl-1H-pyrazol-4-yl)-1H-pyrrolo[3,4-c]pyridin-3(2H)-one (Compound 1 Free Base)

Step 1.

A 1 L, round-bottom flask equipped with an overhead stirrer was charged with Compound 1 citrate, MeCN (120 mL, 6 vol), and water (46 mL). The mixture was stirred at ambient temperature for 5 min followed by addition of NaOH (2 N, 74 mL, 4 equiv) over 5 min, resulting in a slightly orange suspension. The mixture was stirred and heated to 60° C. for 1 h resulting in an orange solution. Water was added over 20 min at 60° C. and the reaction was stirred at 60° C. for 20 min and cooled to ambient temperature over 2 h. The suspension was aged at ambient temperature for 16 h and filtered. The solid was rinsed with water (50 mL) and dried under vacuum for 16 h to afford Compound 1 free base as a slightly pink solid (11.4 g, 88% yield). $^1$H NMR (DMSO-d$_6$, 500 MHz): δ (ppm) 1.32-1.41 (m, 2H), 1.55-1.74 (m, 6H), 3.11-3.15 (m, 1H), 3.31 (br s, 4H), 3.89 (s, 3H), 4.06-4.12 (m, 1H), 4.35 (s, 2H), 6.38 (d, J=6.9 Hz, 1H), 8.24 (s, 1H), 8.25 (s, 1H), 8.78 (s, 1H).

General Methods—X-Ray Powder Diffraction (XRPD)

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for XP/2000 4.1.36 and the data were analyzed and presented using Diffrac Plus EVA v13.0.0.2 or v15.0.0.0.

Samples run under ambient conditions were prepared as flat plate specimens using powder as received without grinding. Approximately 1-2 mg of the sample was lightly pressed on a glass slide to obtain a flat surface.

Samples run under non-ambient conditions were mounted on a silicon wafer with heat-conducting compound. The sample was then heated to the appropriate temperature at 20° C./min and subsequently held isothermally for 1 minute before data collection was initiated.

Alternatively, X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analyzed and presented using Diffrac Plus EVA v13.0.0.2 or v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are: angular range: 2 to 42°2θ; step size: 0.05°2θ; and collection time: 0.5 s/step Differential Scanning Calorimetry (DSC)

DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminum pan, was heated at 10° C./min from 25° C. to 270° C. A purge of dry nitrogen at 50 ml/min was maintained over the sample.

Modulated temperature DSC was carried out using an underlying heating rate of 2° C./min and temperature modulation parameters of ±0.318° C. (amplitude) every 60 seconds (period).

The instrument control software was Advantage for Q Series v2.8.0.394 and Thermal Advantage v5.2.6 and the data were analyzed using Universal Analysis v4.7A or v4.4A.

DSC data were collected on a Mettler DSC 823E equipped with a 34 position auto-sampler. The instrument was calibrated for energy and temperature using certified indium. Typically 0.5-3 mg of each sample, in a pin-holed aluminum pan, was heated at 10° C./min from 25° C. to 270° C. A nitrogen purge at 50 ml/min was maintained over the sample.

The instrument control and data analysis software was STARe v9.20.

Thermo-Gravimetric Analysis (TGA)

TGA data were collected on a Mettler TGA/SDTA 851e equipped with a 34 position auto-sampler. The instrument was temperature calibrated using certified indium. Typically 5-30 mg of each sample was loaded onto a pre-weighed aluminum crucible and was heated at 10° C./min from ambient temperature to 300° C. A nitrogen purge at 50 mL/min was maintained over the sample.

The instrument control and data analysis software was STARe v9.20.

Gravimetric Vapour Sorption (GVS)

Sorption isotherms were obtained using a SMS DVS Intrinsic moisture sorption analyser, controlled by DVS Intrinsic Control software v1.0.0.30. The sample temperature was maintained at 25° C. by the instrument controls. The humidity was controlled by mixing streams of dry and wet nitrogen, with a total flow rate of 200 ml/min The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was undertaken in Microsoft Excel using DVS Analysis Suite v6.0.

Method Parameters for SMS DVS Intrinsic Experiments

| Parameters | Values |
| --- | --- |
| Adsorption - Scan 1 | 40-90 |
| Desorption/Adsorption - Scan 2 | 90-0, 0-40 |
| Intervals (% RH) | 10 |
| Number of Scans | 2 |
| Flow rate (ml/min) | 200 |
| Temperature (° C.) | 25 |
| Stability (° C./min) | 0.2 |
| Sorption Time (hours) | 6 hour time out |

The sample was recovered after completion of the isotherm and re-analyzed by XRPD.

Example 9. Characterization of Crystalline Form of Compound 1 Citrate ("Form 1")

Characterisation data was collected on Compound 1 citrate, prepared as described above. DSC analysis showed one single endothermic event, whilst the TGA thermogram showed no weight loss until the onset of decomposition. The material was non hygroscopic.

The high resolution XRPD data (FIG. 1) showed that the material was crystalline, the material being referred to as Form 1. The thermal data collected (FIGS. 2 and 3) suggested that this form was a non solvated sample with no significant weight loss being observed during heating of the sample in the TGA. The onset of decomposition is located at 226.9° C. on the TGA which coincides with the melting onset on the DSC (233.4° C.).

GVS analysis (FIG. 4) showed that the material was not hygroscopic when subjected to humidity (various RH levels). A subtle mass change of less than 0.3% was observed between 0-90% RH, indicating the presence of surface moisture on the material. No change in form was observed post GVS analysis, nor after storage at 40° C./75% RH and 25° C./97% RH for 1 week.

Samples of Form 1 were submitted for single crystal X-ray diffraction. Analysis revealed that Form 1 was a monoclinic crystal system of space group $P2_1$ with a volume of 1175(5) Å$^3$ and unit cell dimensions as follows:

| a = 9.35(3) Å | α = 90° |
|---|---|
| b = 6.697(17) Å | β = 92.90(2)° |
| c = 18.79(5) Å | γ = 90° |

Example 10. Amorphous Compound 1 Citrate ("Form 2")

Form 1 was dissolved in water (50 mL) at RT and the solution was filtered to remove any potential seeds. The system was frozen over cardice/acetone and set for freeze drying. The obtained solid was examined by XRPD and was found to be essentially non diffracting (absence of Bragg peaks, FIG. 5).

The batch of amorphous Compound 1 citrate contained around 3.3% of water, observed by the weight loss on the TGA (FIG. 7). The DSC curve shows the presence of water below 100° C. followed by a complex thermal profile afterwards (FIG. 6). The material is likely to decompose above 140° C. (observed in both the TGA and DSC curves). GVS analysis showed the material adsorbs moisture in large quantities in the range of 40-80% RH (9% w/w) and undergoes a crystallisation event above 80% RH (FIG. 8). This re-crystallisation is accompanied by a weight loss of 7% between 80% and 90% RH. The amorphous material post exposure to humidity was analyzed by XRPD and showed transformation to Form 1.

Example 11. Characterization of Crystalline Form of Compound 1 Hydrochloride ("Form 3")

Characterisation data was collected on Compound 1 hydrochloride dihydrate, prepared as described above. The high resolution XRPD data (FIG. 9) showed that the material was crystalline, the material being referred to as Form 3. The thermal data collected (FIGS. 10 and 11) suggested that this form was a dihydrate as a weight loss of 8.4% was observed between 50-120° C. in the TGA data, equivalent to 2 moles of water. The DSC data contained a broad endotherm with an onset of 98.3° C. which coincided with the weight loss observed. Karl Fischer analysis confirmed that the sample was in fact a dihydrate giving 8.4% water content. Ion chromatography indicated that the material was a mono hydrochloride salt (0.91 equivalents).

GVS analysis (FIG. 12) showed that the material was subject to dehydration below 20% RH. A mass change of ~6.5% was observed between 0-20% RH, indicating that the water can be removed from the crystal lattice. The amount of water removed by bringing the sample down to 0% was not equal to the full equivalent of a dihydrate. This could be due to the fact that the system did not reach equilibrium after 360 minutes. If longer drying time was allocated in this final step, it is more likely that the material would have lost the total amount of water. During the first sorption scan, the crystalline material was subject to water uptake and reverts back to the starting mass when reaching the 90% RH level. The phenomenon was reversible although differences in the isotherm curve were observed in the first sorption scan. No change in form was observed post GVS analysis, nor after storage at 40° C./75% RH and 25° C./97% RH for 1 week.

Samples of Form 3 were submitted for single crystal X-ray diffraction. The results are shown in Table 14. Analysis revealed that Form 3 was a crystal of space group P2(1)2(1)2(1) with a volume of 1916.81(17) Å$^3$ and unit cell dimensions as follows:

| a = 7.1149(4)Å, | α = 90° |
|---|---|
| b = 15.6028(8)Å, | β = 90°, |
| c = 17.2666(8)Å, | γ = 90° |

The structure solution was obtained by direct methods, full-matrix least-squares refinement on $F^2$ with weighting $w^{-1}=\sigma^2(F_o^2)+(0.0319P)^2+(0.9419P)$, where $P=(F_o^2+2F_c^2)/3$, anisotropic displacement parameters, empirical absorption correction using spherical harmonics, implemented in SCALE3 ABSPACK scaling algorithm, absolute structure parameter=−0.027(19). Final $wR^2=\{\Sigma[w(F_o^2-F_c^2)^2]/\Sigma[w(F_o^2)^2]^{1/2}\}=0.096$ for all data, conventional $R_1=0.0428$ on F values of 3278 reflections with $F_o>4\sigma(F_o)$, S=1.053 for all data and 290 parameters. Final Δ/σ(max) 0.000, Δ/σ(mean), 0.000. Final difference map between +0.231 and −0.214 e Å$^{-3}$.

Example 12. Polymorphism Studies of Form 3

25 mg of Form 3 were placed in HPLC vials with 20 mL of solvent used. These values were derived from the solubility assessment. All slurries were sonicated for 5 seconds. The slurries were stirred at 500 rpm at 5° C. for a period of six days. The solids obtained from this experiment were analyzed by XRPD before being dried in a vacuum oven at 40° C. overnight. The experimental results for this experiment can be found in Table 14.

TABLE 16

| Solvent | XRPD | Solvent | XRPD |
|---|---|---|---|
| Dimethoxyethane | Form 3 | Butyronitrile | Form 3 |
| DMF | Form 4 | DIPE | Form 3 |
| Toluene | Form 3 | Butyl Acetate | Form 3 |
| Cumene | Form 3 | Water | Form 3 |
| DCM | Form 3 | IPA | Form 3 |
| 1,4-Dioxane | Form 3 | n-Heptane | Form 3 |
| Ethyl Acetate | Form 3 | Methyl Acetate | Form 3 |
| Isopropyl Acetate | Form 3 | Dimethoxyethane/5% water | Form 3 |
| THF | Form 3 | DMF/5% water | Form 4 |
| TBME | Form 3 | 1,4-Dioxane/5% water | Form 3 |
| Acetone | Form 3 | Acetone/5% water | Form 3 |
| MEK | Form 3+? | Ethanol/5% water | Form 4 |
| Nitromethane | Form 3 | Methanol/5% water | Form 3 |
| DMSO | n/a | IPA/5% water | Form 3 |
| NMP | n/a | Acetonitrile/5% water | Form 3 |
| Ethanol | Amorphous | Acetonitrile | Form 5 |
| Methanol | Form 3 | | |
| MIBK | Form 3 | | |
| Anisole | Form 3 | | |

25 mg of Form 3 was used per vial with appropriate volumes of solvent. These values were derived from the solubility assessment. All slurries were sonicated for 5 seconds. The slurries were stirred at 500 rpm, cycling between 25° C. and 50° C. (4 h at each temperature) for a period of six days. Any resulting solutions were then allowed to evaporate at room temperature. The solids obtained from this experiment were analyzed by XRPD before being dried in a vacuum oven at 40° C. overnight. The experimental results for this experiment can be found in Table 15.

TABLE 17

| Solvent | XRPD | Solvent | XRPD |
| --- | --- | --- | --- |
| Dimethoxyethane | Form 3 | Anisole | Form 3 |
| DMF | Form 4 | Butyronitrile | Form 4 |
| Toluene | P3 | DIPE | P3 |
| Cumene | Form 3 | Butyl Acetate | Form 3 |
| DCM | Form 7+? | Water | n/a |
| 1,4-Dioxane | Amorphous | IPA | Form 4 |
| Ethyl Acetate | Form 7 | n-Heptane | Form 4 |
| Isopropyl Acetate | Form 3 | Methyl Acetate | Form 3 |
| THF | Form 3 | Dimethoxyethane/5% water | Form 3 |
| TBME | Form 3 | DMF/5% water | Form 4 |
| Acetone | Form 4 | 1,4-Dioxane/5% water | Form 3 |
| MEK | Form 7 | THF/5% water | Form 3 |
| Nitromethane | Form 7 | Acetone/5% water | Form 3 |
| DMSO | n/a | Ethanol/5% water | Form 4 |
| NMP | n/a | Methanol/5% water | Form 4 |
| Ethanol | Amorphous | IPA/5% water | Form 3 |
| Methanol | Form 3 | Acetonitrile/5% water | Form 3 |
| MIBK | Form 3 | Acetonitrile | Form 3 |

Example 13. Characterization of Crystalline Form of Compound 1 Hydrochloride ("Form 4")

Form 4 was prepared using 300 mg of Form 3 to which 20 vol of DMF was added. The experiment was matured by cycling between 25° C. and 50° C. (4 hrs cycle at each temperature for 48 hrs). The resulting material was filtered and dried under suction before being characterised.

XRPD analysis showed that Form 4 was reproducible by slurry maturation of Form 3 in DMF (FIG. 13). Form 4 was analyzed by thermal analysis (FIGS. 14 and 15). TGA data showed no significant weight loss, indicating that the material was anhydrous. The materials did not change form during storage at 25° C./97% RH, 40° C./75% RH, 40° C./97% RH for 10 days, indicating that it was stable to moisture. The solubility profile was similar to the one of Form 3. Form 4 was found to be non-hygroscopic as demonstrated by GVS (FIG. 16).

Example 14. Characterization of Crystalline Form of Compound 1 Hydrochloride ("Form 5")

Form 5 was obtained using a dry heating method. Form 3 was either heated to 250° C. and the sample was maintained at that temperature for 900 min under $N_2$ or Form 3 was heated to 290° C. and maintained at that temperature for 10 min under $N_2$. The recovered solid was analyzed by XRPD (FIG. 17).

Form 5 was found to be a non solvated form of the HCl salt. The material was anhydrous, confirmed by a flat TGA (FIG. 19). The material had a similar solubility profile compared to Form 4 (11 mg/ml). This material did not change form during GVS analysis or during storage at 40° C./97% RH (10 days) indicating that it is stable to moisture (FIG. 20).

Example 15. Characterization of Amorphous Compound 1 Hydrochloride ("Form 6")

Form 3 (41 mg) was dissolved in water (100 vol, 4.1 mL) at RT and the solution was filtered to remove any potential seeds. The system was frozen over cardice and acetone and set for freeze drying. The obtained solid was examined by XRPD and was found to be non diffracting (absence of Bragg peaks).

The XRPD analysis of the material produced by lyophilisation is considered to be essentially amorphous (FIG. 21). The broad peak at around 8° 2θ is not a diffraction peak since no Bragg peak were observed by high resolution XRPD. The material contained around 10% of water (observed by KF) since no vacuum oven drying was applied. The water presence was confirmed by TGA (FIG. 23). The glass transition is above 200° C. with a possible recrystallisation observed at 230° C. (FIG. 22). GVS analysis shows the material adsorbs moisture and undergoes a crystallisation event above 70% RH (FIG. 24). The amorphous material, if exposed to high humidity levels, seems to undergo a phase transformation, possibly leading to Form 9.

Example 16. Characterization of Crystalline Compound 1 Hydrochloride ("Form 7")

Anhydrous Form 7 was unstable to humidity and converted back to a hydrated form (Form 9). Form 7 was characterized by XRPD (FIG. 25). Thermal analysis was also performed on Form 7 (FIGS. 26 and 27). GVS analysis is shown in FIG. 28.

Example 17. Characterization of Crystalline Compound 1 Hydrochloride ("Form 8")

Another hydrated form was found (Form 8). When Form 3 was heated to a high temperature (200° C.), it resulted in a hydrated form (Form 8) and one anhydrous form (Form 5) at 250° C.

Form 8 was characterized by XRPD (FIG. 29). Thermal analysis was also performed on Form 7 (FIGS. 30 and 31). GVS analysis is shown in FIG. 32.

Example 18. Characterization of Crystalline Compound 1 Hydrochloride ("Form 9")

The amorphous material, if exposed to high humidity levels, seems to undergo a phase transformation, possibly leading to Form 9. Anhydrous Form 7 was unstable to humidity and converted back to a hydrated form (Form 9). Form 9 was characterized by XRPD (FIG. 33). Thermal analysis was also performed on Form 7 (FIGS. 34 and 35).

Example 19. Characterization of Crystalline Compound 1 Hydrochloride ("Form 10")

Form 3 was dry heated to 70° C. to provide Form 10. Form 10 was characterized by XRPD (FIG. 36). Thermal analysis was also performed on Form 10 (FIGS. 37 and 38).

Example 20. Characterization of Crystalline Compound 1 Hydrochloride ("Form 11")

Form 3 was dry heated to 80° C. to provide Form 11. Form 11 was characterized by XRPD (FIG. 39). Thermal analysis was also performed on Form 11 (FIGS. 40 and 41).

Example 21. Characterization of Crystalline Compound 1 Free Base

Compound 1 free base was prepared as described above and was characterised using a wide range of techniques to investigate the solid form and chemical properties. Compound 1 free base was found to be a mixture of a methanol solvate and an anhydrous form. Thermal analysis showed that the methanol solvate desolvated at around 120° C. and the anhydrous form transformed to new anhydrous form, Form 10, at around 203° C. Under the GVS experiment conditions and at 40° C.—75% RH, the methanol solvate desolvated, however, the anhydrous form was found to be stable.

Example 22. Characterization of Crystalline Compound 1 Free Base ("Form 12")

Amorphous Compound 1 free base was obtained using ca. 500 mg of Compound 1 free base prepared as described above as a starting material. 24 mL of the solution was freeze-dried in a round bottom flask.

Approximately 70 mg of the amorphous material was slurried in 20 volumes of tert-butyl methyl ether at ambient conditions for 2 days and then filtered and air-dried on a glass slide prior to analysis. XRPD analysis confirmed the formation of Form 12 (FIG. 42). Form 12 was found to be an anhydrous form, with a melting point of 226.5° C. (FIG. 43). No obvious stability issues were noted at 40° C./75% RH; however, at 25° C./97% RH it was not stable. GVS analysis suggested the possibility of the transformation of Form 12 to a hydrated form (FIG. 45). The aqueous solubility of the form was found to be 0.58 mg/mL (pH 9.41).

Example 23. Characterization of Crystalline Compound 1 Free Base ("Form 13")

Approximately 35 mg of amorphous material was slurried in 10 volumes of 2-methyl THF in the presence of small amount of Form 13 seeds overnight. The slurry was continued to mature under the same conditions for another day and the XRPD analysis of the filtered and dried sample confirmed formation of Form 13 (FIG. 46). Form 13 was found to be an anhydrous form. Form 13 transformed to Form 12 at higher temperatures (between 140 and 210° C.). Form 13 was not hygroscopic and no transformation to hydrates was observed during GVS experiment (FIG. 49). It was found to be stable at 40° C./75% RH and 25° C./97% RH. The aqueous solubility of the form was found to be 0.19 mg/mL (pH 9.05).

Example 24. Characterization of Crystalline Compound 1 Free Base ("Form 14")

Approximately 50 mg of Compound 1 free base was slurried in 10 volumes of acetonitrile with 20% water at 50° C. overnight. The sample was filtered and air dried prior to the XRPD analysis and was confirmed to be Form 14 which was a hemi-hydrate (FIG. 50). Form 14 was found to dehydrate at around 55° C. and transformed to Form 12 (FIG. 51). It was stable at 40° C./75% RH and 25° C./97% RH. Between 0 and 90% RH Form 14 exchanged 0.25 eq. of water; however, no change in the XRPD pattern was noted on isolation of the sample at the end of the GVS analysis (FIG. 53).

Example 25. Characterization of Crystalline Compound 1 Free Base ("Form 15")

Figure 57:
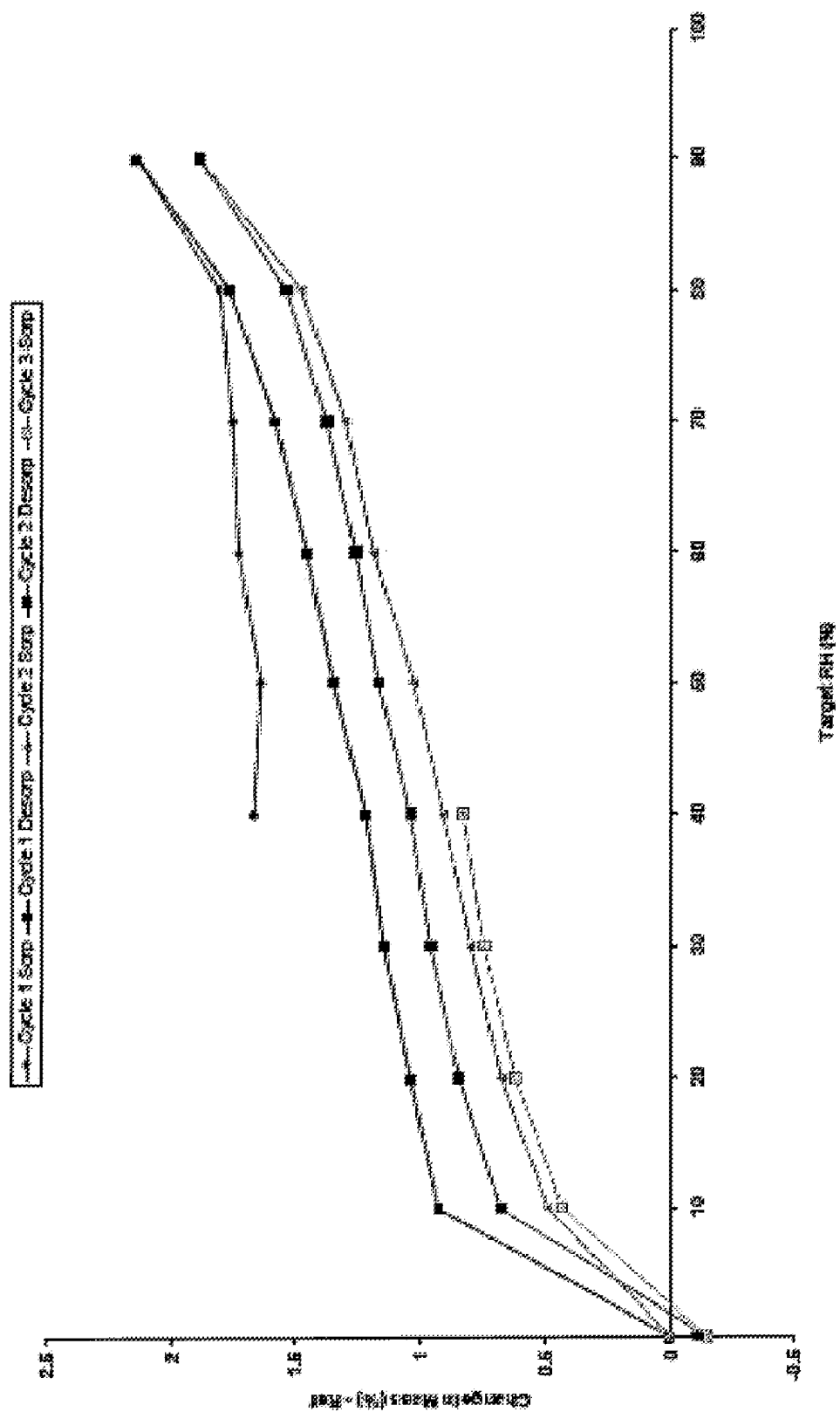
FIG. 57 shows a GVS isotherm plot for crystalline Form 15.

Approximately 60 mg of Compound 1 free base was dissolved in 100 volumes of dimethoxyethane at 50° C. The resulting turbid solution was filtered and evaporated to dryness at RT. The XRPD analysis of the sample confirmed formation of Form 15 which was a mono-hydrate (FIG. 54). Form 15 was found to desolvate at 110° C. and transformed to Form 12 on further heating (FIG. 55). It was stable at 40° C./75% RH and 25° C./97% RH. Between 0 and 90% RH it exchanged 0.4 eq. of water; however, no change in the XRPD pattern was noted on isolation of the sample at the end of the GVS analysis (FIG. 57). The aqueous solubility of the form was found to be 0.71 mg/mL (pH 9.41).

Example 26. Characterization of Crystalline Compound 1 Free Base ("Form 16")

Approximately 60 mg of Compound 1 free base was slurried in water at RT for 4 hours followed by 50° C. for the next 4 hours and the heat/cool cycle was carried out for two days. The sample was filtered and air dried prior to XRPD analysis (FIG. 58). The analysis confirmed Form 16 which was a tris-hydrate. Form 16 was found to desolvate at around 37° C. (FIG. 59). It was stable at and above 30% RH at 25° C. and desolvated below 30% RH. No changes in the XRPD pattern were observed at 40° C./75% RH and 25° C./97% RH. The aqueous solubility of the form was found to be 0.13 mg/mL (pH 9.27).

Example 27. Characterization of Crystalline Compound 1 Free Base ("Form 17")

Approximately 50 mg of the amorphous material was slurried in 10 volumes of THF with 5% water at ambient conditions for 2 days and then filtered and air-dried on a glass slide, prior to XRPD analysis which indicated a mixture of Form 15 and Form 17. Approximately 20 mg of this mixture was slurried in 10 volumes of THF with 5% water at 25° C. for 3 days, filtered and air-dried prior to XRPD analysis (FIG. 62). The sample was confirmed to be Form 17 which was a mono-hydrate. Form 17 was found to desolvate at around 50° C., followed by a series of transformations (FIG. 63). It was stable at 40° C./75% RH and 25° C./97% RH. Between 0 and 90% RH it exchanged 0.3 eq. of water; however, no change in the XRPD pattern was noted on isolation of the sample at the end of the GVS analysis (FIG. 65). The aqueous solubility of the form was found to be 0.18 mg/ml (pH 9.33).

Example 28. Administration of Compound 1 Citrate (Form 1)

Patients aged ≥18 yrs with advanced solid tumors/lymphoma whose disease failed standard therapies received oral Compound 1 citrate (Form 1) daily (QD, 60-120 mg) in 28 day cycles. To determine the maximum tolerated dose, dose escalation proceeded via modified titration design based on dose limiting toxicity or any drug-related grade ≥2 adverse event (AE) during cycle 1. Blood samples for plasma pharmacokinetic assessments were collected pre-dose and post-dose on day 1 and day 15 of cycle 1. Response assessments per RECIST for solid tumors and per IWG criteria for lymphoma were performed between day 22 and day 29 (pre-dose) of cycle 2, 4 and 6, and every 3 cycles thereafter.

At data cut-off, 15 patients were enrolled (11 patients at 60 mg, 7 solid tumor [4 diffuse large B-cell lymphoma, DLBCL] and 4 patients at 120 mg, all solid tumor); patients received a median of 2 cycles at 60 mg and all patients at 120 mg received 1 cycle. Cycle 1 dose limiting toxicity occurred in 1 patient at 60 mg (grade 3 asymptomatic aspartate aminotransferase elevation) and 2 patients at 120 mg (grade 3 and 4 asymptomatic lipase elevation). Grade ≥3 drug-related AEs occurred in 2 (18%) pts at 60 mg and 3 (75%) at 120 mg. Only anemia (1 at 60 mg, 2 at 120 mg) and increased lipase (0 and 2 pts) were seen in >1 pt overall; 3 patients discontinued due to adverse events (1 at 60 mg, 2 at 120 mg) and 4 patients died on study (3 and 1 patient; deaths were not related to study drug). Plasma pharmacokinetic data was evaluated in 11 patients at 60 and 120 mg. The pharmacokinetics of Compound 1 citrate (Form 1) was characterized by rapid absorption (median Tmax 2 h), moderate variability in steady-state exposures (47% coefficient of variation for dl 5 AUCtau), mean peak-to-trough ratio of 2.7 at steady-state, and mean accumulation of 2.7-fold post repeated once daily dosing for 15 days. In 5 response-evaluable patients (4 DLBCL) by data cut-off, 2 DLBCL patients at 60 mg showed signs of response after 2 cycles, 1 partial response and 1 patient with 25% tumor reduction. Post data cut-off, 1 DLBCL patient at 80 mg achieved partial response after 1 cycle.

Compound 1 citrate (Form 1) 60 mg once daily appears to have an acceptable safety and pharmacokinetic profile. Pharmacokinetic results support oral and continuous once-daily administration of Compound 1 citrate (Form 1).

Example 29 Tablet Formulations

The following oral dosage forms were prepared using a wet granulation process:

| | 20 mg Tablet (mg) | 60 mg Tablet (mg) | 100 mg Tablet (mg) |
|---|---|---|---|
| Compound 1 (Form 1) | 20 (31.16) | 60 (93.48) | 100 (155.8) |
| D-Mannitol | 44.34 | 133.02 | 221.7 |
| Microcrystalline cellulose (Ceolus PH101) | 5 | 15 | 25 |
| Hydroxypropyl cellulose (HPC-L) | 3 | 9 | 15 |
| Sodium starch glycolate (Primojel) | 5 | 15 | 25 |
| Microcrystalline cellulose (Ceolus KG802) | 10 | 30 | 50 |
| Magnesium stearate | 1.5 | 4.5 | 7.5 |
| Core tablet weight | 100 | 300 | 500 |
| Opadry red | 2 | 6 | 9 |
| Opadry yellow | 2 | 6 | 9 |
| Coated tablet weight | 104 | 312 | 518 |

The patent and scientific literature referred to herein establishes knowledge that is available to those skilled in the art. Unless otherwise defined, all technical and scientific terms used herein have the same meaning as commonly understood by those skilled in the art to which the invention belongs. The issued patents, applications, and references that are cited herein are hereby incorporated by reference to the same extent as if each was specifically and individually indicated to be incorporated by reference. In the case of inconsistencies, the present disclosure, including definitions, is intended to control.

While a number of embodiments of the invention have been described, it is apparent that the provided basic examples may be altered to convey other embodiments, which utilize the compounds, methods, etc. of the invention. It will thus be appreciated that the scope of the invention has been represented herein by way of example and is not intended to be limited by the specific embodiments.

What is claimed is:

1. A crystal form of 6-((1R,2S)-2-aminocyclohexylamino)-7-fluoro-4-(1-methyl-1H-pyrazol-4-yl)-1H-pyrrolo[3,4-c]pyridine-3(2H)-one citrate, which is in substantially crystalline form, and is characterized by an X-ray powder diffraction (XRPD) pattern using Cu Kα radiation comprising peaks at 2θ angles of 9.4, 16.6, 17.4, 18.9, 19.2, and 20.7°±0.2 degrees.

2. The crystal form of claim 1, characterized by an XRPD pattern using Cu Kα radiation comprising peaks at 2θ angles of 4.7, 9.4, 16.6, 17.4, 18.9, 19.2, 20.7, and 23.0°±0.2 degrees.

3. The crystal form of claim 1, characterized by an XRPD pattern using Cu Kα radiation comprising peaks at 2θ angles of 4.7, 9.4, 13.0, 13.8, 14.1, 16.6, 17.4, 18.4, 18.9, 19.2, 20.7, 23.0, 23.3, 23.6, and 25.0°±0.2 degrees.

4. The crystal form of claim 1, wherein the crystal form is not hygroscopic.

5. A pharmaceutical composition comprising the crystal form of claim 1 and one or more pharmaceutically acceptable carriers.

6. The pharmaceutical composition of claim 5, which is suitable for oral administration.

7. The pharmaceutical composition of claim 6, which is a dosage form selected from a capsule and a tablet.

8. The pharmaceutical composition of claim 7, wherein the dosage form is a tablet.

* * * * *